United States Patent
Park et al.

(10) Patent No.: US 12,279,524 B2
(45) Date of Patent: Apr. 15, 2025

(54) ORGANIC ELECTRIC ELEMENT COMPRISING COMPOUND FOR ORGANIC ELECTRIC ELEMENT AND AN ELECTRONIC DEVICE THEREOF

(71) Applicant: DUK SAN NEOLUX CO., LTD., Chungcheongnam-do (KR)

(72) Inventors: Jong Gwang Park, Chungcheongnam-do (KR); Sun Hee Lee, Chungcheongnam-do (KR); Soung Yun Mun, Chungcheongnam-do (KR); Byoung Yeop Kang, Chungcheongnam-do (KR)

(73) Assignee: DUK SAN NEOLUX CO., LTD., Chungcheongnam-Do (KR)

( * ) Notice: Subject to any disclaimer, the term of this patent is extended or adjusted under 35 U.S.C. 154(b) by 757 days.

(21) Appl. No.: 17/608,610

(22) PCT Filed: Apr. 20, 2020

(86) PCT No.: PCT/KR2020/005208
§ 371 (c)(1),
(2) Date: Nov. 3, 2021

(87) PCT Pub. No.: WO2020/226298
PCT Pub. Date: Nov. 12, 2020

(65) Prior Publication Data
US 2022/0238811 A1    Jul. 28, 2022

(30) Foreign Application Priority Data
May 3, 2019   (KR) .......................... 10-2019-0052128

(51) Int. Cl.
*H10K 85/60*   (2023.01)
*C07C 211/61*   (2006.01)
(Continued)

(52) U.S. Cl.
CPC .......... *H10K 85/636* (2023.02); *C07C 211/61* (2013.01); *C07D 209/86* (2013.01);
(Continued)

(58) Field of Classification Search
CPC ... H10K 85/631; H10K 85/633; H10K 85/636
See application file for complete search history.

(56) References Cited

U.S. PATENT DOCUMENTS

| 2018/0186764 | A1* | 7/2018 | Jung | C07D 307/92 |
| 2019/0259947 | A1* | 8/2019 | Lee | H10K 85/633 |
| 2020/0335698 | A1* | 10/2020 | Park | H01L 27/1255 |

FOREIGN PATENT DOCUMENTS

| KR | 20150007476 A | * | 1/2015 | ............. C09K 11/06 |
| KR | 10-2015-0031892 A | | 3/2015 | |

(Continued)

OTHER PUBLICATIONS

Office action issued on Feb. 27, 2024 from Korean Patent Office in a counterpart Korean Patent Application No. 10-2019-0052128 (all the cited references are listed in this IDS.) (English translation is also submitted herewith.).

(Continued)

*Primary Examiner* — Vu A Nguyen
(74) *Attorney, Agent, or Firm* — The PL Law Group, PLLC

(57) ABSTRACT

An organic electric element according to an embodiment of the present disclosure includes an anode, a cathode, and an organic material layer formed between the anode and the cathode. The organic material layer includes a compound of Formula 1. The driving voltage of the organic electric element can be lowered, and the luminous efficiency and life time of the organic electric element can be improved.

18 Claims, 2 Drawing Sheets

(51) Int. Cl.
- *C07D 209/86* (2006.01)
- *C07D 251/24* (2006.01)
- *C07D 307/91* (2006.01)
- *C07D 333/76* (2006.01)
- *C07D 403/04* (2006.01)
- *C07D 405/04* (2006.01)
- *C07D 405/10* (2006.01)
- *C07D 409/14* (2006.01)
- *C07D 487/16* (2006.01)
- *C07D 495/04* (2006.01)
- *C09K 11/06* (2006.01)
- *H10K 50/11* (2023.01)
- *H10K 50/15* (2023.01)
- *H10K 50/19* (2023.01)
- *H10K 101/10* (2023.01)

(52) U.S. Cl.
CPC ......... *C07D 251/24* (2013.01); *C07D 307/91* (2013.01); *C07D 333/76* (2013.01); *C07D 403/04* (2013.01); *C07D 405/04* (2013.01); *C07D 405/10* (2013.01); *C07D 409/14* (2013.01); *C07D 487/16* (2013.01); *C07D 495/04* (2013.01); *C09K 11/06* (2013.01); *H10K 85/615* (2023.02); *H10K 85/622* (2023.02); *H10K 85/633* (2023.02); *H10K 85/654* (2023.02); *H10K 85/6572* (2023.02); *H10K 85/6574* (2023.02); *H10K 85/6576* (2023.02); *C07C 2603/18* (2017.05); *C07C 2603/40* (2017.05); *C09K 2211/1007* (2013.01); *C09K 2211/1011* (2013.01); *C09K 2211/1014* (2013.01); *C09K 2211/1018* (2013.01); *H10K 50/11* (2023.02); *H10K 50/15* (2023.02); *H10K 50/19* (2023.02); *H10K 2101/10* (2023.02)

(56) References Cited

FOREIGN PATENT DOCUMENTS

| KR | 10-2015-0066429 A | 6/2015 | | |
|----|-------------------|--------|---|---|
| KR | 10-2016-0074376 A | 6/2016 | | |
| KR | 10-2018-0082710 A | 7/2018 | | |
| KR | 10-2018-0112962 A | 10/2018 | | |
| KR | 10-2019-0005522 A | 1/2019 | | |
| KR | 10-2019-0012468 A | 2/2019 | | |
| KR | 10-2019-0019251 A | 2/2019 | | |
| KR | 10-2019-0038254 A | 4/2019 | | |
| KR | 20190038254 A | * | 4/2019 | ........... C07D 409/14 |
| WO | WO-2017122978 A1 | * | 7/2017 | ........... C07C 13/72 |

OTHER PUBLICATIONS

International Search Report for PCT/KR2020/005208 mailed on Aug. 4, 2020.

* cited by examiner

ORGANIC ELECTRIC ELEMENT COMPRISING COMPOUND FOR ORGANIC ELECTRIC ELEMENT AND AN ELECTRONIC DEVICE THEREOF

PRIORITY

This application claims benefit under 35 U.S.C. 119(e), 120, 121, or 365(c), and is a National Stage entry from International Application No. PCT/KR2020/005208, filed on Apr. 20, 2020, which claims priority to the benefit of Korean Patent Application No. 10-2019-0052128 filed in the Korean Intellectual Property Office on May 3, 2019, the entire contents of which are incorporated herein by reference.

BACKGROUND

1. Technical Field

The present invention relates to organic electric element comprising compound for organic electric element and an electronic device thereof.

2. Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function. Further, the light emitting material may be divided into a high molecular weight type and a low molecular weight type according to its molecular weight, and may also be divided into a fluorescent material derived from excited singlet states of electron and a phosphorescent material derived from excited triplet states of electron according to its light emitting mechanism. Further, the light emitting material may be divided into blue, green, and red light emitting material and yellow and orange light emitting material required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to a deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more than more as size of display becomes larger and larger in the portable display market. Therefore, the power consumption is a very important factor in the portable display with a limited power source of the battery, and efficiency and life span issue must also be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase.

However, efficiency cannot be maximized only by simply improving the organic material layer. This is because long life span and high efficiency can be simultaneously achieved when energy levels and $T_1$ values among the respective layers included in the organic material layer, inherent material properties (mobility, interfacial properties, etc.) and the like are optimal combination.

In addition, an emission-auxiliary layer must be present between the hole transport layer and the light emitting layer in order to solve the problem of luminescence in the hole transport layer of recent organic electroluminescent devices, and material of different emission-auxiliary layers have been developed for each of the light emitting layers (R, G, B).

In general, an electron is transferred from an electron transport layer to a light emitting layer and a hole is transferred from a hole transport layer to the light emitting layer, as a result, an exciton is formed by the recombination of the electron and hole. However, the material used for the hole transport layer has a low HOMO value and therefore has a low $T_1$ value. As a result, the exciton generated in the light emitting layer is transferred to the hole transport layer, resulting in a charge unbalance in the light emitting layer and light is emitted at the interface of the hole transport layer.

When light is emitted at the interface of the hole transport layer, the color purity and efficiency of the organic electric element are lowered and a problem occurs in that the life time is shortened. Therefore, it is necessary to develop the emission-auxiliary layer material having a high T1 value and a HOMO level between the hole transport layer and the light emitting layer.

Therefore, it is necessary to use the materials constituting the organic layer, particularly, the materials of a hole transport layer, an emission-auxiliary layer and a light emitting layer, in an appropriate combination in order to sufficiently exhibit the excellent characteristics of an organic electric element.

SUMMARY

The object of the present invention is to provide an organic electric element comprising a compound capable of lowering the driving voltage of the element and improving the luminous efficiency, color purity, stability and life time, and an electronic device thereof.

In an aspect of the present invention, the present invention provides an organic electric element comprising a compound represented by the following formula.

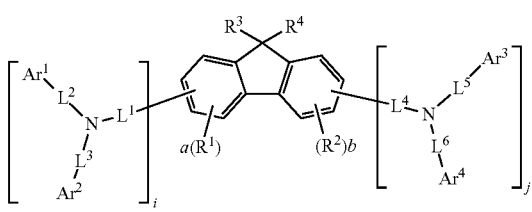

In another aspect of the present invention, the present invention provides an organic electric element employing the compound represented by formula above and an electronic device thereof.

By employing the compound represented by Formula 1 of the present invention to the organic material layer of the organic electric element, the driving voltage can be lowered, and the luminous efficiency and lifetime of the element can be improved.

BRIEF DESCRIPTION OF THE DRAWINGS

The FIGS. 1 to 3 illustrate an example of an organic electroluminescent element according to an embodiment of the present invention.

DETAILED DESCRIPTION

Figure 1:
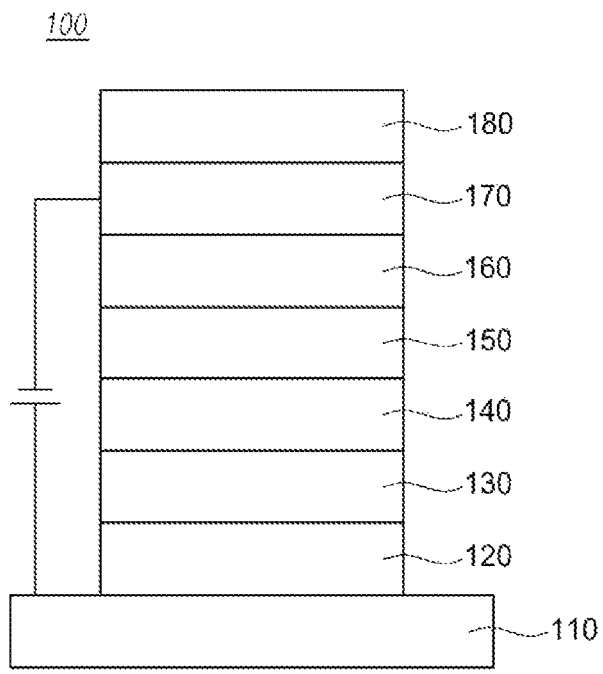

Unless otherwise stated, the term "aryl group" or "arylene group" as used herein has, but not limited to, 6 to 60 carbon atoms. The aryl group or arylene group in the present invention may comprise a monocyclic ring, ring assemblies, a fused polycyclic system, spiro compounds and the like. In addition, unless otherwise stated, a fluorenyl group may be comprised in an aryl group and a fluorenylene group may be comprised in an arylene group.

The term "fluorenyl group" used in the present invention refers to a substituted or unsubstituted fluorenyl group, and "fluorenylene group" refers to a substituted or unsubstituted fluorenyl group, and the fluorenyl group or fluorenylene group used in the present invention comprises case in which R and R' are bonded to each other in the following structure to form a spiro compound together with the carbon to which they are bonded.

"Substituted fluorenyl group" or "substituted fluorenylene group" means that at least any one of R, R' and R" is a substituent other than hydrogen, and in this specification, a fluorenyl group, a fluoreneylene group, and a fluorenetriyl group may be referred to as a fluorene group regardless of the valence.

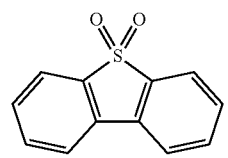

The term "spiro compound" as used herein has a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

The term "heterocyclic group" used in the specification comprises a non-aromatic ring as well as an aromatic ring like "heteroaryl group" or "heteroarylene group". Unless otherwise stated, the term "heterocyclic group" means, but not limited to, a ring containing one or more heteroatoms and having 2 to 60 carbon atoms. Unless otherwise stated, the term "heteroatom" as used herein represents N, O, S, P or Si and the heterocyclic group means a monocyclic, ring assemblies, fused polycyclic system or spiro compound containing a heteroatom. In addition, heterocyclic group comprises the compound comprising the heteroatom group such as $SO_2$, $P=O$ etc. instead of carbon forming a ring such as the following compound.

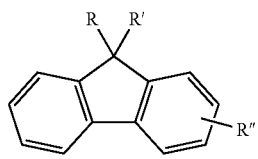

The term "aliphatic ring group" as used herein refers to a cyclic hydrocarbon except for aromatic hydrocarbons, and comprises a monocyclic ring, ring assemblies, a fused polycyclic system, spiro compounds, and the like, and unless otherwise specified, it means a ring of 3 to 60 carbon atoms, but not limited thereto. For example, a fused ring formed by benzene being an aromatic ring with cyclohexane being a non-aromatic ring corresponds to aliphatic ring group.

In this specification, a 'group name' corresponding to an aryl group, an arylene group, a heterocyclic group, and the like exemplified for each symbol and its substituent may be written in the name of functional group reflecting the valence, and may also be described as the name of a parent compound. For example, in the case of phenanthrene which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

In addition, in the present specification, the numbers and alphabets indicating a position may be omitted when describing a compound name or a substituent name, For example, pyrido[4,3-d]pyrimidine, benzofuro[2,3-d]pyrimidine and 9,9-dimethyl-9H-fluorene can be described as pyridopyrimidine, benzofuropyrimidine and dimethylfluorene, respectively. Therefore, both benzo[g]quinoxaline and benzo[f]quinoxaline can be described as benzoquinoxaline.

In addition, unless otherwise expressed, where any formula of the present invention is represented by the following formula, the substituent according to the index may be defined as follows.

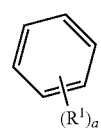

In the above formula, where a is an integer of zero, the substituent R¹ is absent, that is, hydrogen atoms are bonded to all the carbon constituting the benzene ring. Here, chemical formulas or compounds may be written without explicitly describing the hydrogen. In addition, one substituent R¹ is bonded to any carbon of the carbons forming the benzene ring when "a" is an integer of 1. Similarly, where "a" is an integer of 2 or 3, substituents R¹s may be bonded to the carbon of the benzene ring, for example, as followings. Also, where "a" is an integer of 4 to 6, substituents R¹s are bonded to the carbon of the benzene ring in a similar manner. Further, where "a" is an integer of 2 or more, R¹s may be the same or different from each other.

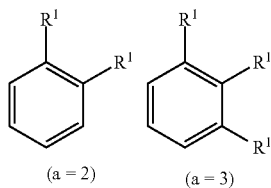

In addition, unless otherwise specified in the present specification, the ring formed by bonding between adjacent groups may be selected from the group consisting of a $C_6$-$C_{60}$ aromatic ring group, a fluorenyl group, a $C_2$-$C_{60}$ heterocyclic group containing at least one heteroatom selected from the group consisting of O, N, S, Si, and P, and a $C_3$-$C_{60}$ aliphatic ring.

Hereinafter, referring to FIGS. 1 to 3, a lamination structure of an organic electric element including the compound of the present invention will be described.

In the reference numbers assigned to the components of each drawing, it should be noted that the same elements will be designated by the same reference numerals although they are shown in different drawings. In addition, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It will be understood that the expression "one component is "connected," "coupled" or "joined" to another component comprises the case where a third component may be "connected," "coupled," and "joined" between the first and second components as well as the case where the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

Figure 2:
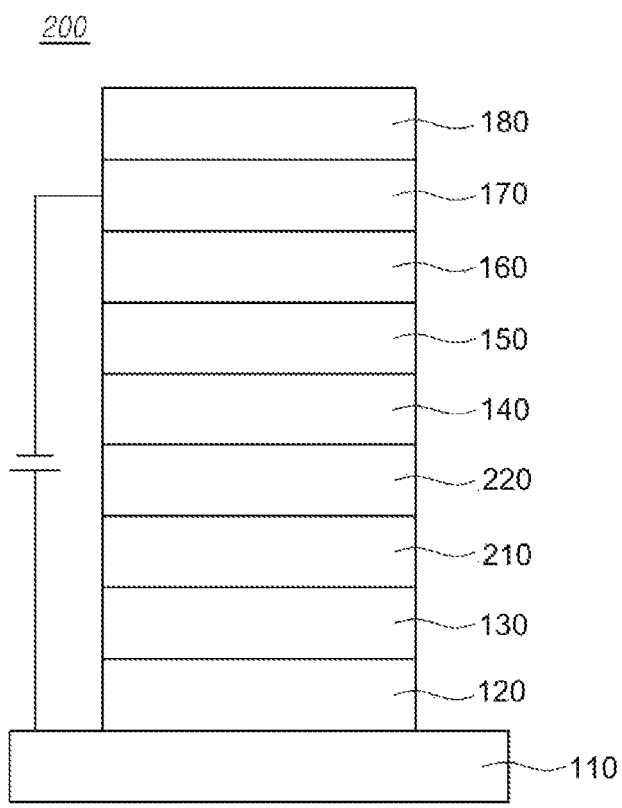
Figure 3:
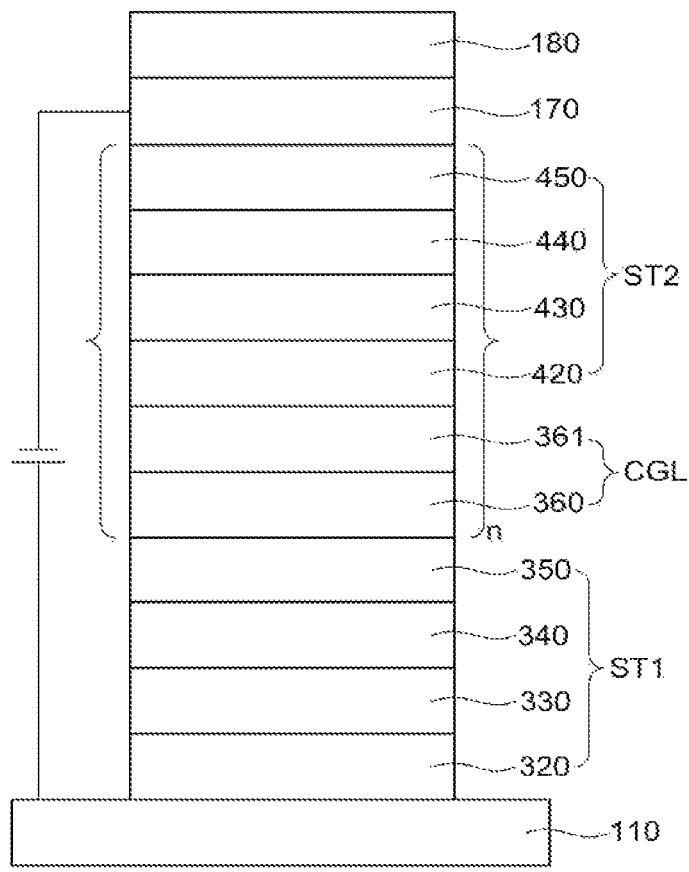
Figure 4:
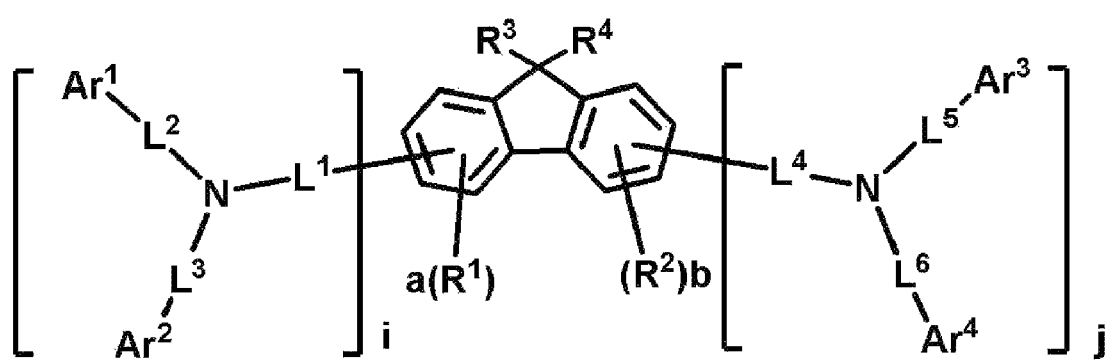
FIG. 4 shows Formula comprised in an organic material layer of the present invention.

The FIGS. 1 to 3 are structures for showing an example of an organic electric element according to an embodiment of the present invention, respectively.

Referring to the FIG. 1, an organic electric element 100 according to an embodiment of the present invention includes a first electrode 110 formed on a substrate (not shown), a second electrode 170, and an organic material layer formed between the first electrode 110 and the second electrode 170.

The first electrode 110 may be an anode (positive electrode), and the second electrode 170 may be a cathode (negative electrode). In the case of an inverted organic electric element, the first electrode may be a cathode, and the second electrode may be an anode.

The organic material layer may be comprised a hole injection layer 120, a hole transport layer 130, a light emitting layer 140, an electron transport layer 150, and an electron injection layer 160. Specifically, a hole injection layer 120, a hole transport layer 130, a light emitting layer 140, an electron transport layer 150, and an electron injection layer 160 are formed on the first electrode 110 in sequence.

Preferably, a layer for improving the luminous efficiency 180 may be formed one side of sides of the first electrode 110 and the second electrode 170, wherein one side is not facing the organic material layer, as a result the luminous efficiency of an organic electric element can be improved.

For example, the light efficiency improving layer 180 may be formed on the second electrode 170, as a result, in the case of a top emission organic light emitting diode, the optical energy loss due to Surface Plasmon Polaritons (SPPs) at the second electrode 170 may be reduced and in the case of a bottom emission organic light emitting diode, the light efficiency improving layer 180 may serve as a buffer for the second electrode 170.

A buffer layer 210 or an emission-auxiliary layer 220 may be further formed between the hole transport layer 130 and the light emitting layer 140. This will be described with reference to FIG. 2.

Referring to FIG. 2, the organic electric element 200 according to another embodiment of the present invention may comprise a hole injection layer 120, a hole transport layer 130, a buffer layer 210, an emission-auxiliary layer 220, a light emitting layer 140, the electron transport layer 150, the electron injection layer 160, and a second electrode 170 formed on a first electrode 110 in sequence, and a light efficiency improving layer 180 may be formed on the second electrode 170.

Although not shown in FIG. 2, an electron transport auxiliary layer may be further formed between the light emitting layer 140 and the electron transport layer 150.

In addition, according to another embodiment of the present invention, the organic material layer may be a form consisting of a plurality of stacks, wherein the stacks comprise a hole transport layer, a light emitting layer, and an electron transport layer, respectively. This will be described with reference to FIG. 3.

Referring to FIG. 3, two or more sets of stacks of the organic material layers ST1 and ST2 may be formed between the first electrode 110 and the second electrode 170 in the organic electric element 300 according to another embodiment of the present invention, wherein the organic material layers are consisted of multiple layers, respectively, and the charge generation layer CGL may be formed between the stacks of the organic material layer.

Specifically, the organic electric element according to the embodiment of the present invention may comprise the first electrode 110, the first stack ST1, the charge generation layer CGL, the second stack ST2, and the second electrode 170 and the light efficiency improving layer 180.

The first stack ST1 is an organic layer formed on the first electrode 110, and the first stack ST1 may comprise the first hole injection layer 320, the first hole transport layer 330, the first light emitting layer 340 and the first electron transport layer 350 and the second stack ST2 may comprise a second hole injection layer 420, a second hole transport layer 430, a second light emitting layer 440 and a second electron transport layer 450. As such, the first stack and the second stack may be the organic layers having the same or different stacked structures.

The charge generation layer CGL may be formed between the first stack ST1 and the second stack ST2. The charge generation layer CGL may comprise a first charge generation layer 360 and a second charge generation layer 361. The charge generating layer CGL is formed between the first light emitting layer 340 and the second light emitting layer 440 to increase the current efficiency generated in each light emitting layer and to smoothly distribute charges.

The first light emitting layer 340 may comprise a light emitting material comprising a blue host doped with a blue fluorescent dopant and the second light emitting layer 440 may comprise a light emitting material comprising a green host doped with a greenish yellow dopant and a red dopant together, but the material of the first light emitting layer 340 and the second light emitting layer 440 according to an embodiment of the present invention is not limited thereto.

In FIG. 3, n may be an integer of 1 to 5 and the charge generation layer CGL and the third stack may be further stacked on the second stack ST2 when n is 2.

When a plurality of light emitting layers are formed in a multi-layer stack structure as shown in FIG. 3, it is possible to manufacture an organic electroluminescent element that emits not only white light but also various colors, wherein the white light is emitted by the mixing effect of light emitted from each light emitting layer.

The mixture of the compound represented by Formula 1 can be used as material of a hole injection layer 120, 320, 420, a hole transport layer 130, 330, 430, a buffer layer 210, an emission-auxiliary layer 220, an electron transport layer 150, 350, 450, an electron injection layer 160, a light emitting layer 140, 340, 440, or a layer for improving luminous efficiency 180, preferably as material of three layers of a hole transport layer 130, 330, 430, an emission-auxiliary layer 220 and a light emitting layer 140, 340, 440.

Even if the core is the same core, the band gap, the electrical characteristics, the interface characteristics and the like may be different depending on which substituent is bonded at which position. Therefore, it is necessary to study the selection of the core and the combination of the core and the sub-substituent bonded to the core. In particular, long life span and high efficiency can be simultaneously achieved when the optimal combination of energy levels and $T_1$ values, inherent material properties (mobility, interfacial properties, etc.), and the like among the respective layers of an organic material layer is achieved.

Therefore, energy level and $T_1$ value between the respective layers of the organic material layer, inherent material properties (mobility, interfacial properties, etc.) and the like can be optimized by employing the compound represented by Formula 1 as material of three layers of a hole transport layer 130, 330, 430, an emission-auxiliary layer 220 and a light emitting layer 140, 340, 440. As a result, the lifetime and efficiency of the organic electric element can be improved simultaneously.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 110, forming the organic material layer comprising the hole injection layer 120, the hole transport layer 130, the light emitting layer 140, the electron transport layer 150, and the electron injection layer 160 thereon, and then depositing a material, which can be used as the cathode 170, thereon. Also, an emission-auxiliary layer 220 may be formed between a hole transport layer 130 and a light emitting layer 140, and an electron transport auxiliary layer (not shown) may be further formed between a light emitting layer 140 and an electron transport layer 150 and, as described above, a stack structure may be formed.

In addition, the organic material layer may be manufactured in such a manner that the fewer layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

In addition, the organic electric element according to an embodiment of the present invention may be selected from the group consisting of an organic light emitting diode, an organic solar cell, an organic photo conductor, an organic transistor, an element for monochromatic illumination and an element for quantum dot display.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electric element according to an aspect of the present invention will be described.

An organic electric element according to an aspect of the present invention comprises an anode, a cathode, and an organic material layer formed between the anode and the cathode, wherein the organic material layer comprises a light emitting layer, a hole transport layer formed between the light emitting layer and the anode, and an emission-auxiliary layer formed between the hole transport layer and the light emitting layer, and the hole transport layer, the emission-auxiliary layer and the light emitting layer comprise a compound of Formula 1, respectively.

<Formula 1>

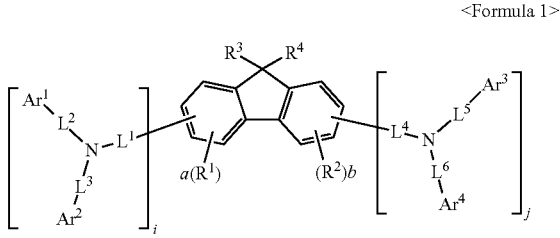

In Formula 1, each of symbols may be defined as follows.

$R^1$ and $R^2$ are each independently selected from the group consisting of hydrogen, deuterium, tritium, halogen, a cyano group, a nitro group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a $C_1$-$C_{30}$ alkyl group, a $C_2$-$C_{30}$ alkenyl group, a $C_2$-$C_{30}$ alkynyl group, a $C_1$-$C_{30}$ alkoxyl group, a $C_6$-$C_{30}$ aryloxy group and a $C_6$-$C_{30}$ arylthio group, and adjacent groups may be optionally bonded to each other to form a ring.

a is an integer of 0 to 4, and a plurality of $R^1$s are each the same as or different from each other when a is an integer of 2 or more, b is an integer of 0 to 3, and a plurality of $R^2$s are each the same as or different from each other when b is an integer of 2 or more.

When $R^1$ and $R^2$ are each an aryl group, the aryl group may be preferably a $C_6$-$C_{30}$ aryl group, more preferably a $C_6$-$C_{18}$ aryl group, for example, phenyl, biphenyl, naphthyl, terphenyl, phenanthrene and the like.

When $R^1$ and $R^2$ are each an alkyl group, the alkyl group may be preferably a $C_1$-$C_{20}$ alkyl group, more preferably a $C_1$-$C_{10}$ alkyl group, for example, methyl, ethyl, propyl, t-butyl and the like.

When $R^1$ and $R^2$ are each a heterocyclic group, the heterocyclic group may be preferably a $C_2$-$C_{30}$ heterocyclic group, more preferably a $C_2$-$C_{20}$ heterocyclic group, for example, pyridine, quinoline, dibenzothiophene, dibenzofuran, and the like.

The ring formed by bonding between neighboring $R^1$s and/or neighboring $R^2$s may be selected from the group consisting of a $C_6$-$C_{60}$ aromatic ring group, a fluorenyl group, a $C_2$-$C_{60}$ heterocyclic group containing at least one heteroatom of O, N, S, Si and P, and a $C_3$-$C_{60}$ aliphatic ring.

When an aromatic ring is formed by neighboring $R^1$s and/or neighboring $R^2$s, the aromatic ring may be preferably a $C_6$-$C_{30}$ aromatic ring, more preferably, a $C_6$-$C_{14}$ aromatic ring, for example, benzene, naphthalene, phenanthrene or the like.

$R^3$ and $R^4$ are each independently selected from the group consisting of hydrogen, deuterium, tritium, halogen, a cyano group, a nitro group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a $C_1$-$C_{30}$ alkyl group, a $C_2$-$C_{30}$ alkenyl group, a $C_2$-$C_{30}$ alkynyl group, a $C_1$-$C_{30}$ alkoxyl group, a $C_6$-$C_{30}$ aryloxy group and -L'-N($R_a$)($R_b$), and $R^3$ and $R^4$ may be optionally bonded to each other to form a ring.

When $R^3$ and $R^4$ are each an alkyl group, the alkyl group may be preferably a $C_1$-$C_{20}$ alkyl group, more preferably a $C_1$-$C_{10}$ alkyl group, for example, methyl, ethyl, propyl, t-butyl and the like.

When $R^3$ and $R^4$ are each an alkenyl group, the alkenyl group may be preferably a $C_2$-$C_{20}$ alkenyl group, more preferably a $C_2$-$C_{10}$ alkenyl group, for example, ethene, propene and the like.

When $R^3$ and $R^4$ are each an aryl group, the aryl group may be preferably a $C_6$-$C_{30}$ aryl group, more preferably a $C_6$-$C_{18}$ aryl group, for example, phenyl, naphthyl, biphenyl, terphenyl and the like.

When $R^3$ and $R^4$ are each a heterocyclic group, the heterocyclic group may be preferably a $C_2$-$C_{30}$ heterocyclic group, more preferably a $C_2$-$C_{20}$ heterocyclic group, for example, pyridine, quinoline, dibenzothiophene, dibenzofuran, and the like.

When $R^3$ and $R^4$ are bonded to each other to form a ring, a spiro compound may be formed together with C to which they are bonded.

$Ar^1$ to $Ar^4$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, and a $C_3$-$C_{60}$ aliphatic ring.

When $Ar^1$ to $Ar^4$ are each an aryl group, the aryl group may be preferably a $C_6$-$C_{30}$ aryl group, more preferably a $C_6$-$C_{18}$ aryl group, for example, phenyl, biphenyl, naphthyl, terphenyl, phenanthrene, triphenylene, anthracene, and the like.

When $Ar^1$ to $Ar^4$ are each a heterocyclic group, the heterocyclic group may be preferably a $C_2$-$C_{30}$ heterocyclic group, more preferably a $C_2$-$C_{22}$ heterocyclic group, for example, pyridine, triazine, quinoline, isoquinoline, quinoxaline, quinazoline, dibenzothiophene, dibenzofuran, carbazole, phenyl-carbazole, benzocarbazole, phenyl-benzocarbazole, benzonaphthothiophene, benzonaphthofuran, cyanthrene, benzoindole, and the like.

When $Ar^1$ to $Ar^4$ are each a fluorenyl group, the fluorenyl group may be 9,9-dimethyl-9H-fluorene, 9,9-diphenyl-9H-fluorene, 9,9'-spirobifluorene, spiro[benzo[b]fluorene-11,9'-fluorene], benzo[b] fluorene, 11,11-diphenyl-11H-benzo[b] fluorene, 9-(naphthalen-2-yl)9-phenyl-9H-fluorene and the like.

When $Ar^1$ to $Ar^4$ are each an aryloxy group, the aryloxy group may be preferably a $C_6$-$C_{20}$ aryloxy group, more preferably a $C_6$-$C_{18}$ aryloxy group, for example, phenyloxy, naphthyloxy, and the like.

When $Ar^1$ to $Ar^4$ are each an arylthio group, the arylthio group may be preferably a $C_6$-$C_{20}$ arylthio group, more preferably a $C_6$-$C_{18}$ arylthio group, for example, phenylthio, naphthylthio, and the like.

$L^1$ to $L^6$ are each independently selected from the group consisting of a single bond, a $C_6$-$C_{60}$ arylene group, a fluorenylene group, a $C_3$-$C_{60}$ aliphatic ring, and a $C_2$-$C_{60}$ heterocyclic group comprising at least one heteroatom selected from the group consisting of O, N, S, Si and P.

When $L^1$ to $L^6$ are each an arylene group, the arylene group may be preferably a $C_6$-$C_{30}$ arylene group, more preferably a $C_6$-$C_{18}$ arylene group, for example, phenylene, biphenyl, naphthalene, terphenyl and the like.

When $L^1$ to $L^6$ are each a heterocyclic group, the heterocyclic group may be preferably a $C_2$-$C_{30}$ heterocyclic group, more preferably a $C_2$-$C_{18}$ heterocyclic group, for example, dibenzothiophene, dibenzofuran, carbazole, phenylcarbazole, and the like.

i and j are each an integer of 0 to 2, and when both i and j are 0, one of $R^3$ and $R^4$ has to contain -L'-N($R_a$)($R_b$).

A plurality of $Ar^1$s, a plurality of $Ar^2$s, a plurality of $L^1$s, a plurality of $L^2$s, a plurality of $L^3$s are the same as or different from each other when i is an integer of 2, and a plurality of $Ar^3$s, a plurality of $Ar^4$s, a plurality of $L^4$s, a plurality of $L^5$s, a plurality of $L^6$s are the same as or different from each other when j is an integer of 2.

L' is selected from the group consisting of a single bond, a $C_6$-$C_{60}$ arylene group, a fluorenylene group, a $C_3$-$C_{60}$ aliphatic ring, and a $C_2$-$C_{60}$ heterocyclic group comprising at least one heteroatom selected from the group consisting of O, N, S, Si and P.

$R_a$ and $R_b$ are each independently selected from the group consisting of a $C_6$-$C_{60}$ aryl group, a fluorenyl group, a $C_3$-$C_{60}$ aliphatic ring, and a $C_2$-$C_{60}$ heterocyclic group comprising at least one heteroatom selected from the group consisting of O, N, S, Si and P.

$R^1$ to $R^4$, $Ar^1$ to $Ar^4$, $L^1$ to $L^6$, L', $R_a$, $R_b$, the ring formed by adjacent groups, and the ring formed by $R^3$ and $R^4$ may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ aliphatic ring group, a $C_7$-$C_{20}$ arylalkyl group, $C_6$-$C_{20}$ arylalkenyl group and -L'-N($R_a$)($R_b$). Here, L', $R_a$ and $R_b$ are as defined above.

Preferably, Formula 1 can be represented by one of Formula 2 to Formula 6.

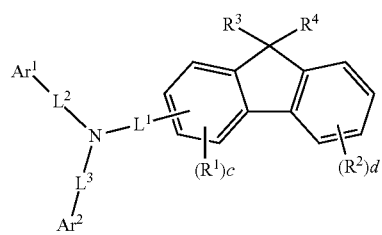

<Formula 2>

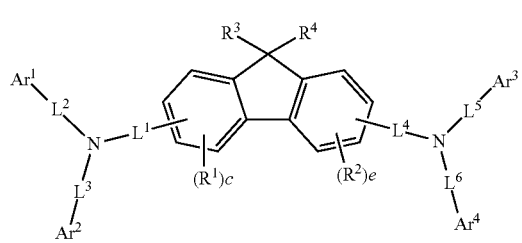

<Formula 3>

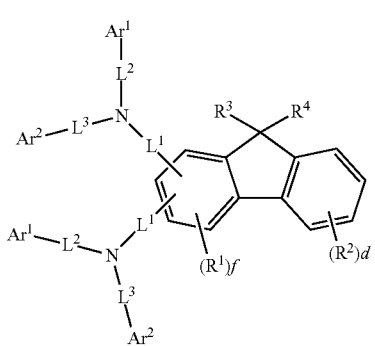

<Formula 4>

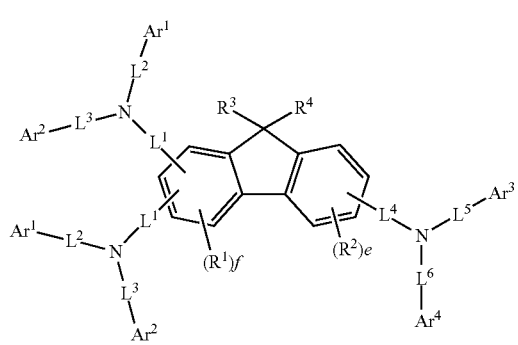

<Formula 5>

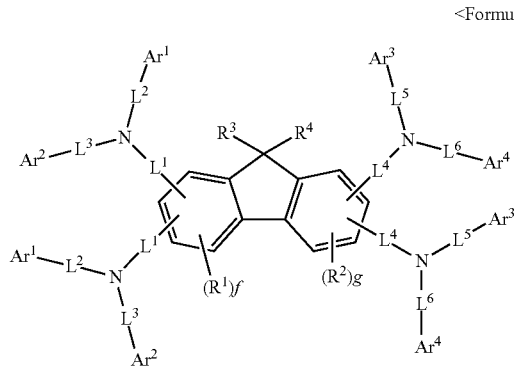

<Formula 6>

In Formula 2 to Formula 6, $R^1$ to $R^4$, $Ar^1$ to $Ar^4$, and $L^1$ to $L^6$ are the same as defined in Formula 1.

c is an integer of 0 to 3, and when c is an integer of 2 or more, a plurality of $R^1$s are each the same as or different from each other, d is an integer of 0 to 4, and when d is an integer of 2 or more, a plurality of $R^2$s are each the same as or different from each other, e is an integer of 0 to 3, and when e is an integer of 2 or more, a plurality of $R^2$s are each the same as or different from each other, f is an integer of 0 to 2, and when f is an integer of 2 or more, a plurality of $R^1$s are each the same as or different from each other, and g is an integer of 0 to 2, and when c is an integer of 2 or more, a plurality of $R^2$s are each the same as or different from each other.

In addition, preferably, Formula 1 may be represented by one of Formula 7 to Formula 11.

<Formula 7>
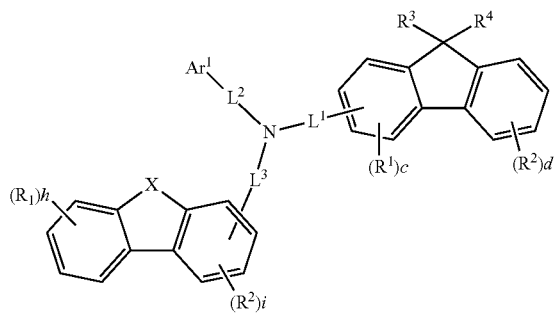
<Formula 8>
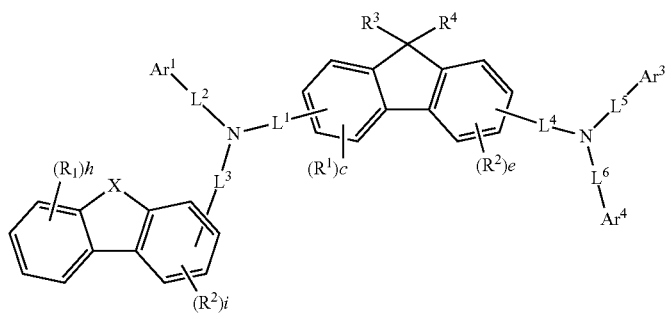
<Formula 9>
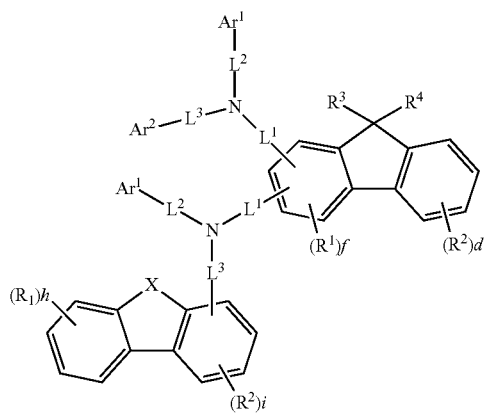
<Formula 10>
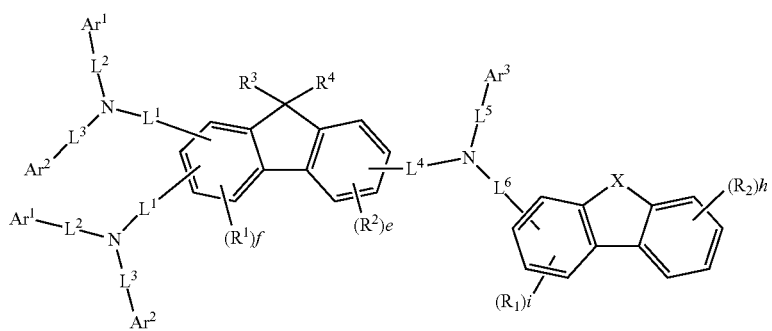

-continued

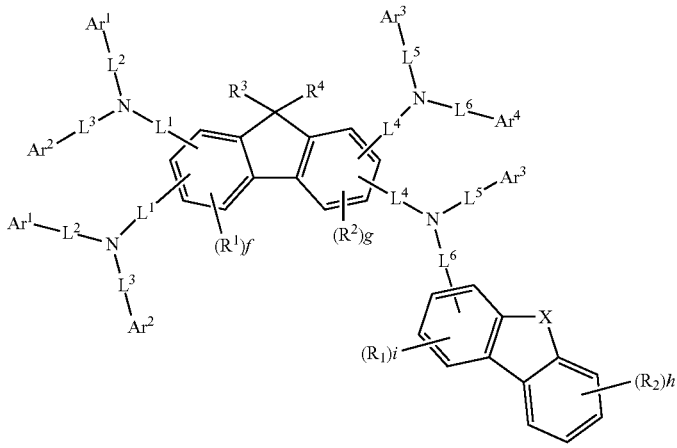

<Formula 11>

In Formula 7 to Formula 11, $R^1$ to $R^4$, $Ar^1$ to $Ar^4$, and $L^1$ to $L^6$ are the same as defined for Formula 1 and X is O, S, C(R')(R'') or N($R_3$).

$R_1$, $R_2$, R' and R'' are each independently selected from the group consisting of hydrogen, deuterium, halogen, a silane group unsubstituted or substituted with a $C_1$-$C_{20}$ alkyl group or a $C_6$-$C_{20}$ aryl group, a cyano group, a nitro group, a $C_1$-$C_{20}$ alkoxy group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group containing at least one heteroatom of O, N, S, Si, and P, and a $C_3$-$C_{20}$ aliphatic ring group, and adjacent $R_1$s or adjacent $R_2$s may be bonded to each other to form a ring, and R' and R' may be bonded to each other to form a ring.

$R_3$ is selected from the group consisting of a $C_6$-$C_{20}$ aryl group, a fluorenyl group, a $C_2$-$C_{20}$ heterocyclic group containing at least one heteroatom of O, N, S, Si, and P, and a $C_3$-$C_{20}$ aliphatic ring group, c is an integer of 0 to 3, and when c is an integer of 2 or more, a plurality of $R^1$s are each the same as or different from each other, d is an integer of 0 to 4, and when d is an integer of 2 or more, a plurality of $R^2$s are each the same as or different from each other, e is an integer of 0 to 3, and when e is an integer of 2 or more, a plurality of $R^2$s are each the same as or different from each other, f is an integer of 0 to 2, and when f is an integer of 2 or more, a plurality of $R^1$s are each the same as or different from each other, g is an integer of 0 to 2, and when c is an integer of 2 or more, a plurality of $R^2$s are each the same as or different from each other, h is an integer of 0 to 4, and when h is an integer of 2 or more, a plurality of $R_1$s are each the same as or different from each other, and i is an integer of 0 to 3, and when i is an integer of 2 or more, a plurality of $R_2$s are each the same as or different from each other.

In another embodiment of the present invention, the light emitting layer may further comprise compound represented by Formula 12 or Formula 13.

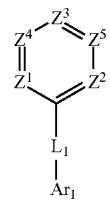

<Formula 12>

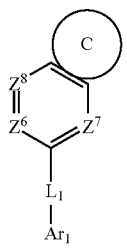

<Formula 13>

In Formula 12 and Formula 13, each of symbols may be defined as follows.

$Z^1$ to $Z^5$ are each independently N or C($R_3$), and at least one of $Z^1$ to $Z^5$ is N, $Z^6$ to $Z^8$ are each independently N or C($R_3$), and at least one of $Z^6$ to $Z^8$ is N.

$L_1$ is selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, and a $C_3$-$C_{60}$ aliphatic ring.

When $L_1$ is an arylene group, the arylene group may be preferably a $C_6$-$C_{30}$ arylene group, more preferably a $C_6$-$C_{18}$ arylene group, for example, phenylene, biphenyl, naphthalene, terphenyl and the like.

When $L_1$ is a heterocyclic group, the heterocyclic group may be preferably a $C_2$-$C_{30}$ heterocyclic group, more preferably a $C_2$-$C_{22}$ heterocyclic group, for example, dibenzothiophene, dibenzofuran, carbazole, phenylcarbazole, benzocarbazole, phenyl-benzocarbazole, benzonaphthothiophene, benzonaphthofuran, and the like.

$Ar_1$ is selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, and a $C_3$-$C_{60}$ aliphatic ring.

When $Ar_1$ is an aryl group, the aryl group may be preferably a $C_6$-$C_{30}$ aryl group, more preferably a $C_6$-$C_{18}$ aryl group, for example, phenyl, biphenyl, naphthyl, terphenyl, phenanthrene, and the like.

When $Ar_1$ is a heterocyclic group, the heterocyclic group may be preferably a $C_2$-$C_{30}$ heterocyclic group, more preferably a $C_2$-$C_{26}$ heterocyclic group, for example, pyridine, pyrimidine, triazine, quinazoline, quinoxaline, dibenzothiophene, benzonaphthothiophene, dibenzofuran, benzonaphthofuran, carbazole, phenylcarbazole, benzocarbazole, phenyl-benzocarbazole, dibenzocarbazole, indolocarbazole, and the like.

When $Ar_1$ is a fluorenyl group, the fluorenyl group may be 9,9-dimethyl-9H-fluorene, 9,9-diphenyl-9H-fluorene, 9,9'-spirobifluorene, spiro[benzo[b]fluorene-11,9'-fluorene], benzo[b] fluorene, 11,11-diphenyl-11H-benzo[b]fluorene, 9-(naphthalen-2-yl)9-phenyl-9H-fluorene and the like.

C ring is selected from the group consisting of a $C_6$-$C_{60}$ aromatic ring, a $C_2$-$C_{60}$ heterocyclic group comprising at least one heteroatom selected from the group consisting of O, N, S, Si and P, and a $C_3$-$C_{60}$ aliphatic ring, and C ring may be further substituted with one or more $R_4$, When C ring is an aromatic ring, the aromatic ring may be preferably a $C_6$-$C_{30}$ aromatic ring, more preferably, a $C_6$-$C_{14}$ aromatic ring, for example, benzene, naphthalene, phenanthrene, anthracene or the like.

When C ring is a heterocyclic group, the heterocyclic group may be preferably a $C_2$-$C_{30}$ heterocyclic group, more preferably, a $C_6$-$C_{16}$ heterocyclic ring group, for example, benzothiophene, benzofuran, naphthothiophene, naphthofuran, phenanthrofuran, or the like.

$R_3$ and $R_4$ are each independently selected from the group consisting of hydrogen, deuterium, tritium, halogen, a cyano group, a nitro group, a $C_6$-$C_{60}$ aryl group, a fluorenyl group, a $C_2$-$C_{30}$ heterocyclic group comprising at least one heteroatom selected from the group consisting of O, N, S, Si and P, and a $C_3$-$C_{60}$ aliphatic ring, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_6$-$C_{30}$ aryloxy group, and -L'-N($R_a$)($R_b$), and adjacent $R_3$s may be bonded to each other to form a ring, L' is selected from the group consisting of a single bond, a $C_6$-$C_{30}$ arylene group, a fluorenylene group, a $C_3$-$C_{60}$ aliphatic ring, and a $C_2$-$C_{60}$ heterocyclic group comprising at least one heteroatom selected from the group consisting of O, N, S, Si and P.

$R_a$ and $R_b$ are each independently selected from the group consisting of a $C_6$-$C_{60}$ aryl group, a fluorenyl group, a $C_3$-$C_{30}$ aliphatic ring, and a $C_2$-$C_{30}$ heterocyclic group comprising at least one heteroatom selected from the group consisting of O, N, S, Si and P.

$Ar_1$, $L_1$, L', $R_3$, $R_4$, $R_a$, $R_b$, the ring formed by adjacent $R_3$s may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ aliphatic ring group, a $C_7$-$C_{20}$ arylalkyl group, $C_8$-$C_{20}$ arylalkenyl group and -L'-N($R_a$)($R_b$).

Formula 13 may be represented by one of Formula 13-1 to Formula 13-6.

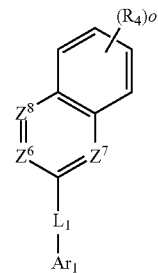

<Formula 13-1>

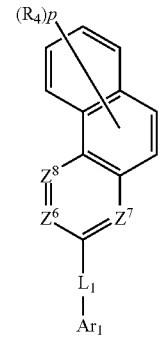

<Formula 13-2>

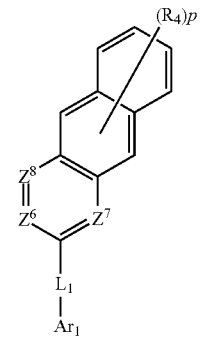

<Formula 13-3>

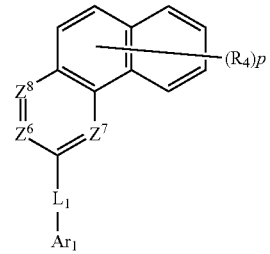

<Formula 13-4>

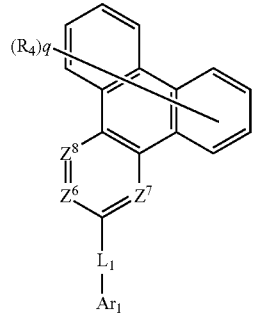

<Formula 13-5>

<Formula 13-6>

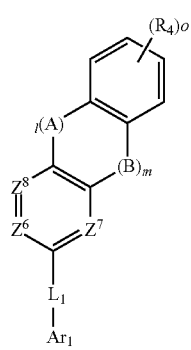

In Formula 13-1 to Formula 13-6, $Z^6$ to $Z^8$, $L_1$, $Ar_1$, $R_4$ are the same as defined for Formula 13, A and B are each independently O, N, S or $C(R_5)(R_6)$, l and m are each an integer of 0 or 1, and at least one of l and m is 1, o is an integer of 0 to 4, p is an integer of 0 to 6, q is an integer of 0 to 8, and when o, p, q are each an integer of 2 or more, a plurality of $R_4$s are each the same as or different from each other.

Preferably, a hole transport layer comprises compound of Formula 2, and preferably, a hole transport layer may also comprise compound Formula 7.

In addition, preferably, a hole transport layer and an emission-auxiliary layer may comprise compound of Formula 2.

In addition, preferably, the hole transport layer, the emission-auxiliary layer and the light emitting layer may comprise compound of Formula 2, respectively.

Specifically, the compound represented by Formula 1 may be one of the following compounds, but there is no limitation thereto.

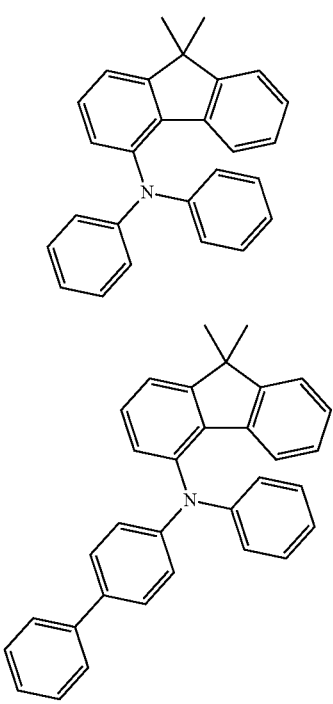

P-1

P-2

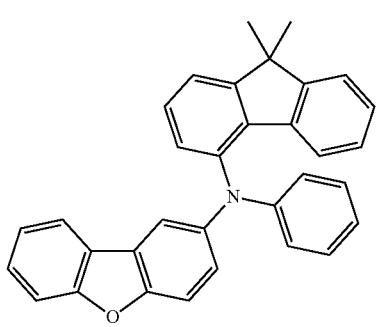

P-3

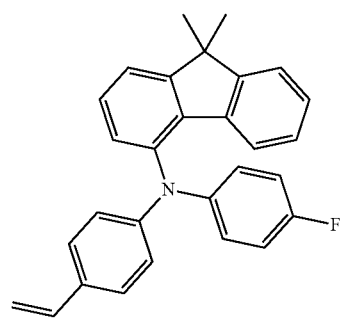

P-4

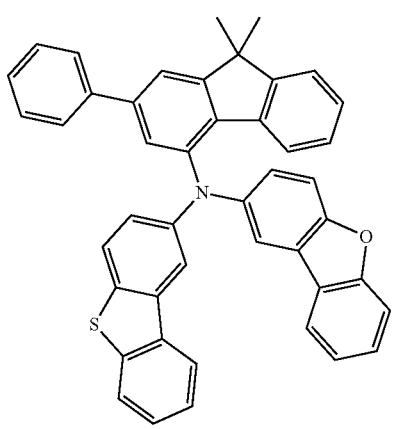

P-5

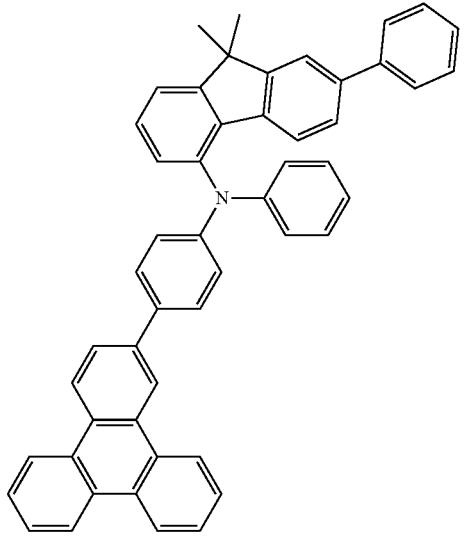

P-6

P-7
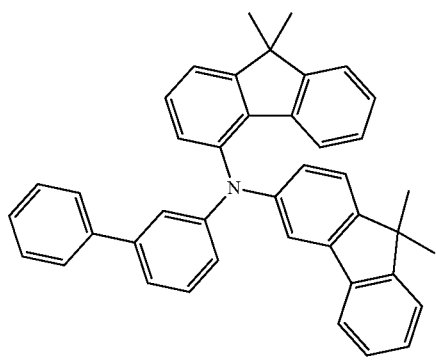
P-8
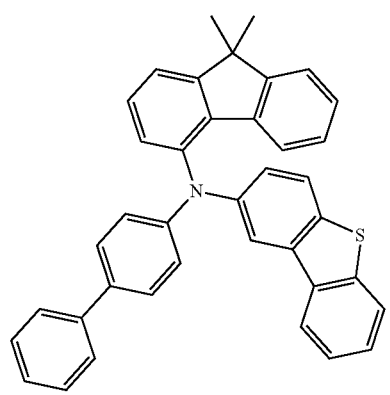
P-9
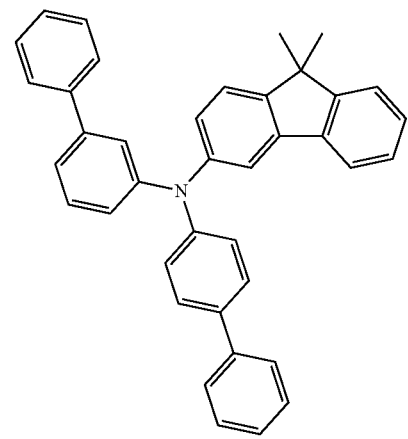
P-10
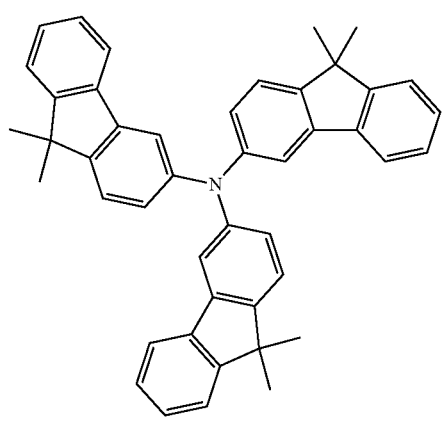
P-11
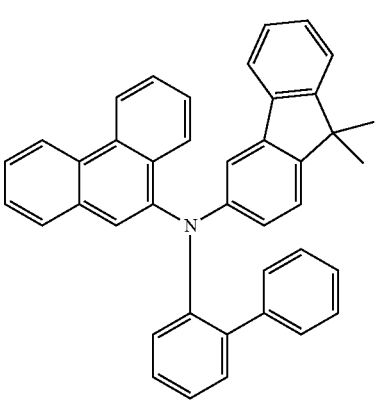
P-12
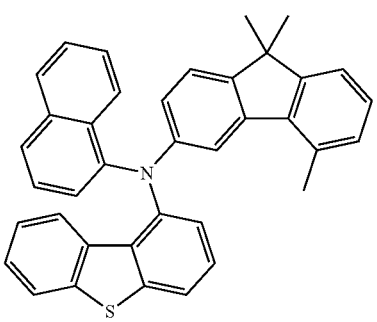
P-13
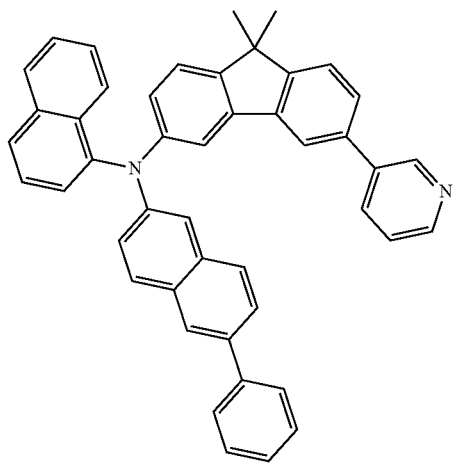
P-14
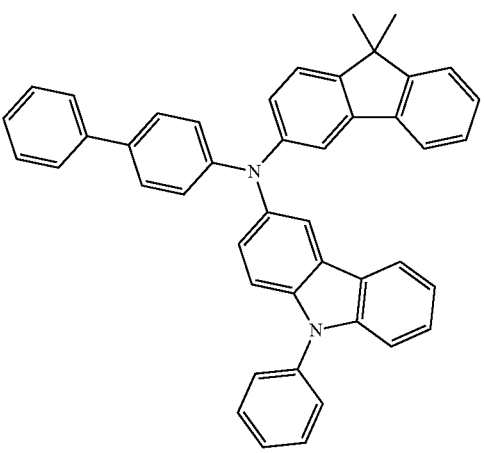

P-15
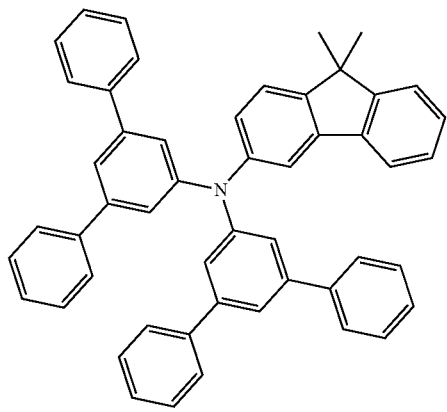
P-16
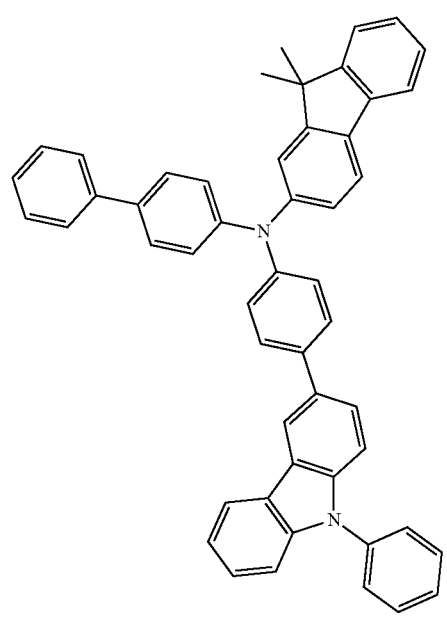
P-17
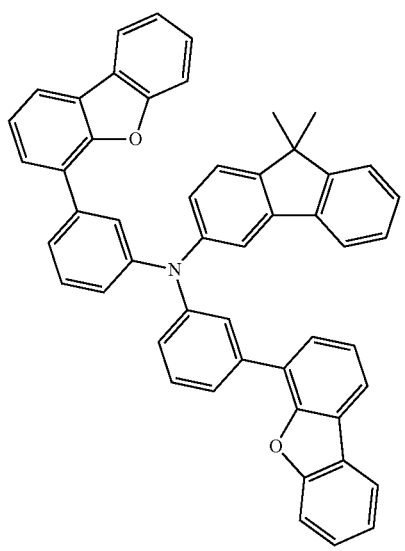
P-18
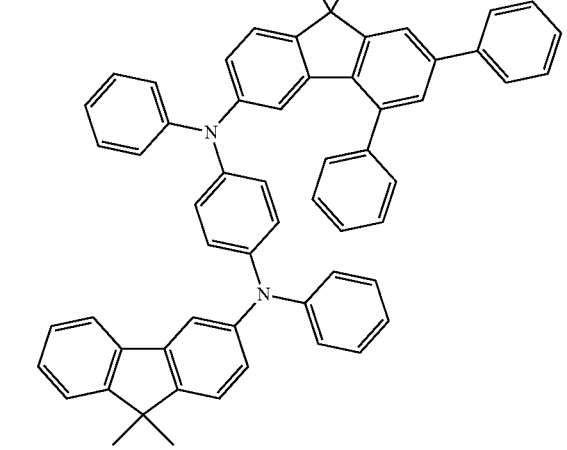
P-19
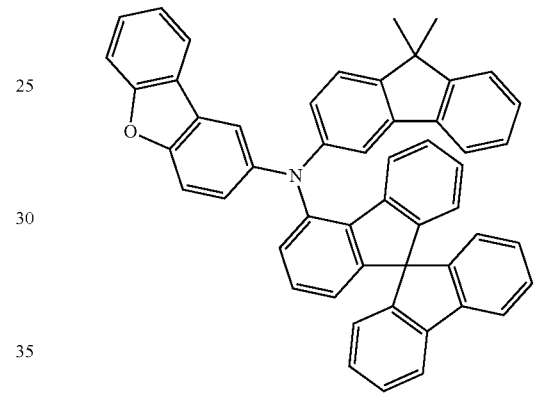
P-20
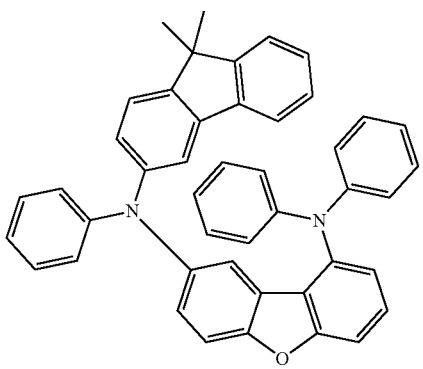
P-21
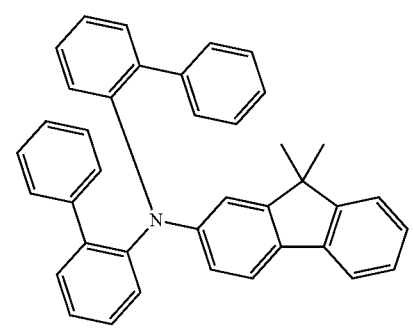

P-22
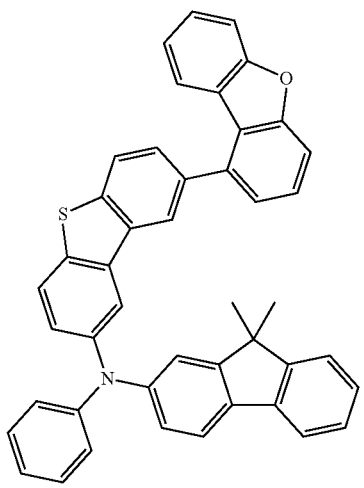
P-23
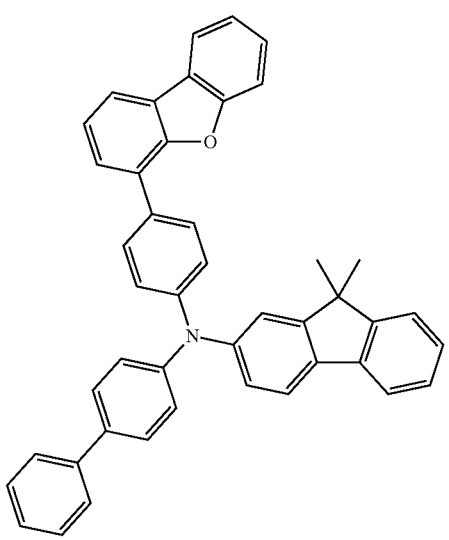
P-24
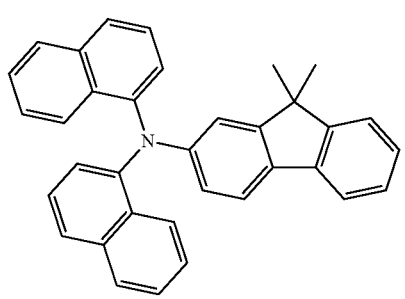
P-25
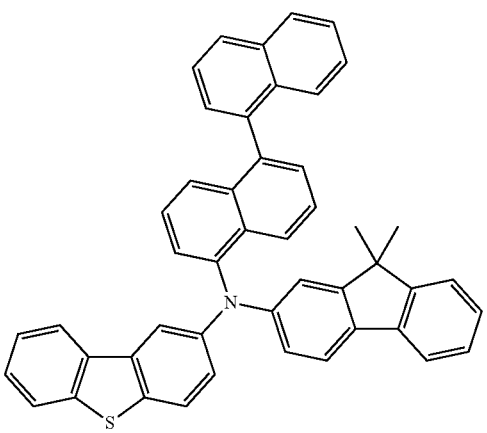
P-26
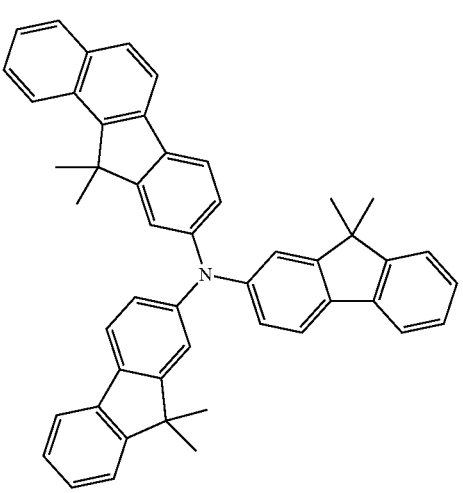
P-27
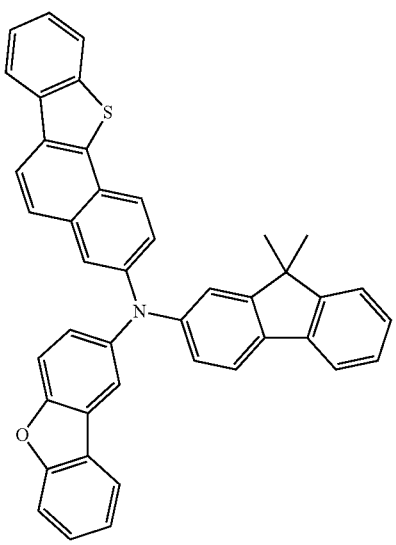

-continued
P-28
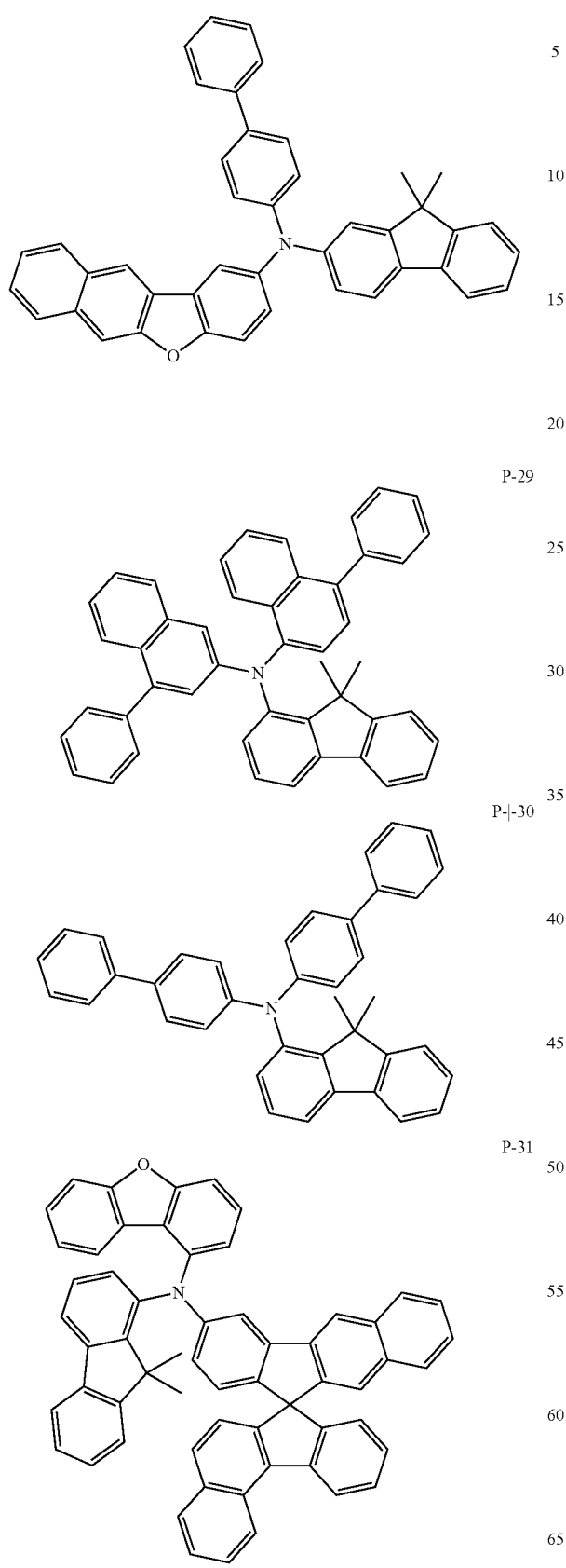
P-29
P-|-30
P-31
-continued
P-32
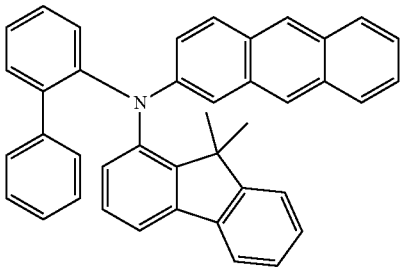
P-33
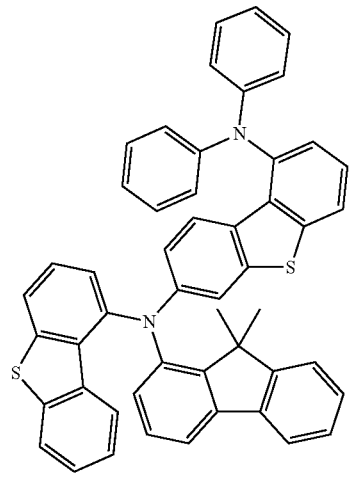
P-34
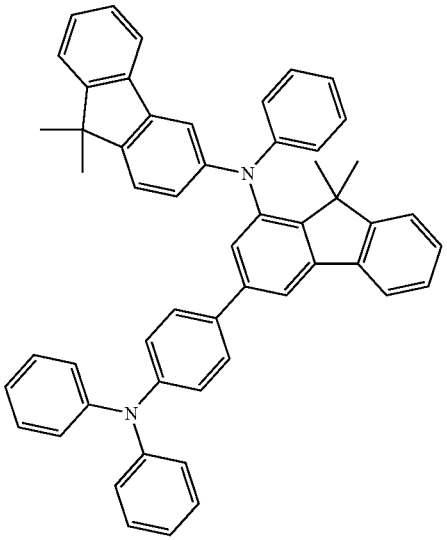
P-35
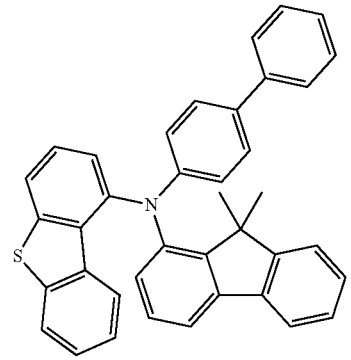

P-36
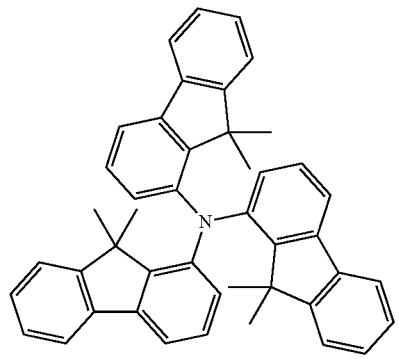
P-37
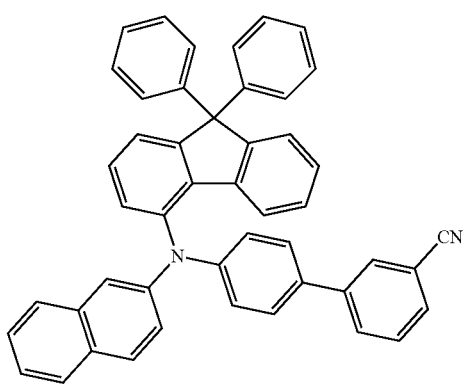
P-38
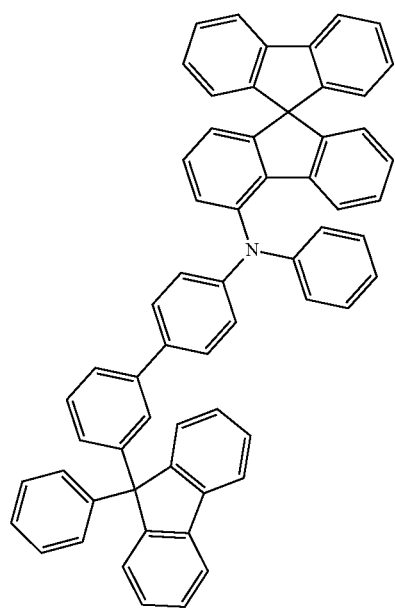
P-39
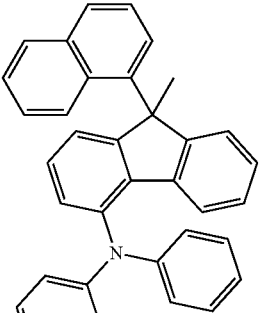
P-40
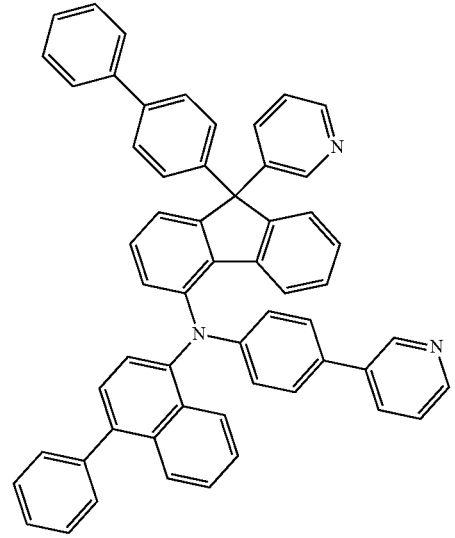
P-41
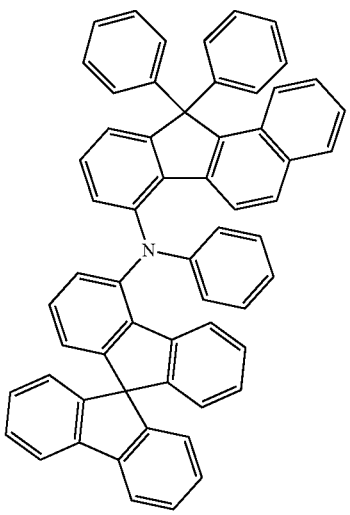

P-42
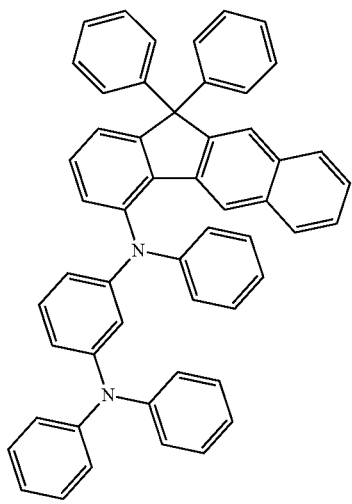
P-45
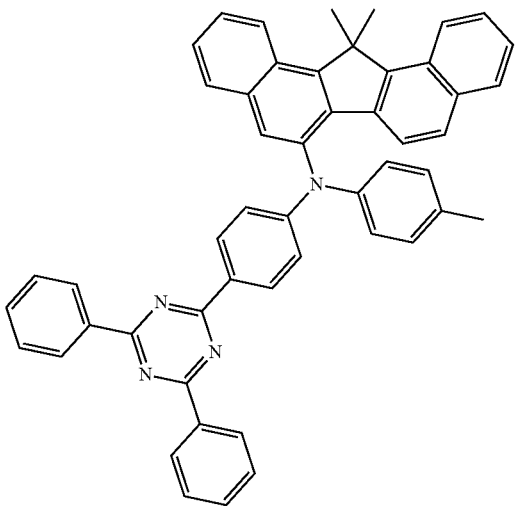
P-43
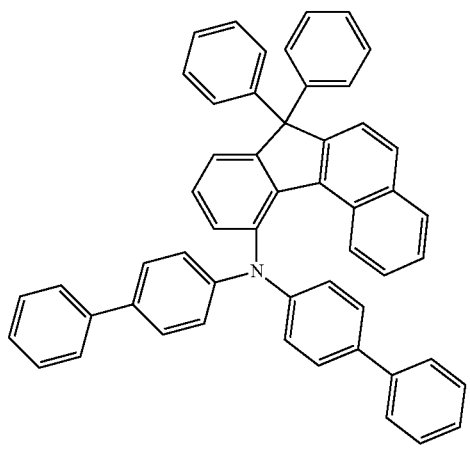
P-46
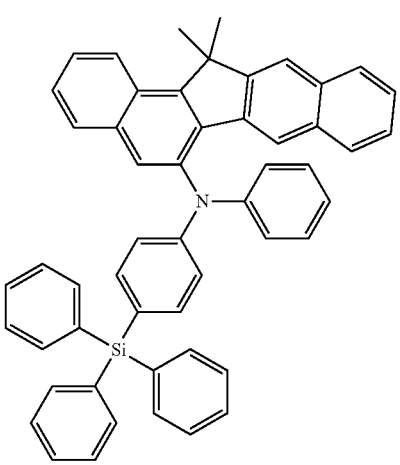
P-44
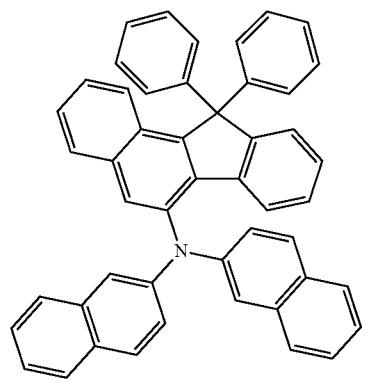
P-47
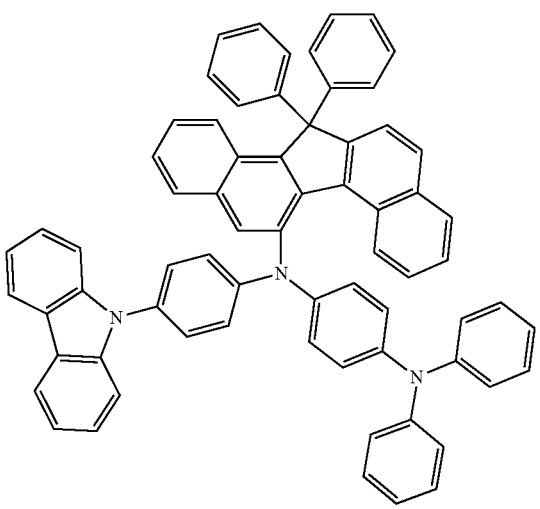

P-48
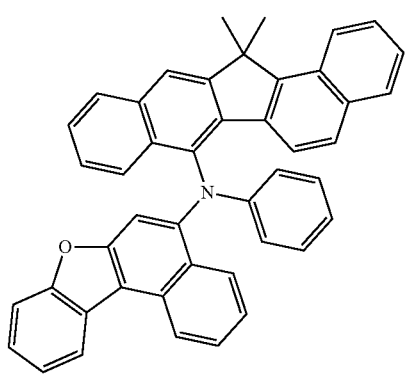
P-49
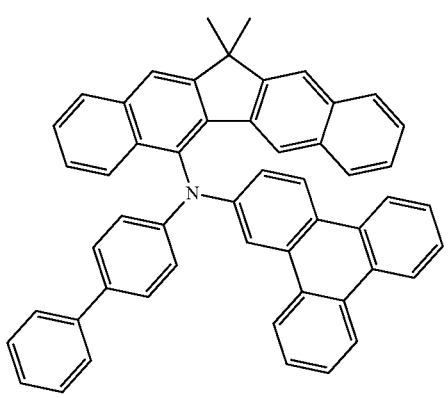
P-50
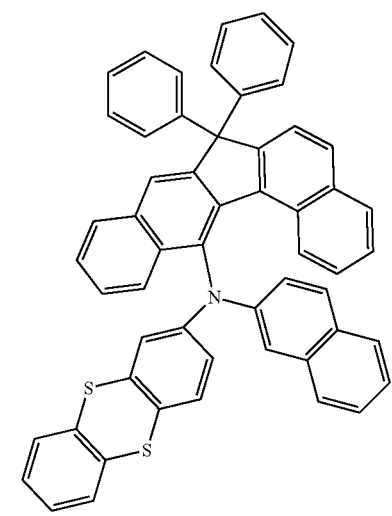
P-51
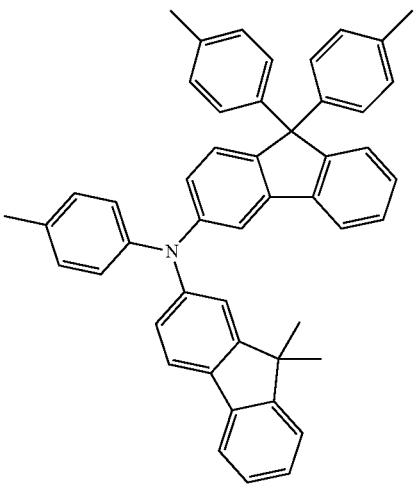
P-52
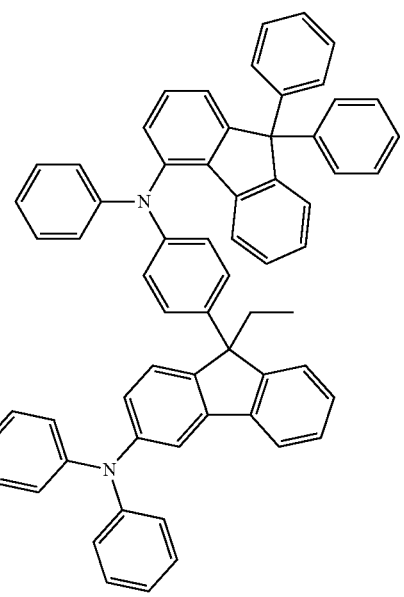
P-53
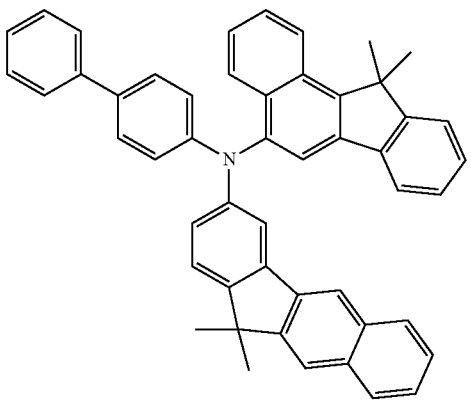

-continued
P-54
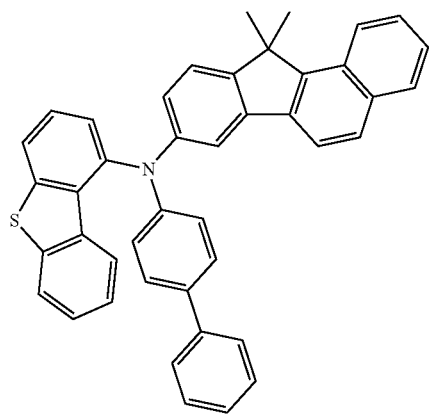
P-55
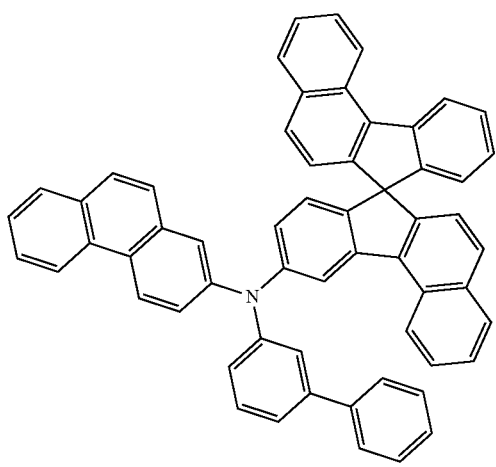
P-56
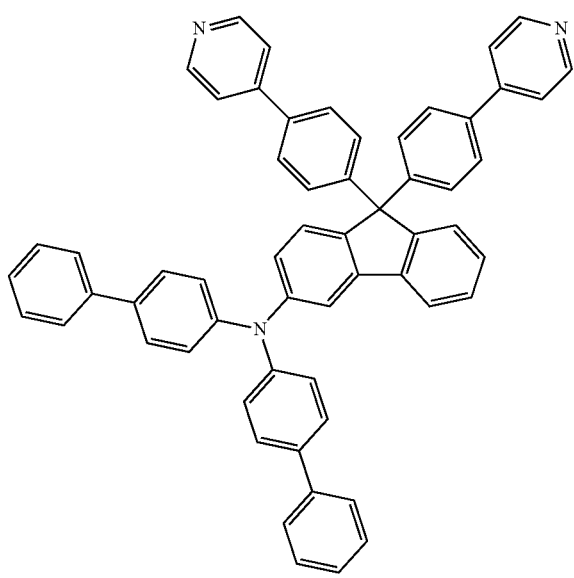
-continued
P-57
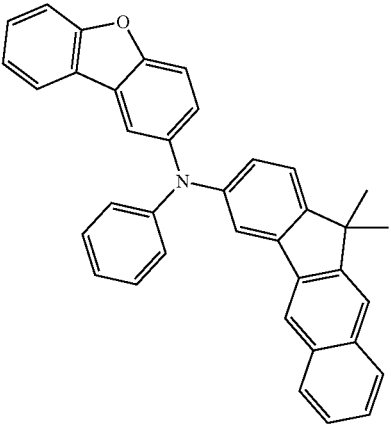
P-58
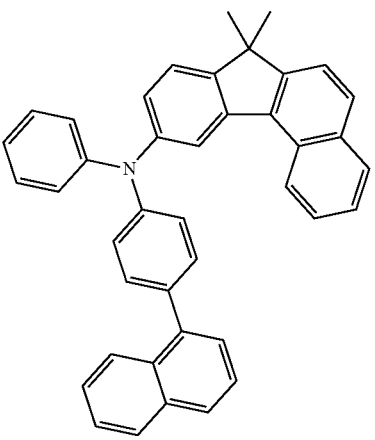
P-59
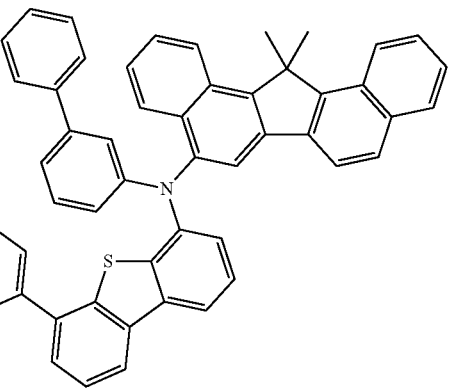
P-60
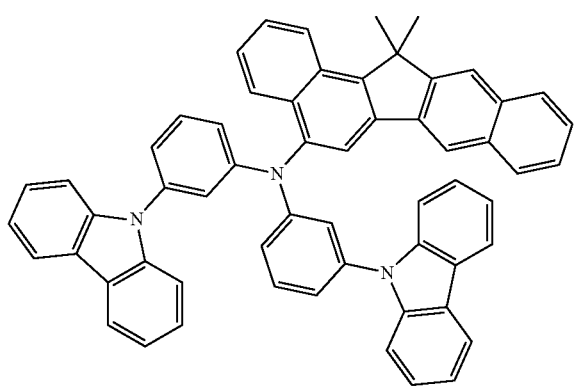

P-61
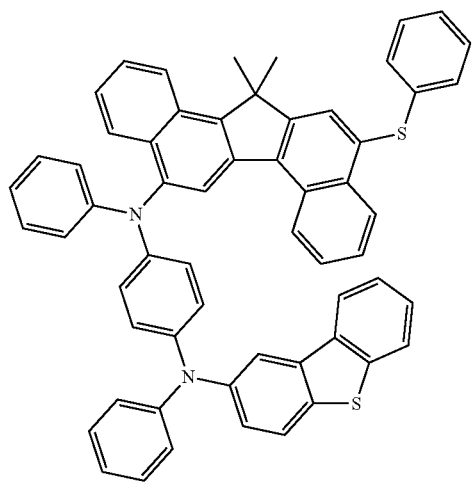
P-62
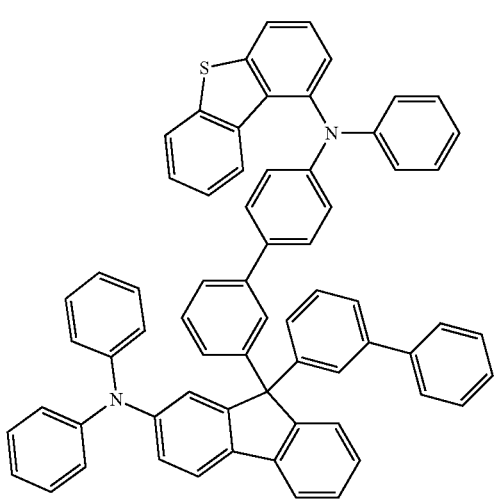
P-63
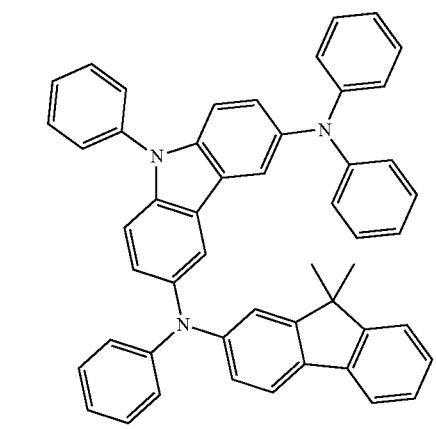
P-64
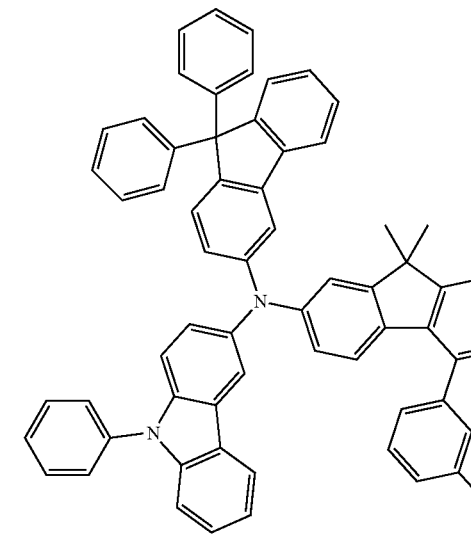
P-65
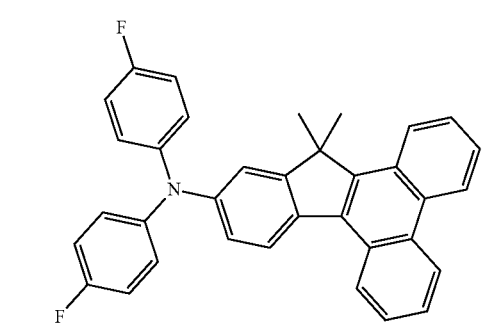
P-66
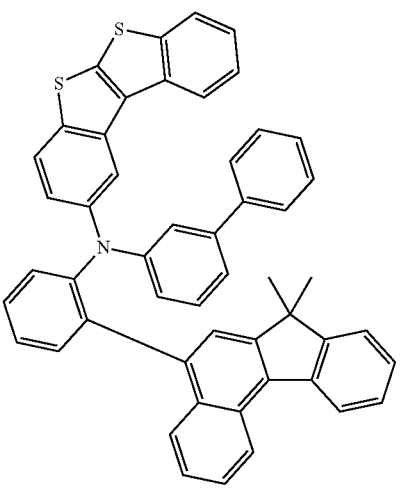

P-67
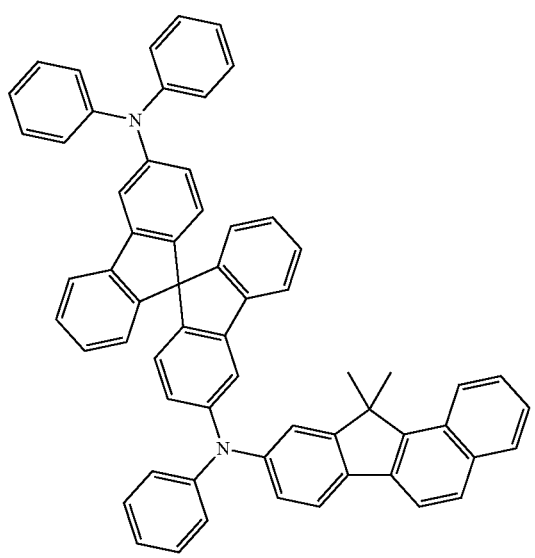
P-68
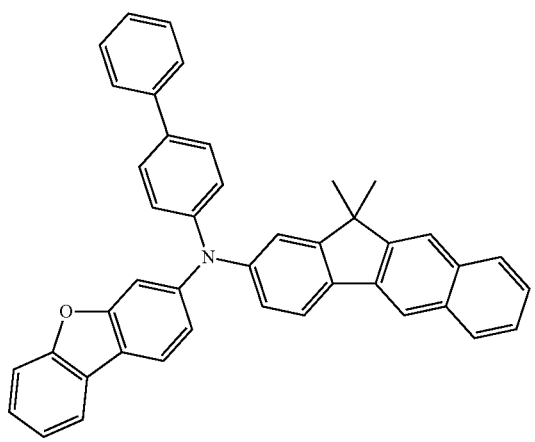
P-69
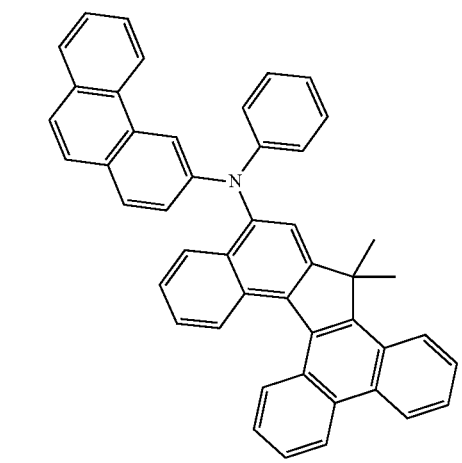
P-70
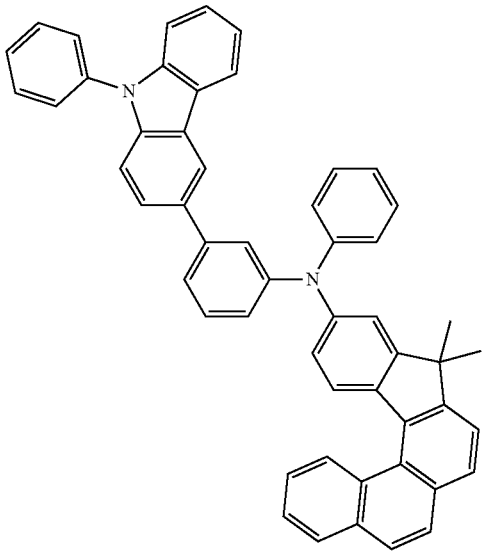
P-71
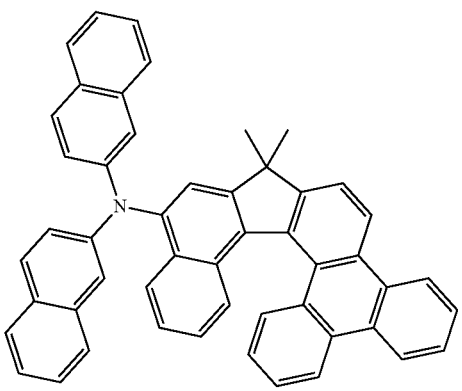
P-72
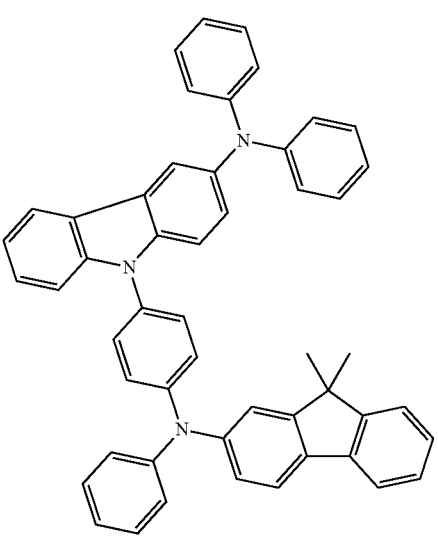

P-73
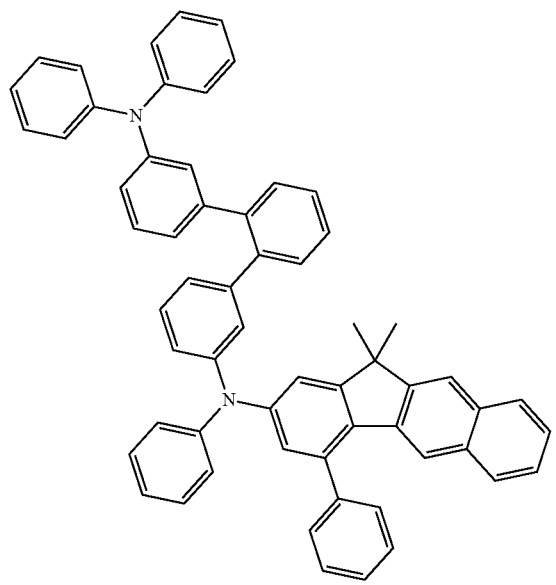
P-74
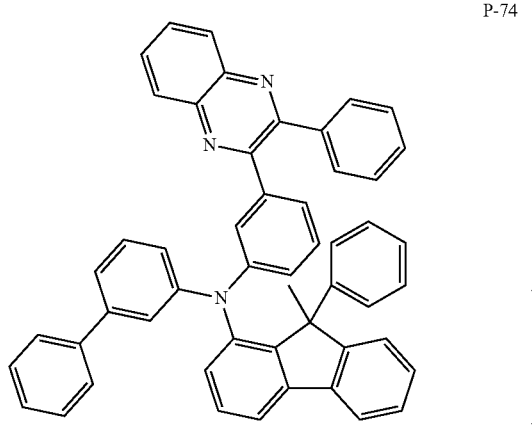
P-75
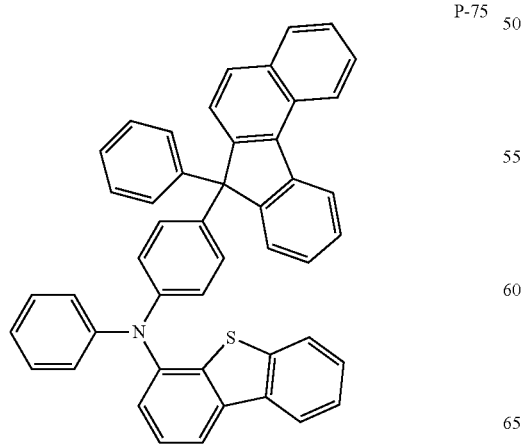
P-76
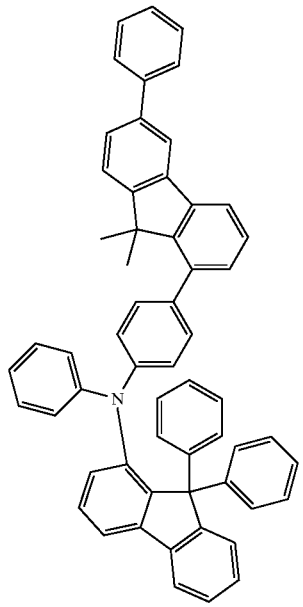
P-77
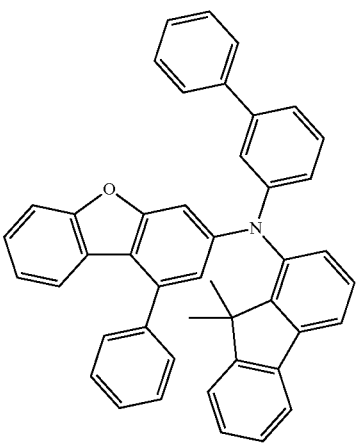
P-78
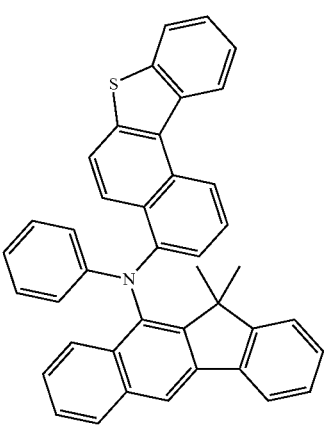

P-79
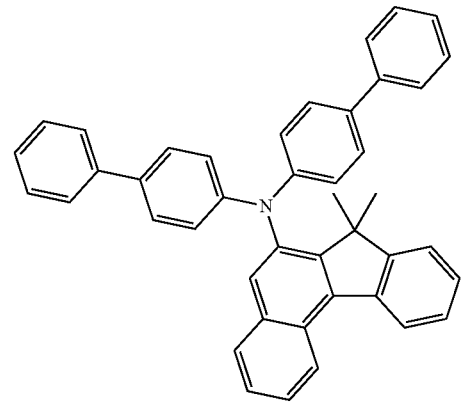
P-80
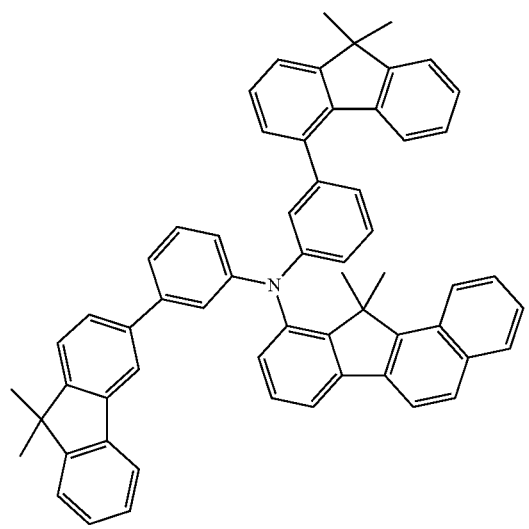
P-81
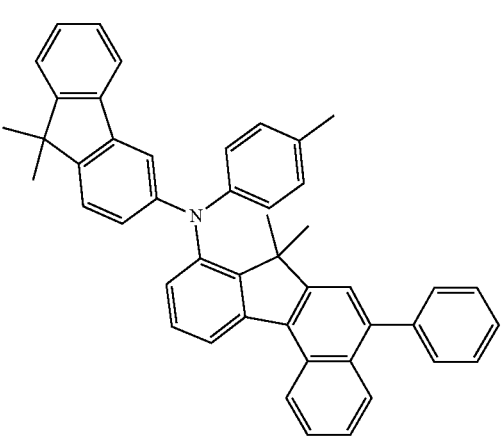
P-82
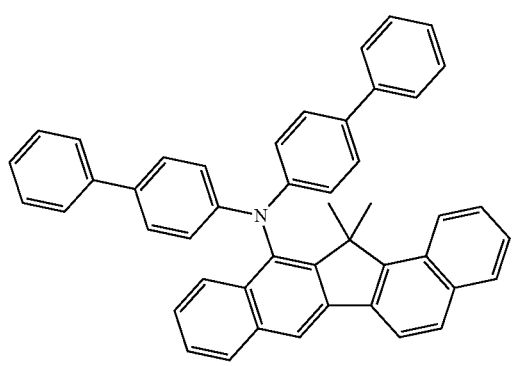
P-83
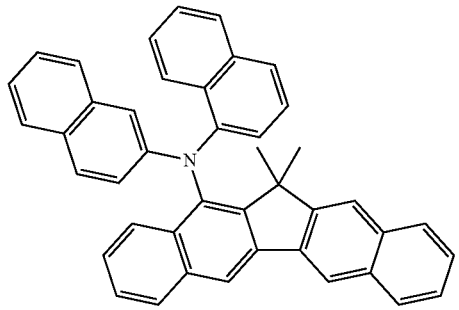
P-84
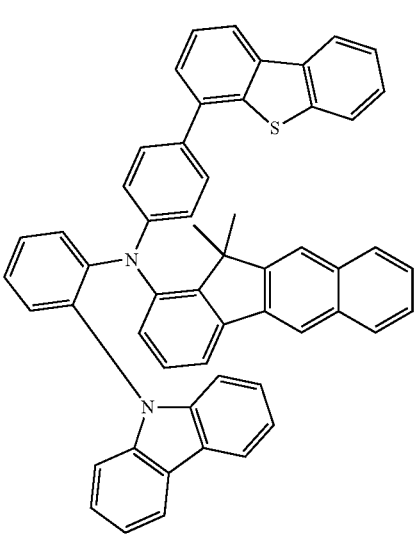
P-85
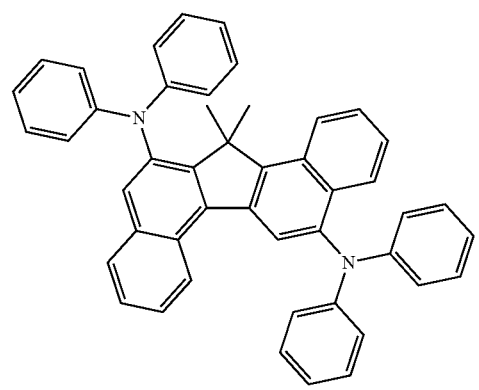

-continued
P-86
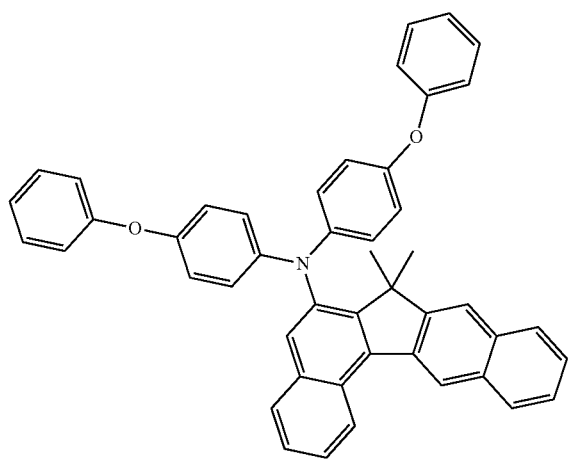
P-89
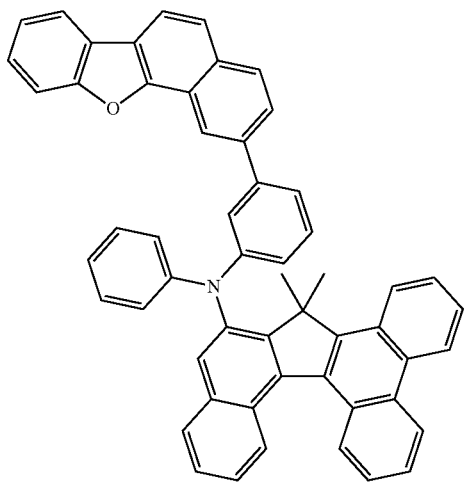
P-87
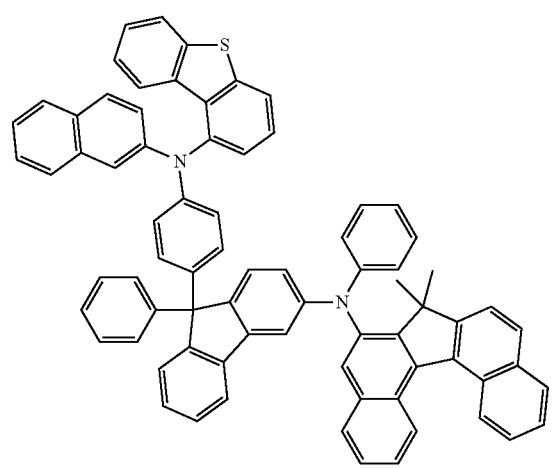
P-90
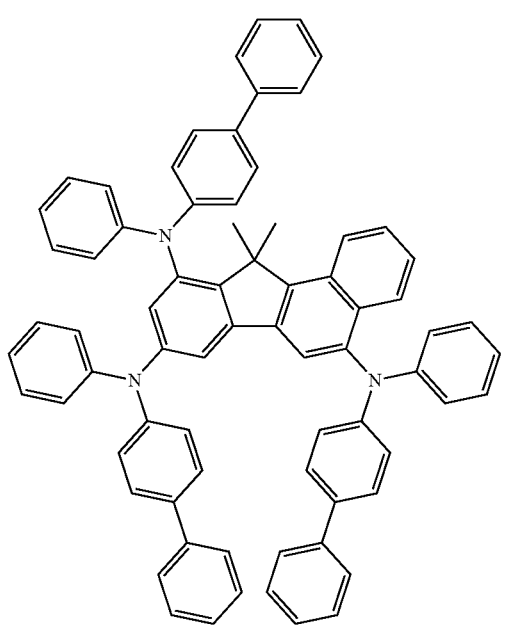
P-88
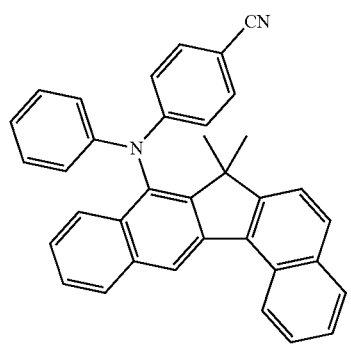
P-91
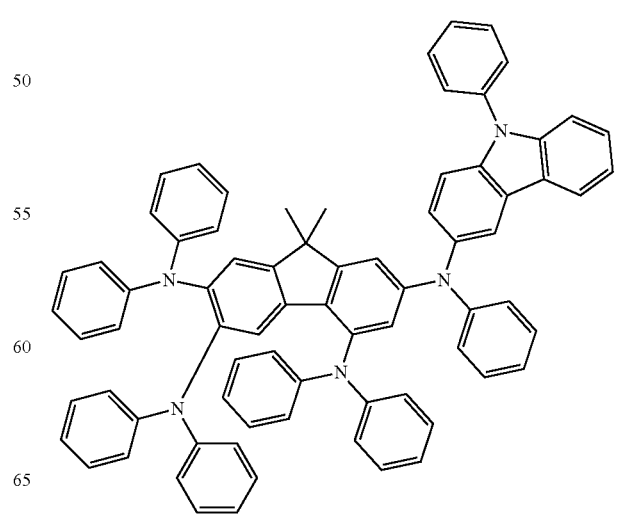

P-92
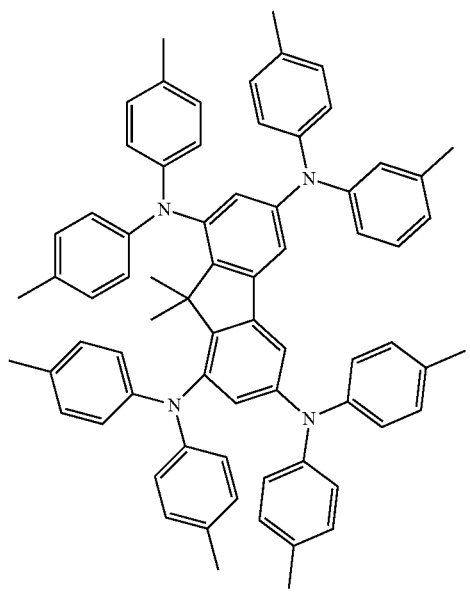
P-93
P-94
P-95
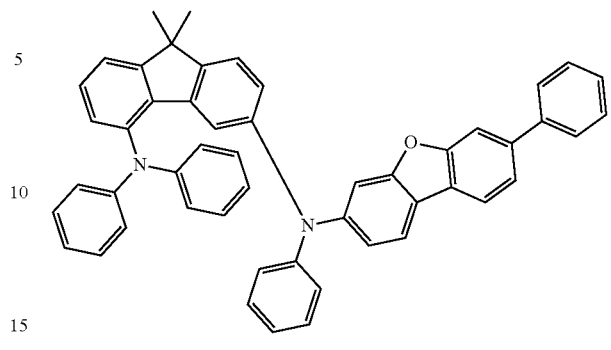
P-96
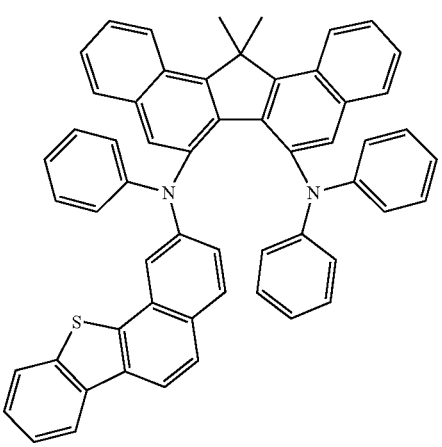
P-97
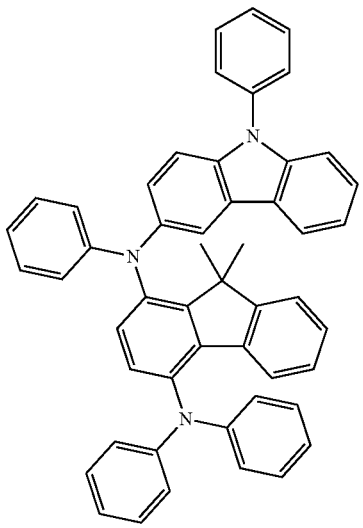

P-98
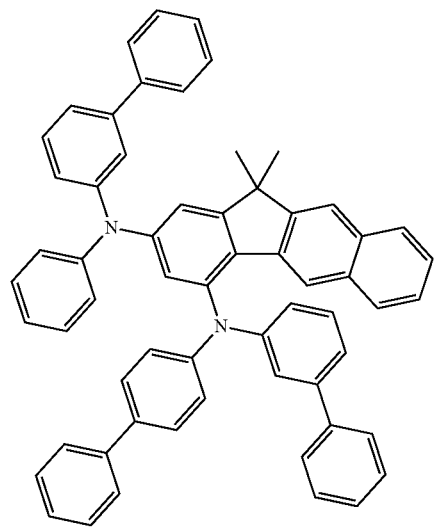
P-101
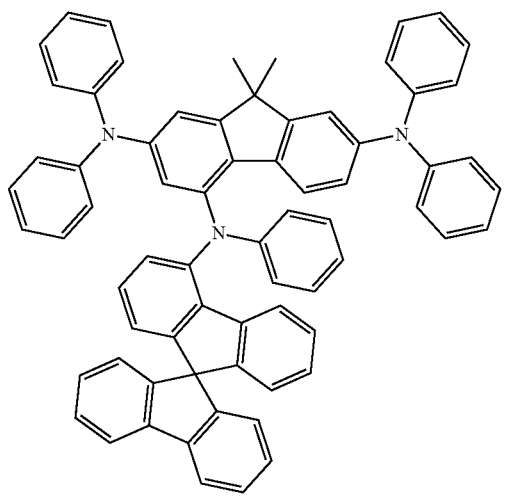
P-99
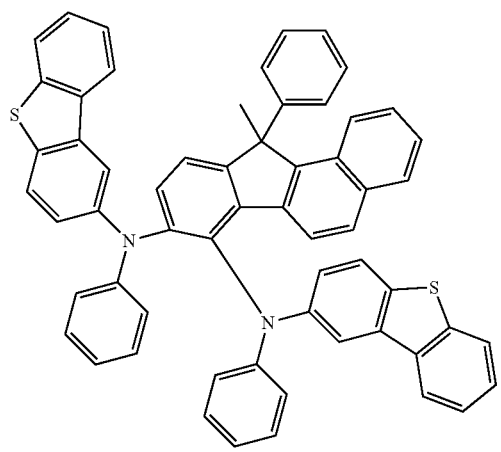
P-100
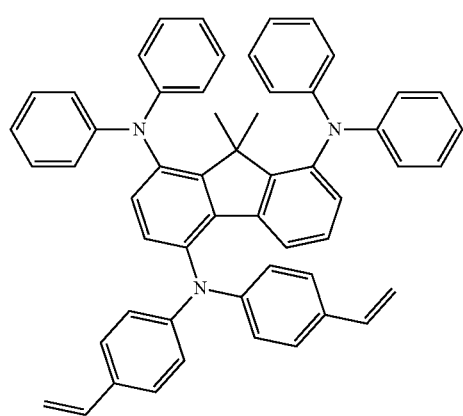
P-102
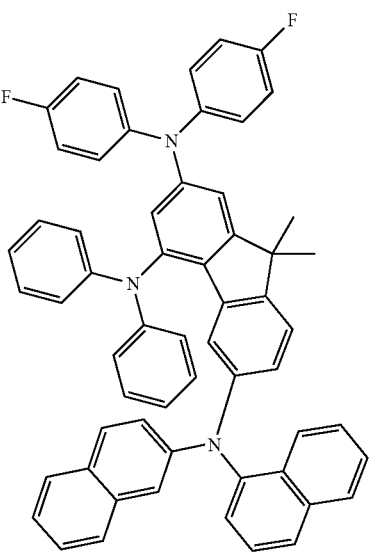

P-103
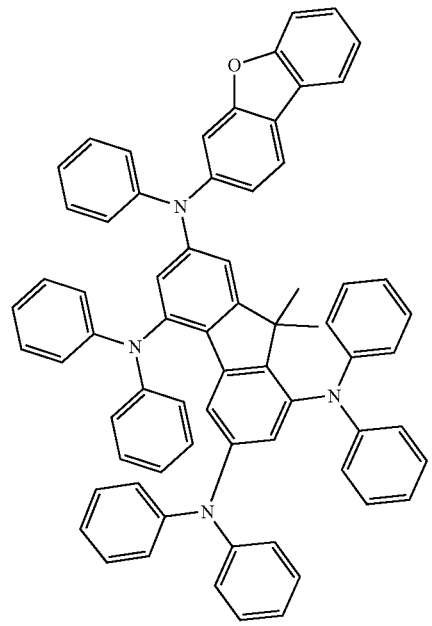
P-104
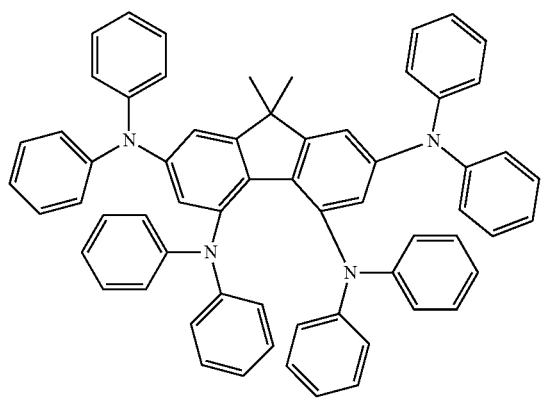
P-105
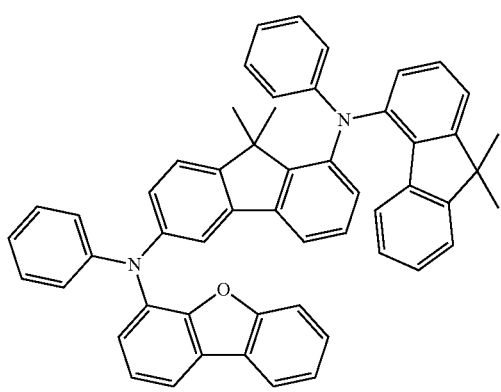
P-106
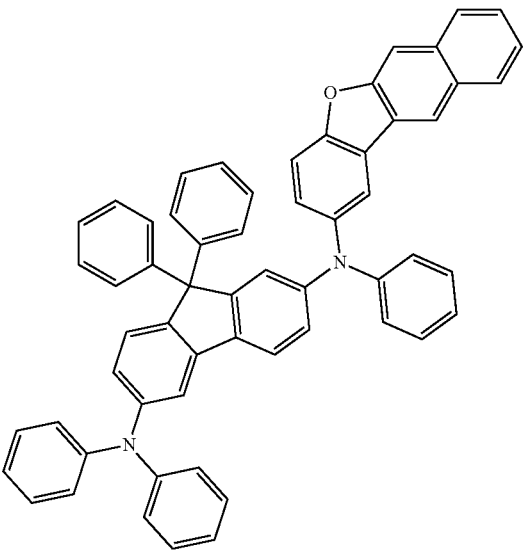
P-107
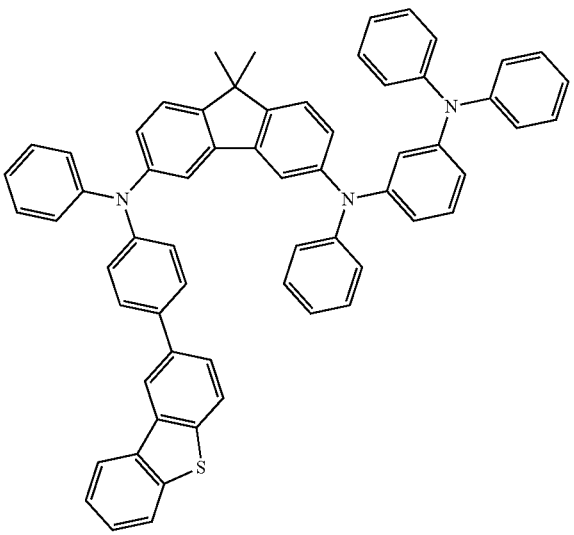
P-108
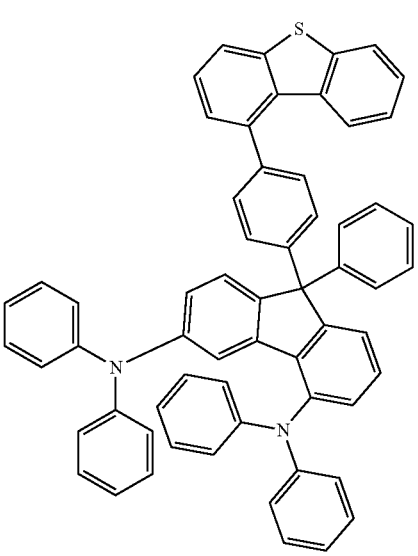

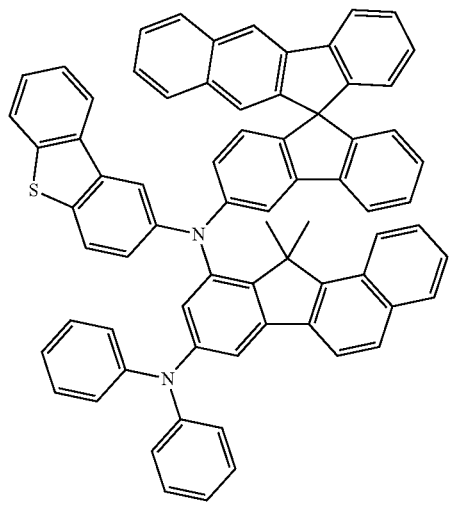
P-109
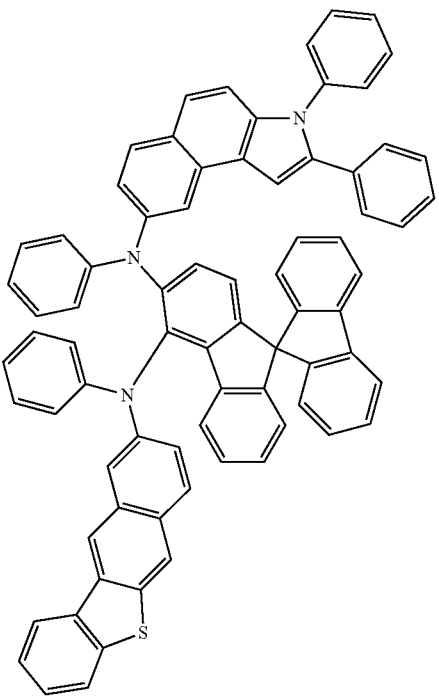
P-111
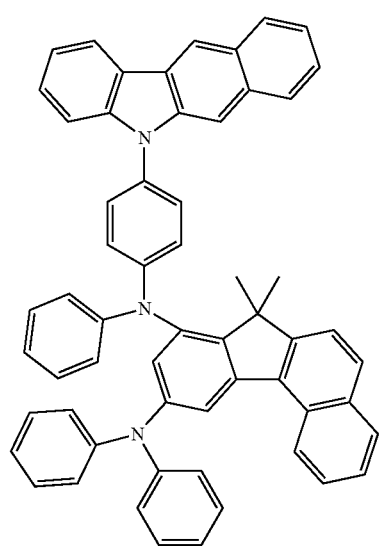
P-110
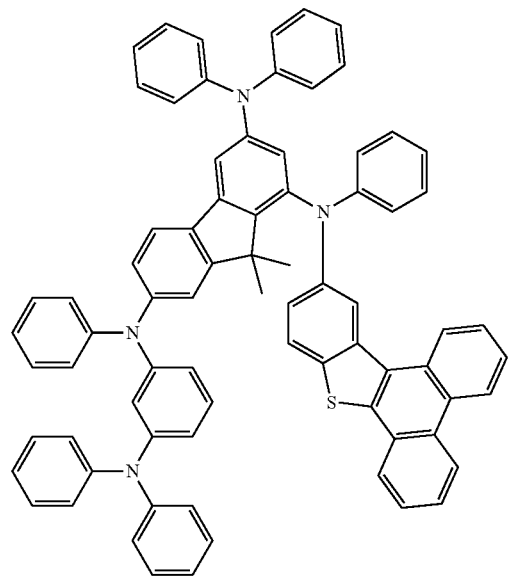
P-112

P-113
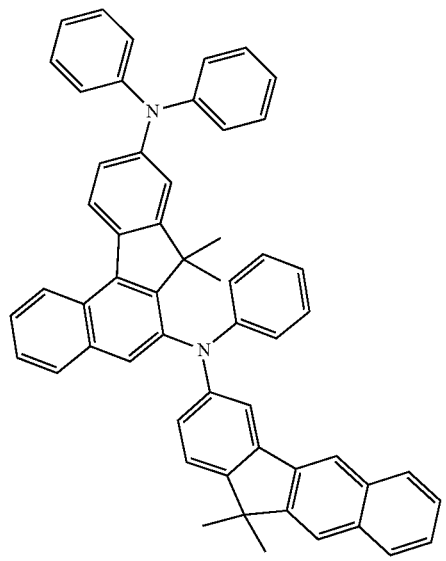
P-114
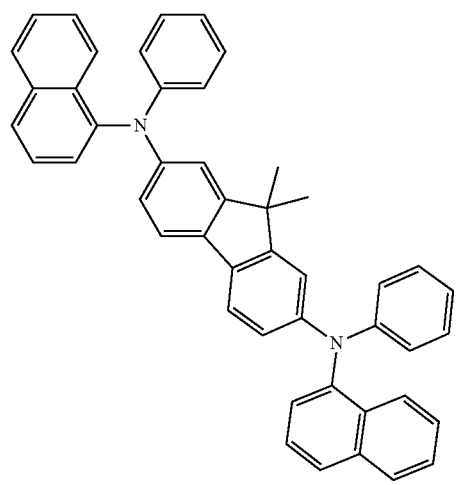
P-115
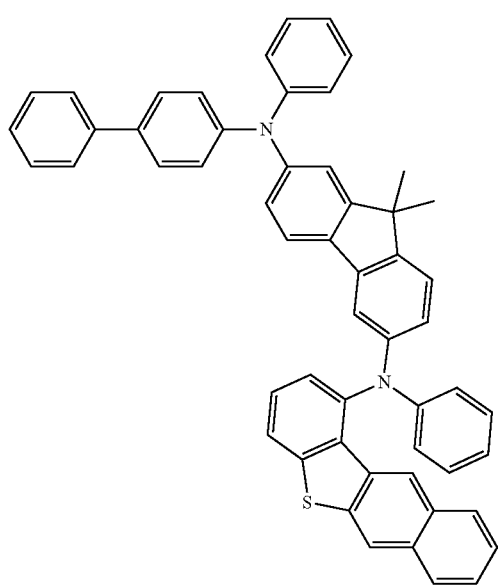
P-116
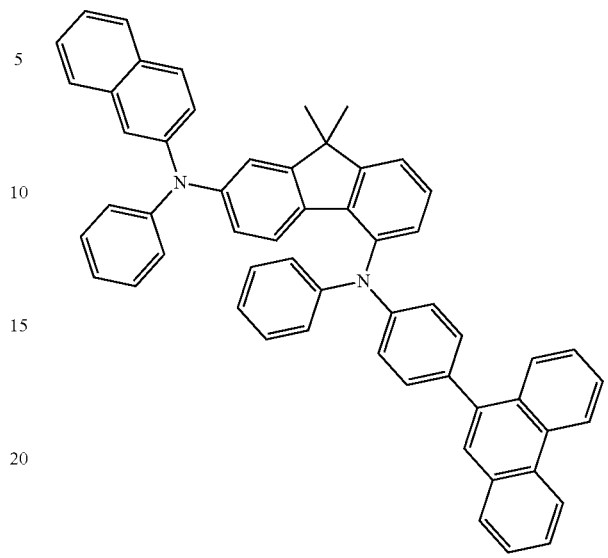
P-117
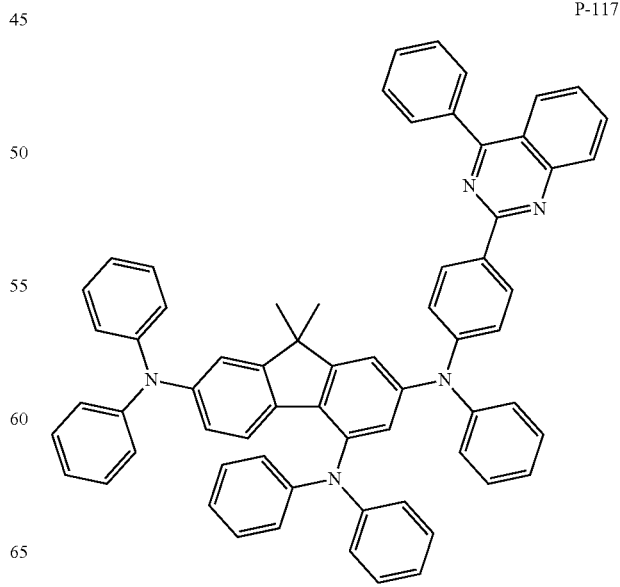

-continued
P-118
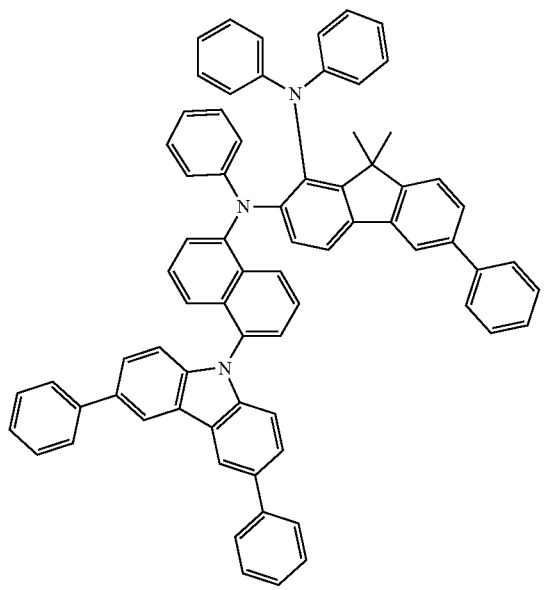
P-119
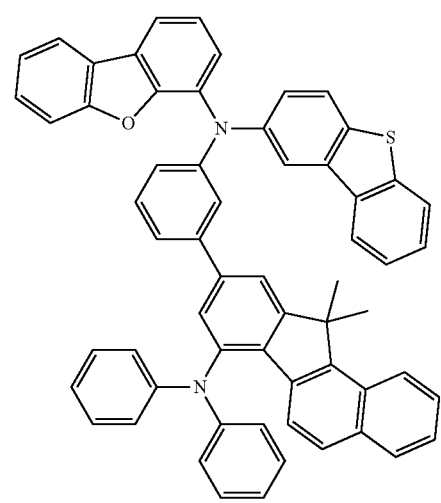
P-120
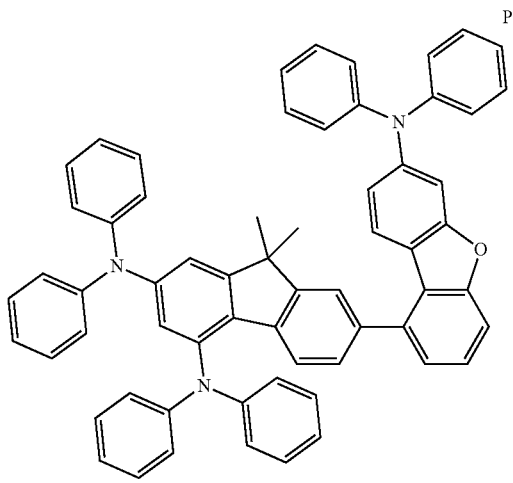
-continued
P-121
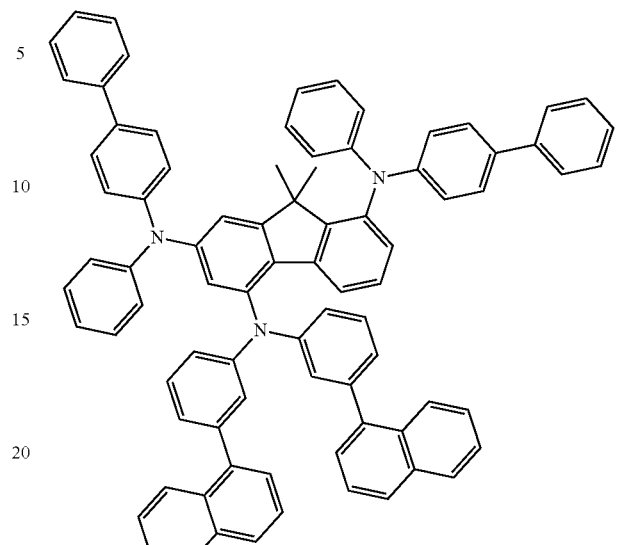
P-122
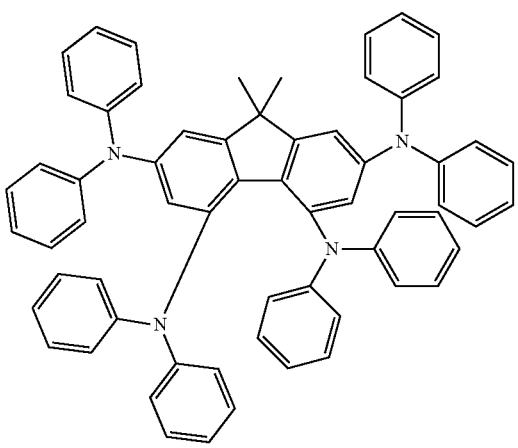
P-123
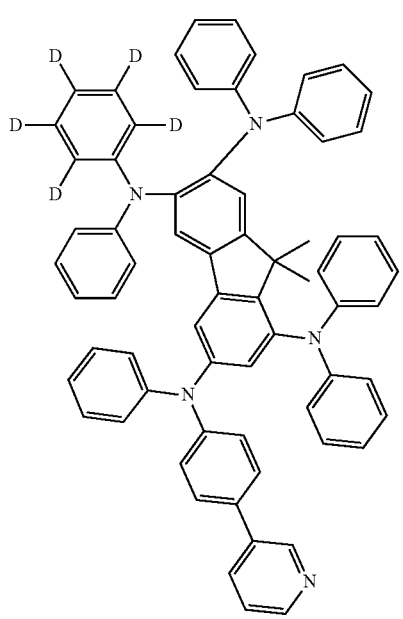

P-124
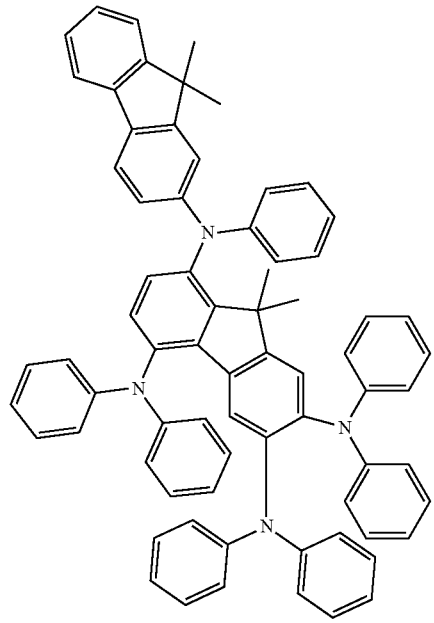
P-125
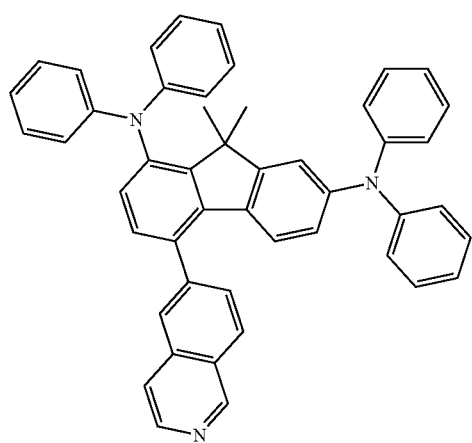
P-126
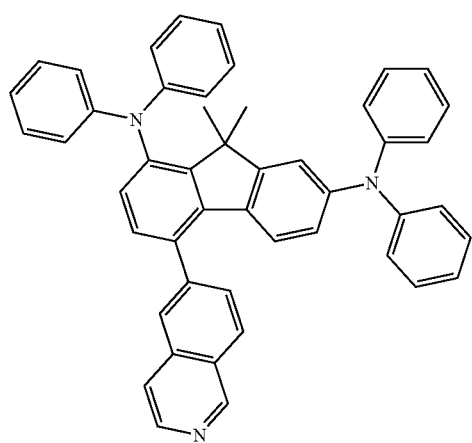
P-127
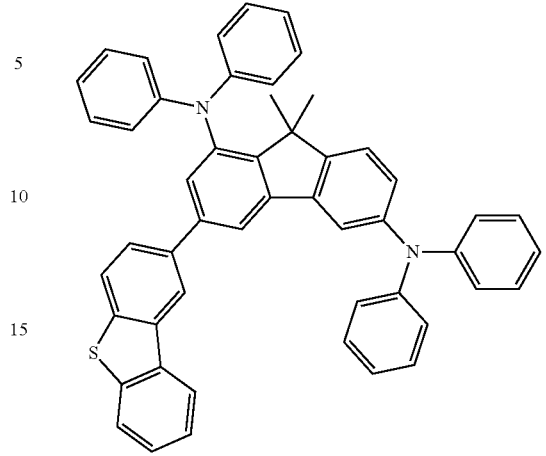
P-128
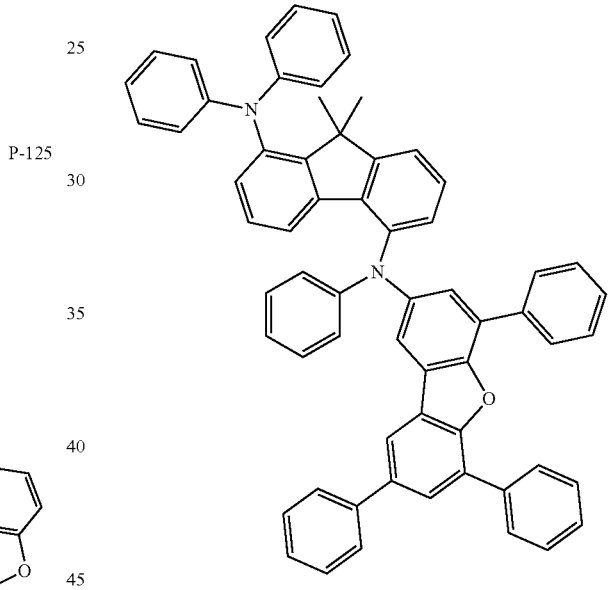
P-129
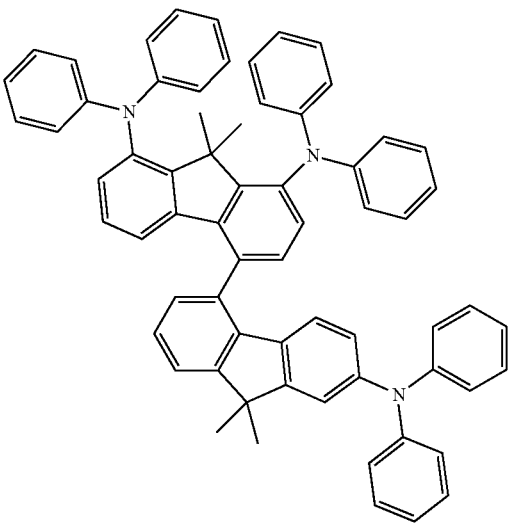

P-130
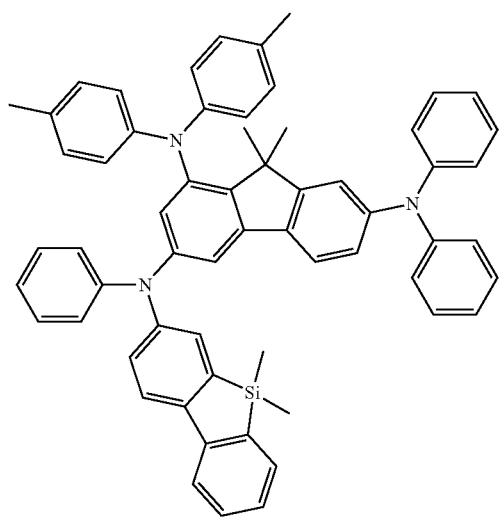
P-131
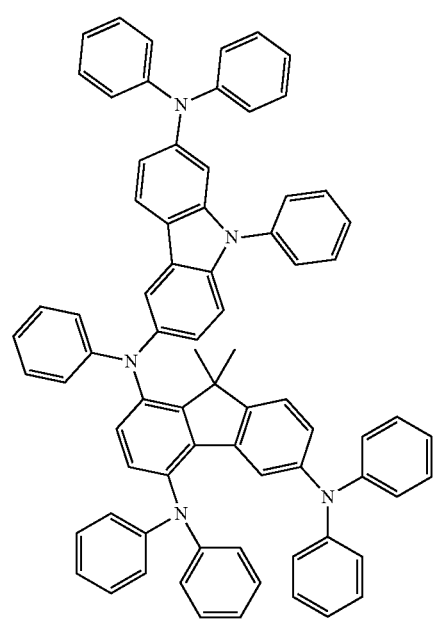
P-132
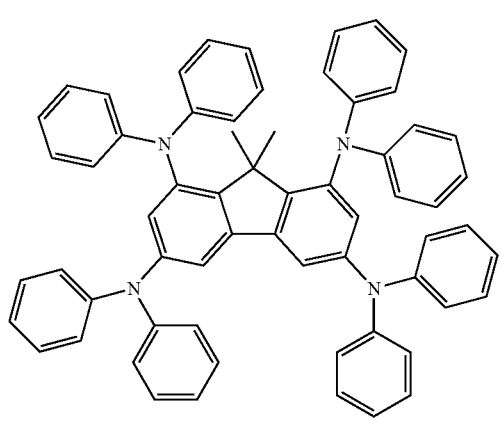
P-133
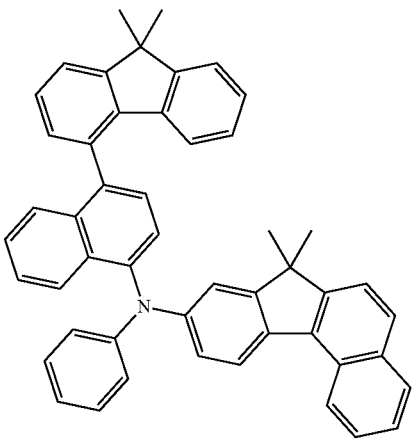
P-134
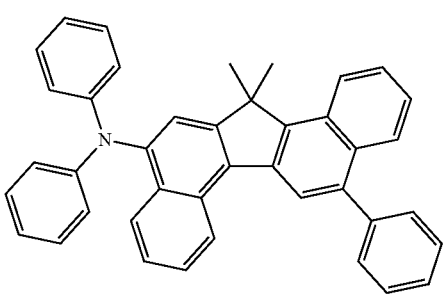
P-135
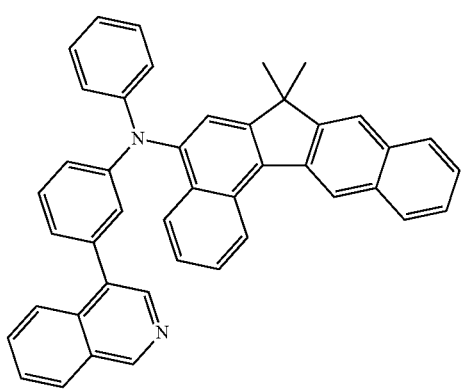
P-136
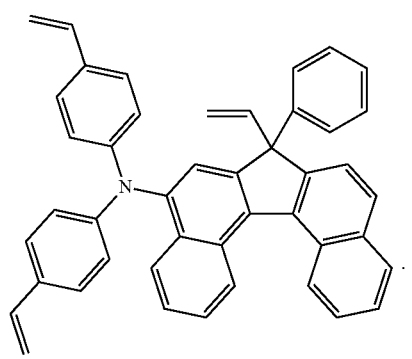
Specifically, the compound represented by formula 12 may be one of the following compounds, but there is no limitation thereto.

P2-1
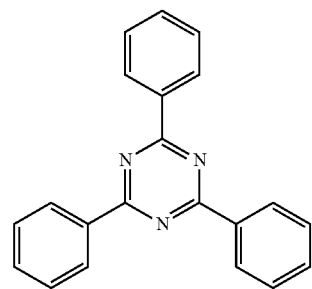
P2-4
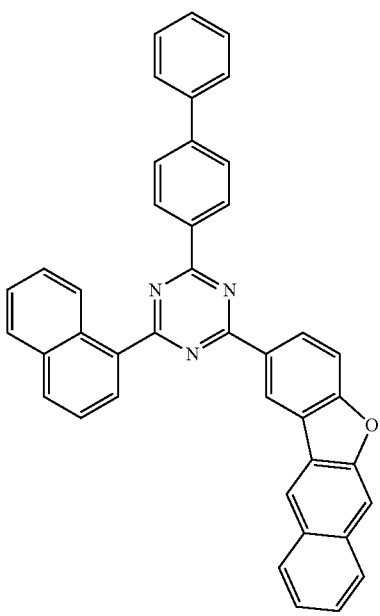
P2-2
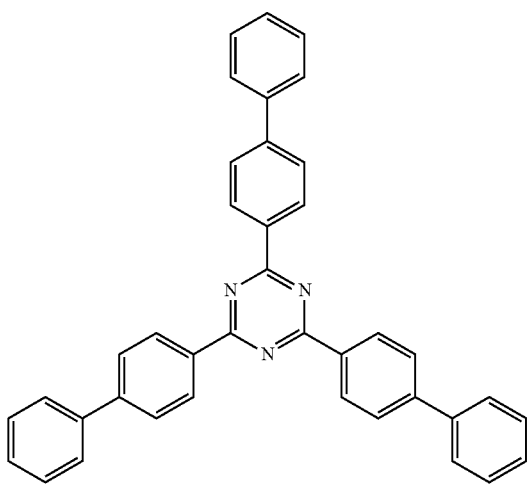
P2-5
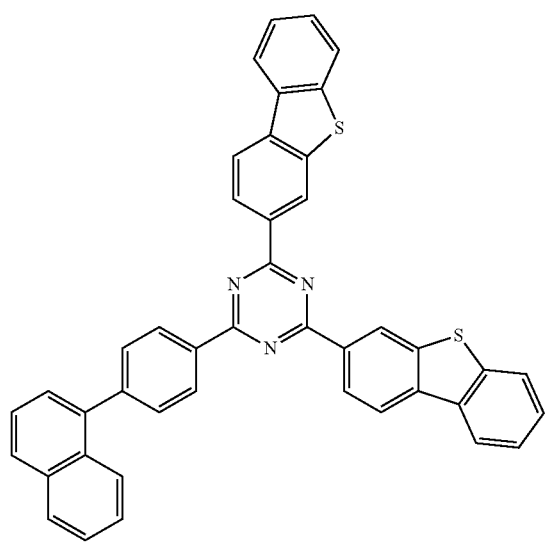
P2-3
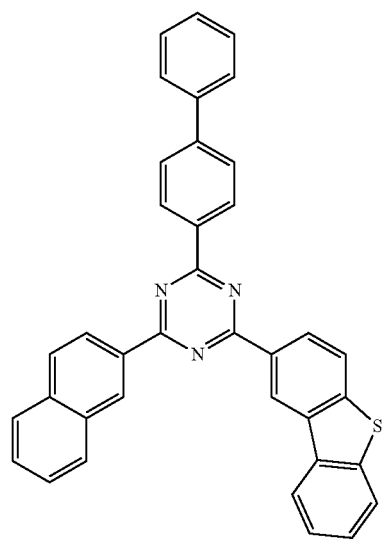
P2-6

P2-7
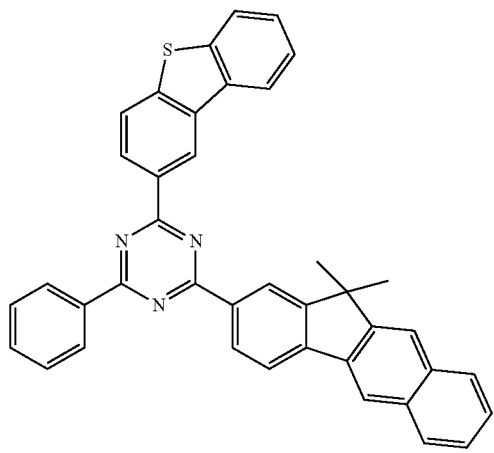
P2-8
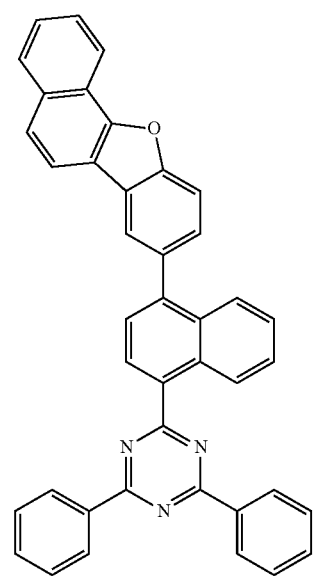
P2-9
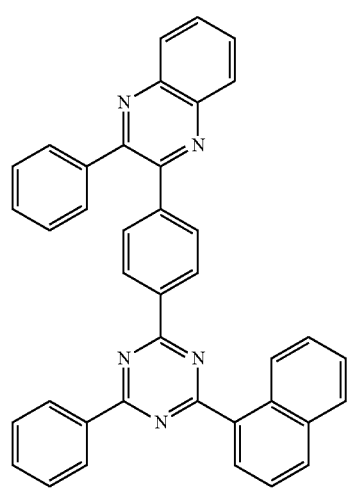
P2-10
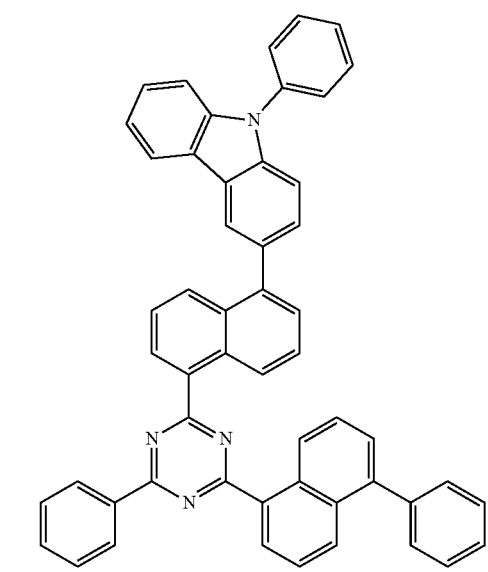
P2-11
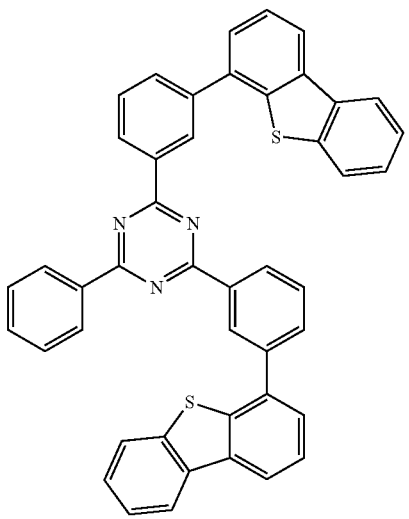

-continued
P2-12
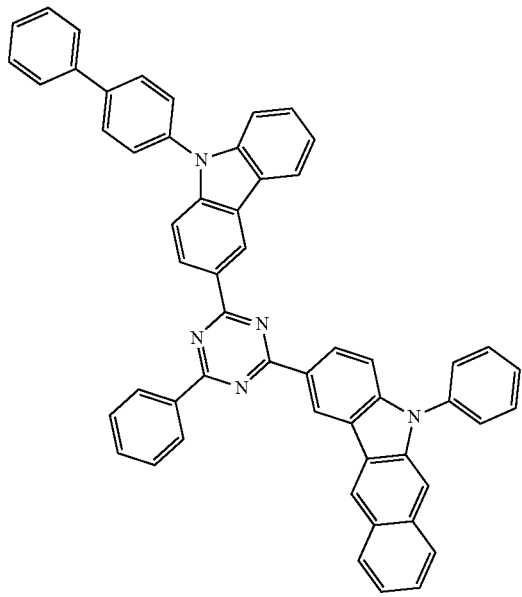
P2-13
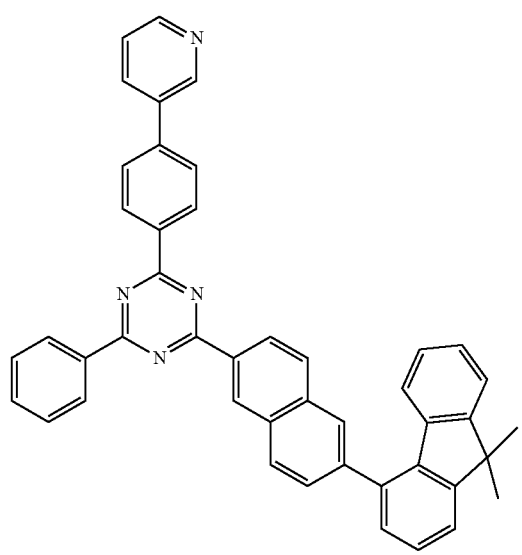
P2-14
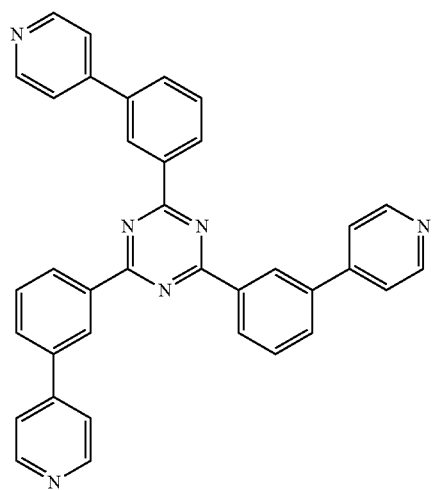
-continued
P2-15
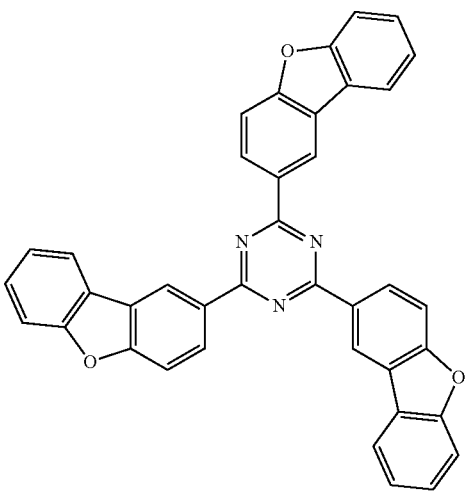
P2-16
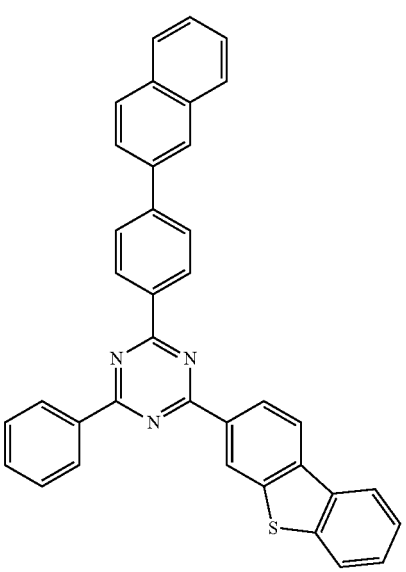
P2-17
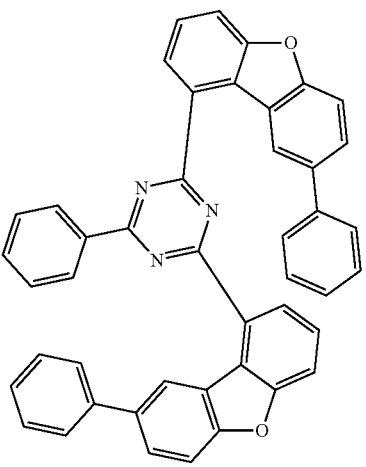

P2-18
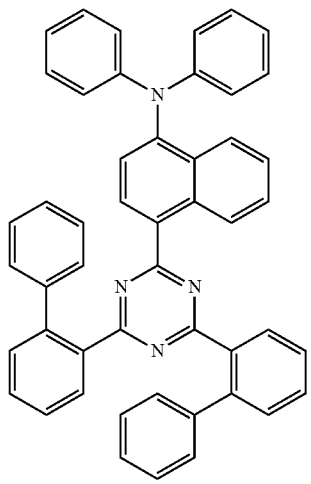
P2-19
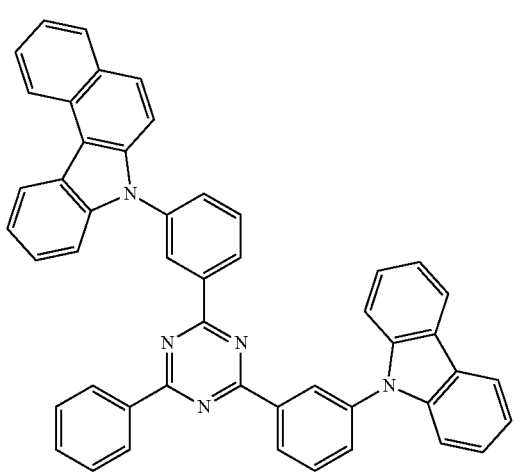
P2-20
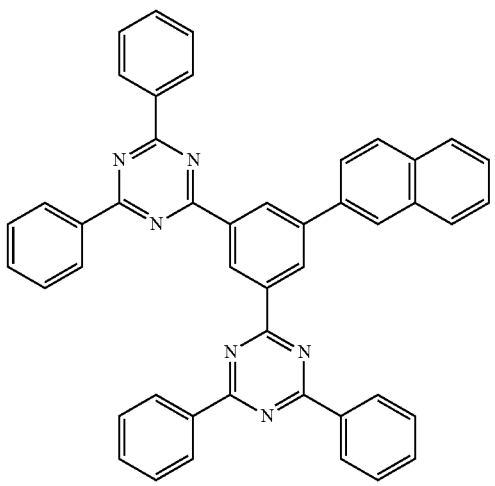
P2-21
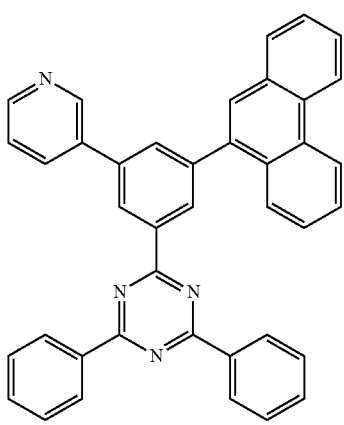
P2-22
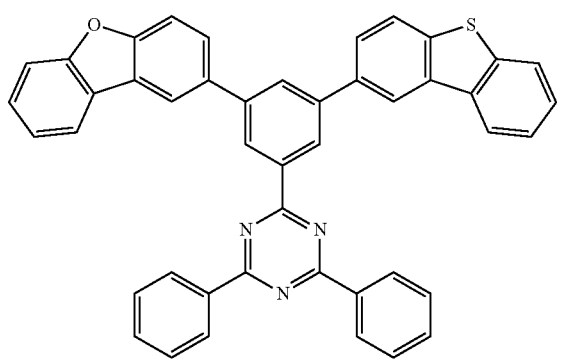
P2-23
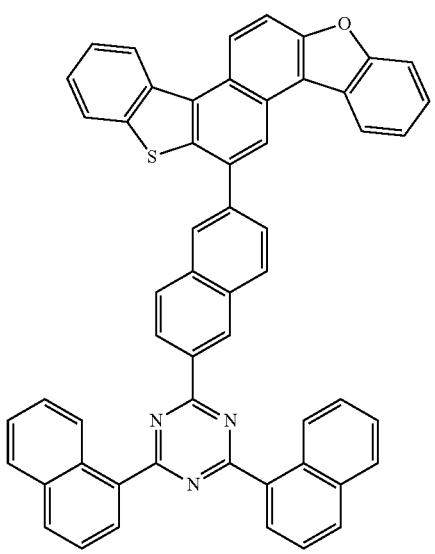

P2-24
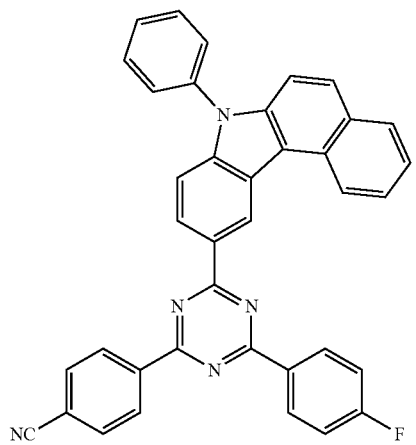
P2-25
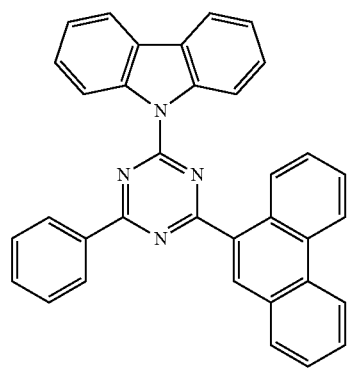
P2-26
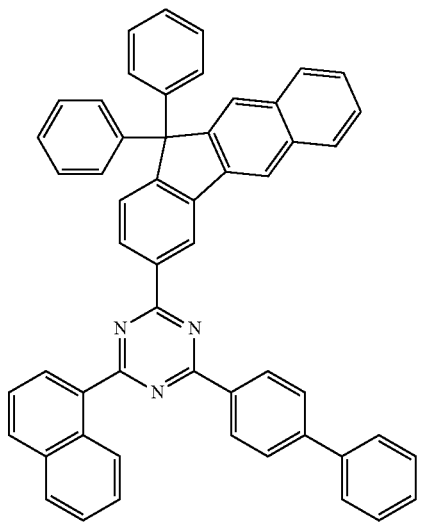
P2-27
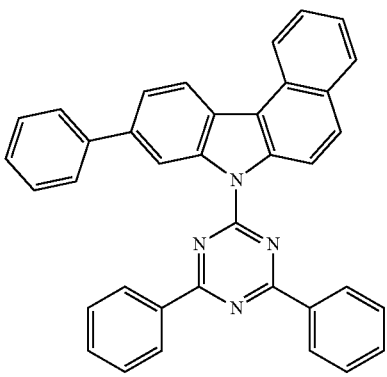
P2-28
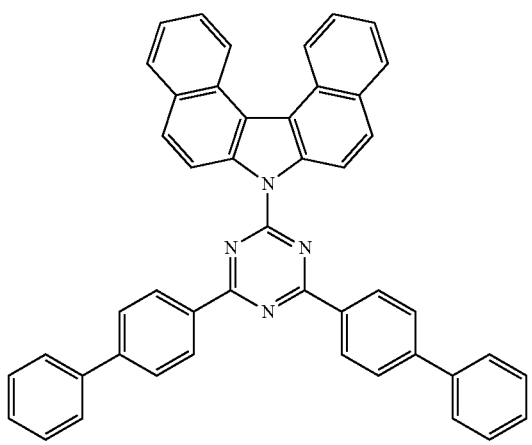
P2-29
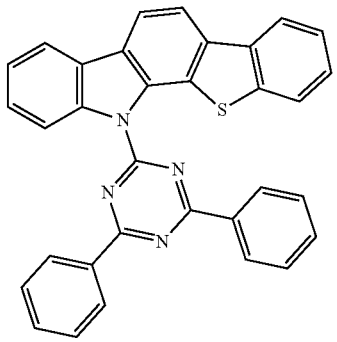
P2-30
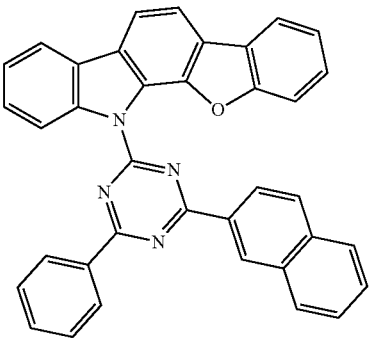

-continued
P2-31
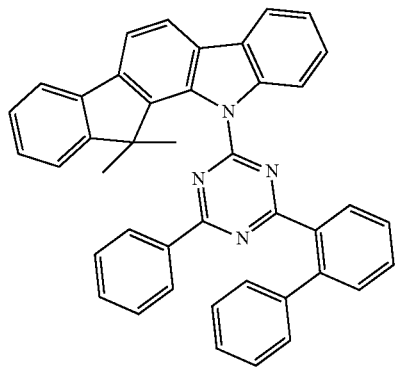
P2-32
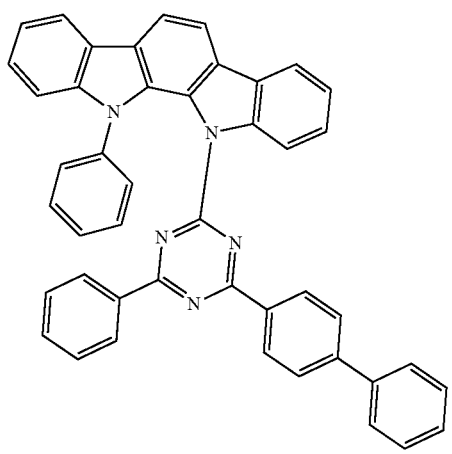
P2-33
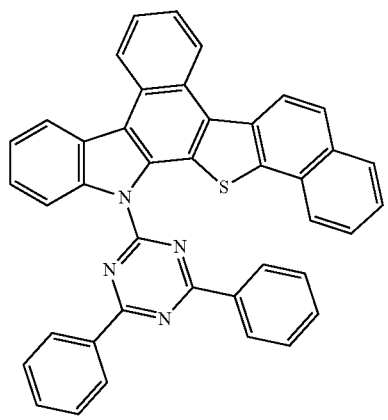
P2-34
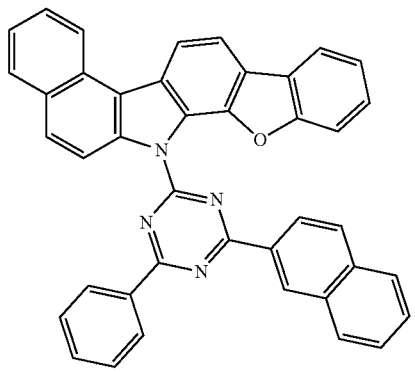
-continued
P2-35
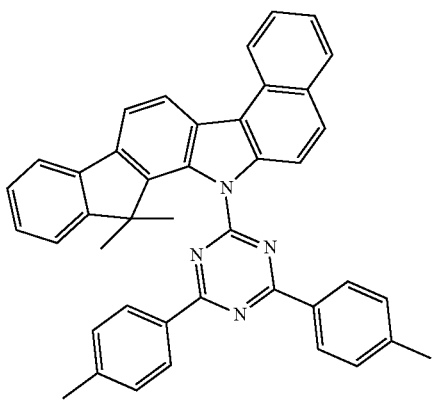
P2-36
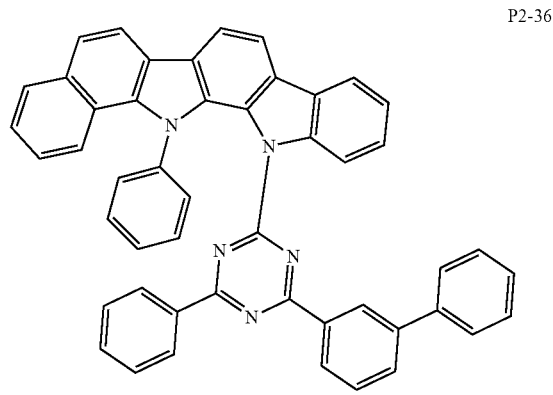
P2-37
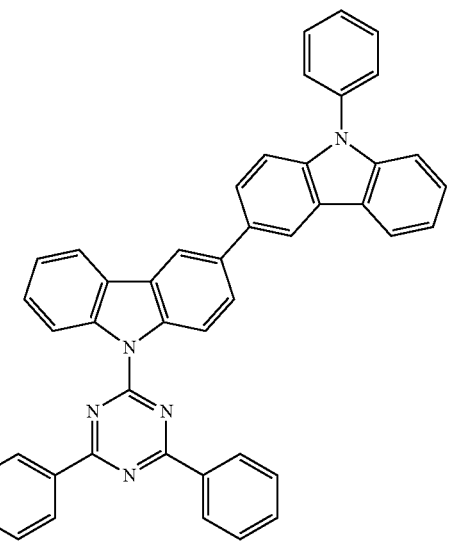

-continued
P2-38
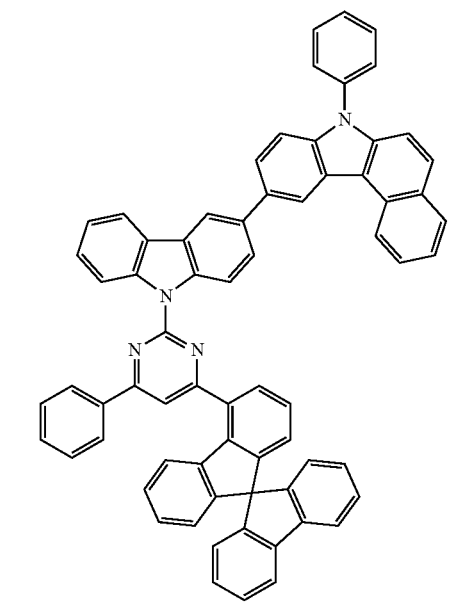
P2-39
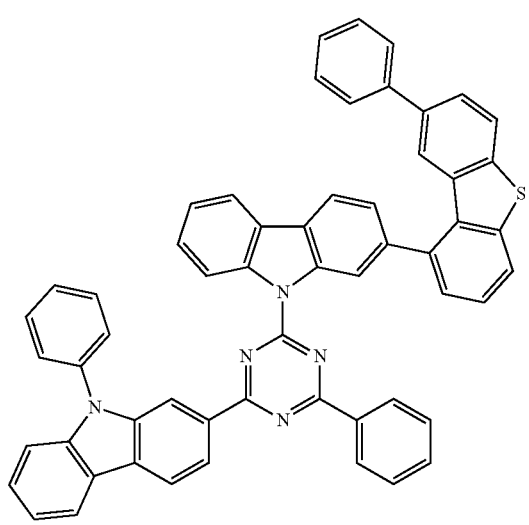
P2-40
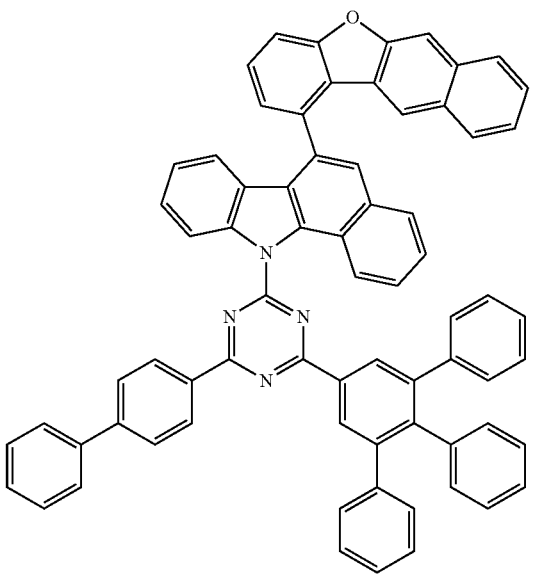
P2-41
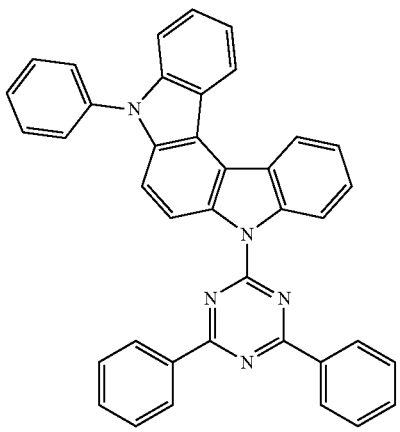
P2-42
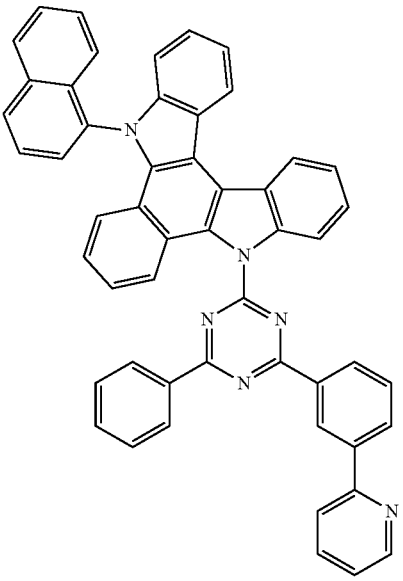

P2-43
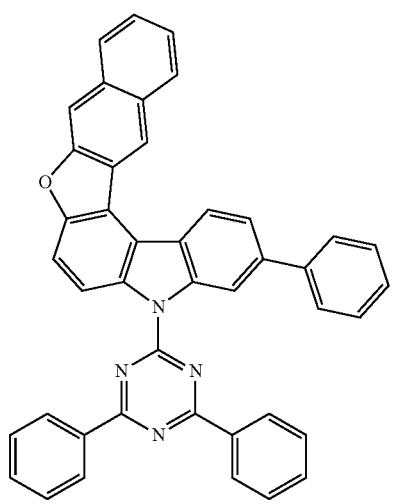
P2-44
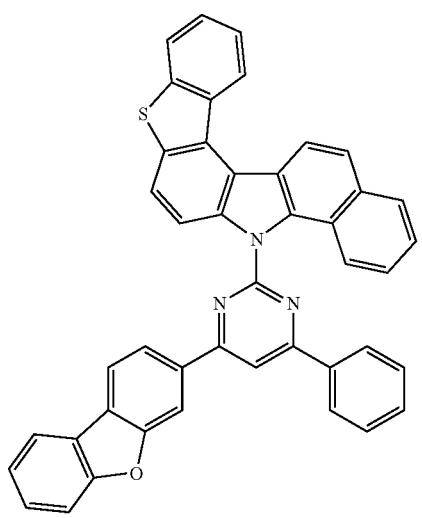
P2-45
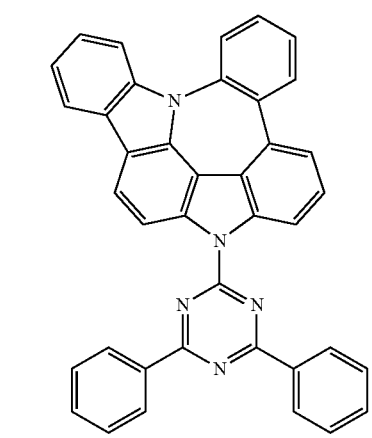
P2-46
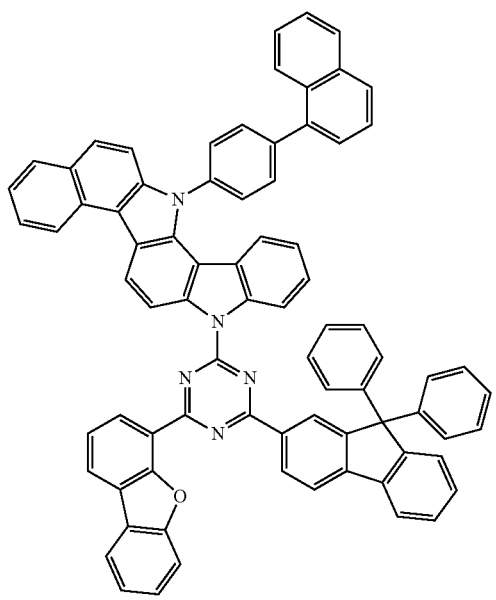
P2-47
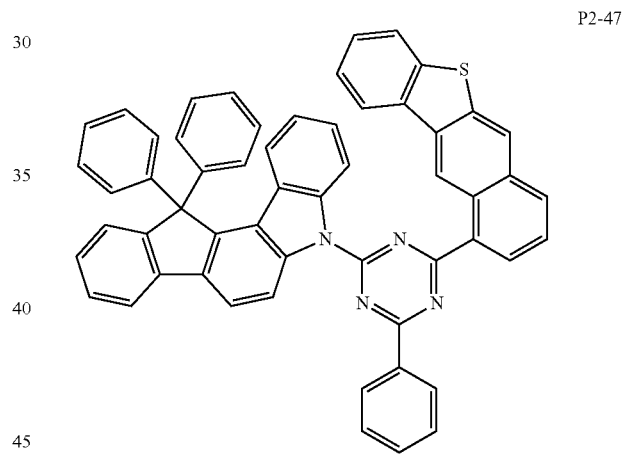
P2-48
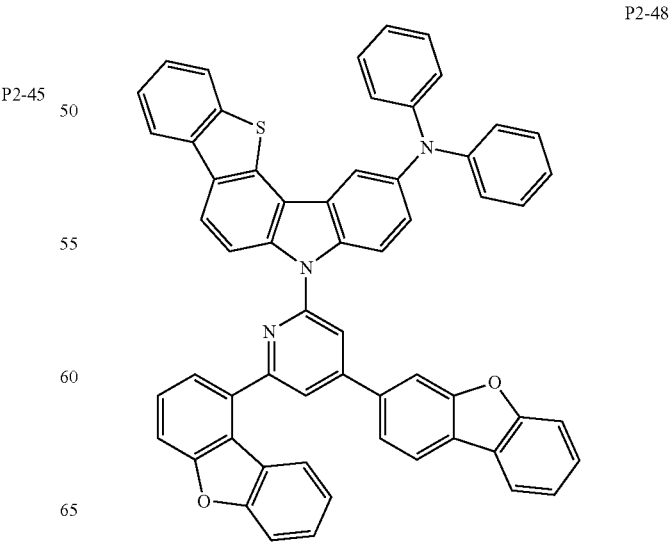

-continued
P2-49
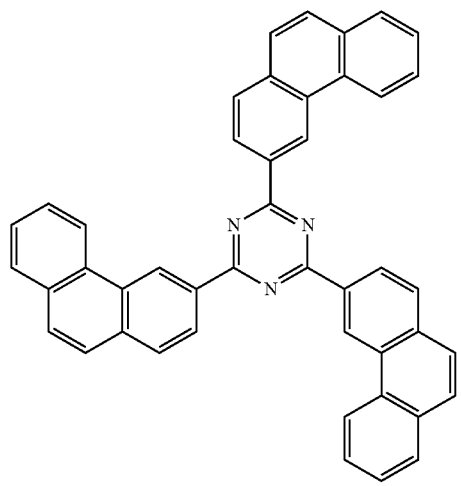
P2-50
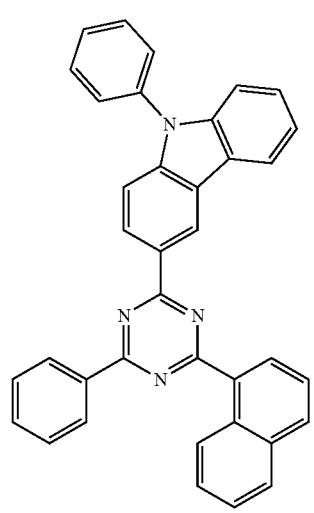
P2-51
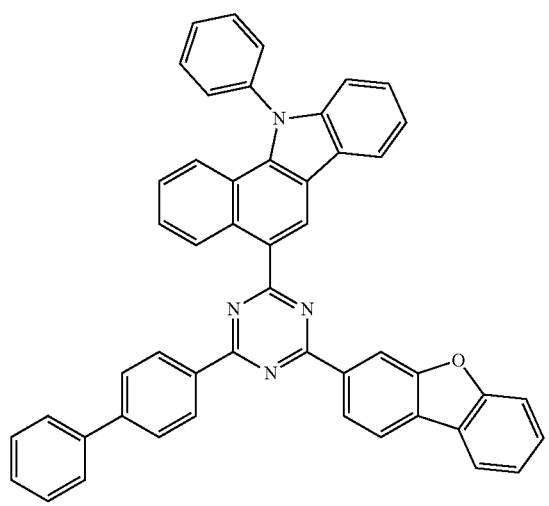
-continued
P2-52
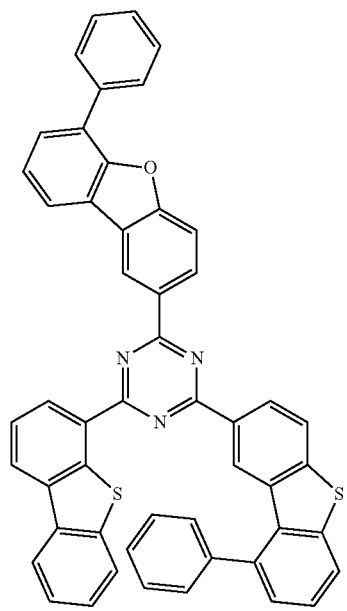
P2-53
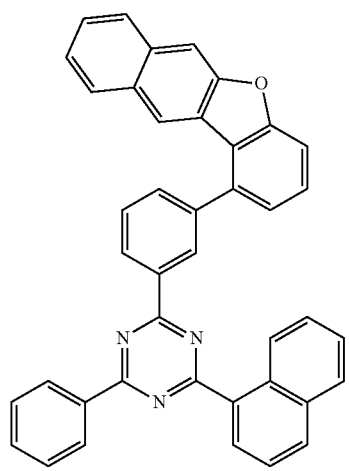
P2-54
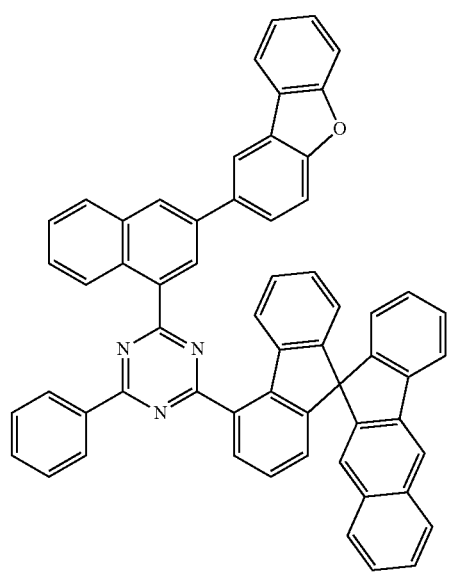

-continued
P2-55
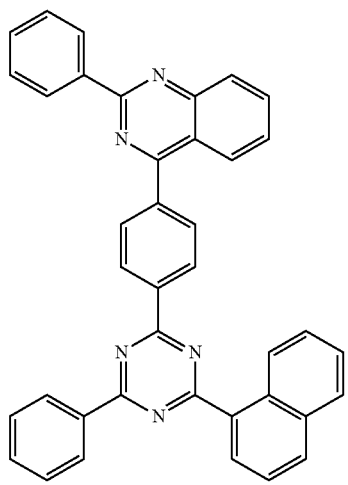
P2-56
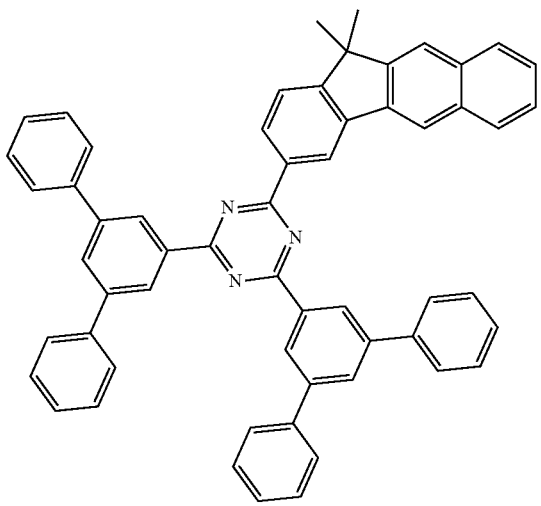
P2-57
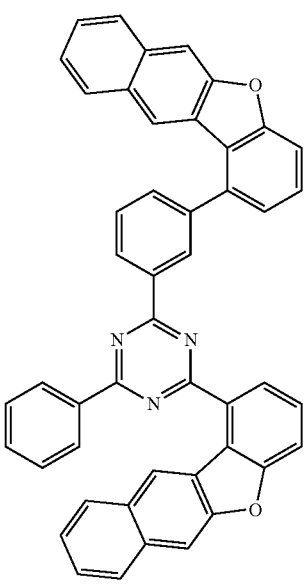
-continued
P2-58
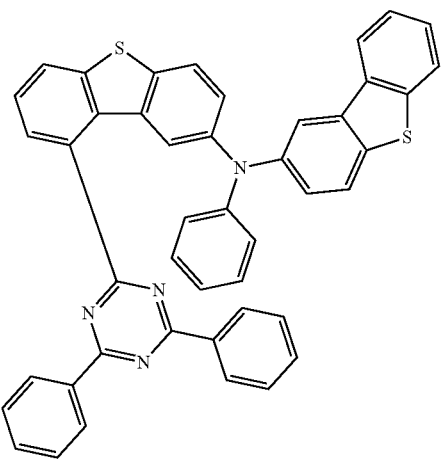
P2-59
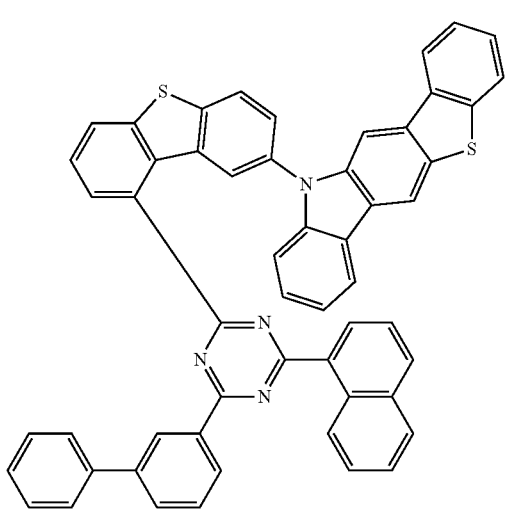
P2-60
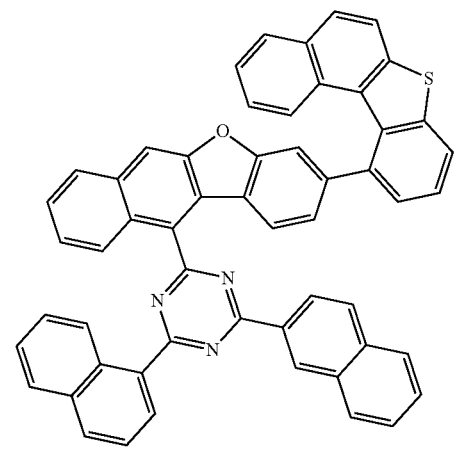

P2-61
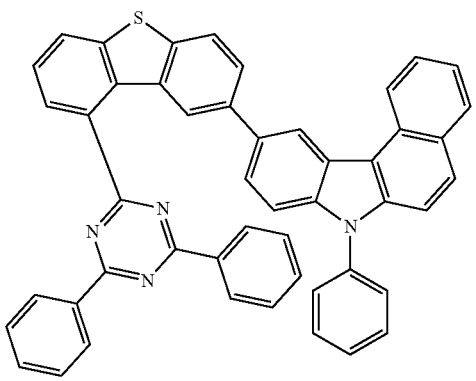
P2-62
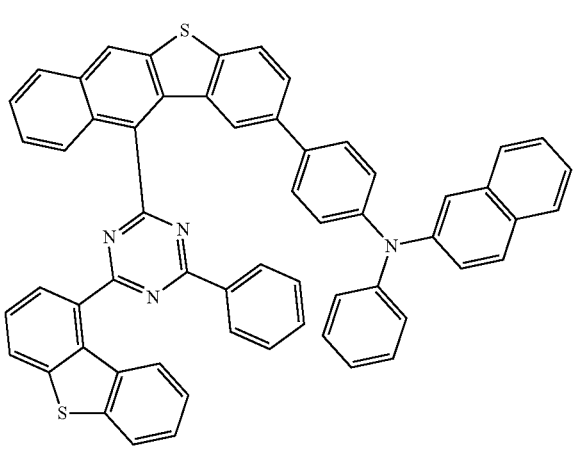
P2-63
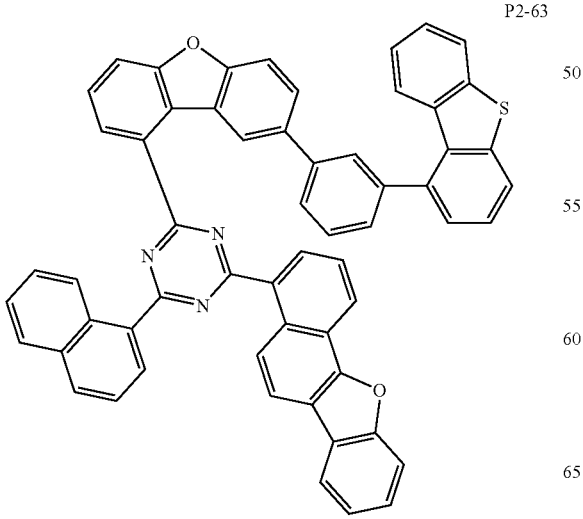
P2-64
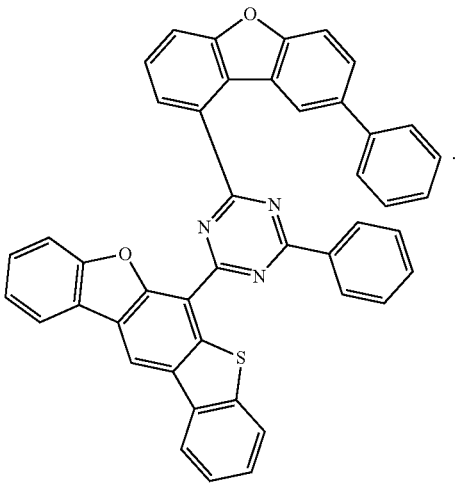
Specifically, the compound represented by formula 13 may be one of the following compounds, but there is no limitation thereto.
P2-65
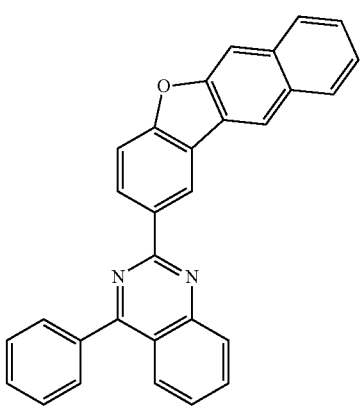
P2-66
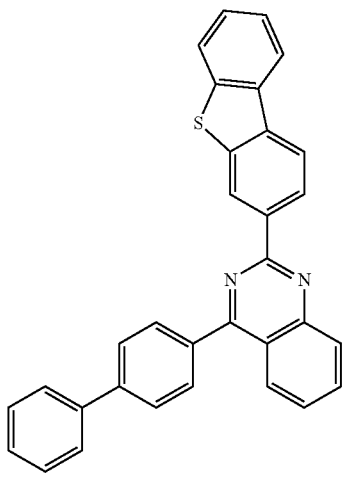

P2-67
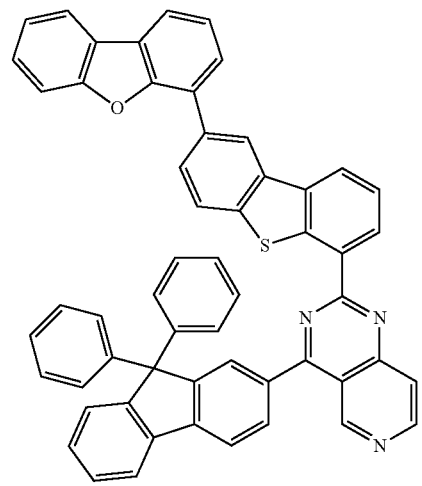
P2-68
P2-69
P2-70
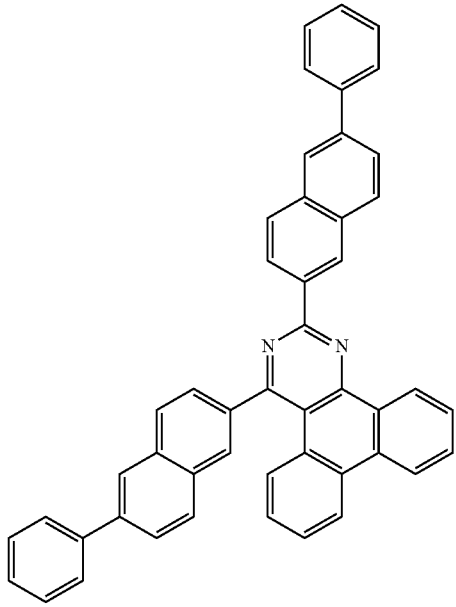
P2-71
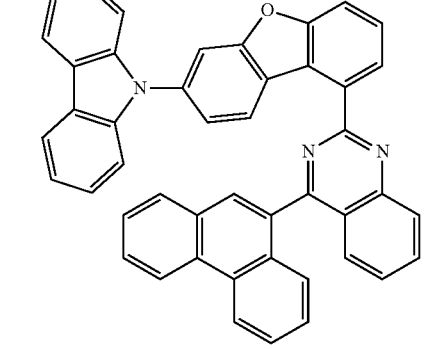
P2-72
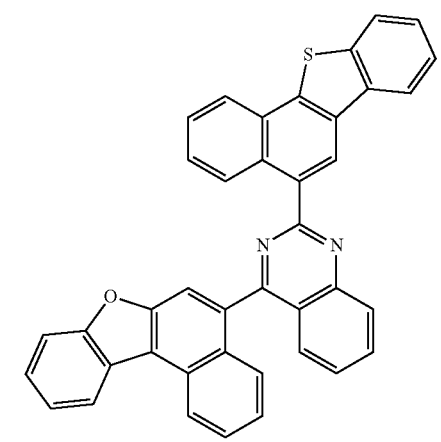

P2-73
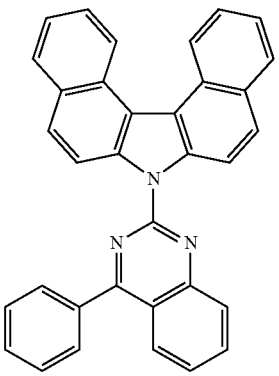
P2-74
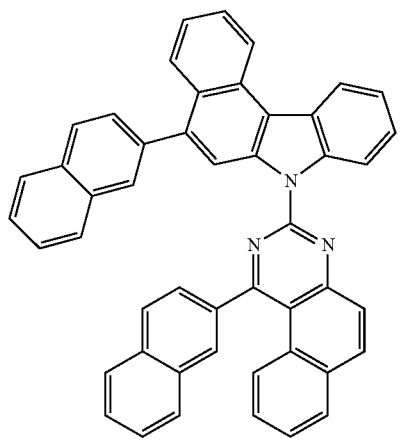
P2-75
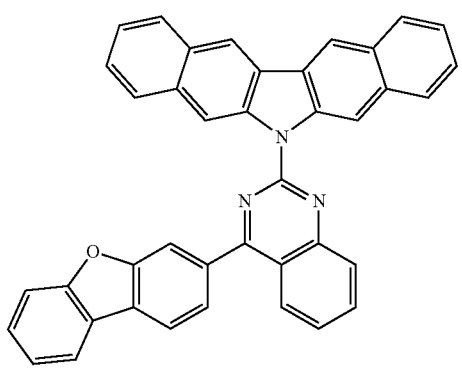
P2-76
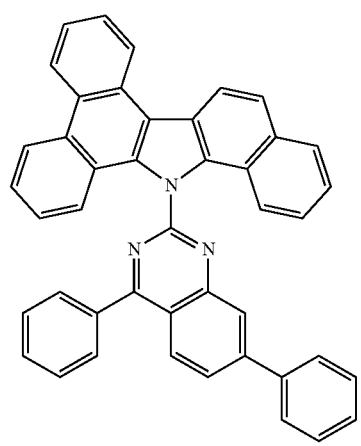
P2-77
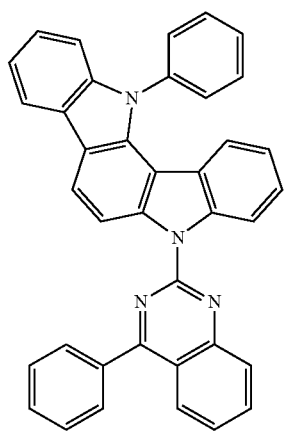
P2-78
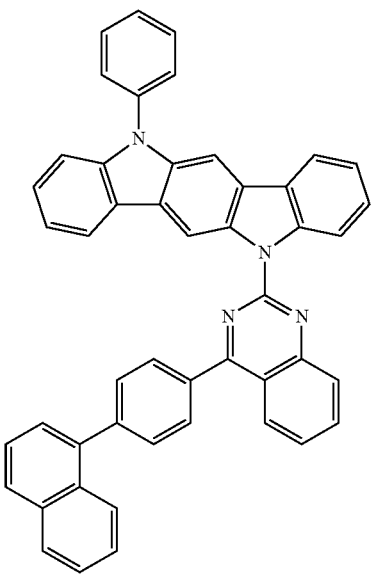
P2-79
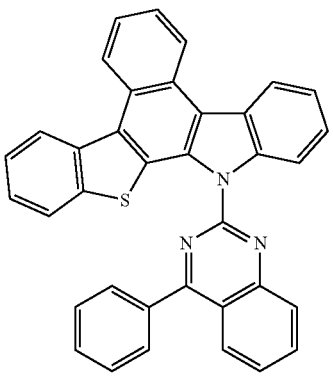

P2-80
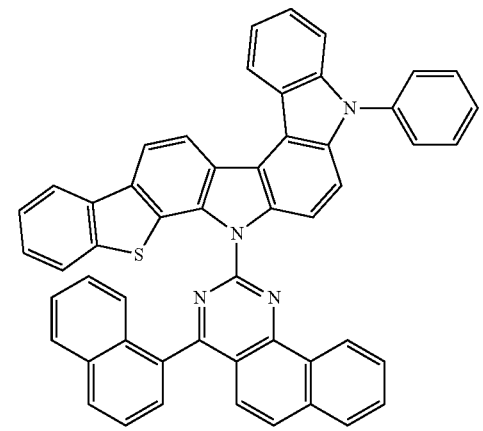
P2-81
P2-82
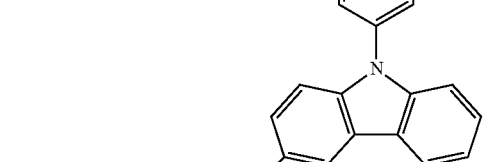
P2-83
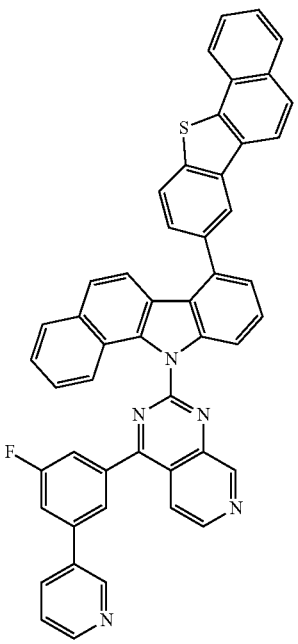
P2-84
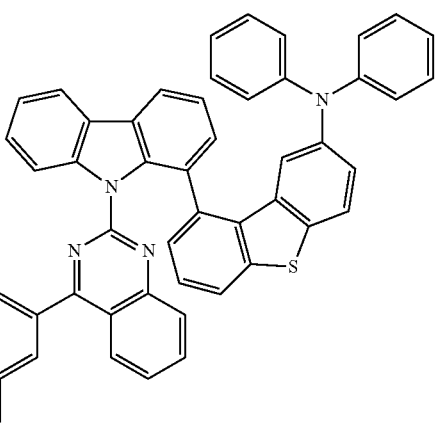
P2-85
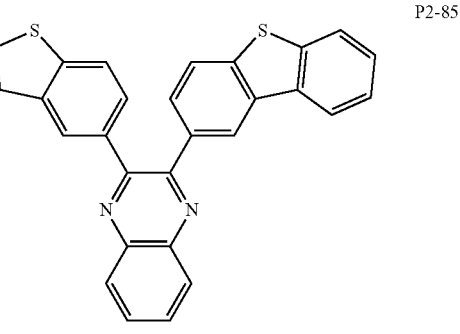

-continued
P2-86
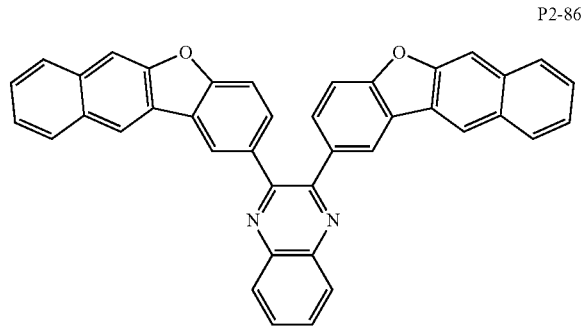
P2-87
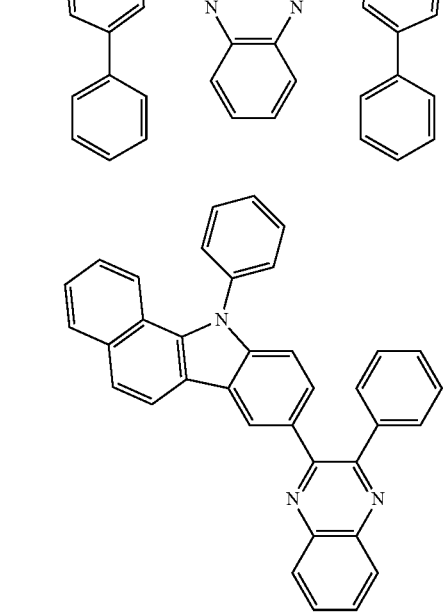
P2-88
P2-89
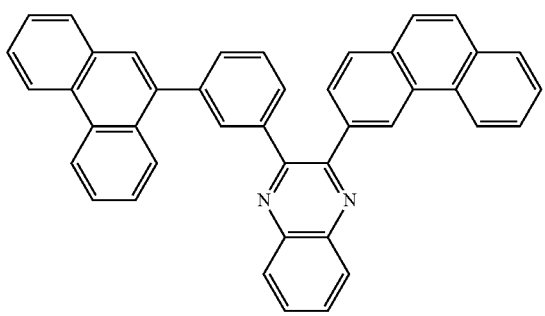
-continued
P2-90
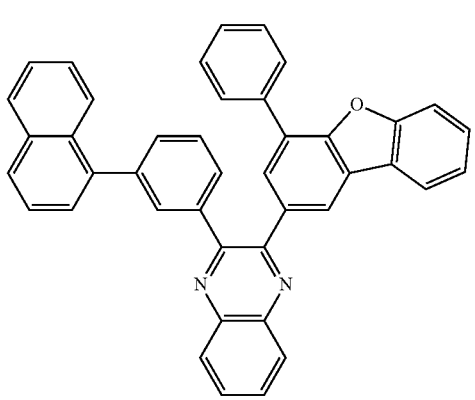
P2-91
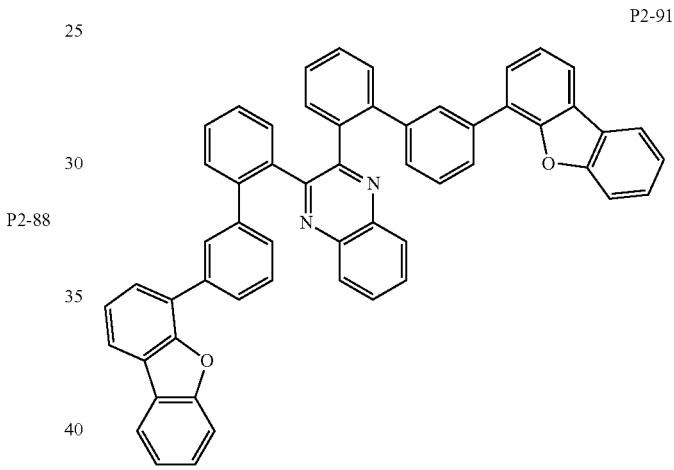
P2-92
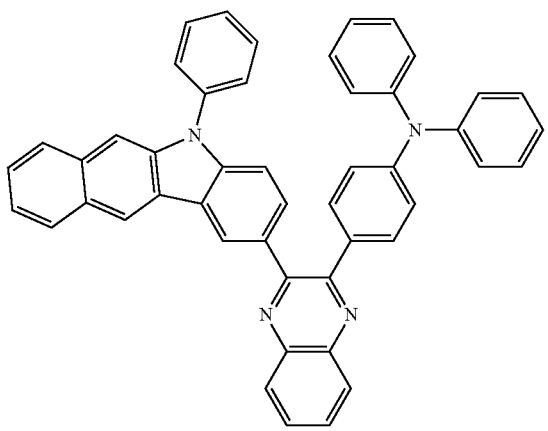

-continued
P2-93
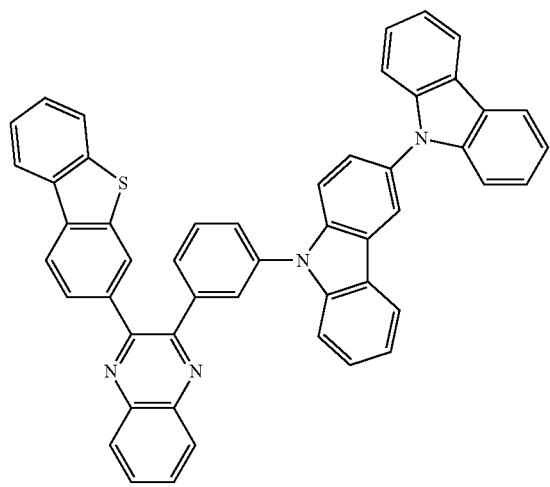
P2-94
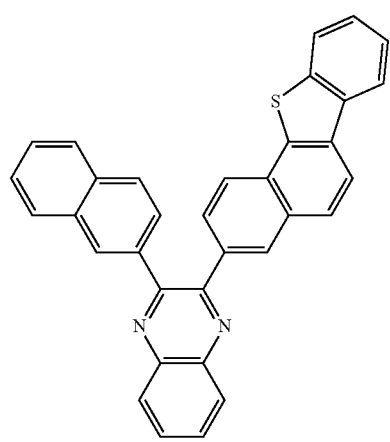
P2-95
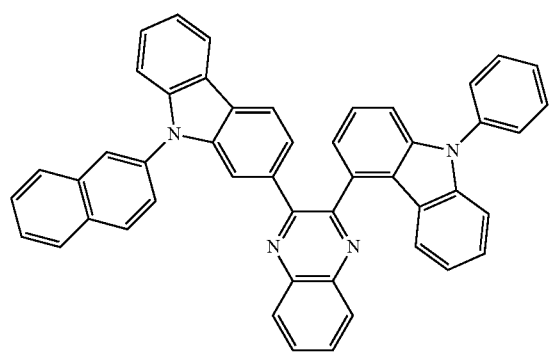
-continued
P2-96
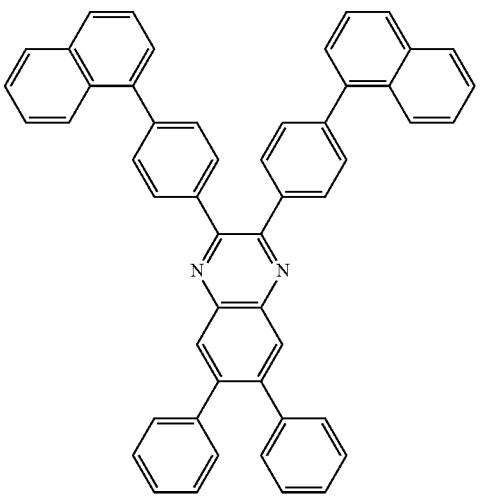
P2-97
P2-98
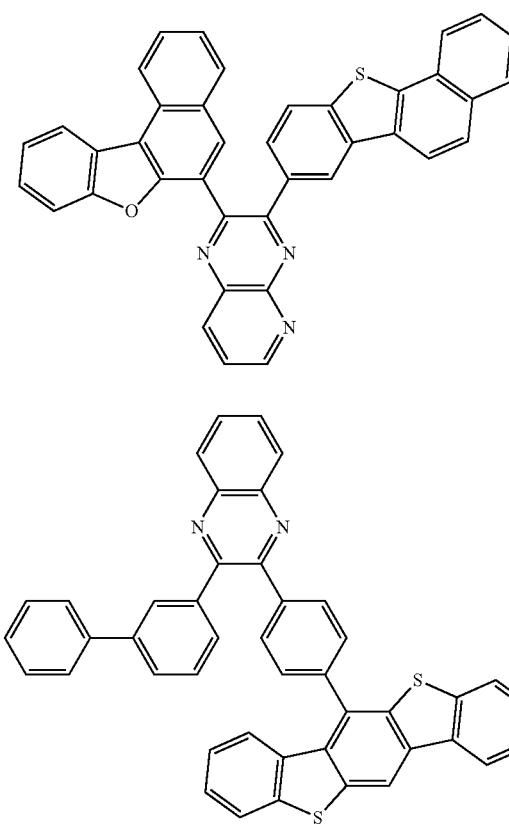
P2-99
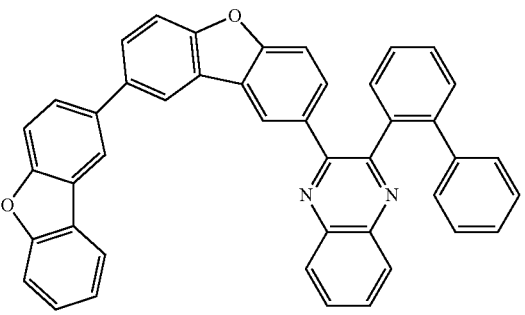

P2-100
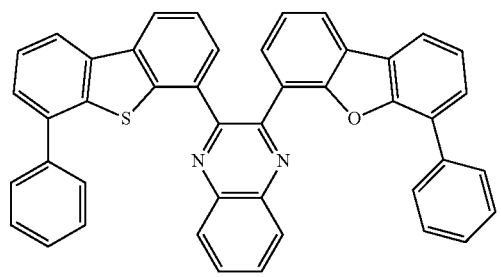
P2-101
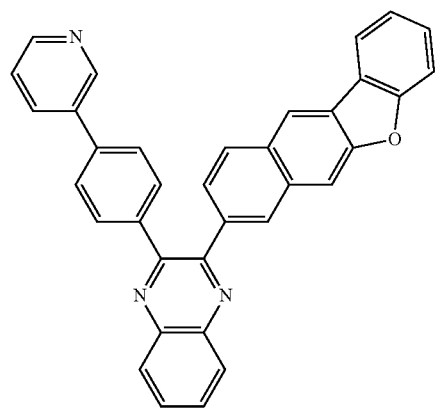
P2-102
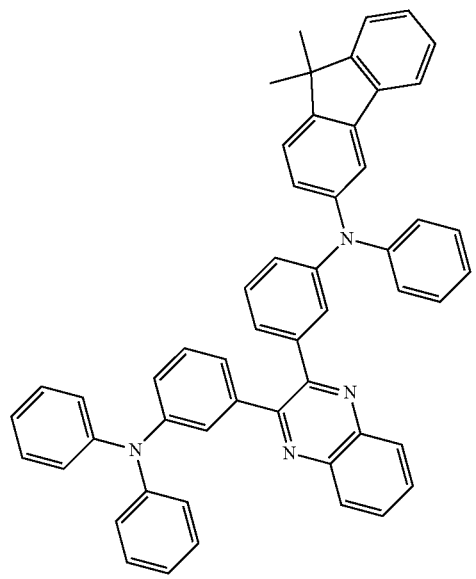
P2-103
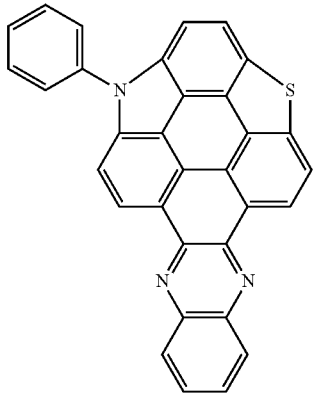
P2-104
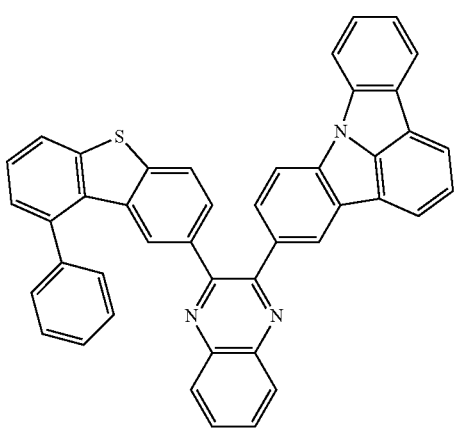
P2-105
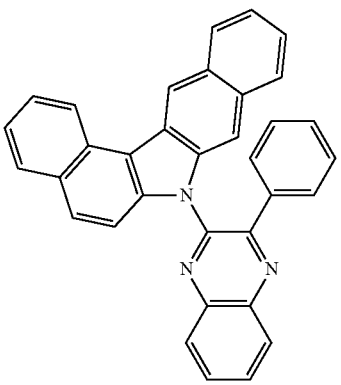

P2-106
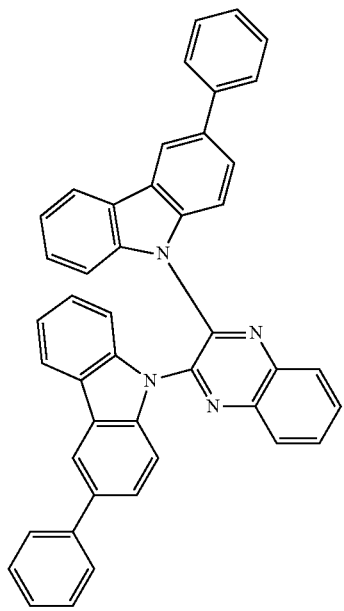
P2-107
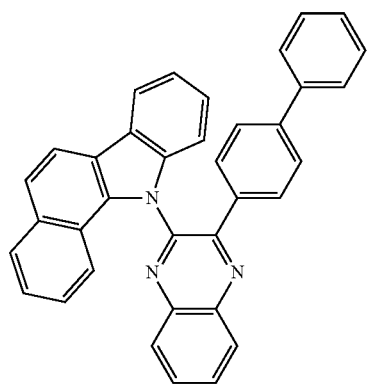
P2-108
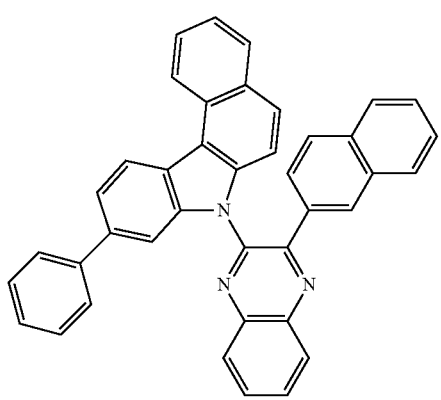
P2-109
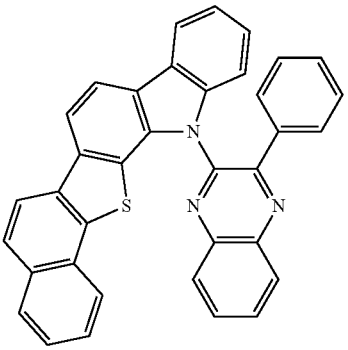
P2-110
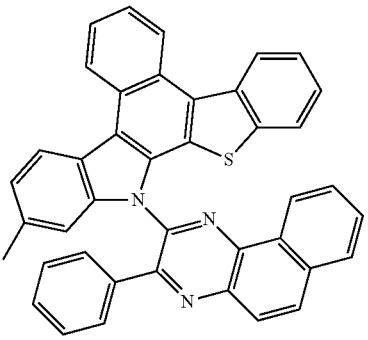
P2-111
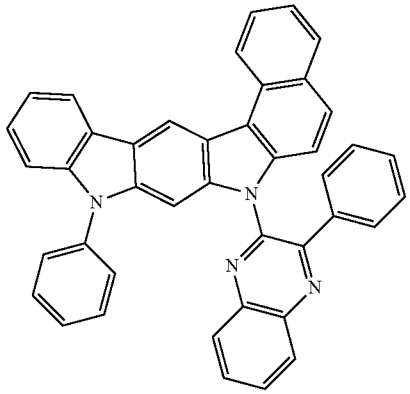
P2-112
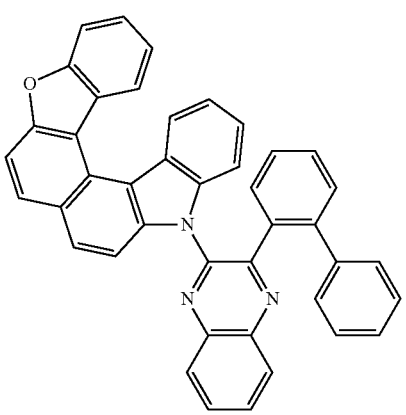

P2-113
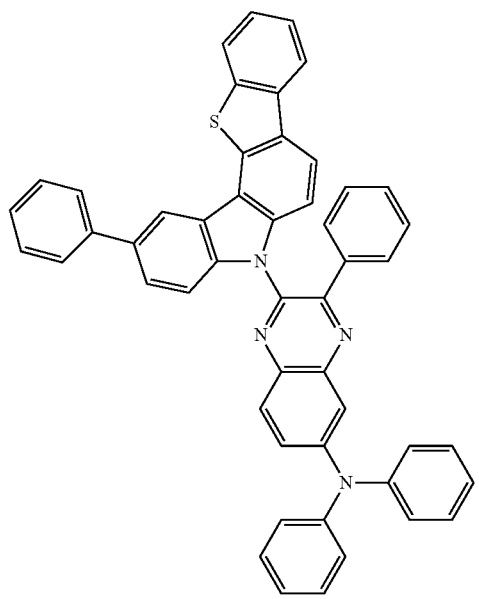
P2-116
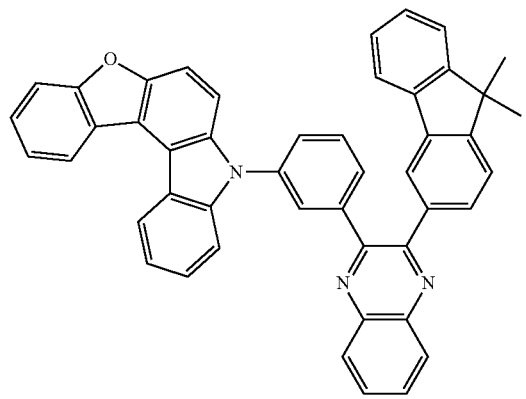
P2-114
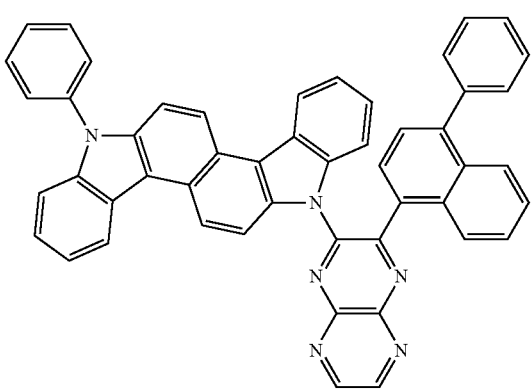
P2-117
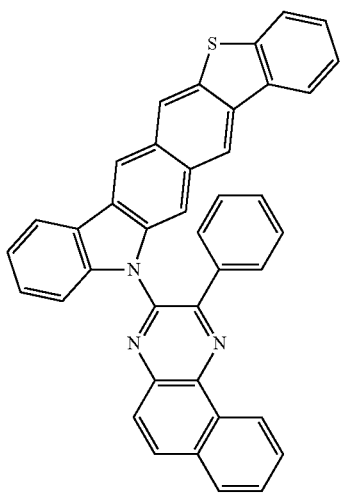
P2-115
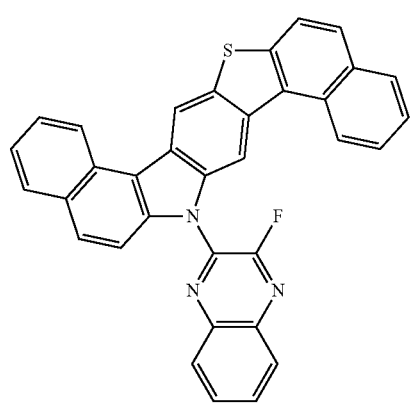
P2-118
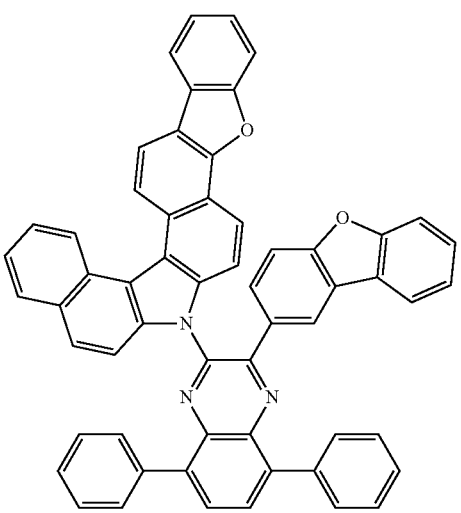

-continued
P2-119
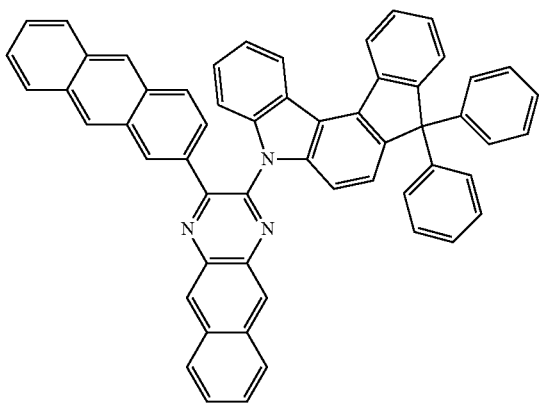
P2-120
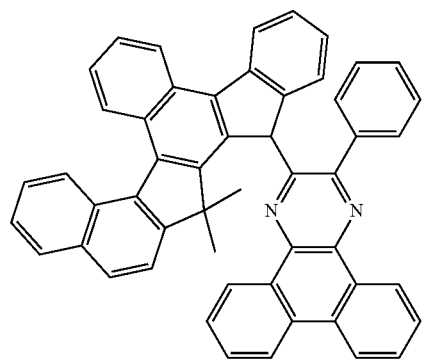
P2-121
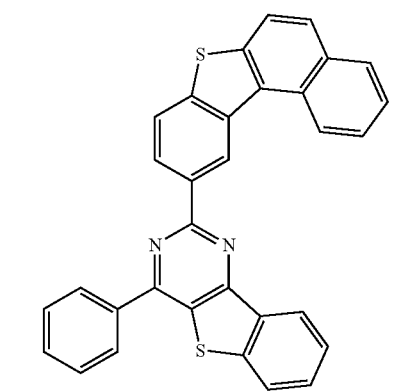
P2-122
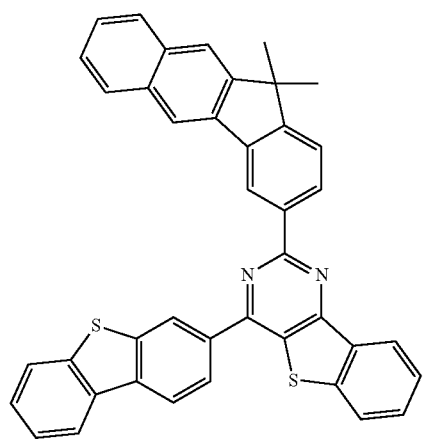
P2-123
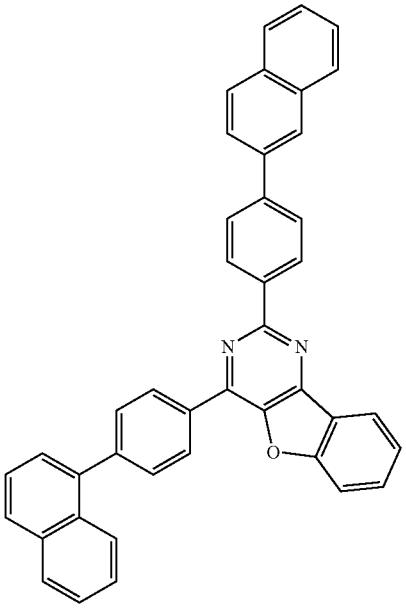
P2-124
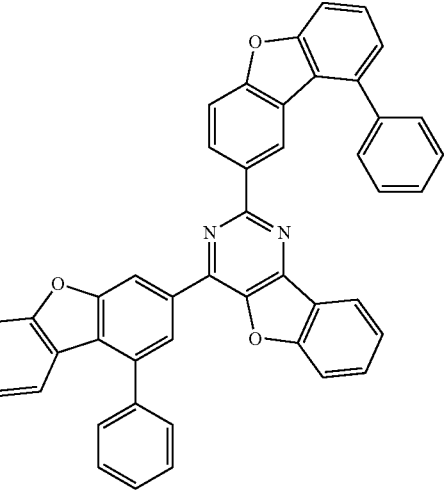
P2-125
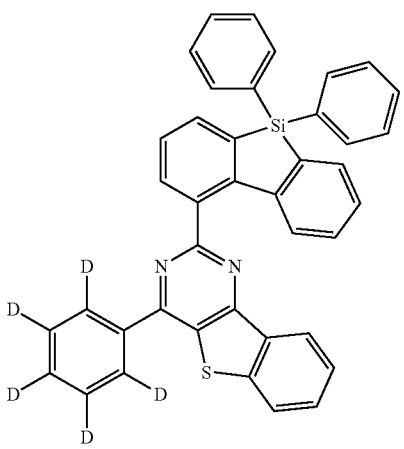

P2-126
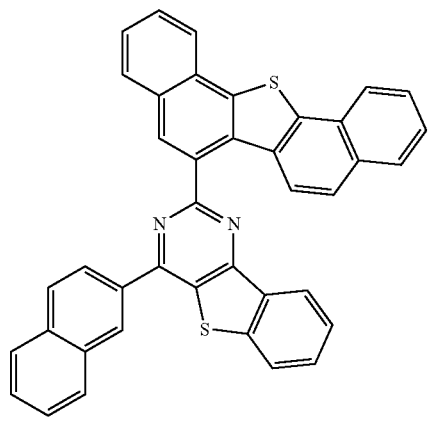
P2-129
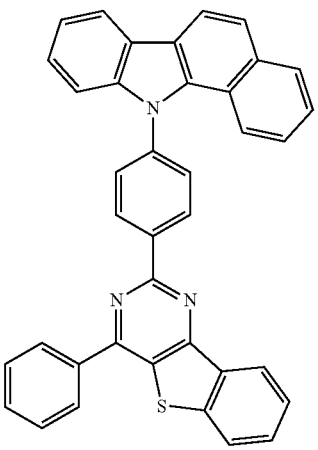
P2-127
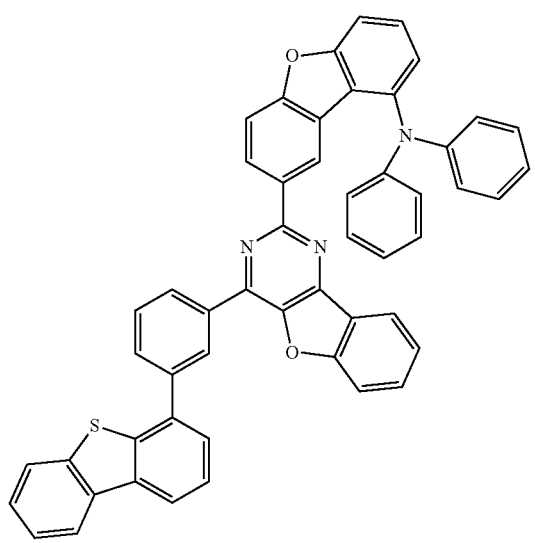
P2-130
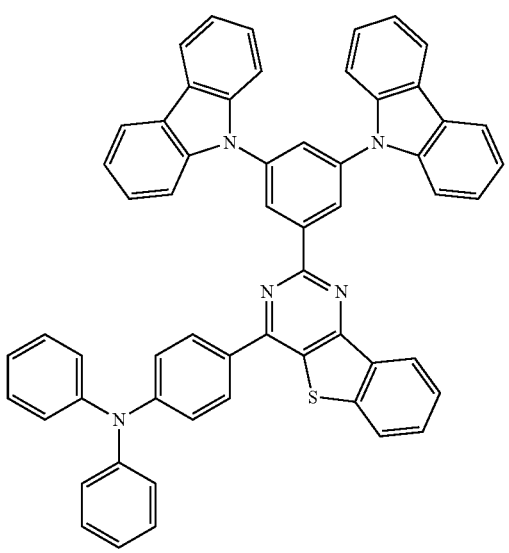
P2-128
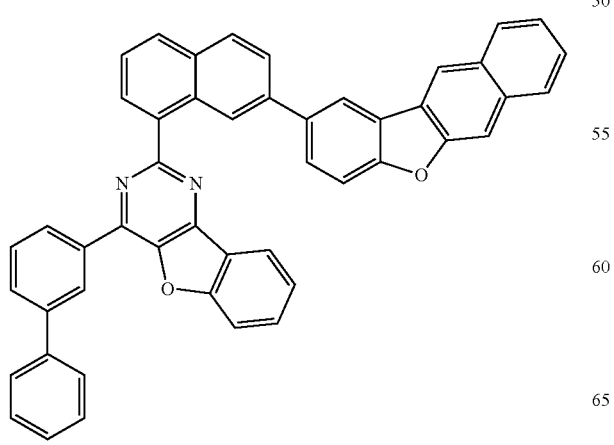
P2-131
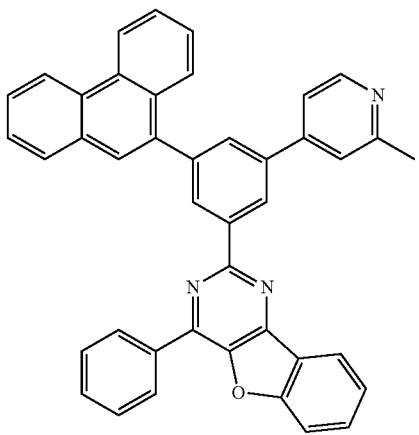

P2-132
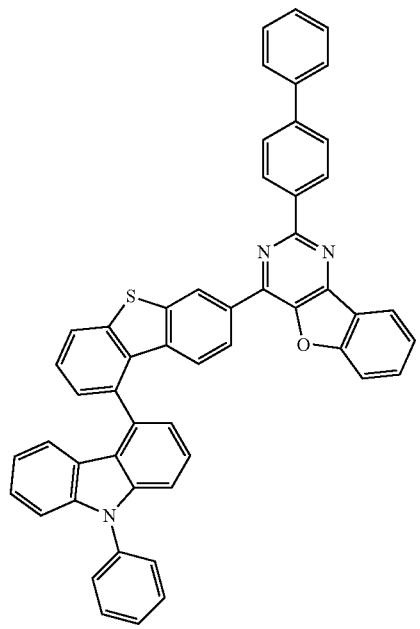
P2-133
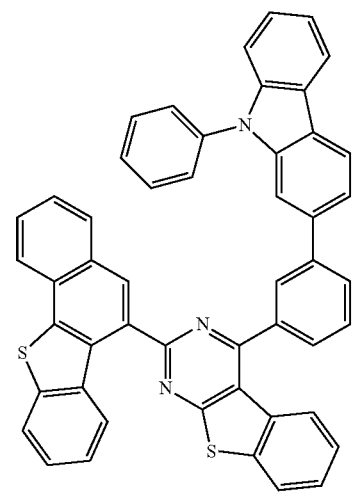
P2-134
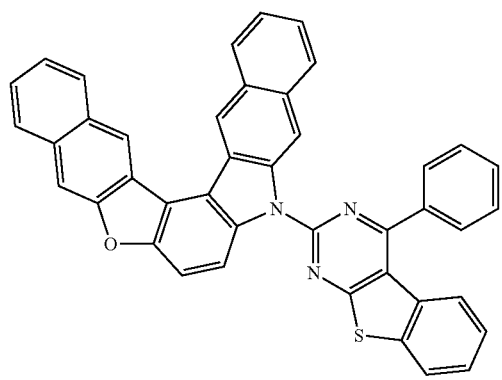
P2-135
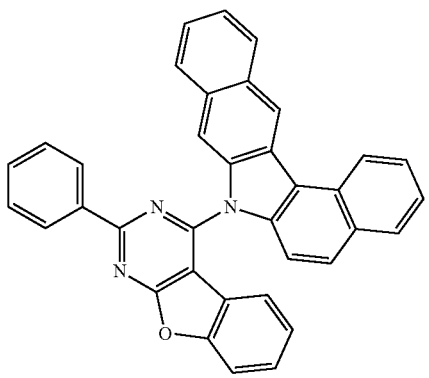
P2-136
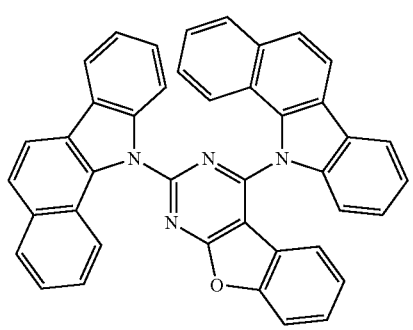
P2-137
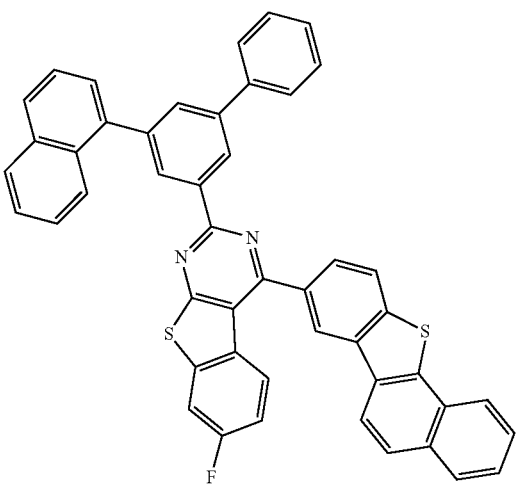
P2-138
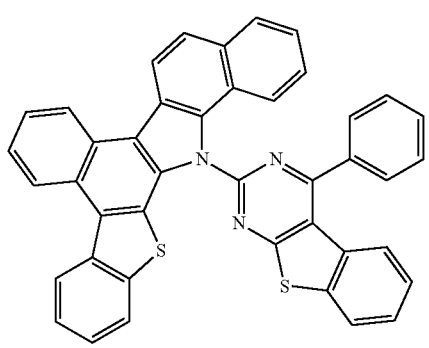

P2-139
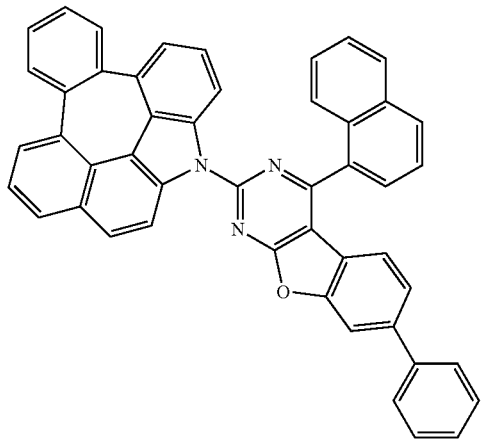
P2-140
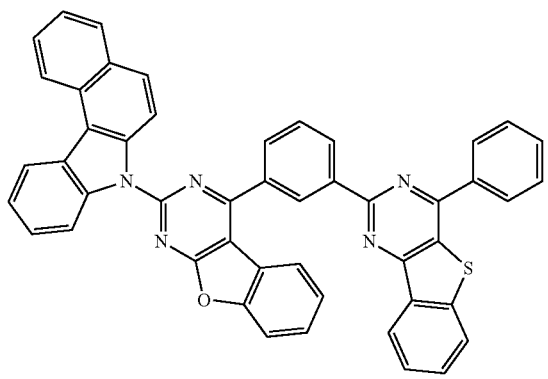
P2-141
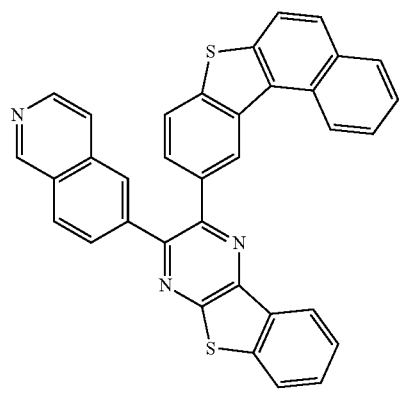
P2-142
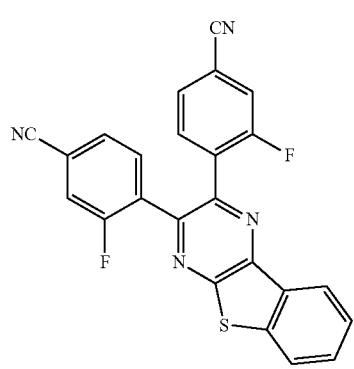
P2-143
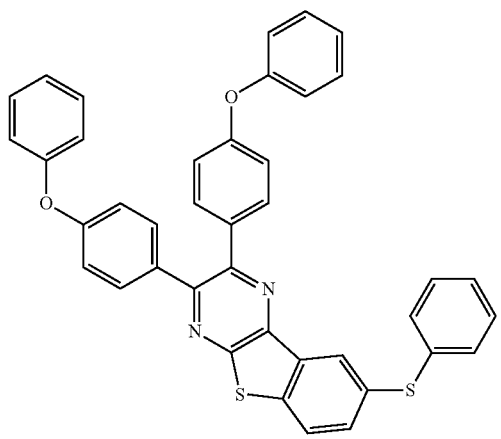
P2-144
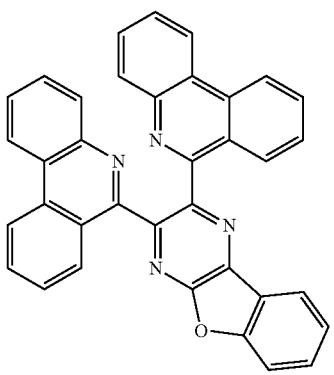
P2-145
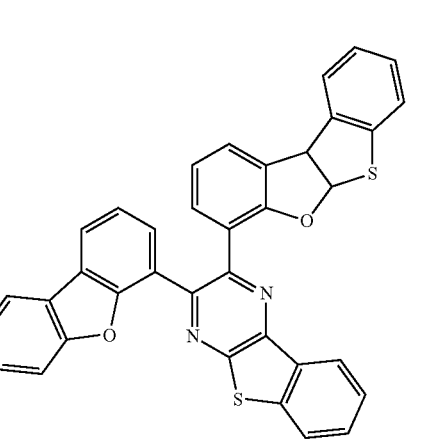

P2-146
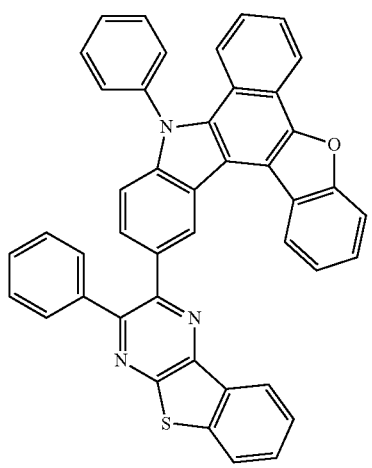
P2-147
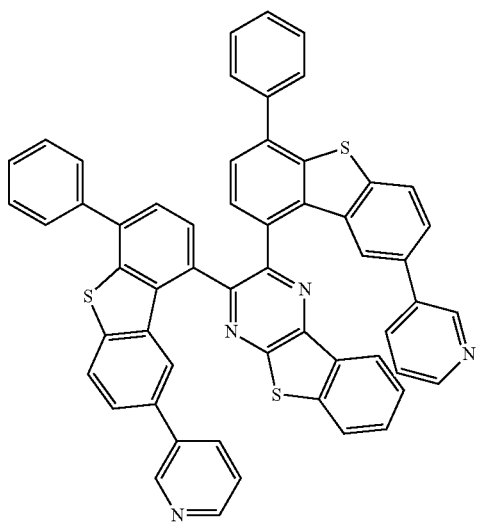
P2-148
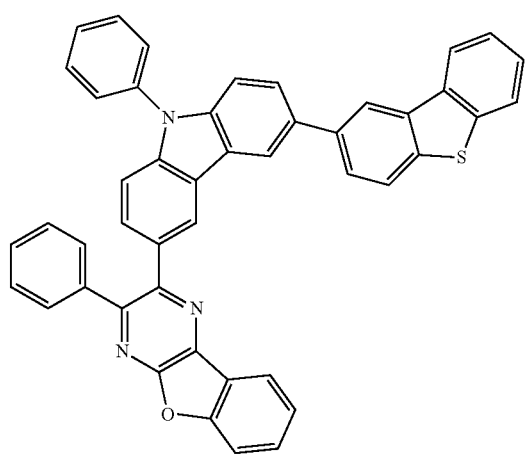
P2-149
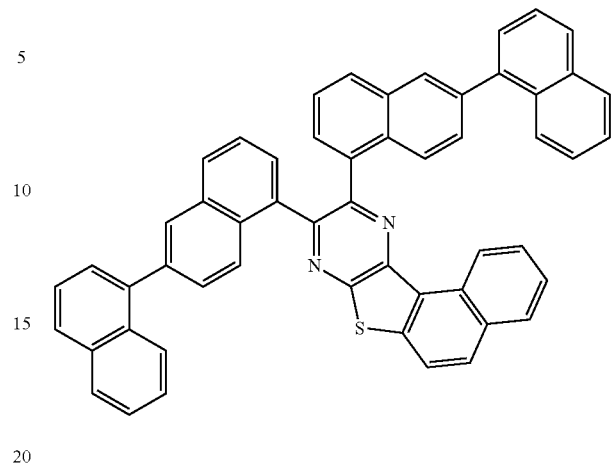
P2-150
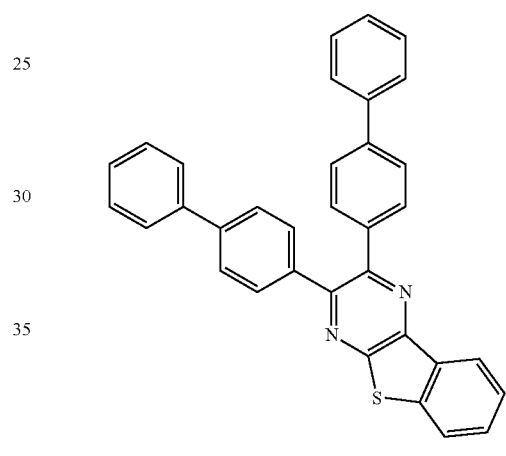
P2-151
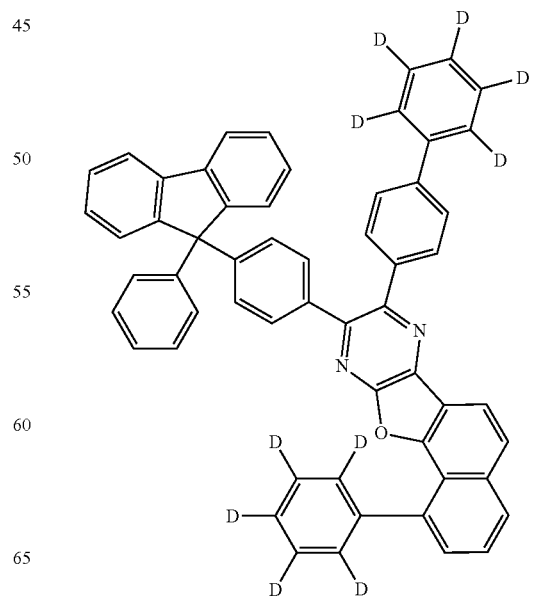

P2-152

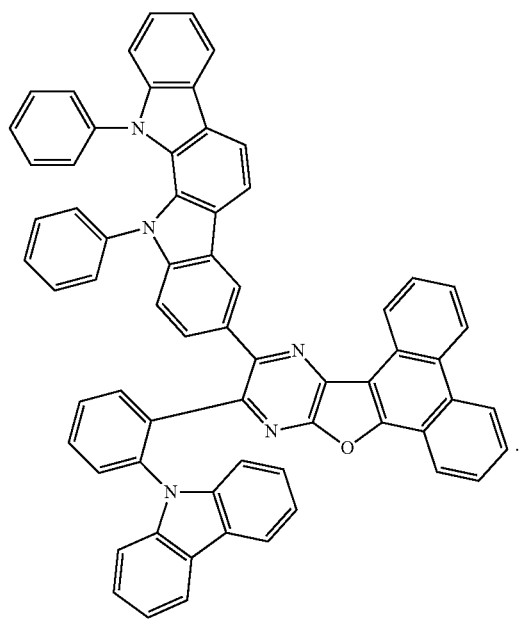

Hereinafter, synthesis example of the compound represented by Formula 1 and preparation method of an organic electric element according to the present invention will be described in detail by way of examples. However, the present invention is not limited to the following examples.

Synthesis Example

Synthesis of P-8

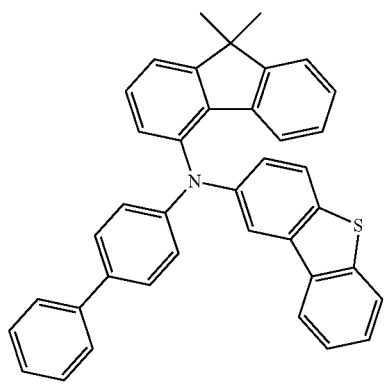

P-8

Sub 1-1 (20 g, 0.07 mol), Sub 2-1 (25.7 g, 0.07 mol), Pd$_2$(dba)$_3$ (2 g, 0.002 mol), P(t-Bu)$_3$ (1.8 g, 0.004 mol), NaOt-Bu (21.1 g, 0.22 mmol) and toluene (150 mL) were added in a round bottom flask and the mixture was stirred at 90° C. When the reaction was completed, the temperature of the reactant was cooled to room temperature, toluene was removed, and the remaining organic material was separated by a silica gel column and recrystallized to obtain 30 g (75.3%) of product P-8.

Synthesis of P-16

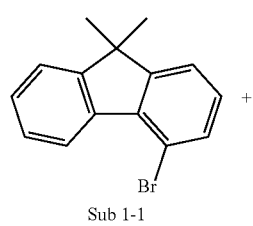

Sub 1-1

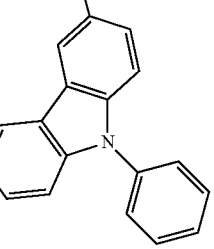

Sub 1-7

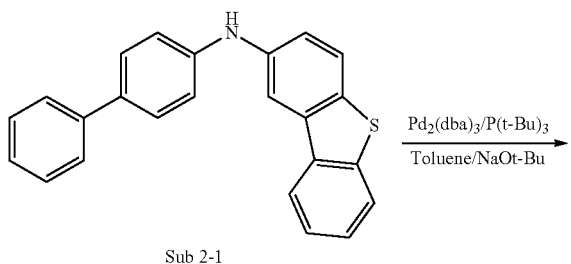

Sub 2-1

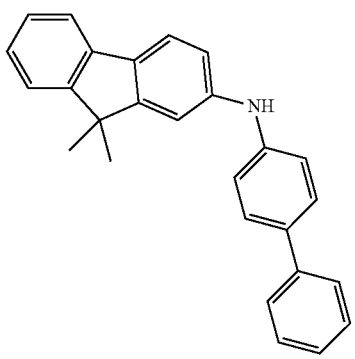

Sub 2-2

-continued

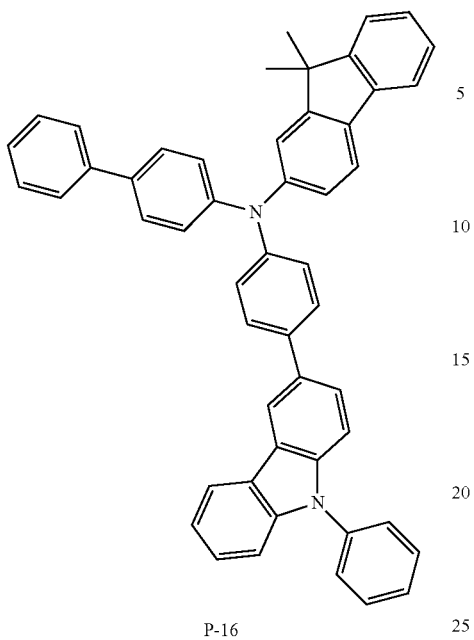

P-16

Sub 1-7 (20 g, 0.05 mol), Sub 2-2 (18.1 g, 0.05 mol), Pd$_2$(dba)$_3$ (1.4 g, 0.002 mol), P(t-Bu)$_3$ (1.2 g, 0.003 mol), NaOt-Bu (14.5 g, 0.15 mol) and toluene (100 mL) were added in a round bottom flask and the reaction was carried out in the same manner as in the synthesis method of P-8 to obtain 32 g (yield: 93.8%) of the product P-16.

Synthesis of P-28

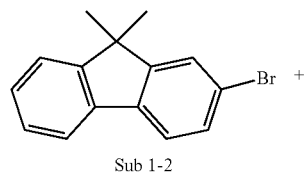

Sub 1-2

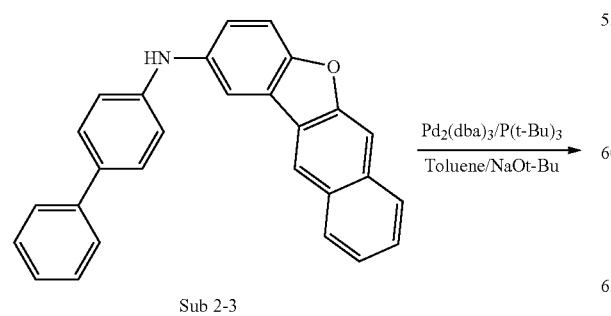

Sub 2-3

-continued

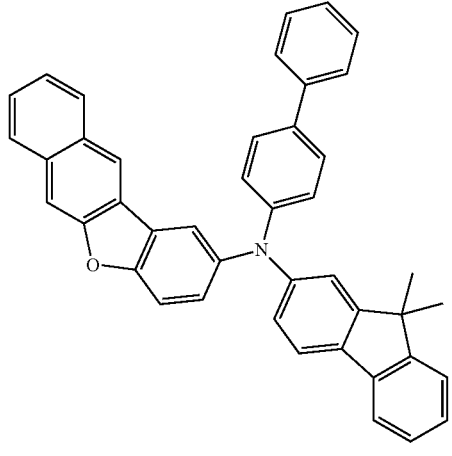

P-28

Sub 1-2 (30 g, 0.11 mol), Sub 2-3 (42.3 g, 0.11 mol), Pd$_2$(dba)$_3$ (3 g, 0.003 mol), P(t-Bu)$_3$ (2.7 g, 0.007 mol), NaOt-Bu (31.7 g, 0.33 mol) and toluene (220 mL) were added in a round bottom flask and the reaction was carried out in the same manner as in the synthesis method of P-28 to obtain 50 g (yield: 78.8%) of the product P-28.

Synthesis of P-42

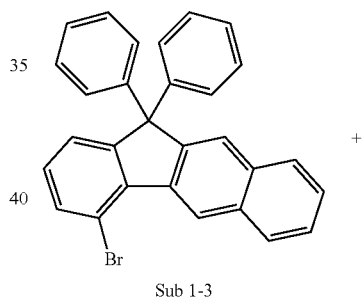

Sub 1-3

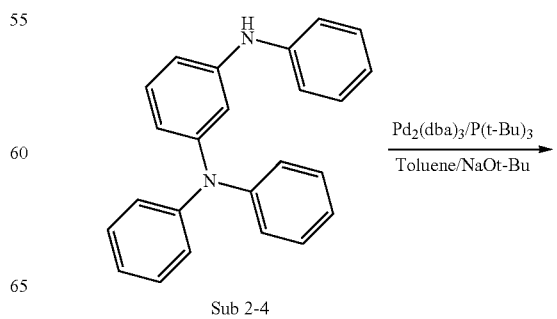

Sub 2-4

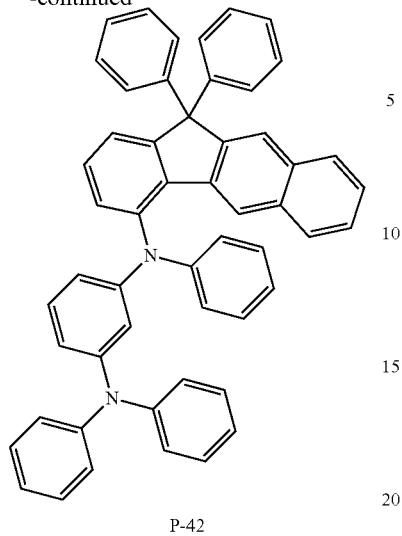

P-42

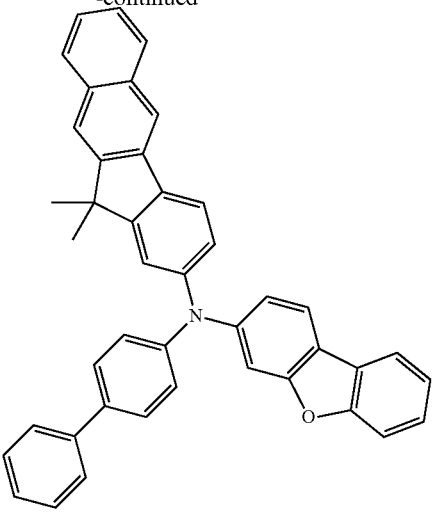

P-68

Sub 1-3 (15 g, 0.03 mol), Sub 2-4 (11.3 g, 0.03 mol), Pd$_2$(dba)$_3$ (0.9 g, 0.001 mol), P(t-Bu)$_3$ (0.8 g, 0.002 mol), NaOt-Bu (9.7 g, 0.1 mol) and toluene (80 mL) were added in a round bottom flask and the reaction was carried out in the same manner as in the synthesis method of P-8 to obtain 20 g (yield: 84.8%) of the product P-42.

Synthesis of P-68

Sub 1-4 (20 g, 0.06 mol), Sub 2-5 (20.7 g, 0.06 mol), Pd$_2$(dba)$_3$ (1.7 g, 0.002 mol), P(t-Bu)$_3$ (1.5 g, 0.004 mol), NaOt-Bu (17.9 g, 0.2 mol) and toluene (123 mL) were added in a round bottom flask and the reaction was carried out in the same manner as in the synthesis method of P-8 to obtain 31 g (yield: 86.8%) of the product P-68.

Synthesis of P-95

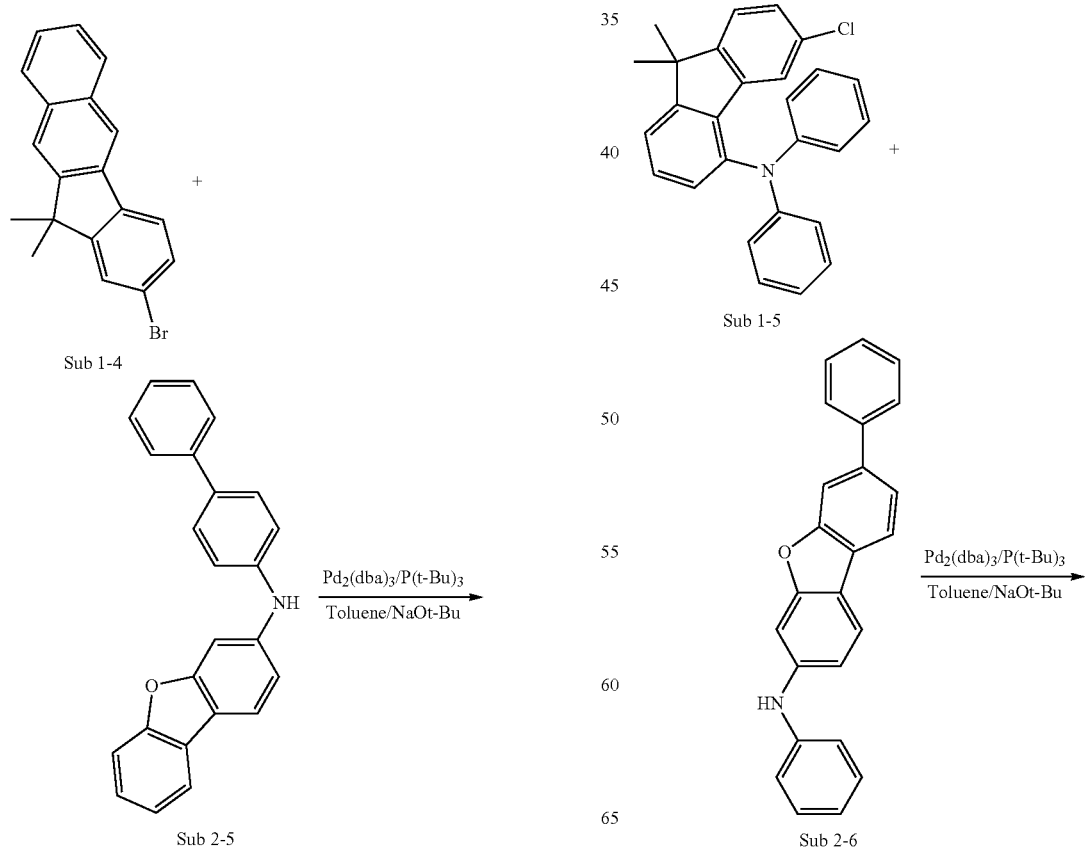

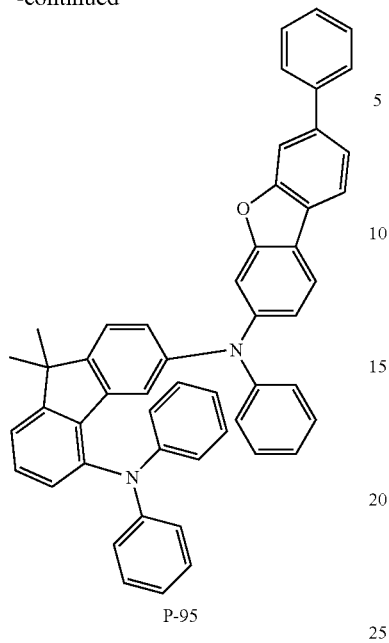

P-95

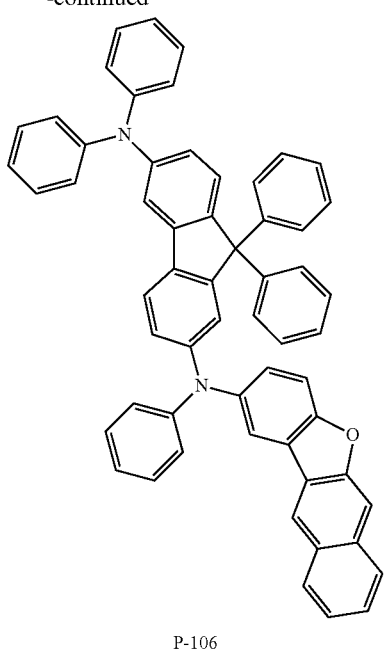

P-106

Sub 1-5 (20 g, 0.05 mol), Sub 2-6 (16.9 g, 0.05 mol), Pd$_2$(dba)$_3$ (1.4 g, 0.002 mol), P(t-Bu)$_3$ (1.2 g, 0.003 mol), NaOt-Bu (14.6 g, 0.2 mol) and toluene (101 mL) were added in a round bottom flask and the reaction was carried out in the same manner as in the synthesis method of P-8 to obtain 32 g (yield: 91.1%) of the product P-95.

Synthesis of P-106

Sub 1-6 (30 g, 0.06 mol), Sub 2-7 (17.8 g, 0.06 mol), Pd$_2$(dba)$_3$ (1.6 g, 0.002 mol), P(t-Bu)$_3$ (1.4 g, 0.004 mol), NaOt-Bu (16.6 g, 0.2 mol) and toluene (115 mL) were added in a round bottom flask and the reaction was carried out in the same manner as in the synthesis method of P-8 to obtain 40 g (yield: 87.4%) of the product P-106.

Synthesis of P-132

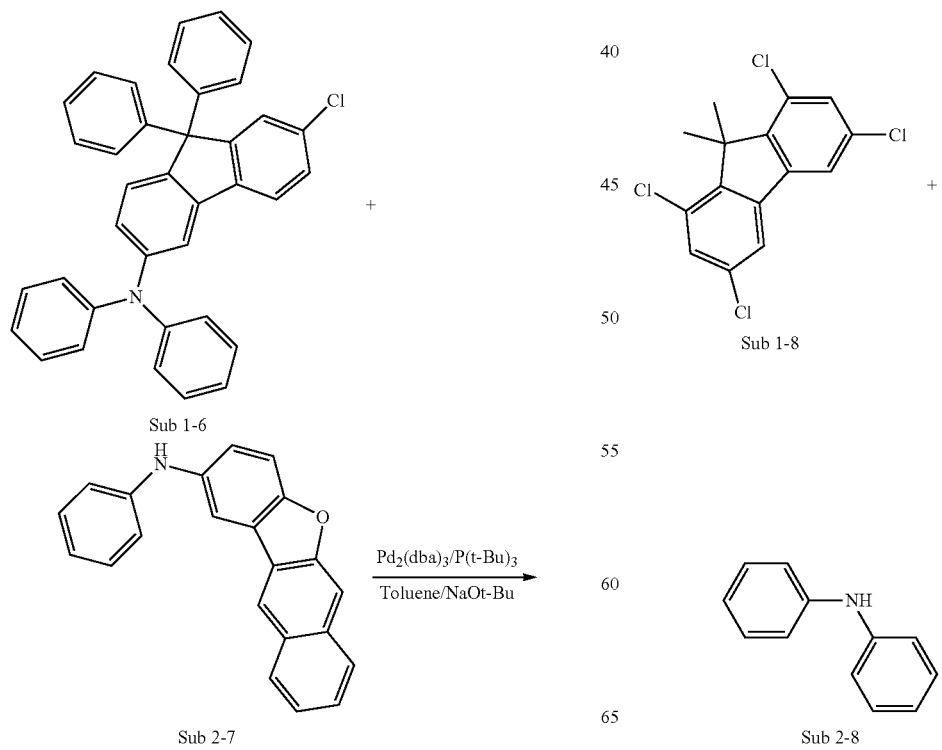

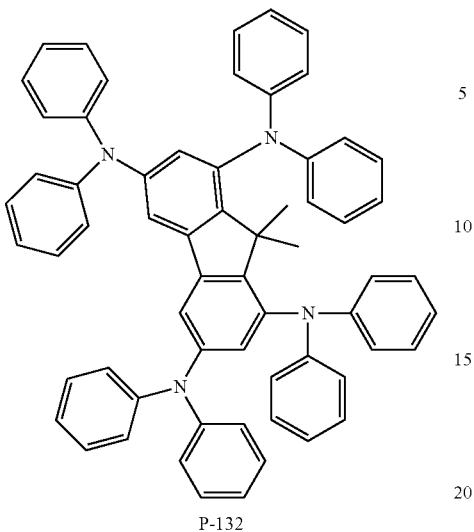

P-132

Sub 1-8 (30 g, 0.09 mol), Sub 2-8 (76.4 g, 0.45 mol), Pd$_2$(dba)$_3$ (2.5 g, 0.003 mol), P(t-Bu)$_3$ (2.2 g, 0.005 mol), NaOt-Bu (26.1 g, 0.27 mol) and toluene (181 mL) were added in a round bottom flask and the reaction was carried out in the same manner as in the synthesis method of P-8 to obtain 45 g (yield: 62.8%) of the product P-132.

Synthesis of P2-4

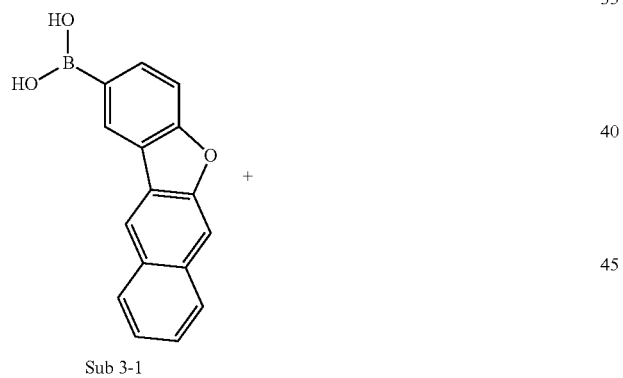

Sub 3-1

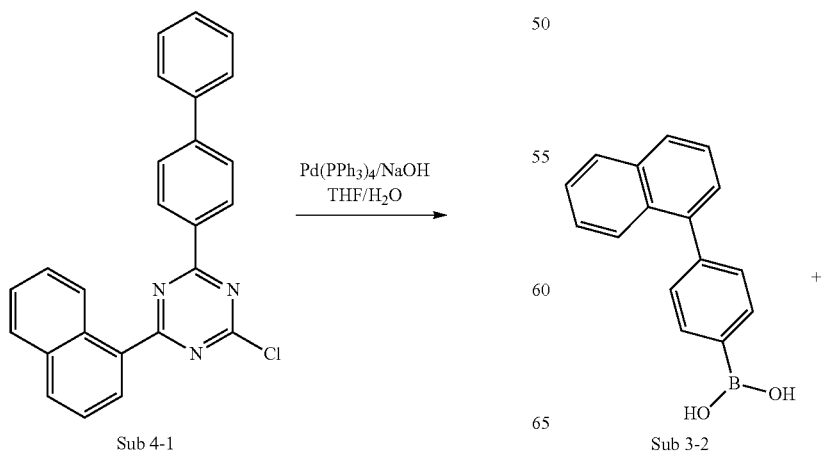

Sub 4-1

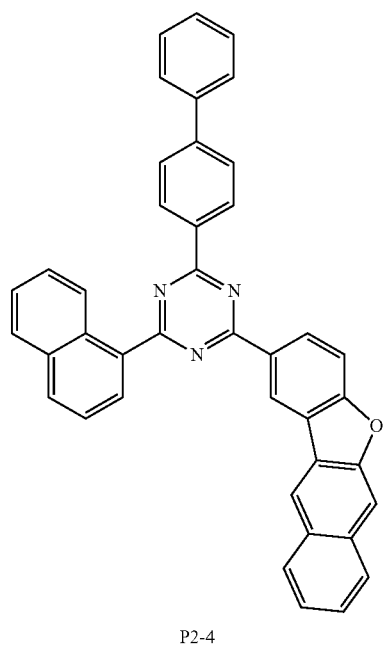

P2-4

Sub 3-1 (20 g, 0.08 mol), Sub 4-1 (30 g, 0.08 mol), Pd(PPh$_3$)$_4$ (2.6 g, 0.001 mol), NaOH (9.2 g, 0.23 mmol), THF (150 mL) and H$_2$O (50 mL) were added in a round bottom flask and stirred at 90° C. When the reaction was completed, the temperature of the reactant was cooled to room temperature, THF and water were removed, and the remaining organic material was separated by a silica gel column and recrystallized to obtain 30 g (68.2%) of product P2-4.

Synthesis of P2-5

Sub 3-2

-continued

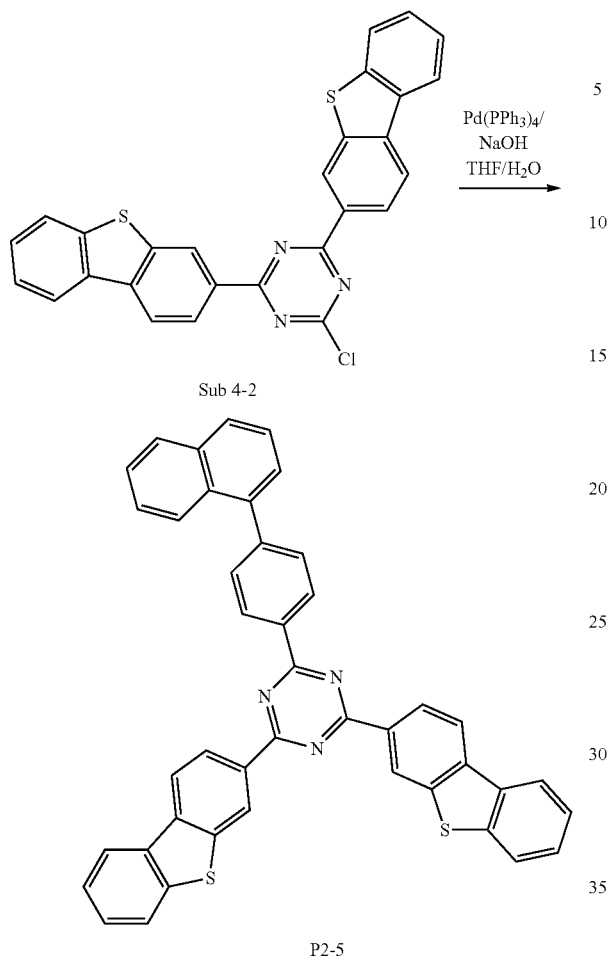

Sub 3-2 (20 g, 0.08 mol), Sub 4-2 (38.7 g, 0.08 mol), Pd(PPh₃)₄ (2.6 g, 0.001 mol), NaOH (9.2 g, 0.23 mmol), THF (161 mL) and H₂O (50 mL) were added in a round bottom flask and the reaction was carried out in the same manner as in the synthesis method of P2-4 to obtain 47 g (yield: 89.9%) of the product P2-5.

Synthesis of P2-26

-continued

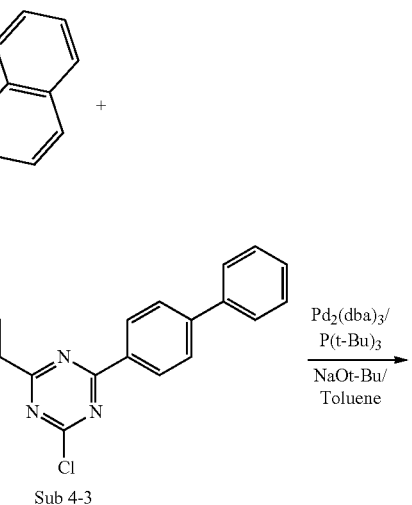

Sub 3-3 (35 g, 0.08 mol), Sub 4-1 (33.5 g, 0.08 mol), Pd(PPh₃)₄ (2.6 g, 0.001 mol), NaOH (10.2 g, 0.25 mmol), THF (170 mL) and H₂O (55 mL) were added in a round bottom flask and the reaction was carried out in the same manner as in the synthesis method of P2-4 to obtain 52 g (yield: 84.4%) of the product P2-26.

Synthesis of P2-28

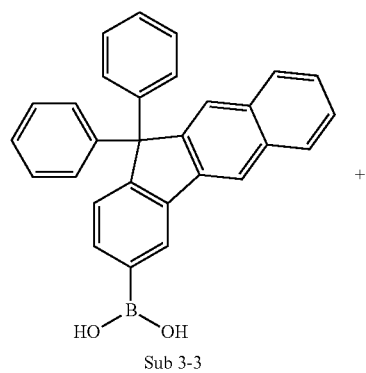

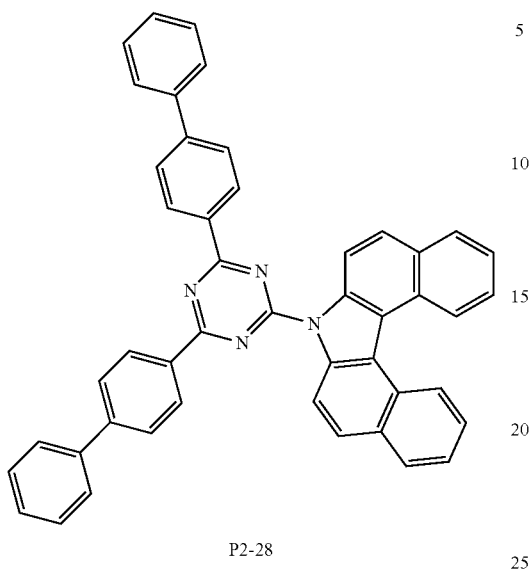

P2-28

Sub 3-4 (20 g, 0.07 mol), Sub 4-3 (31.5 g, 0.07 mol), Pd$_2$(dba)$_3$ (2.1 g, 0.002 mol), P(t-Bu)$_3$ (1.8 g, 0.005 mol), NaOt-Bu (21.6 g, 0.22 mol) and toluene (150 mL) were added in a round bottom flask and the reaction was carried out in the same manner as in the synthesis method of P-8 to obtain 43 g (yield: 88.2%) of the product P2-28.

Synthesis of P2-45

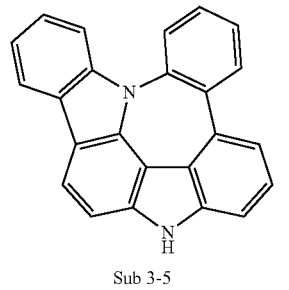

Sub 3-5

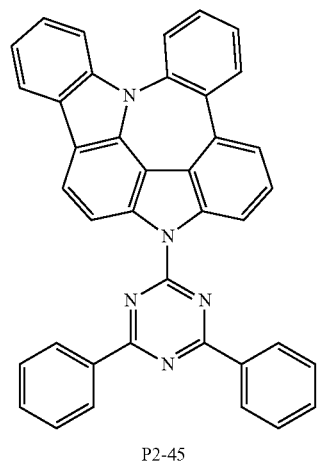

P2-45

Sub 3-5 (20 g, 0.06 mol), Sub 4-4 (16.2 g, 0.06 mol), Pd$_2$(dba)$_3$ (1.7 g, 0.002 mol), P(t-Bu)$_3$ (1.5 g, 0.004 mol), NaOt-Bu (17.5 g, 0.18 mol) and toluene (121 mL) were added in a round bottom flask and the reaction was carried out in the same manner as in the synthesis method of P-8 to obtain 30 g (yield: 88.2%) of the product P2-45.

Synthesis of P2-53

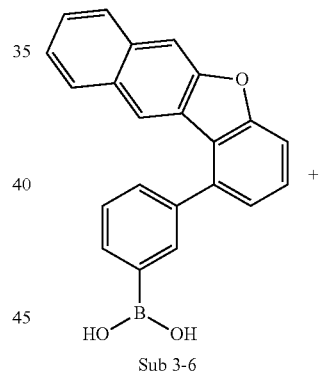

Sub 3-6

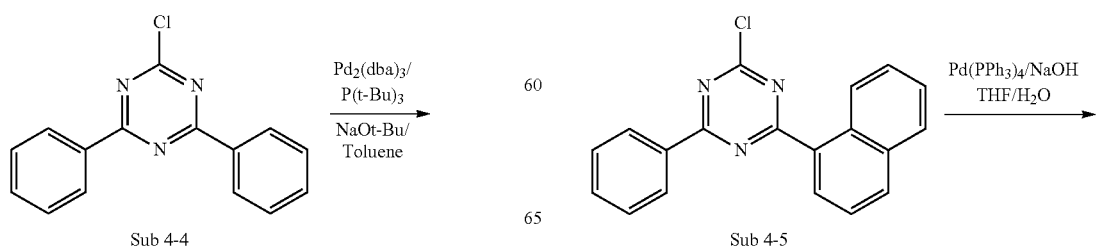

125

-continued

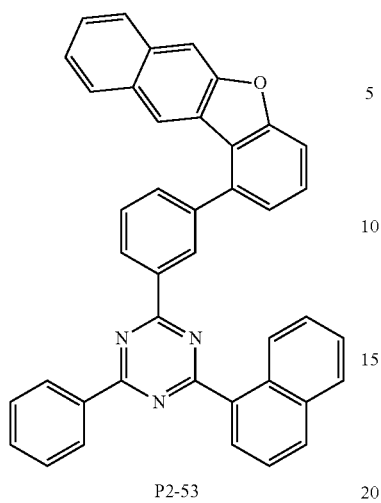

P2-53

Sub 3-6 (28 g, 0.08 mol), Sub 4-5 (26.3 g, 0.08 mol), Pd(PPh₃)₄ (2.9 g, 0.001 mol), NaOH (10 g, 0.25 mmol), THF (170 mL) and H₂O (55 mL) were added in a round bottom flask and the reaction was carried out in the same manner as in the synthesis method of P2-4 to obtain 40 g (yield: 83.9%) of the product P2-53.

Synthesis of P2-79

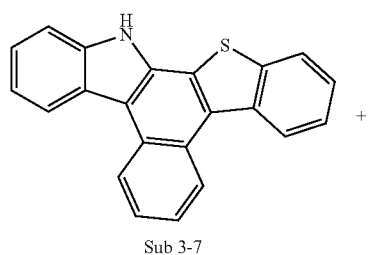

Sub 3-7

+

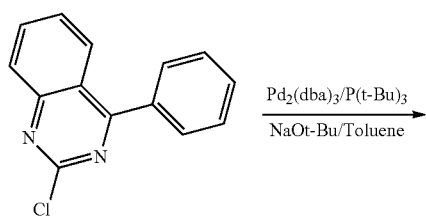

Sub 4-6

$\xrightarrow{\text{Pd}_2(\text{dba})_3/\text{P(t-Bu)}_3}{\text{NaOt-Bu/Toluene}}$

126

-continued

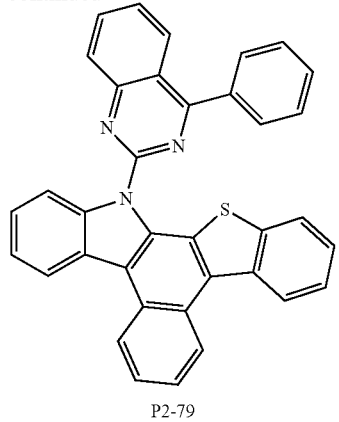

P2-79

Sub 3-7 (18 g, 0.06 mol), Sub 4-6 (13.4 g, 0.06 mol), Pd₂(dba)₃ (1.5 g, 0.002 mol), P(t-Bu)₃ (1.4 g, 0.004 mol), NaOt-Bu (16.1 g, 0.17 mol) and toluene (111 mL) were added in a round bottom flask and the reaction was carried out in the same manner as in the synthesis method of P-8 to obtain 24 g (yield: 81.7%) of the product P2-79.

Synthesis of P2-109

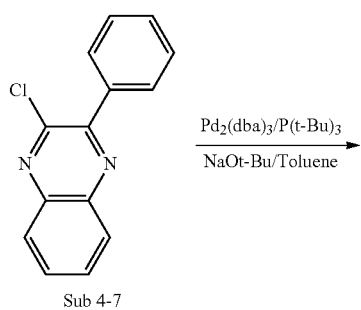

Sub 3-8

+

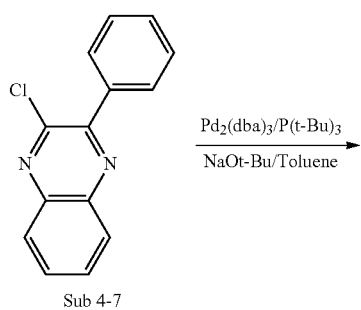

Sub 4-7

$\xrightarrow{\text{Pd}_2(\text{dba})_3/\text{P(t-Bu)}_3}{\text{NaOt-Bu/Toluene}}$ -continued

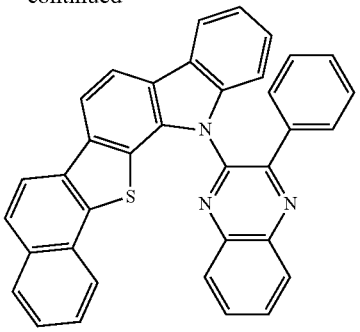

P2-109

Sub 3-8 (25 g, 0.08 mol), Sub 4-7 (18.7 g, 0.08 mol), Pd$_2$(dba)$_3$ (2.1 g, 0.002 mol), P(t-Bu)$_3$ (1.9 g, 0.005 mol), NaOt-Bu (22.3 g, 0.23 mol) and toluene (160 mL) were added in a round bottom flask and the reaction was carried out in the same manner as in the synthesis method of P-8 to obtain 34 g (yield: 83.4%) of the product P2-109.

Manufacturing and Evaluation of Organic Electric Element

[Test Example 1] to [Test Example 140] Red Organic Electric Element

A hole injection layer having a thickness of 60 nm was formed by vacuum-deposition of 4,4',4"-tris[2-naphthyl(phenyl)amino]triphenylamine (hereinafter, abbreviated as 2-TNATA) on an ITO layer (anode). Thereafter, as shown in Table 1 below, the compound represented by Formula 1 of the present invention was vacuum-deposited to a thickness of 60 nm to form a hole transport layer.

Next, as shown in Table 1 below, the compound represented by Formula 1 of the present invention was vacuum-deposited to a thickness of 30 nm to form an emission-auxiliary layer.

Thereafter, as shown in Table 1 below, a light emitting layer having a thickness of 30 nm was formed on the emission-auxiliary layer. As shown in Table 1 below, a mixture of the compound of Formula 1 (first host) of the present invention and the compound of Formula 12 or Formula 13 (second host) in a 3:7 ratio was used as a host, bis-(1-phenylisoquinolyl)iridium(III)acetylacetonate (hereinafter abbreviated as "(piq)$_2$Ir(acac)" was used as a dopant, and the dopant was doped so that the host and dopant were in a 95:5 weight ratio.

Next, (1,1'-biphenyl-4-olato)bis(2-methyl-8-quinolinolato)aluminum (hereinafter, abbreviated as BAlq) was vacuum-deposited to a thickness of 10 nm on the light emitting layer to form a hole blocking layer.

Subsequently, tris-(8-hydroxyquinoline)aluminum (hereinafter, abbreviated as "Alq$_3$") was vacuum-deposited to a thickness of 40 nm on the hole blocking layer to form an electron transport layer. Thereafter, LiF was deposited to a thickness of 0.2 nm to form an electron injection layer, and then Al was deposited to a thickness of 150 nm to form a cathode. In this way, an organic electric element was manufactured.

Comparative Example 1

As shown in Table 1 below, the organic electric element was manufactured in the same manner as described in Example 1 except that 4,4'-bis[N-(1-naphthyl)-N-phenylamino]biphenyl(hereinafter, abbreviated as "NPB") was used as material of a hole transport layer instead of the compound of the present invention, 4'-N,N'-dicarbazole-biphenyl (hereinafter, abbreviated as "CBP") was used as a host instead of the compound of the present invention, and an emission-auxiliary layer was not formed.

Comparative Example 2

As shown in Table 1 below, the organic electric element was manufactured in the same manner as described in Example 1 except that NPB was used as material of a hole transport layer instead of the compound of the present invention, CBP was used as a host instead of the compound of the present invention, and an emission-auxiliary layer was formed using compound P-8 of the present invention.

Comparative Example 3

As shown in Table 1 below, the organic electric element was manufactured in the same manner as described in Example 1 except that CBP was used as a host. Here, a hole transport layer was formed using compound P-14 of the present invention and an emission-auxiliary layer was formed using compound P-8 of the present invention.

Comparative Example 4

As shown in Table 1 below, the organic electric element was manufactured in the same manner as described in Example 1 except that NPB was used as material of a hole transport layer instead of the compound of the present invention. Here, n emission-auxiliary layer was formed using compound P-8 of the present invention and a mixture of compound P-7 and compound P2-51 was used as the host of a light emitting layer.

TABLE 1

| | Cpd of HTL | Cpd of EAL | Cpd of EML |
|---|---|---|---|
| Comparative Ex.(1) | NPB | — | CBP |
| Comparative Ex.(2) | NPB | P-8 | CBP |
| Comparative Ex.(3) | P-14 | P-8 | CBP |
| Comparative Ex.(4) | NPB | P-8 | P-7, P2-51 |
| Test Ex.(1) | P-16 | P-68 | P-68, P2-4 |
| Test Ex.(2) | | | P-14, P2-15 |
| Test Ex.(3) | | | P-23, P2-27 |
| Test Ex.(4) | | | P-10, P2-79 |
| Test Ex.(5) | | | P-33, P2-37 |
| Test Ex.(6) | | | P-101, P2-5 |
| Test Ex.(7) | | | P-124, P2-9 |
| Test Ex.(8) | | P-23 | P-68, P2-4 |
| Test Ex.(9) | | | P-14, P2-15 |
| Test Ex.(10) | | | P-23, P2-27 |
| Test Ex.(11) | | | P-10, P2-79 |
| Test Ex.(12) | | | P-33, P2-37 |
| Test Ex.(13) | | | P-101, P2-5 |
| Test Ex.(14) | | | P-124, P2-9 |
| Test Ex.(15) | | P-7 | P-68, P2-4 |
| Test Ex.(16) | | | P-14, P2-15 |
| Test Ex.(17) | | | P-23, P2-27 |
| Test Ex.(18) | | | P-10, P2-79 |
| Test Ex.(19) | | | P-33, P2-37 |
| Test Ex.(20) | | | P-101, P2-5 |
| Test Ex.(21) | | | P-124, P2-9 |
| Test Ex.(22) | | P-20 | P-68, P2-4 |
| Test Ex.(23) | | | P-14, P2-15 |
| Test Ex.(24) | | | P-23, P2-27 |
| Test Ex.(25) | | | P-10, P2-79 |
| Test Ex.(26) | | | P-33, P2-37 |
| Test Ex.(27) | | | P-101, P2-5 |
| Test Ex.(28) | | | P-124, P2-9 |
| Test Ex.(29) | | P-100 | P-68, P2-4 |

TABLE 1-continued

|  | Cpd of HTL | Cpd of EAL | Cpd of EML |
|---|---|---|---|
| Test Ex.(30) |  |  | P-14, P2-15 |
| Test Ex.(31) |  |  | P-23, P2-27 |
| Test Ex.(32) |  |  | P-10, P2-79 |
| Test Ex.(33) |  |  | P-33. P2-37 |
| Test Ex.(34) |  |  | P-101, P2-5 |
| Test Ex.(35) |  |  | P-124, P2-9 |
| Test Ex.(36) | P-20 | P-14 | P-68, P2-4 |
| Test Ex.(37) |  |  | P-14, P2-15 |
| Test Ex.(38) |  |  | P-23, P2-27 |
| Test Ex.(39) |  |  | P-10, P2-79 |
| Test Ex.(40) |  |  | P-33. P2-37 |
| Test Ex.(41) |  |  | P-101, P2-5 |
| Test Ex.(42) |  |  | P-124, P2-9 |
| Test Ex.(43) |  | P-75 | P-68, P2-4 |
| Test Ex.(44) |  |  | P-14, P2-15 |
| Test Ex.(45) |  |  | P-23, P2-27 |
| Test Ex.(46) |  |  | P-10, P2-79 |
| Test Ex.(47) |  |  | P-33. P2-37 |
| Test Ex.(48) |  |  | P-101, P2-5 |
| Test Ex.(49) |  |  | P-124, P2-9 |
| Test Ex.(50) |  | P-16 | P-68, P2-4 |
| Test Ex.(51) |  |  | P-14, P2-15 |
| Test Ex.(52) |  |  | P-23, P2-27 |
| Test Ex.(53) |  |  | P-10, P2-79 |
| Test Ex.(54) |  |  | P-33. P2-37 |
| Test Ex.(55) |  |  | P-101, P2-5 |
| Test Ex.(56) |  |  | P-124, P2-9 |
| Test Ex.(57) |  | P-98 | P-68, P2-4 |
| Test Ex.(58) |  |  | P-14, P2-15 |
| Test Ex.(59) |  |  | P-23, P2-27 |
| Test Ex.(60) |  |  | P-10, P2-79 |
| Test Ex.(61) |  |  | P-33. P2-37 |
| Test Ex.(62) |  |  | P-101, P2-5 |
| Test Ex.(63) |  |  | P-124, P2-9 |
| Test Ex.(64) |  | P-104 | P-68, P2-4 |
| Test Ex.(65) |  |  | P-14, P2-15 |
| Test Ex.(66) |  |  | P-23, P2-27 |
| Test Ex.(67) |  |  | P-10, P2-79 |
| Test Ex.(68) |  |  | P-33. P2-37 |
| Test Ex.(69) |  |  | P-101, P2-5 |
| Test Ex.(70) |  |  | P-124, p2-9 |
| Test Ex.(71) | P-43 | P-28 | P-68, P2-4 |
| Test Ex.(72) |  |  | P-14, P2-15 |
| Test Ex.(73) |  |  | P-23, P2-27 |
| Test Ex.(74) |  |  | P-10, P2-79 |
| Test Ex.(75) |  |  | P-33. P2-37 |
| Test Ex.(76) |  |  | P-101, P2-5 |
| Test Ex.(77) |  |  | P-124, P2-9 |
| Test Ex.(78) |  | P-8 | P-68, P2-4 |
| Test Ex.(79) |  |  | P-14, P2-15 |
| Test Ex.(80) |  |  | P-23, P2-27 |
| Test Ex.(81) |  |  | P-10, P2-79 |
| Test Ex.(82) |  |  | P-33. P2-37 |
| Test Ex.(83) |  |  | P-101, P2-5 |
| Test Ex.(84) |  |  | P-124, P2-9 |
| Test Ex.(85) |  | P-19 | P-68, P2-4 |
| Test Ex.(86) |  |  | P-14, P2-15 |
| Test Ex.(87) |  |  | P-23, P2-27 |
| Test Ex.(88) |  |  | P-10, P2-79 |
| Test Ex.(89) |  |  | P-33. P2-37 |
| Test Ex.(90) |  |  | P-101, P2-5 |
| Test Ex.(91) |  |  | P-124, P2-9 |
| Test Ex.(92) |  | P-85 | P-68, P2-4 |
| Test Ex.(93) |  |  | P-14, P2-15 |
| Test Ex.(94) |  |  | P-23, P2-27 |
| Test Ex.(95) |  |  | P-10, P2-79 |
| Test Ex.(96) |  |  | P-33. P2-37 |
| Test Ex.(97) |  |  | P-101, P2-5 |
| Test Ex.(98) |  |  | P-124, P2-9 |
| Test Ex.(99) |  | P-130 | P-68, P2-4 |
| Test Ex.(100) |  |  | P-14, P2-15 |
| Test Ex.(101) |  |  | P-23, P2-27 |
| Test Ex(102) |  |  | P-10, P2-79 |
| Test Ex.(103) |  |  | P-33. P2-37 |
| Test Ex.(104) |  |  | P-101, P2-5 |
| Test Ex.(105) |  |  | P-124, P2-9 |
| Test Ex.(106) | P-90 | P-43 | P-68, P2-4 |
| Test Ex.(107) |  |  | P-14, P2-15 |
| Test Ex.(108) |  |  | P-23, P2-27 |
| Test Ex.(109) |  |  | P-10, P2-79 |
| Test Ex.(110) |  |  | P-33. P2-37 |
| Test Ex.(111) |  |  | P-101, P2-5 |
| Test Ex.(112) |  |  | P-124, P2-9 |
| Test Ex.(113) |  | P-9 | P-68, P2-4 |
| Test Ex.(114) |  |  | P-14, P2-15 |
| Test Ex.(115) |  |  | P-23, P2-27 |
| Test Ex.(116) |  |  | P-10, P2-79 |
| Test Ex.(117) |  |  | P-33. P2-37 |
| Test Ex.(118) |  |  | P-101, P2-5 |
| Test Ex.(119) |  |  | P-124, P2-9 |
| Test Ex.(120) |  | P-106 | P-68, P2-4 |
| Test Ex.(121) |  |  | P-14, P2-15 |
| Test Ex.(122) |  |  | P-23, P2-27 |
| Test Ex.(123) |  |  | P-10, P2-79 |
| Test Ex.(124) |  |  | P-33. P2-37 |
| Test Ex.(125) |  |  | P-101, P2-5 |
| Test Ex.(126) |  |  | P-124, P2-9 |
| Test Ex.(127) |  | P-120 | P-68, P2-4 |
| Test Ex.(128) |  |  | P-14, P2-15 |
| Test Ex.(129) |  |  | P-23, P2-27 |
| Test Ex.(130) |  |  | P-10, P2-79 |
| Test Ex.(131) |  |  | P-33. P2-37 |
| Test Ex.(132) |  |  | P-101, P2-5 |
| Test Ex.(133) |  |  | P-124, P2-9 |
| Test Ex.(134) |  | P-123 | P-68, P2-4 |
| Test Ex.(135) |  |  | P-14, P2-15 |
| Test Ex.(136) |  |  | P-23, P2-27 |
| Test Ex.(137) |  |  | P-10, P2-79 |
| Test Ex.(138) |  |  | P-33. P2-37 |
| Test Ex.(139) |  |  | P-101, P2-5 |
| Test Ex.(140) |  |  | P-124, P2-9 |

Electroluminescence characteristics were measured with a PR-650 from Photo research company by applying a forward bias DC voltage to the organic electric elements manufactured in Test Examples 1 to 140 of the present invention and Comparative Examples 1 to 4. T(95) life time was measured using a life time measuring apparatus manufactured by Mc science Inc. at reference brightness of 2500 cd/m$^2$. The results of measurement are shown in the table 2 below.

TABLE 2

|  | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|
| Comp.Ex(1) | 6.0 | 32.9 | 2500.0 | 7.6 | 62.1 | 0.64 | 0.34 |
| Comp.Ex(2) | 6.1 | 24.5 | 2500.0 | 10.2 | 90.4 | 0.64 | 0.34 |
| Comp.Ex(3) | 5.8 | 18.7 | 2500.0 | 13.4 | 97.8 | 0.64 | 0.32 |
| Comp.Ex(4) | 5.7 | 16.4 | 2500.0 | 15.2 | 95.4 | 0.63 | 0.32 |
| Test Ex.(1) | 4.7 | 8.3 | 2500.0 | 30.0 | 120.0 | 0.64 | 0.32 |
| Test Ex.(2) | 4.8 | 8.4 | 2500.0 | 29.7 | 119.4 | 0.61 | 0.34 |
| Test Ex.(3) | 4.8 | 8.5 | 2500.0 | 29.3 | 118.8 | 0.63 | 0.31 |
| Test Ex.(4) | 4.8 | 8.6 | 2500.0 | 29.0 | 118.2 | 0.61 | 0.31 |
| Test Ex.(5) | 4.9 | 8.7 | 2500.0 | 28.7 | 117.6 | 0.60 | 0.32 |
| Test Ex.(6) | 4.9 | 8.8 | 2500.0 | 28.3 | 117.0 | 0.60 | 0.35 |
| Test Ex.(7) | 4.7 | 8.9 | 2500.0 | 28.0 | 116.3 | 0.62 | 0.33 |
| Test Ex.(8) | 4.8 | 8.4 | 2500.0 | 29.6 | 119.3 | 0.64 | 0.34 |
| Test Ex.(9) | 4.8 | 8.5 | 2500.0 | 29.3 | 118.7 | 0.63 | 0.33 |
| Test Ex.(10) | 4.8 | 8.6 | 2500.0 | 28.9 | 118.0 | 0.65 | 0.30 |
| Test Ex.(11) | 4.9 | 8.7 | 2500.0 | 28.6 | 117.4 | 0.62 | 0.34 |
| Test Ex.(12) | 4.9 | 8.8 | 2500.0 | 28.3 | 116.8 | 0.63 | 0.31 |
| Test Ex.(13) | 4.9 | 8.9 | 2500.0 | 27.9 | 116.2 | 0.63 | 0.32 |
| Test Ex.(14) | 4.7 | 9.1 | 2500.0 | 27.6 | 115.6 | 0.64 | 0.33 |
| Test Ex.(15) | 4.8 | 8.6 | 2500.0 | 29.2 | 118.5 | 0.64 | 0.32 |
| Test Ex.(16) | 4.8 | 8.7 | 2500.0 | 28.9 | 117.9 | 0.61 | 0.34 |
| Test Ex.(17) | 4.9 | 8.8 | 2500.0 | 28.5 | 117.3 | 0.64 | 0.32 |
| Test Ex.(18) | 4.9 | 8.9 | 2500.0 | 28.2 | 116.7 | 0.63 | 0.31 |
| Test Ex.(19) | 4.9 | 9.0 | 2500.0 | 27.9 | 116.1 | 0.60 | 0.34 |
| Test Ex.(20) | 5.0 | 9.1 | 2500.0 | 27.5 | 115.5 | 0.63 | 0.34 |

TABLE 2-continued

| | Voltage (V) | Current Density (mA/cm²) | Brightness (cd/m²) | Efficiency (cd/A) | Lifetime T(95) | CIE x | CIE y |
|---|---|---|---|---|---|---|---|
| Test Ex.(21) | 4.8 | 9.2 | 2500.0 | 27.2 | 114.9 | 0.60 | 0.35 |
| Test Ex.(22) | 4.9 | 8.7 | 2500.0 | 28.8 | 117.8 | 0.65 | 0.32 |
| Test Ex.(23) | 4.9 | 8.8 | 2500.0 | 28.5 | 117.2 | 0.63 | 0.31 |
| Test Ex.(24) | 4.9 | 8.9 | 2500.0 | 28.1 | 116.6 | 0.61 | 0.33 |
| Test Ex.(25) | 4.9 | 9.0 | 2500.0 | 27.8 | 116.0 | 0.65 | 0.33 |
| Test Ex.(26) | 5.0 | 9.1 | 2500.0 | 27.5 | 115.4 | 0.60 | 0.31 |
| Test Ex.(27) | 5.0 | 9.2 | 2500.0 | 27.1 | 114.8 | 0.64 | 0.33 |
| Test Ex.(28) | 4.8 | 9.3 | 2500.0 | 26.8 | 114.1 | 0.61 | 0.34 |
| Test Ex.(29) | 5.1 | 8.8 | 2500.0 | 28.4 | 117.1 | 0.62 | 0.33 |
| Test Ex.(30) | 5.1 | 8.9 | 2500.0 | 28.1 | 116.5 | 0.64 | 0.31 |
| Test Ex.(31) | 5.2 | 9.0 | 2500.0 | 27.7 | 115.8 | 0.63 | 0.34 |
| Test Ex.(32) | 5.2 | 9.1 | 2500.0 | 27.4 | 115.2 | 0.61 | 0.32 |
| Test Ex.(33) | 5.2 | 9.2 | 2500.0 | 27.1 | 114.6 | 0.64 | 0.33 |
| Test Ex.(34) | 5.2 | 9.4 | 2500.0 | 26.7 | 114.0 | 0.65 | 0.33 |
| Test Ex.(35) | 5.1 | 9.5 | 2500.0 | 26.4 | 113.4 | 0.62 | 0.35 |
| Test Ex.(36) | 4.9 | 8.8 | 2500.0 | 28.5 | 117.0 | 0.62 | 0.31 |
| Test Ex.(37) | 4.9 | 8.9 | 2500.0 | 28.1 | 116.4 | 0.64 | 0.32 |
| Test Ex.(38) | 4.9 | 9.0 | 2500.0 | 27.8 | 115.7 | 0.61 | 0.32 |
| Test Ex.(39) | 5.0 | 9.1 | 2500.0 | 27.5 | 115.1 | 0.60 | 0.33 |
| Test Ex.(40) | 5.0 | 9.2 | 2500.0 | 27.1 | 114.5 | 0.63 | 0.31 |
| Test Ex.(41) | 5.0 | 9.3 | 2500.0 | 26.8 | 113.9 | 0.63 | 0.30 |
| Test Ex.(42) | 4.9 | 9.4 | 2500.0 | 26.5 | 113.3 | 0.65 | 0.35 |
| Test Ex.(43) | 4.9 | 8.9 | 2500.0 | 28.1 | 116.2 | 0.62 | 0.34 |
| Test Ex.(44) | 5.0 | 9.0 | 2500.0 | 27.7 | 115.6 | 0.63 | 0.35 |
| Test Ex.(45) | 5.0 | 9.1 | 2500.0 | 27.4 | 115.0 | 0.61 | 0.31 |
| Test Ex.(46) | 5.0 | 9.2 | 2500.0 | 27.1 | 114.4 | 0.65 | 0.34 |
| Test Ex.(47) | 5.0 | 9.4 | 2500.0 | 26.7 | 113.8 | 0.64 | 0.31 |
| Test Ex.(48) | 5.1 | 9.5 | 2500.0 | 26.4 | 113.2 | 0.61 | 0.32 |
| Test Ex.(49) | 4.9 | 9.6 | 2500.0 | 26.1 | 112.6 | 0.65 | 0.34 |
| Test Ex.(50) | 5.0 | 12.1 | 2500.0 | 20.7 | 115.5 | 0.61 | 0.32 |
| Test Ex.(51) | 5.0 | 12.3 | 2500.0 | 20.4 | 114.9 | 0.63 | 0.33 |
| Test Ex.(52) | 5.0 | 12.5 | 2500.0 | 20.0 | 114.3 | 0.63 | 0.32 |
| Test Ex.(53) | 5.1 | 12.7 | 2500.0 | 19.7 | 113.7 | 0.62 | 0.31 |
| Test Ex.(54) | 5.1 | 12.9 | 2500.0 | 19.4 | 113.1 | 0.64 | 0.30 |
| Test Ex.(55) | 5.1 | 13.1 | 2500.0 | 19.0 | 112.5 | 0.64 | 0.33 |
| Test Ex.(56) | 4.9 | 13.4 | 2500.0 | 18.7 | 111.8 | 0.61 | 0.32 |
| Test Ex.(57) | 5.0 | 9.2 | 2500.0 | 27.3 | 114.8 | 0.64 | 0.33 |
| Test Ex.(58) | 5.0 | 9.3 | 2500.0 | 26.9 | 114.2 | 0.64 | 0.34 |
| Test Ex.(59) | 5.1 | 9.4 | 2500.0 | 26.6 | 113.5 | 0.61 | 0.34 |
| Test Ex.(60) | 5.1 | 9.5 | 2500.0 | 26.3 | 112.9 | 0.61 | 0.30 |
| Test Ex.(61) | 5.1 | 9.6 | 2500.0 | 25.9 | 112.3 | 0.63 | 0.31 |
| Test Ex.(62) | 5.2 | 9.8 | 2500.0 | 25.6 | 111.7 | 0.62 | 0.35 |
| Test Ex.(63) | 5.0 | 9.9 | 2500.0 | 25.3 | 111.1 | 0.63 | 0.33 |
| Test Ex.(64) | 5.0 | 9.3 | 2500.0 | 26.9 | 114.0 | 0.62 | 0.35 |
| Test Ex.(65) | 5.1 | 9.4 | 2500.0 | 26.5 | 113.4 | 0.64 | 0.33 |
| Test Ex.(66) | 5.1 | 9.5 | 2500.0 | 26.2 | 112.8 | 0.63 | 0.33 |
| Test Ex.(67) | 5.1 | 9.7 | 2500.0 | 25.9 | 112.2 | 0.60 | 0.33 |
| Test Ex.(68) | 5.2 | 9.8 | 2500.0 | 25.5 | 111.6 | 0.64. | 0.34. |
| Test Ex.(69) | 5.2 | 9.9 | 2500.0 | 25.2 | 111.0 | 0.61 | 0.35 |
| Test Ex.(70) | 5.0 | 10.1 | 2500.0 | 24.9 | 110.4 | 0.63 | 0.31 |
| Test Ex.(71) | 4.8 | 8.6 | 2500.0 | 29.2 | 118.2 | 0.60 | 0.30 |
| Test Ex.(72) | 4.8 | 8.7 | 2500.0 | 28.9 | 117.5 | 0.64 | 0.33 |
| Test Ex.(73) | 4.9 | 8.8 | 2500.0 | 28.6 | 116.9 | 0.62 | 0.35 |
| Test Ex.(74) | 4.9 | 8.9 | 2500.0 | 28.2 | 116.3 | 0.62 | 0.31 |
| Test Ex.(75) | 4.9 | 9.0 | 2500.0 | 27.9 | 115.7 | 0.62 | 0.33 |
| Test Ex.(76) | 5.0 | 9.1 | 2500.0 | 27.6 | 115.1 | 0.65 | 0.35 |
| Test Ex.(77) | 4.8 | 9.2 | 2500.0 | 27.2 | 114.5 | 0.62 | 0.30 |
| Test Ex.(78) | 4.8 | 8.7 | 2500.0 | 28.8 | 117.4 | 0.61 | 0.31 |
| Test Ex.(79) | 4.9 | 8.8 | 2500.0 | 28.5 | 116.8 | 0.62 | 0.35 |
| Test Ex.(80) | 4.9 | 8.9 | 2500.0 | 28.2 | 116.2 | 0.63 | 0.34 |
| Test Ex.(81) | 4.9 | 9.0 | 2500.0 | 27.8 | 115.6 | 0.61 | 0.32 |
| Test Ex.(82) | 5.0 | 9.1 | 2500.0 | 27.5 | 115.0 | 0.62 | 0.33 |
| Test Ex.(83) | 5.0 | 9.2 | 2500.0 | 27.2 | 114.4 | 0.63 | 0.33 |
| Test Ex.(84) | 4.8 | 9.3 | 2500.0 | 26.8 | 113.8 | 0.63 | 0.33 |
| Test Ex.(85) | 4.9 | 8.8 | 2500.0 | 28.4 | 116.7 | 0.63 | 0.31 |
| Test Ex.(86) | 4.9 | 8.9 | 2500.0 | 28.1 | 116.1 | 0.62 | 0.34 |
| Test Ex.(87) | 4.9 | 9.0 | 2500.0 | 27.8 | 115.5 | 0.65 | 0.33 |
| Test Ex.(88) | 5.0 | 9.1 | 2500.0 | 27.4 | 114.9 | 0.61 | 0.33 |
| Test Ex.(89) | 5.0 | 9.2 | 2500.0 | 27.1 | 114.2 | 0.64 | 0.34 |
| Test Ex.(90) | 5.0 | 9.3 | 2500.0 | 26.8 | 113.6 | 0.60 | 0.31 |
| Test Ex.(91) | 4.9 | 9.5 | 2500.0 | 26.4 | 113.0 | 0.60 | 0.32 |
| Test Ex.(92) | 4.9 | 8.9 | 2500.0 | 28.0 | 116.0 | 0.65 | 0.32 |
| Test Ex.(93) | 5.0 | 9.0 | 2500.0 | 27.7 | 115.3 | 0.62 | 0.33 |
| Test Ex.(94) | 5.0 | 9.1 | 2500.0 | 27.4 | 114.7 | 0.63 | 0.33 |
| Test Ex.(95) | 5.0 | 9.2 | 2500.0 | 27.0 | 114.1 | 0.63 | 0.33 |
| Test Ex.(96) | 5.0 | 9.4 | 2500.0 | 26.7 | 113.5 | 0.65 | 0.35 |
| Test Ex.(97) | 5.1 | 9.5 | 2500.0 | 26.4 | 112.9 | 0.65 | 0.34 |
| Test Ex.(98) | 4.9 | 9.6 | 2500.0 | 26.0 | 112.3 | 0.63 | 0.31 |
| Test Ex.(99) | 5.0 | 9.0 | 2500.0 | 27.6 | 115.2 | 0.64 | 0.31 |
| Test Ex.(100) | 5.0 | 9.2 | 2500.0 | 27.3 | 114.6 | 0.61 | 0.34 |
| Test Ex.(101) | 5.0 | 9.3 | 2500.0 | 27.0 | 114.0 | 0.61 | 0.33 |
| Test Ex.(102) | 5.1 | 9.4 | 2500.0 | 26.6 | 113.4 | 0.64 | 0.32 |
| Test Ex.(103) | 5.1 | 9.5 | 2500.0 | 26.3 | 112.8 | 0.65 | 0.32 |
| Test Ex.(104) | 5.1 | 9.6 | 2500.0 | 26.0 | 112.2 | 0.65 | 0.34 |
| Test Ex.(105) | 4.9 | 9.8 | 2500.0 | 25.6 | 111.6 | 0.61 | 0.30 |
| Test Ex.(106) | 5.0 | 9.0 | 2500.0 | 27.7 | 115.8 | 0.64 | 0.31 |
| Test Ex.(107) | 5.0 | 9.1 | 2500.0 | 27.4 | 115.2 | 0.62 | 0.31 |
| Test Ex.(108) | 5.0 | 9.2 | 2500.0 | 27.0 | 114.6 | 0.65 | 0.34 |
| Test Ex.(109) | 5.1 | 9.4 | 2500.0 | 26.7 | 114.0 | 0.63 | 0.32 |
| Test Ex.(110) | 5.1 | 9.5 | 2500.0 | 26.4 | 113.3 | 0.61 | 0.30 |
| Test Ex.(111) | 5.1 | 9.6 | 2500.0 | 26.0 | 112.7 | 0.61 | 0.32 |
| Test Ex.(112) | 4.9 | 9.7 | 2500.0 | 25.7 | 112.1 | 0.64 | 0.32 |
| Test Ex.(113) | 5.0 | 9.2 | 2500.0 | 27.3 | 115.1 | 0.64 | 0.30 |
| Test Ex.(114) | 5.0 | 9.3 | 2500.0 | 27.0 | 114.4 | 0.61 | 0.33 |
| Test Ex.(115) | 5.1 | 9.4 | 2500.0 | 26.6 | 113.8 | 0.61 | 0.32 |
| Test Ex.(116) | 5.1 | 9.5 | 2500.0 | 26.3 | 113.2 | 0.63 | 0.35 |
| Test Ex.(117) | 5.1 | 9.6 | 2500.0 | 26.0 | 112.6 | 0.60 | 0.34 |
| Test Ex.(118) | 5.2 | 9.8 | 2500.0 | 25.6 | 112.0 | 0.61 | 0.33 |
| Test Ex.(119) | 5.0 | 9.9 | 2500.0 | 25.3 | 111.4 | 0.63 | 0.31 |
| Test Ex.(120) | 5.0 | 9.3 | 2500.0 | 26.9 | 114.3 | 0.65 | 0.31 |
| Test Ex.(121) | 5.1 | 9.4 | 2500.0 | 26.6 | 113.7 | 0.62 | 0.31 |
| Test Ex.(122) | 5.1 | 9.5 | 2500.0 | 26.2 | 113.1 | 0.63 | 0.30 |
| Test Ex.(123) | 5.1 | 9.7 | 2500.0 | 25.9 | 112.5 | 0.61 | 0.33 |
| Test Ex.(124) | 5.2 | 9.8 | 2500.0 | 25.6 | 111.9 | 0.63 | 0.35 |
| Test Ex.(125) | 5.2 | 9.9 | 2500.0 | 25.2 | 111.3 | 0.60 | 0.33 |
| Test Ex.(126) | 5.0 | 10.0 | 2500.0 | 24.9 | 110.7 | 0.65 | 0.32 |
| Test Ex.(127) | 5.1 | 9.4 | 2500.0 | 26.5 | 113.6 | 0.62 | 0.33 |
| Test Ex.(128) | 5.1 | 9.6 | 2500.0 | 26.2 | 113.0 | 0.64 | 0.32 |
| Test Ex.(129) | 5.1 | 9.7 | 2500.0 | 25.8 | 112.4 | 0.63 | 0.31 |
| Test Ex.(130) | 5.2 | 9.8 | 2500.0 | 25.5 | 111.8 | 0.63 | 0.31 |
| Test Ex.(131) | 5.2 | 9.9 | 2500.0 | 25.2 | 111.1 | 0.63 | 0.32 |
| Test Ex.(132) | 5.2 | 10.1 | 2500.0 | 24.8 | 110.5 | 0.63 | 0.31 |
| Test Ex.(133) | 5.1 | 10.2 | 2500.0 | 24.5 | 109.9 | 0.64 | 0.30 |
| Test Ex.(134) | 5.1 | 9.6 | 2500.0 | 26.1 | 112.9 | 0.61 | 0.34 |
| Test Ex.(135) | 5.2 | 9.7 | 2500.0 | 25.8 | 112.2 | 0.64 | 0.31 |
| Test Ex.(136) | 5.2 | 9.8 | 2500.0 | 25.4 | 111.6 | 0.64 | 0.33 |
| Test Ex.(137) | 5.2 | 10.0 | 2500.0 | 25.1 | 111.0 | 0.60 | 0.32 |
| Test Ex.(138) | 5.2 | 10.1 | 2500.0 | 24.8 | 110.4 | 0.62 | 0.34 |
| Test Ex.(139) | 5.3 | 10.2 | 2500.0 | 24.4 | 109.8 | 0.64 | 0.32 |
| Test Ex.(140) | 5.1 | 10.4 | 2500.0 | 24.1 | 109.2 | 0.63 | 0.33 |

As can be seen from the results of Table 2, the case where each of the hole transport layer, the light emitting auxiliary layer, and the light emitting layer compared compound of Formula 1, the driving voltage can be significantly lowered, and the luminous efficiency and lifespan are significantly improved, compared to the case where one or two layers of these comprises compound of Formula 1, or the case where these layers do not comprise the compound of Formula 1.

Specifically, the driving voltage, efficiency and life time are remarkably improved in Comparative Examples 2 to 4 using compound represented by Formula 1 of the present invention as an emission-auxiliary layer rather than Comparative Example 1 using NPB as a hole transport compound and CBP as compound of a light emitting layer. In addition, the driving voltage, efficiency and life time are improved in Comparative Examples 3 and 4 using compound of the present invention represented by Formula 1 in two layers rather than in Comparative Example 2 using the compound in one layer.

It seems that this is because the compound represented by Formula 1 is always used in three layers, and their combination electrochemically synergizes to improve the overall performance of the element, such as charge balance. Moreover, since the light emitting layer according to an embodiment of the present invention includes a mixture, electrons and holes move and energy is transferred not only along the energy level of each material, but also a new region(exciplex) having a new energy level formed by mixing. As a result, it seems that efficiency and lifetime are further improved, compared to the case where a single compound is used.

Although the exemplary embodiments of the present invention have been described for illustrative purposes, those skilled in the art to which the present invention pertains will be capable of various modifications without departing from the essential characteristics of the present invention. Therefore, the embodiment disclosed herein is intended to illustrate the scope of the technical idea of the present invention, and the spirit and scope of the present invention are not limited by the embodiments. The scope of the present invention shall be construed on the basis of the accompanying claims, and it shall be construed that all of the technical ideas included within the scope equivalent to the claims belong to the present invention.

What is claimed is:

1. An organic electric element comprising:
   an anode;
   a cathode; and
   an organic material layer formed between the anode and the cathode, the organic material layer comprising:
     a light emitting layer;
     a hole transport layer formed between the light emitting layer and the anode; and
     an emission-auxiliary layer formed between the hole transport layer and the light emitting layer,
     wherein the hole transport layer, the emission-auxiliary layer and the light emitting layer comprise a compound of Formula 1, respectively:

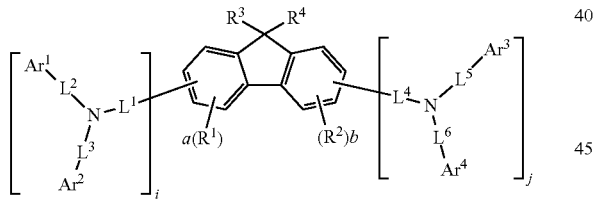

[Formula 1]

wherein:
   $R^1$ and $R^2$ are each independently selected from the group consisting of hydrogen, deuterium, halogen, a cyano group, a nitro group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a $C_1$-$C_{30}$ alkyl group, a $C_2$-$C_{30}$ alkenyl group, a $C_2$-$C_{30}$ alkynyl group, a $C_1$-$C_{30}$ alkoxyl group, a $C_6$-$C_{30}$ aryloxy group and a $C_6$-$C_{30}$ arylthio group, and adjacent groups may be bonded to each other to form a ring,
   a and b are each an integer of 0 to 4, and when each of these is an integer of 2 or more, a plurality of $R^1$s are each the same as or different from each other and a plurality of $R^2$s are each the same as or different from each other,
   $R^3$ and $R^4$ are each independently selected from the group consisting of hydrogen, deuterium, halogen, a cyano group, a nitro group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a $C_1$-$C_{30}$ alkyl group, a $C_2$-$C_{30}$ alkenyl group, a $C_2$-$C_{30}$ alkynyl group, a $C_1$-$C_{30}$ alkoxyl group, a $C_6$-$C_{30}$ aryloxy group and -L'-N($R_a$)($R_b$), and $R^3$ and $R^4$ may be bonded to each other to form a ring,
   $Ar^1$ to $Ar^4$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, and a $C_3$-$C_{60}$ aliphatic ring,
   $L^1$ to $L^6$ are each independently selected from the group consisting of a single bond, a $C_6$-$C_{60}$ arylene group, a fluorenylene group, a $C_3$-$C_{60}$ aliphatic ring, and a $C_2$-$C_{60}$ heterocyclic group comprising at least one heteroatom selected from the group consisting of O, N, S, Si and P,
   i and j are each an integer of 0 to 2, and when both i and j are 0, one of $R^3$ and $R^4$ contain -L'-N($R_a$)($R_b$), with a proviso that i+j is an integer greater than or equal to 1 for the compound of Formula 1 included in the light emitting layer,
   when i is an integer of 2, a plurality of $Ar^1$s, a plurality of $Ar^2$s, a plurality of $L^1$s, a plurality of $L^2$s, a plurality of $L^3$s are the same as or different from each other,
   when j is an integer of 2, a plurality of $Ar^3$s, a plurality of $Ar^4$s, a plurality of $L^4$s, a plurality of $L^5$s, a plurality of $L^6$s are the same as or different from each other,
   L' is selected from the group consisting of a single bond, a $C_6$-$C_{60}$ arylene group, a fluorenylene group, a $C_3$-$C_{60}$ aliphatic ring, and a $C_2$-$C_{60}$ heterocyclic group comprising at least one heteroatom selected from the group consisting of O, N, S, Si and P,
   $R_a$ and $R_b$ are each independently selected from the group consisting of a $C_6$-$C_{60}$ aryl group, a fluorenyl group, a $C_3$-$C_{60}$ aliphatic ring, and a $C_2$-$C_{60}$ heterocyclic group comprising at least one heteroatom selected from the group consisting of O, N, S, Si and P, and
   $R^1$ to $R^4$, $Ar^1$ to $Ar^4$, $L^1$ to $L^6$, L', $R_a$, $R_b$, the ring formed by adjacent groups or by $R^3$ and $R^4$ may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ aliphatic ring group, a $C_7$-$C_{20}$ arylalkyl group, $C_8$-$C_{20}$ arylalkenyl group and -L'-N($R_a$)($R_b$).

2. The organic electric element of claim 1, wherein Formula 1 is represented by one of Formula 2 to Formula 6:

<Formula 2>

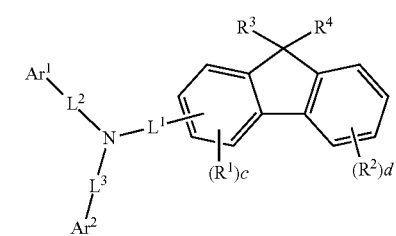

<Formula 3>

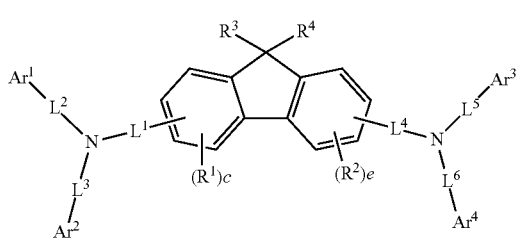

<Formula 4>

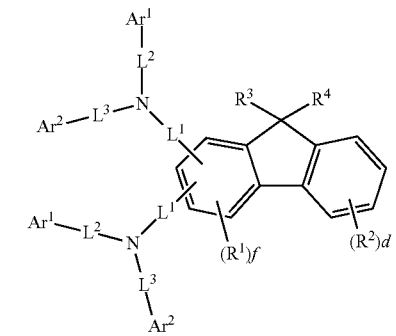

<Formula 5>

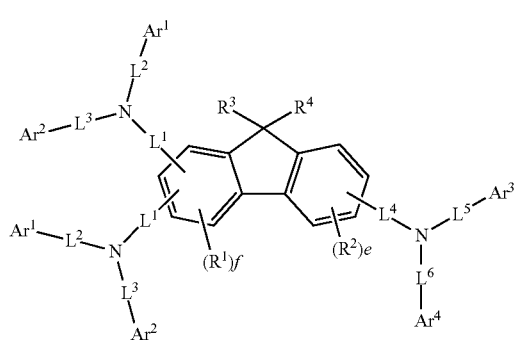

<Formula 6>

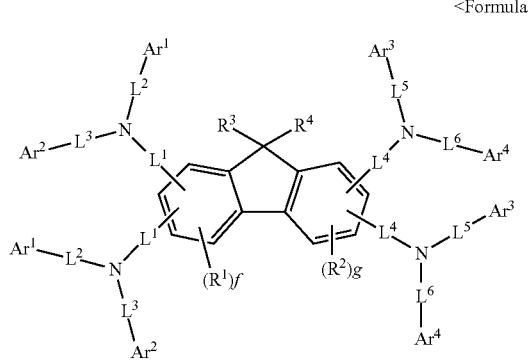

wherein:

$R^1$ to $R^4$, $Ar^1$ to $Ar^4$, and $L^1$ to $L^6$ are the same as defined in claim 1, c is an integer of 0 to 3, and when c is an integer of 2 or more, a plurality of $R^1$s are each the same as or different from each other, d is an integer of 0 to 4, and when d is an integer of 2 or more, a plurality of $R^2$s are each the same as or different from each other, e is an integer of 0 to 3, and when e is an integer of 2 or more, a plurality of $R^2$s are each the same as or different from each other, f is an integer of 0 to 2, and when f is an integer of 2 or more, a plurality of $R^1$s are each the same as or different from each other, and g is an integer of 0 to 2, and when c is an integer of 2 or more, a plurality of $R^2$s are each the same as or different from each other.

3. The organic electric element of claim 1, wherein the compound of Formula 1 is a compound represented by one of Formula 7 to Formula 11:

<Formula 7>

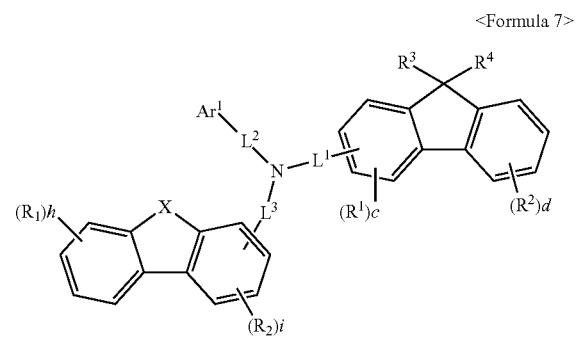

<Formula 8>

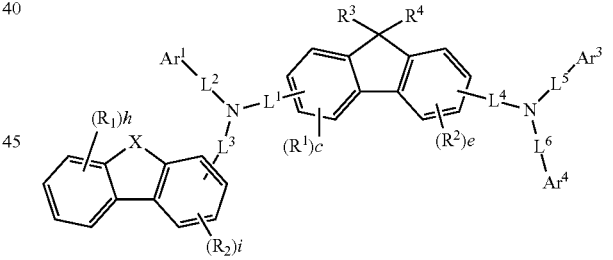

<Formula 9>

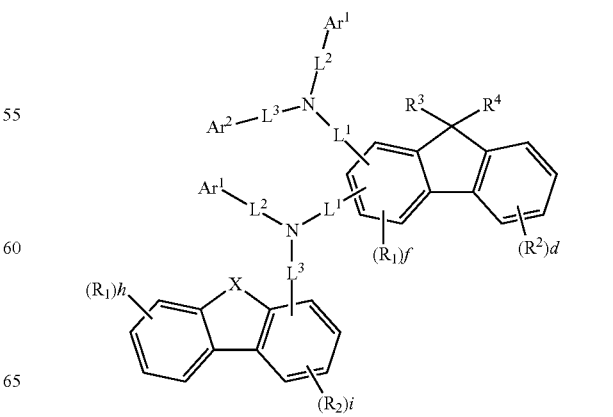

-continued

<Formula 10>

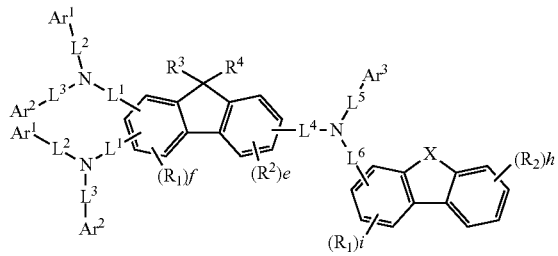

<Formula 11>

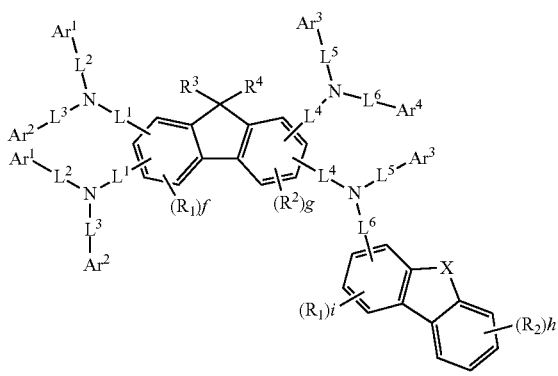

wherein:
R¹ to R⁴, Ar¹ to Ar⁴, and L¹ to L⁶ are the same as defined in claim 1,
X is O, S, C(R')(R") or N(R₃),
$R_1$, $R_2$, R' and R" are each independently selected from the group consisting of hydrogen, deuterium, halogen, a silane group unsubstituted or substituted with a $C_1$-$C_{20}$ alkyl group or a $C_6$-$C_{20}$ aryl group, a cyano group, a nitro group, a $C_1$-$C_{20}$ alkoxy group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group containing at least one heteroatom of O, N, S, Si, and P, and a $C_3$-$C_{20}$ aliphatic ring group, and adjacent $R_1$s or adjacent $R_2$s may be bonded to each other to form a ring, and R' and R" may be bonded to each other to form a ring,
$R_3$ is selected from the group consisting of a $C_6$-$C_{20}$ aryl group, a fluorenyl group, a $C_2$-$C_{20}$ heterocyclic group containing at least one heteroatom of O, N, S, Si, and P, and a $C_3$-$C_{20}$ aliphatic ring group,
c is an integer of 0 to 3, and when c is an integer of 2 or more, a plurality of $R^1$s are each the same as or different from each other,
d is an integer of 0 to 4, and when d is an integer of 2 or more, a plurality of $R^2$s are each the same as or different from each other,
e is an integer of 0 to 3, and when e is an integer of 2 or more, a plurality of $R^2$s are each the same as or different from each other,
f is an integer of 0 to 2, and when f is an integer of 2 or more, a plurality of $R^1$s are each the same as or different from each other,
g is an integer of 0 to 2, and when c is an integer of 2 or more, a plurality of $R^2$s are each the same as or different from each other,
h is an integer of 0 to 4, and when h is an integer of 2 or more, a plurality of $R_1$s are each the same as or different from each other, and i is an integer of 0 to 3, and when i is an integer of 2 or more, a plurality of $R_2$s are each the same as or different from each other.

4. The organic electric element of claim 1, wherein the light emitting layer further comprises at least one of a compound represented by Formula 12 and a compound represented by Formula 13:

<Formula 12>

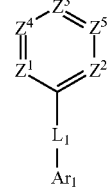

<Formula 13>

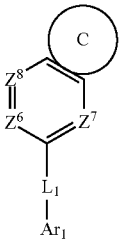

wherein:
$Z^1$ to $Z^5$ are each independently N or C($R_3$), and at least one of $Z^1$ to $Z^5$ is N,
$Z^6$ to $Z^8$ are each independently N or C($R_3$), and at least one of $Z^6$ to $Z^8$ is N,
$L_1$ is selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, and a $C_3$-$C_{60}$ aliphatic ring,
$Ar_1$ is selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, and a $C_3$-$C_{60}$ aliphatic ring,
C ring is selected from the group consisting of a $C_6$-$C_{60}$ aromatic ring, a $C_2$-$C_{60}$ heterocyclic group comprising at least one heteroatom selected from the group consisting of O, N, S, Si and P, and a $C_3$-$C_{60}$ aliphatic ring, and C ring may be further substituted with one or more $R_4$,
$R_3$ and $R_4$ are each independently selected from the group consisting of hydrogen, deuterium, halogen, a cyano group, a nitro group, a $C_6$-$C_{60}$ aryl group, a fluorenyl group, a $C_2$-$C_{60}$ heterocyclic group comprising at least one heteroatom selected from the group consisting of O, N, S, Si and P, and a $C_3$-$C_{60}$ aliphatic ring, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_6$-$C_{30}$ aryloxy group, and -L'-N($R_a$)($R_b$), and adjacent $R_3$s may be bonded to each other to form a ring,
L' is selected from the group consisting of a single bond, a $C_6$-$C_{60}$ arylene group, a fluorenylene group, a $C_3$-$C_{60}$ aliphatic ring, and a $C_2$-$C_{60}$ heterocyclic group comprising at least one heteroatom selected from the group consisting of O, N, S, Si and P,
$R_a$ and $R_b$ are each independently selected from the group consisting of a $C_6$-$C_{60}$ aryl group, a fluorenyl group, a $C_3$-$C_{60}$ aliphatic ring, and a $C_2$-$C_{60}$ heterocyclic group comprising at least one heteroatom selected from the group consisting of O, N, S, Si and P, and $Ar_1$, $L_1$, L', $R_3$, $R_4$, $R_a$, $R_b$, the ring formed by adjacent $R_3$s may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ aliphatic ring group, a $C_7$-$C_{20}$ arylalkyl group, $C_8$-$C_{20}$ arylalkenyl group and -L'-N($R_a$)($R_b$).

5. The organic electric element of claim 4, wherein the light emitting layer comprises a compound represented by one of Formula 13-1 to Formula 13-6:

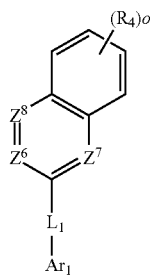
<Formula 13-1>

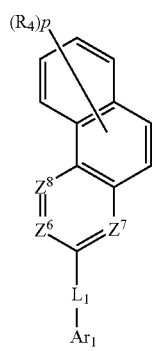
<Formula 13-2>

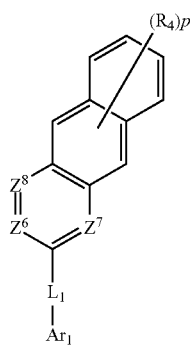
<Formula 13-3>

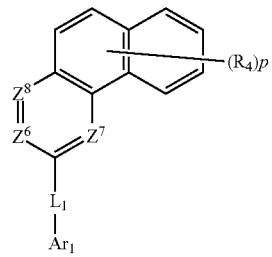
<Formula 13-4>

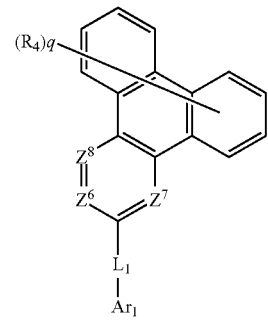
<Formula 13-5>

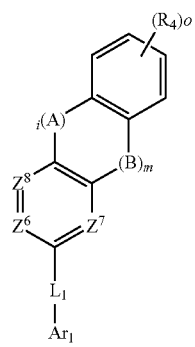
<Formula 13-6> wherein:

$Z^6$ to $Z^8$, $L_1$, $Ar_1$, $R_4$ are the same as defined in claim 4,

A and B are each independently O, N, S or C($R_5$)($R_6$), 1 and m are each an integer of 0 or 1, and at least one of l and m is 1, and is an integer of 0 to 4, p is an integer of 0 to 6, q is an integer of 0 to 8, and when o, p and q are each an integer of 2 or more, a plurality of $R_4$s are each the same as or different from each other.

6. The organic electric element of claim 2, wherein the hole transport layer comprises the compound of Formula 2.

7. The organic electric element of claim 3, wherein the hole transport layer comprises the compound of Formula 7.

8. The organic electric element of claim 2, wherein the hole transport layer and the emission-auxiliary layer comprise the compound of Formula 2.

9. The organic electric element of claim 2, wherein the hole transport layer, the emission-auxiliary layer and the light emitting layer comprise the compound of Formula 2.

10. The organic electric element of claim 4, wherein the light emitting layer comprises the compound of Formula 12.

11. The organic electric element of claim 1, wherein the compound represented by Formula 1 is one of the following compounds:

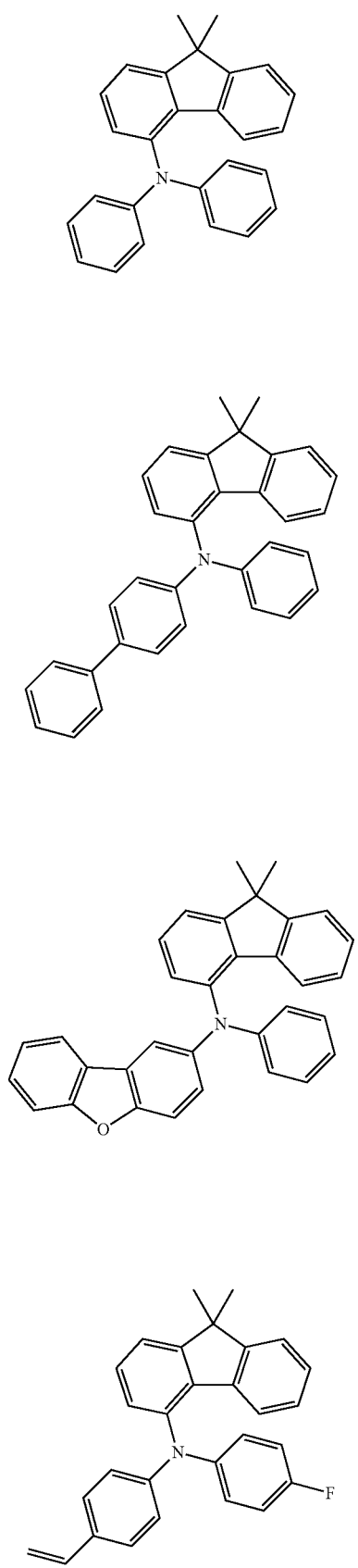

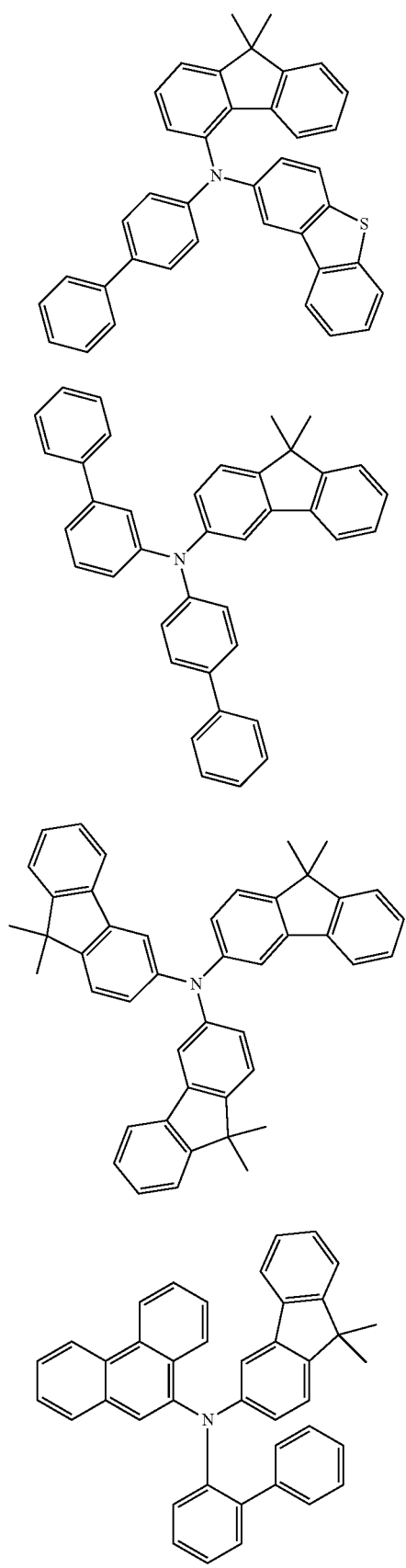
P-8
P-9
P-10
P-11
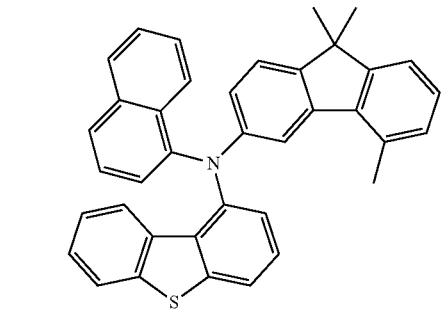
P-12
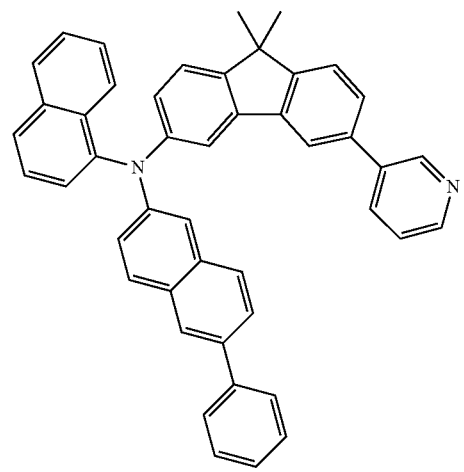
P-13
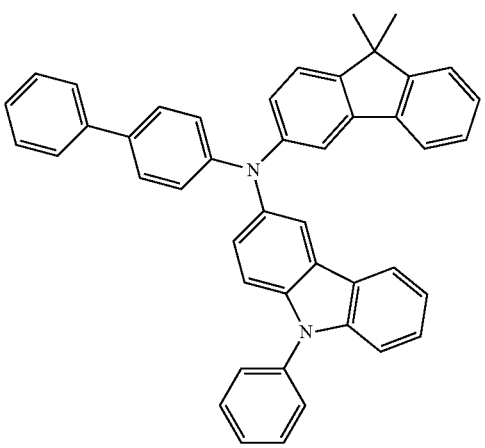
P-14
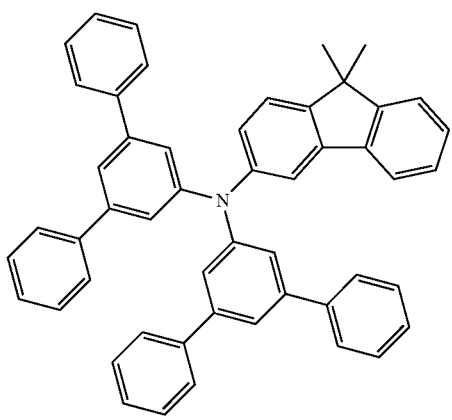
P-15

P-16
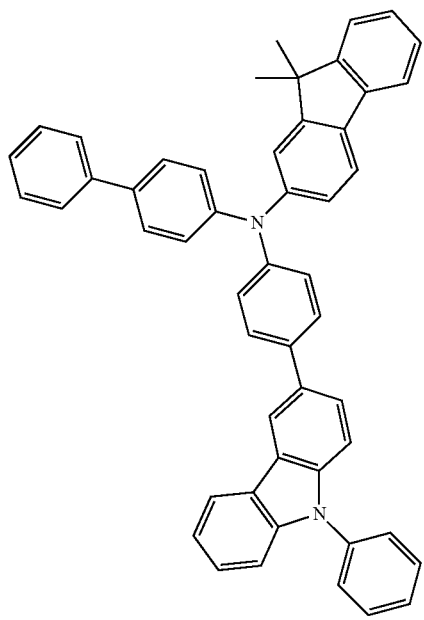
P-17
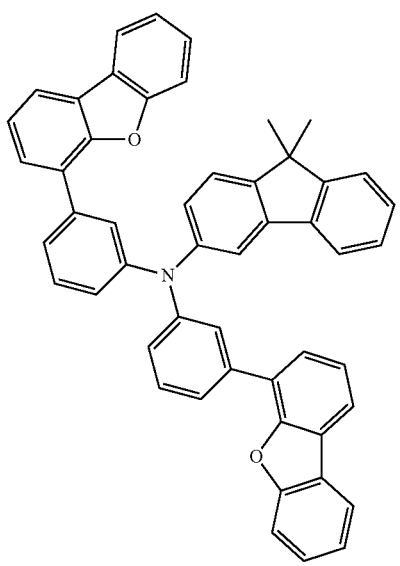
P-18
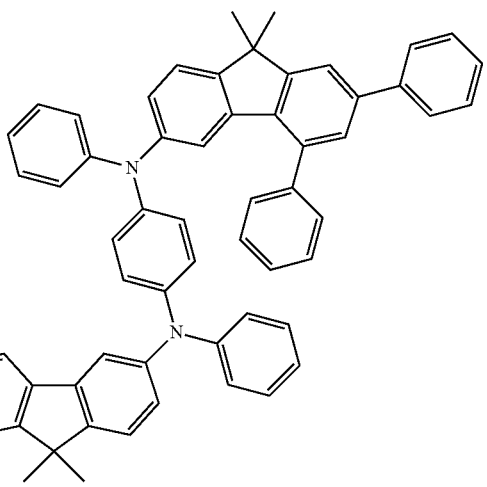
P-19
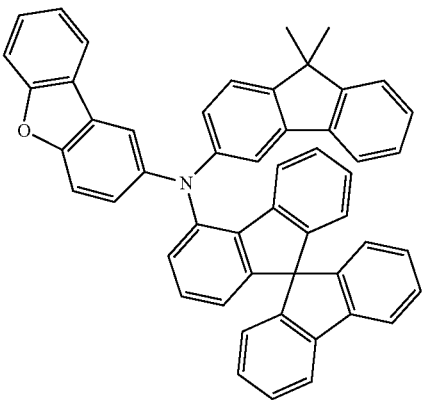
P-20
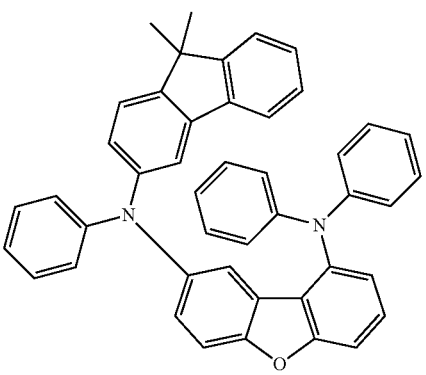
P-21
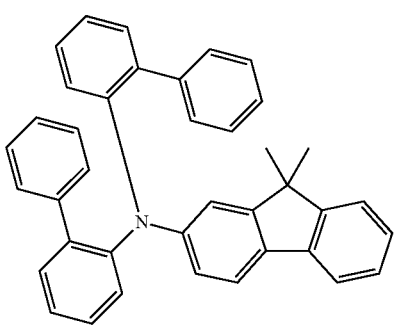

-continued
P-22
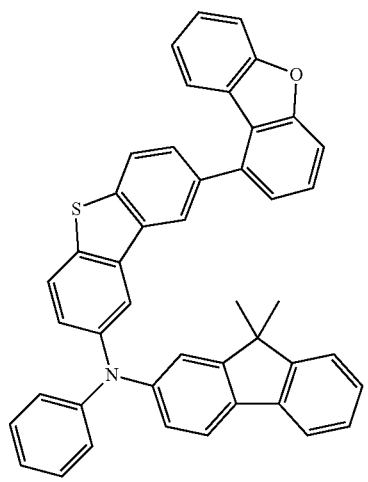
P-23
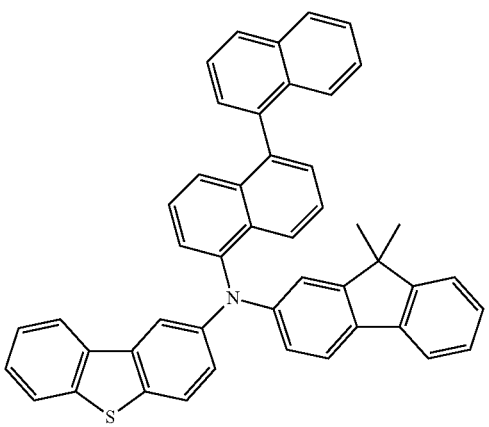
P-24
-continued
P-25
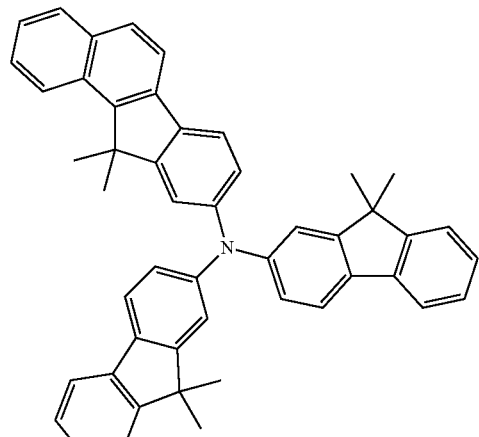
P-26
P-27
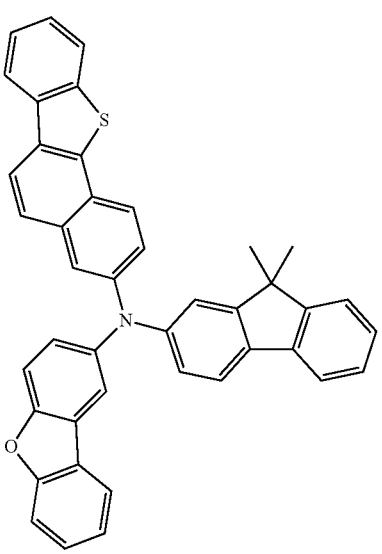

-continued
P-28
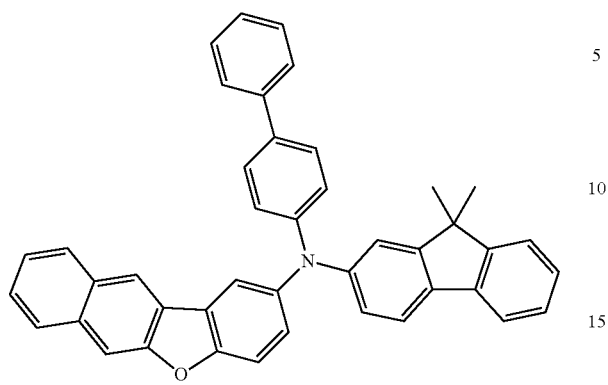
P-29
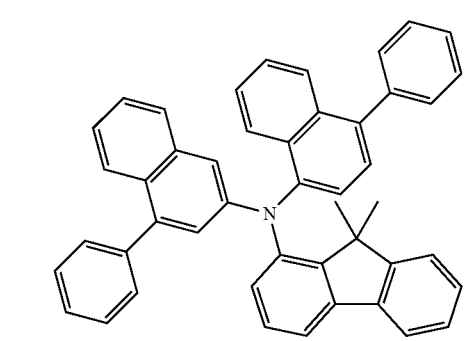
P-30
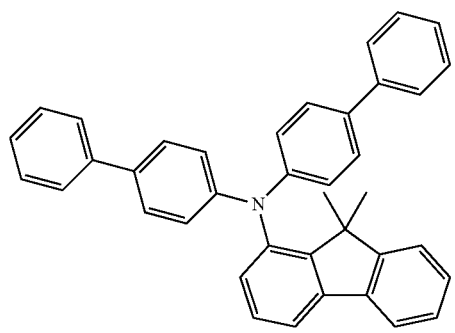
P-31
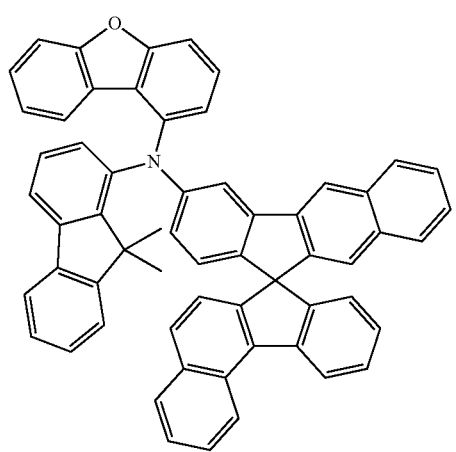
-continued
P-32
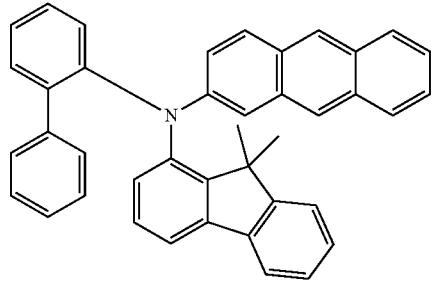
P-33
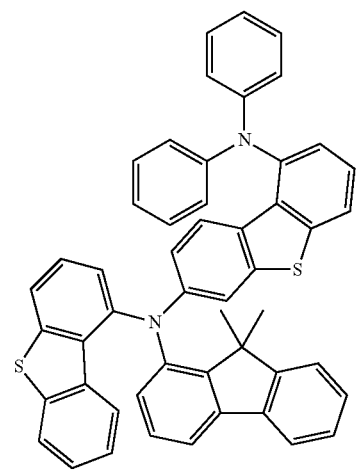
P-34
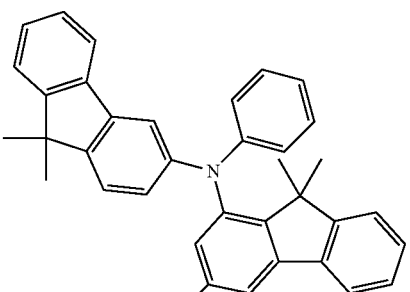
P-35
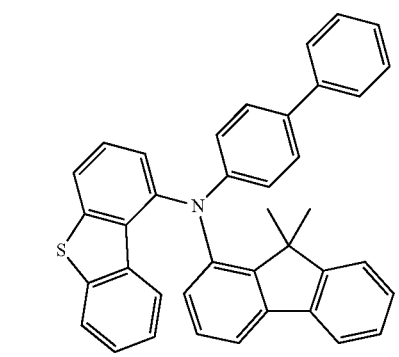

P-36
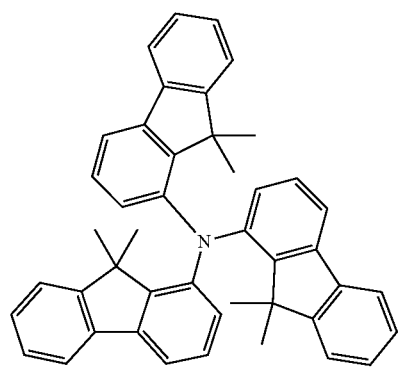
P-37
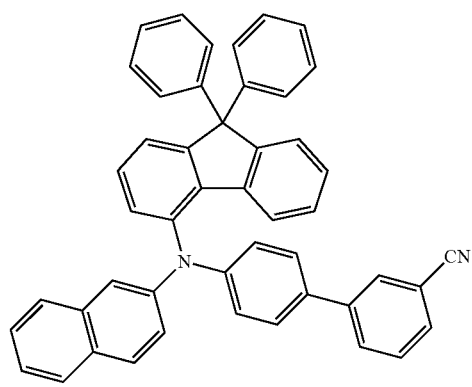
P-38
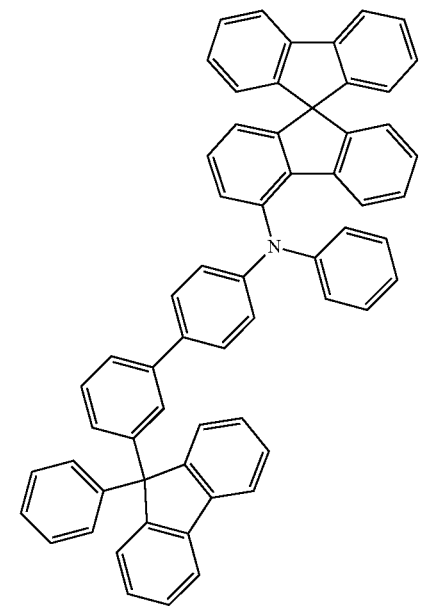
P-39
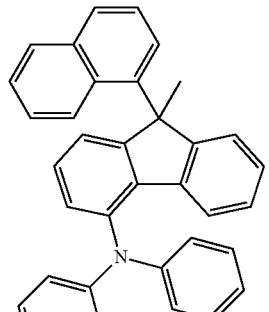
P-40
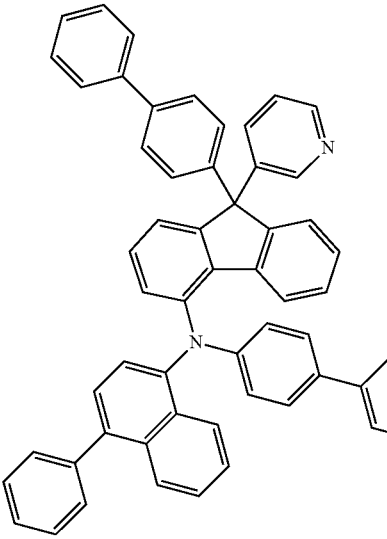
P-41
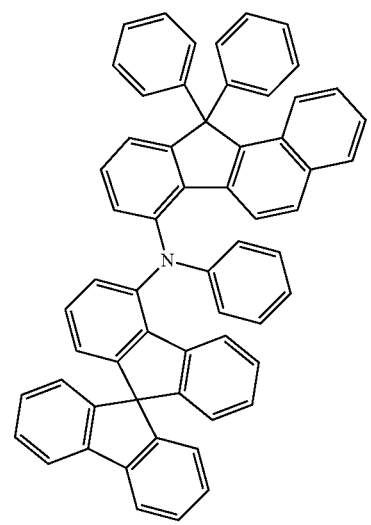

-continued
P-42
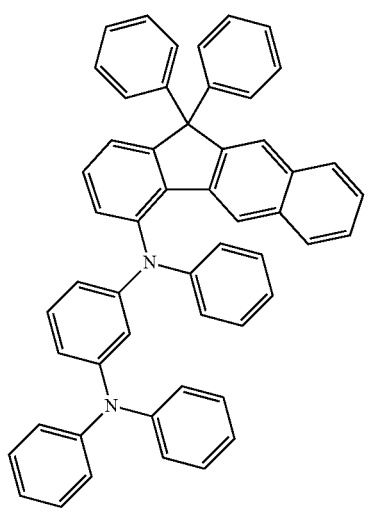
P-43
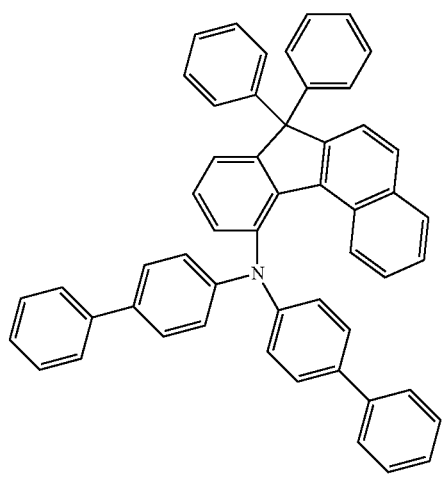
P-44
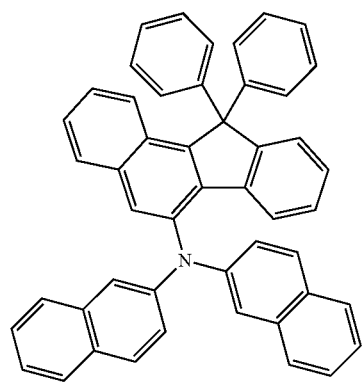
P-45
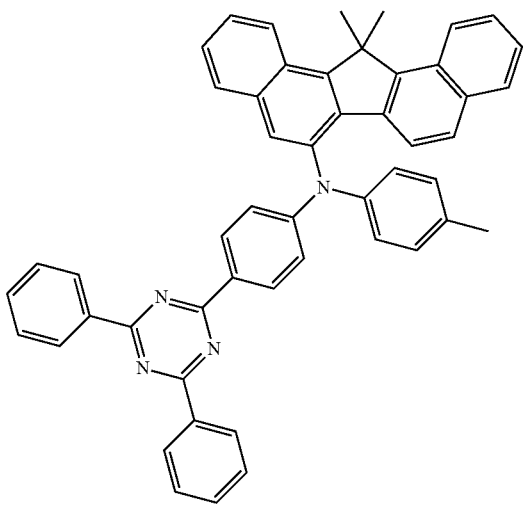
P-46
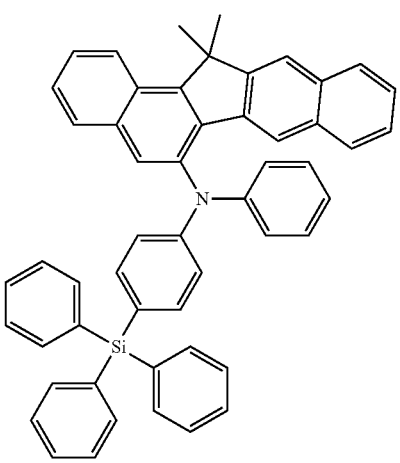
P-47
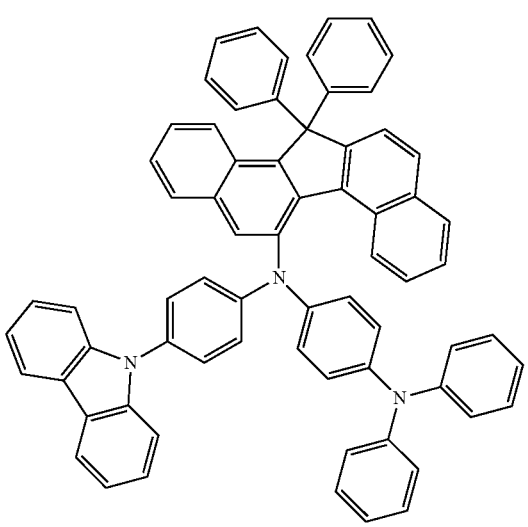

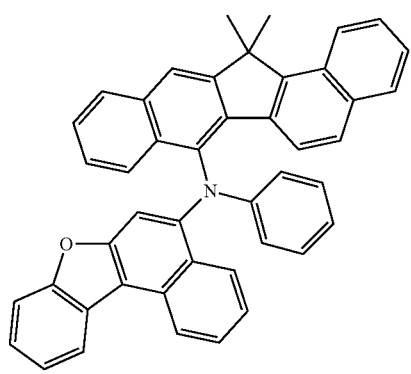
P-48
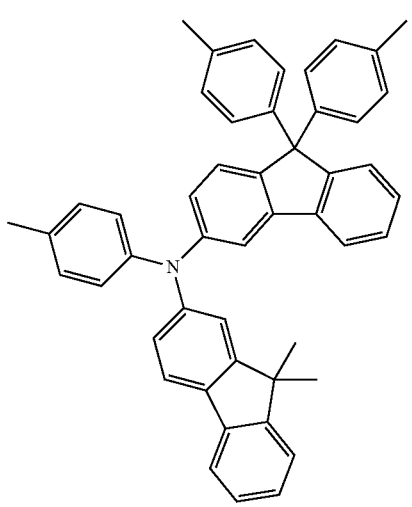
P-51
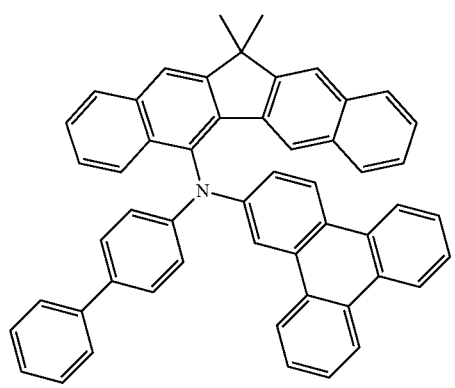
P-49
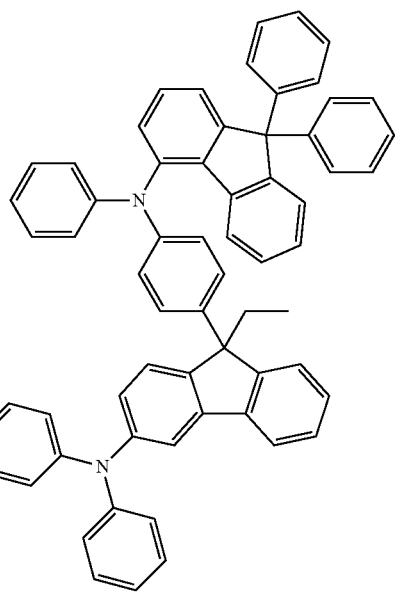
P-52
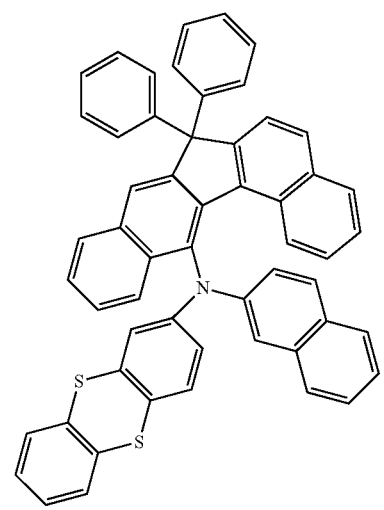
P-50
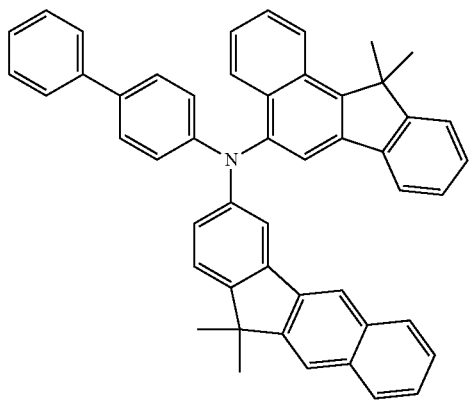
P-53

P-54
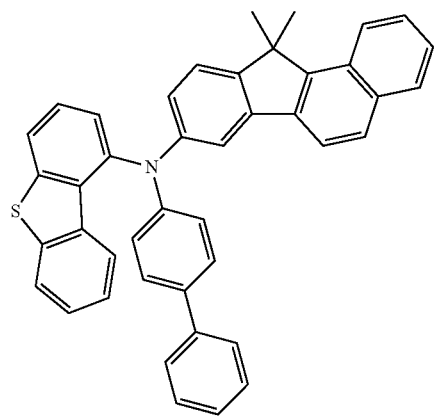
P-55
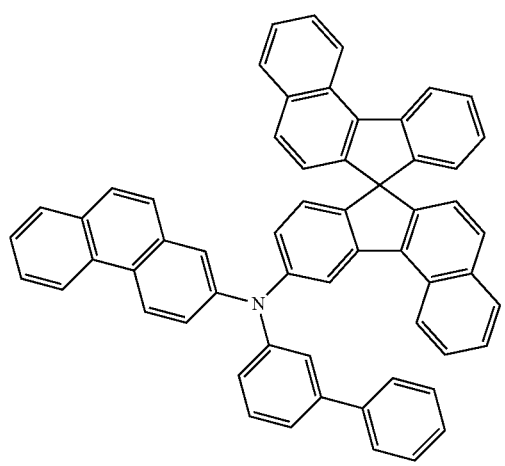
P-56
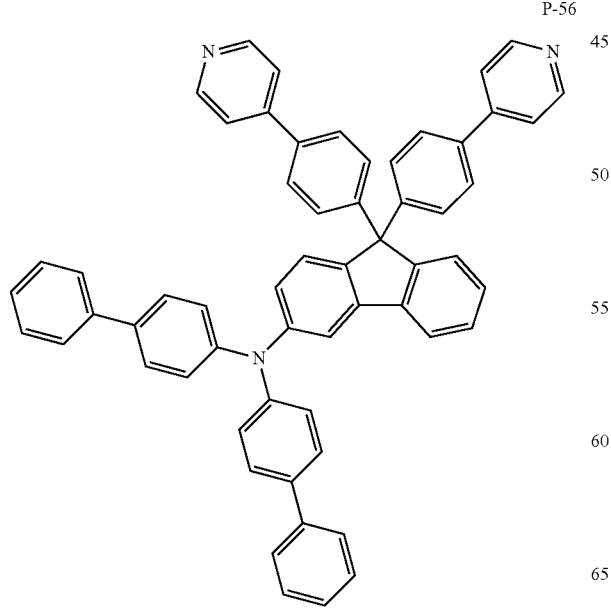
P-57
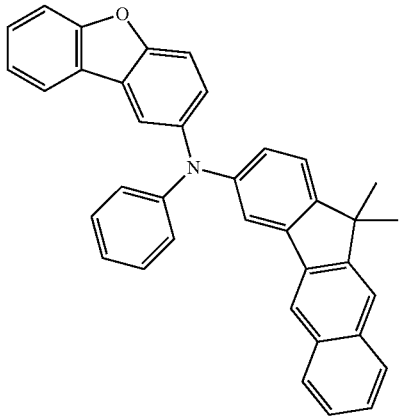
P-58
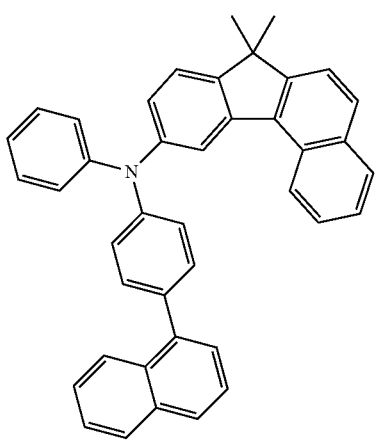
P-59
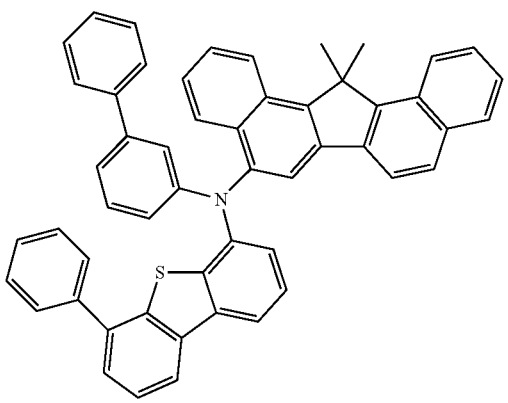

-continued
P-60
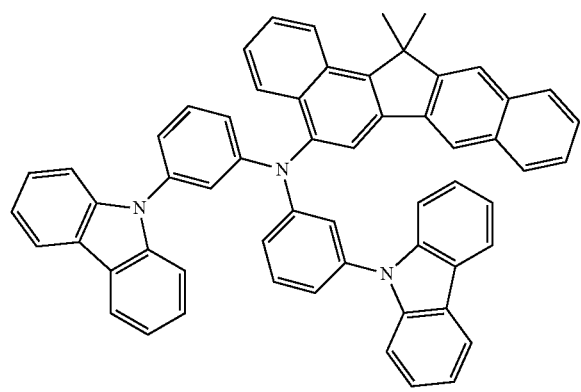
P-61
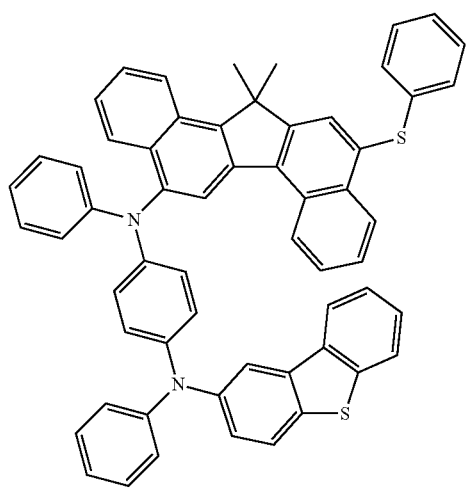
P-62
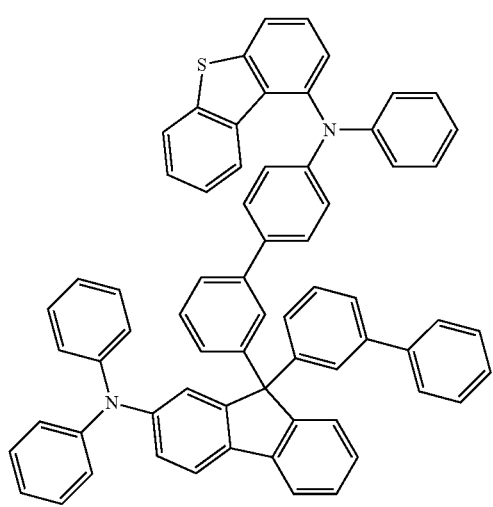
-continued
P-63
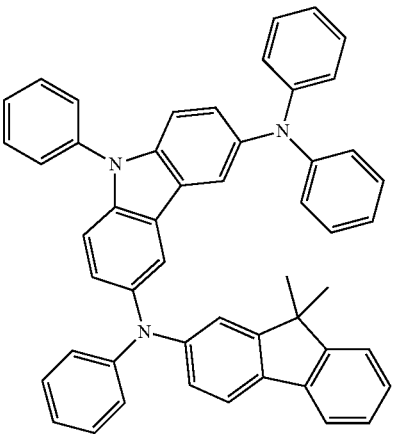
P-64
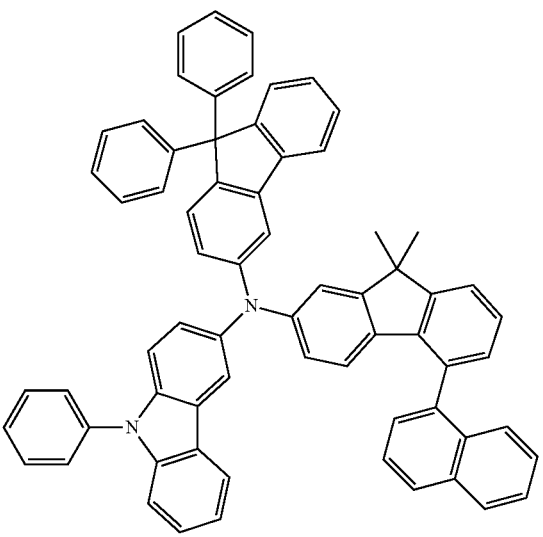
P-65
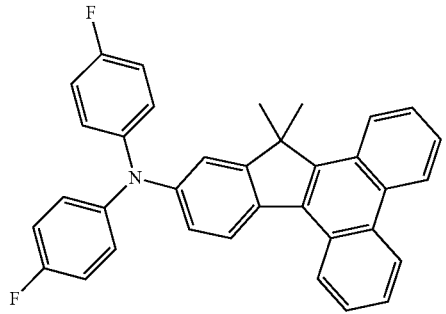

P-66
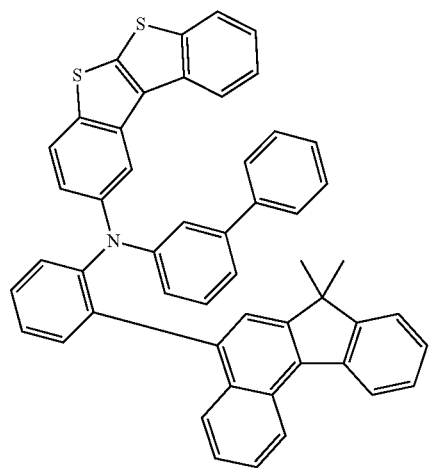
P-67
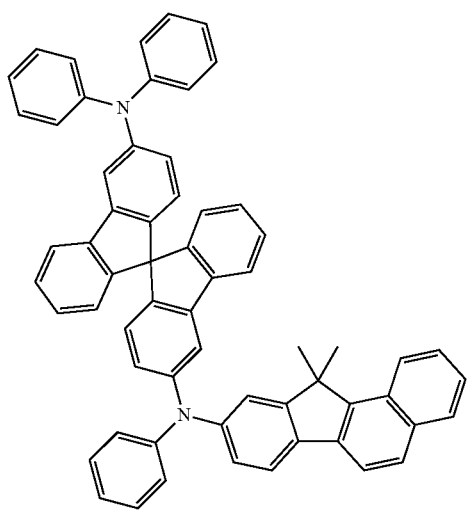
P-68
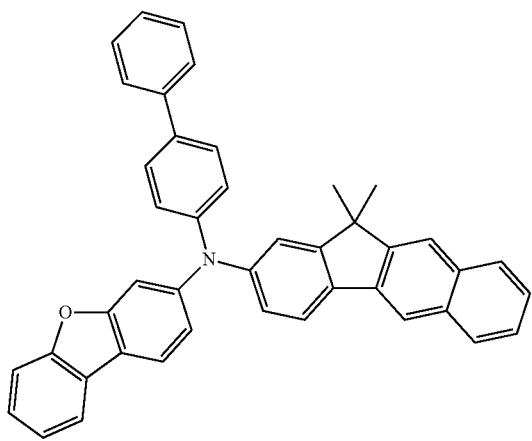
P-69
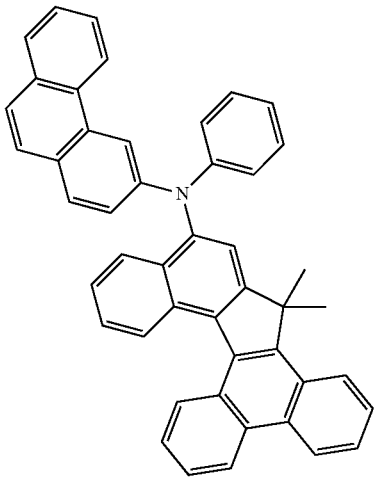
P-70
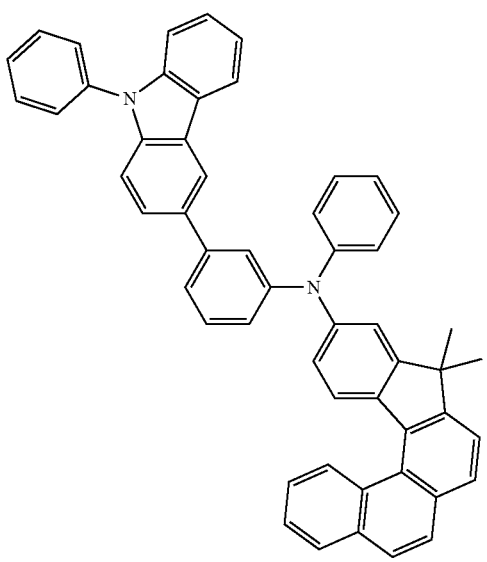
P-71
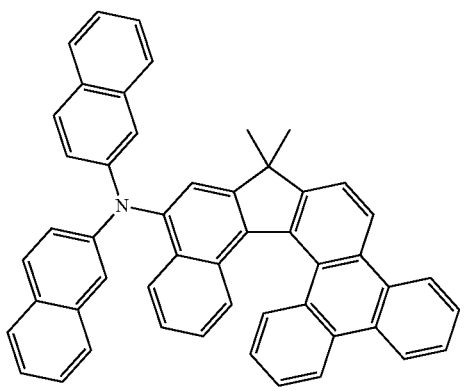

-continued
P-72
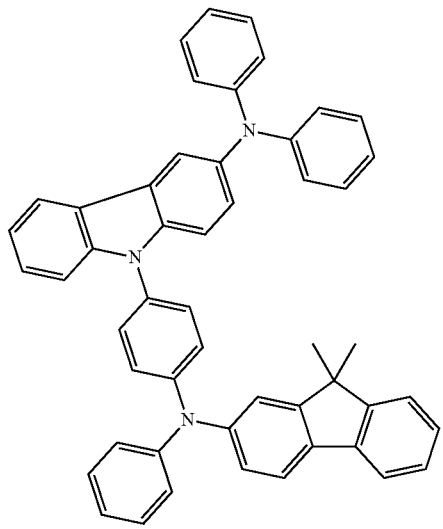
P-73
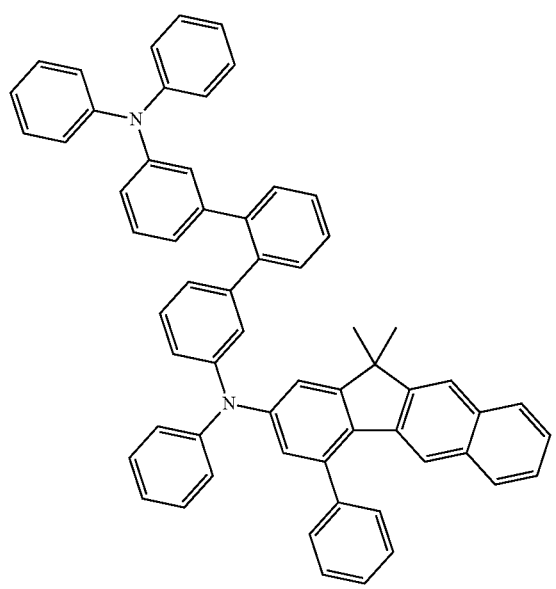
P-74
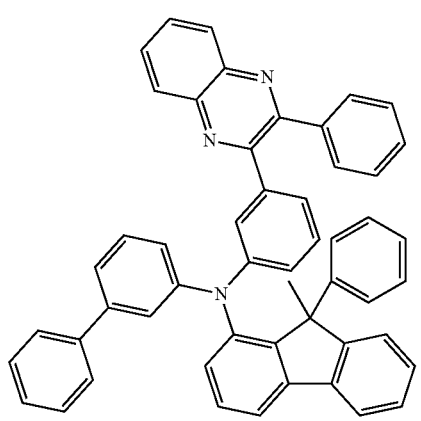
-continued
P-75
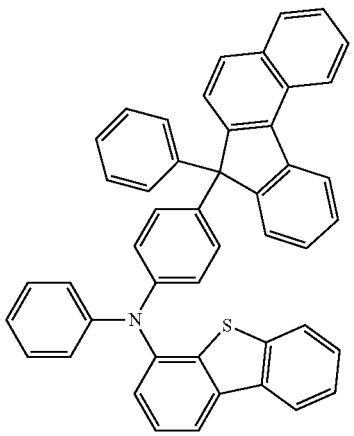
P-76
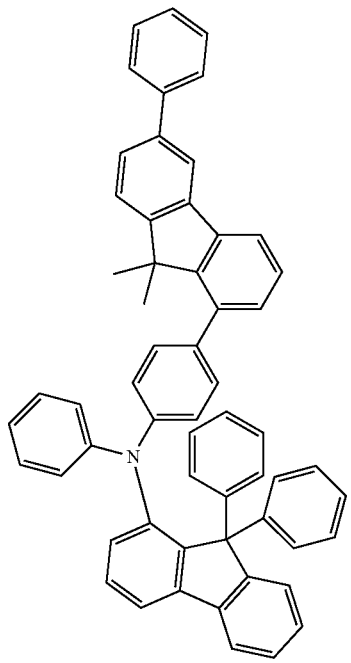
P-77
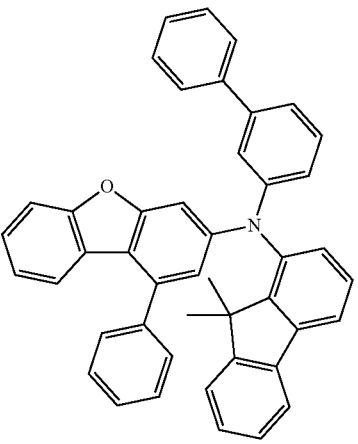

P-78
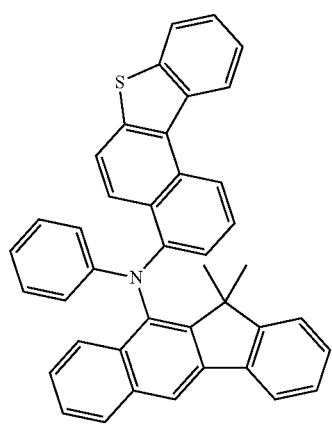
P-79
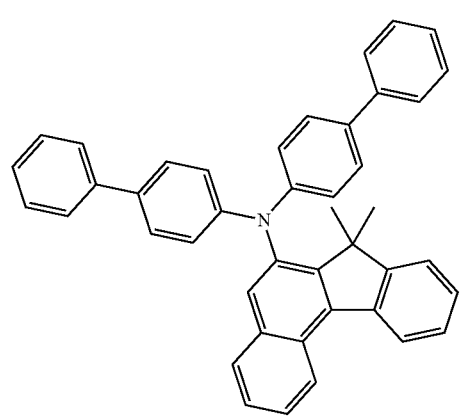
P-80
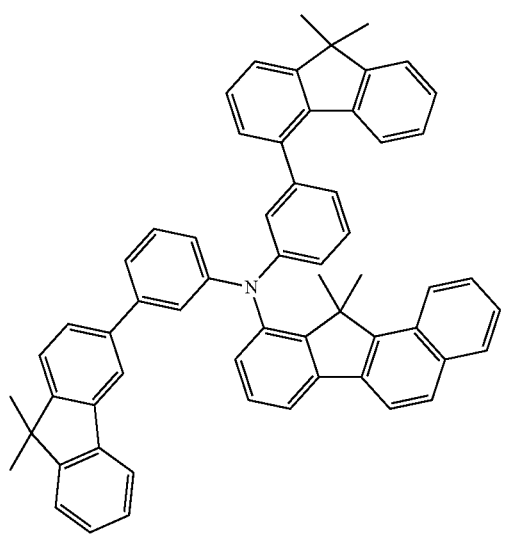
P-81
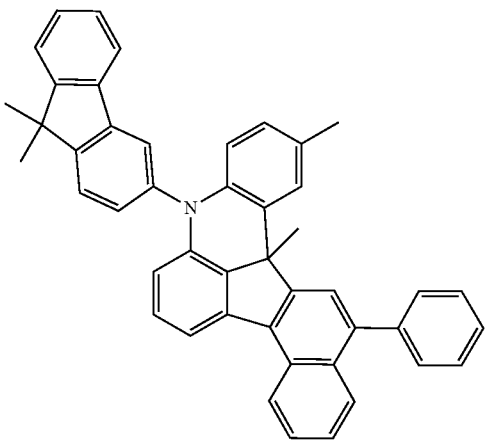
P-82
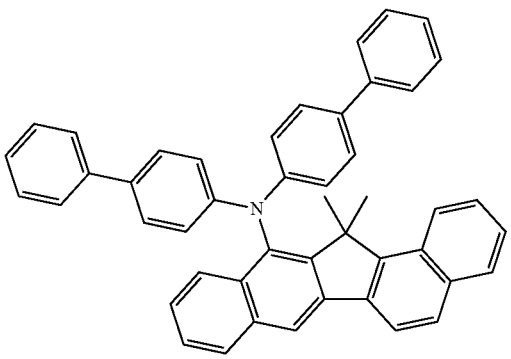
P-83
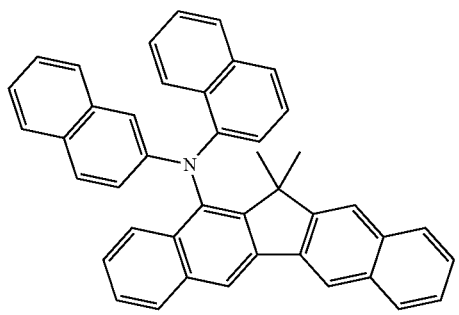

P-84
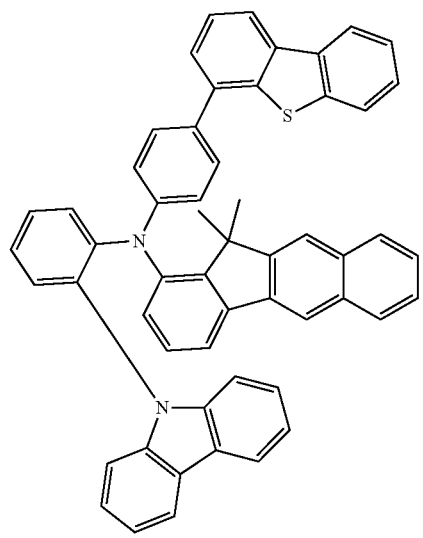
P-85
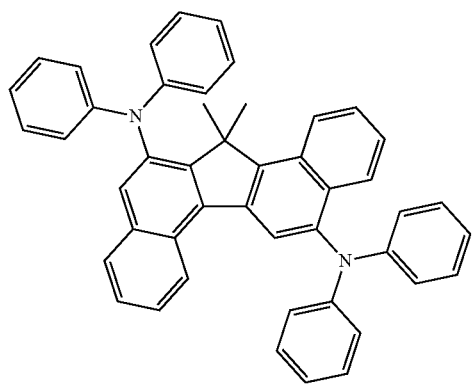
P-86
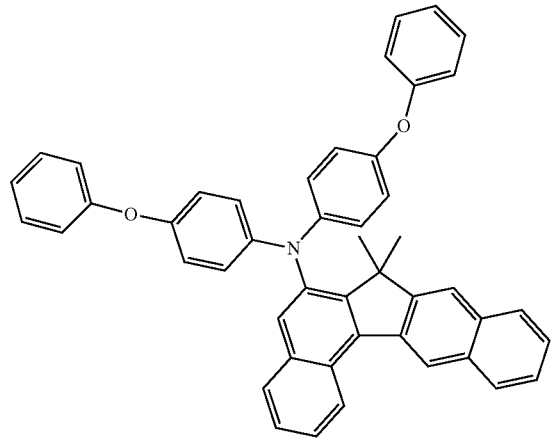
P-87
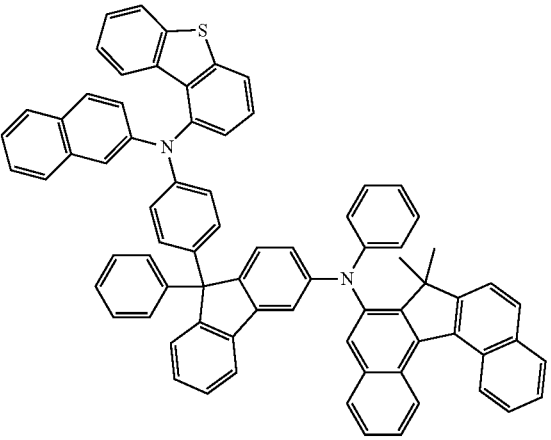
P-88
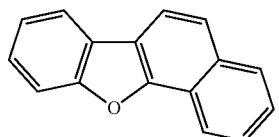
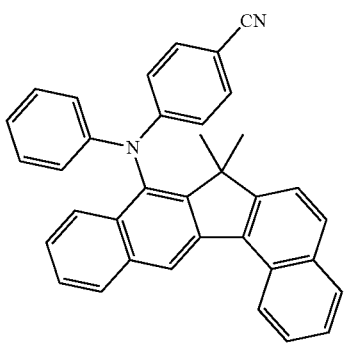
P-89
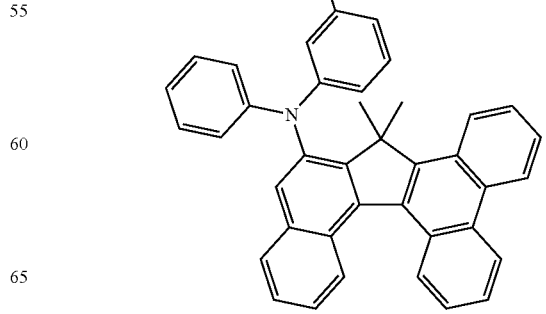

-continued
P-90
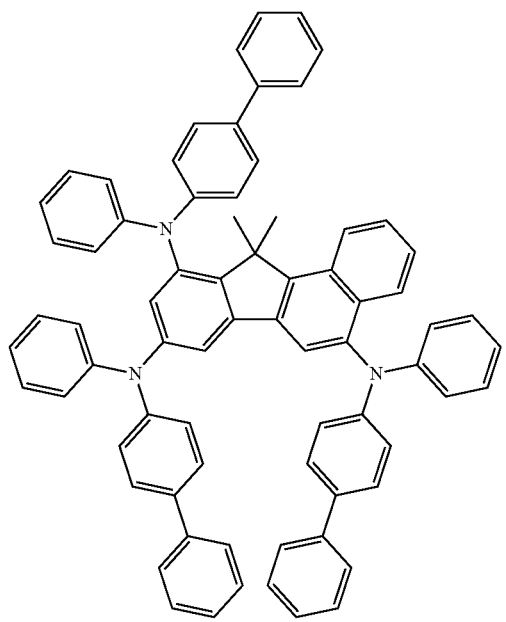
P-91
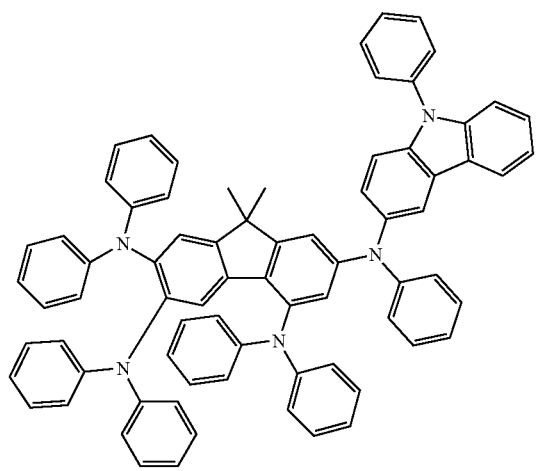
-continued
P-92
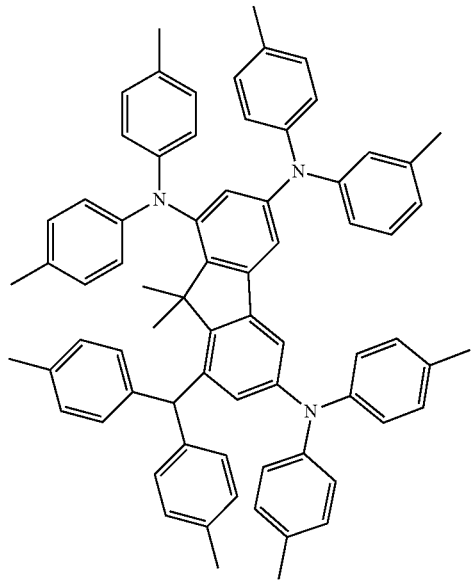
P-93
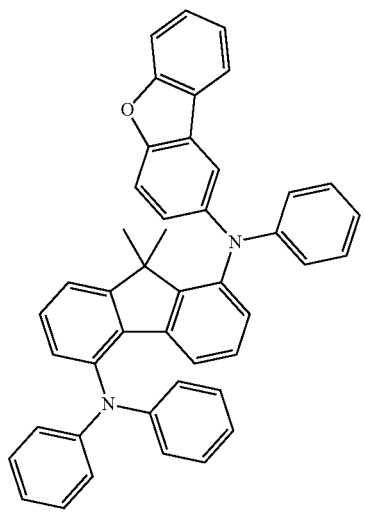
P-94
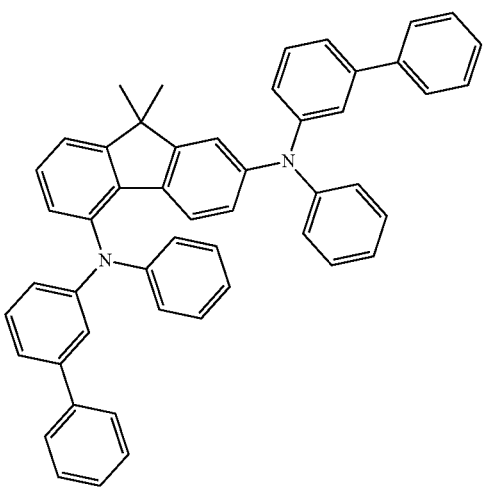

P-95
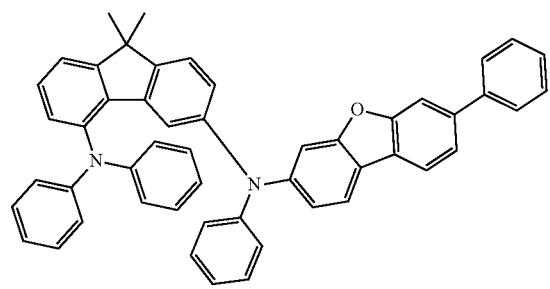
P-98
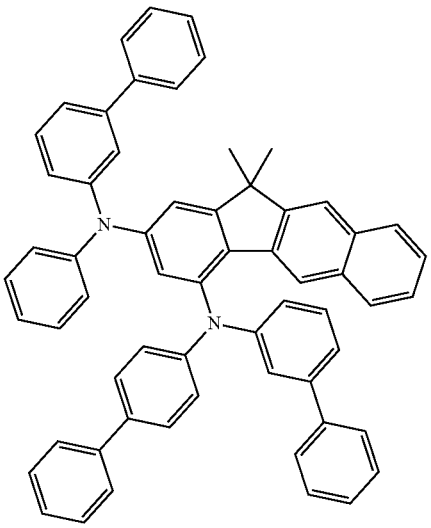
P-96
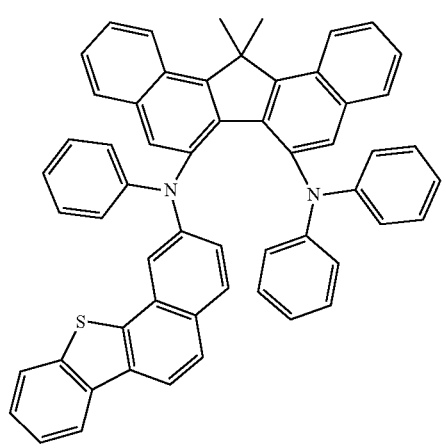
P-99
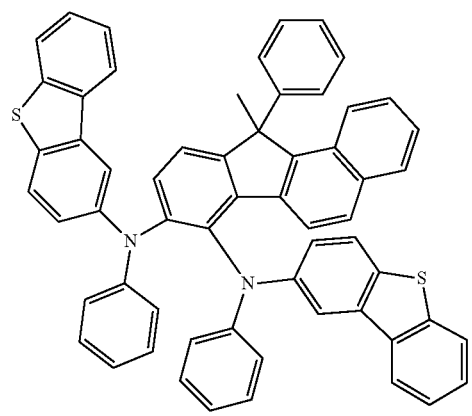
P-97
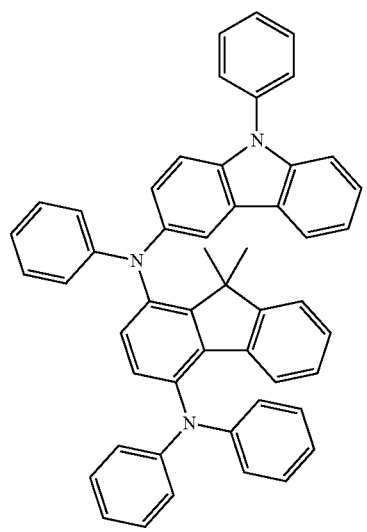
P-100
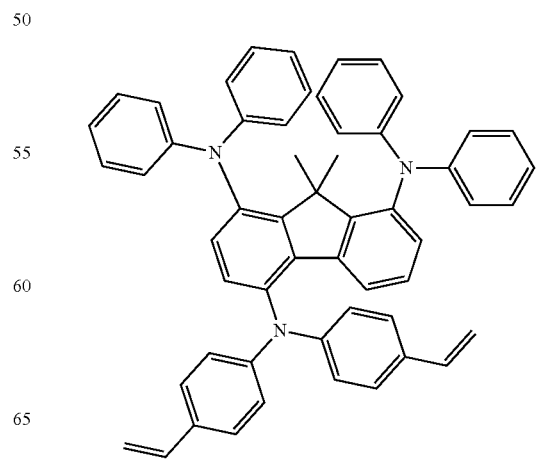

-continued
P-101
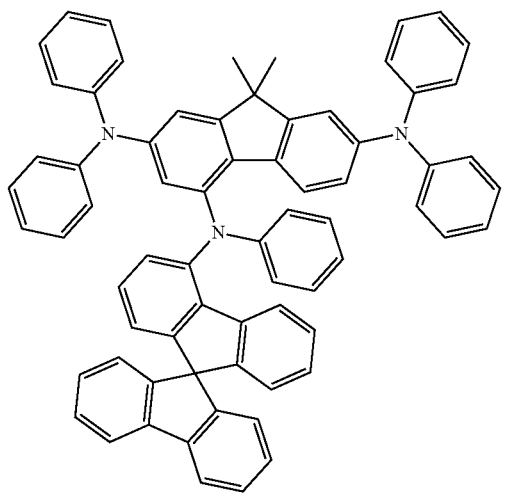
P-102
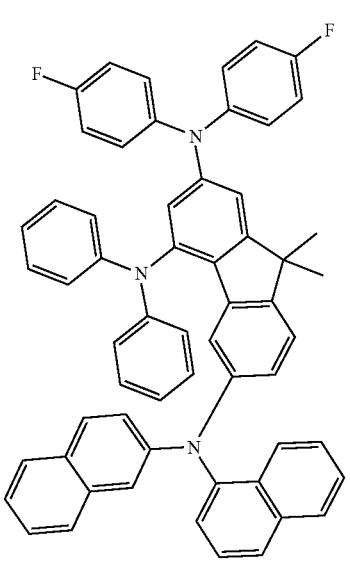
P-103
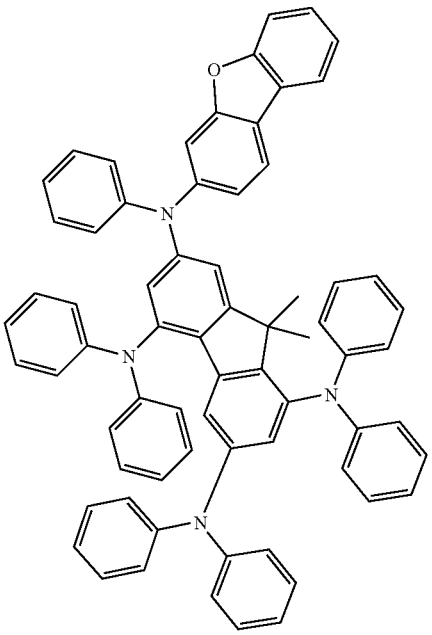
P-104
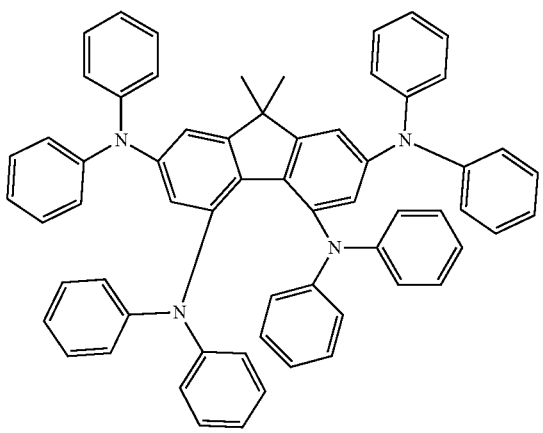
P-105
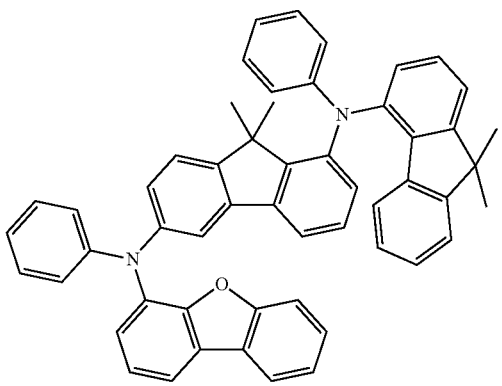

P-106
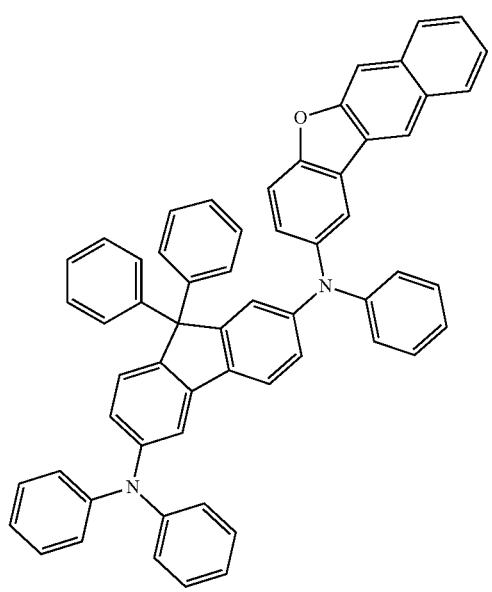
P-109
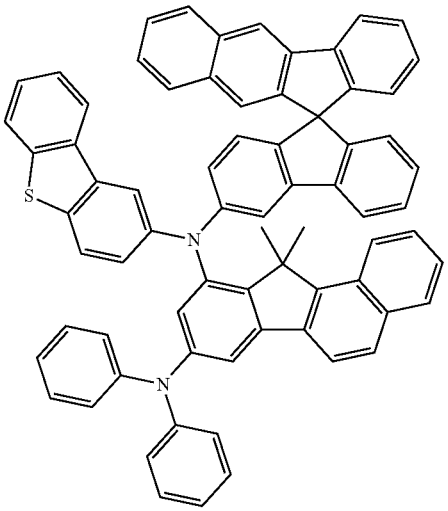
P-107
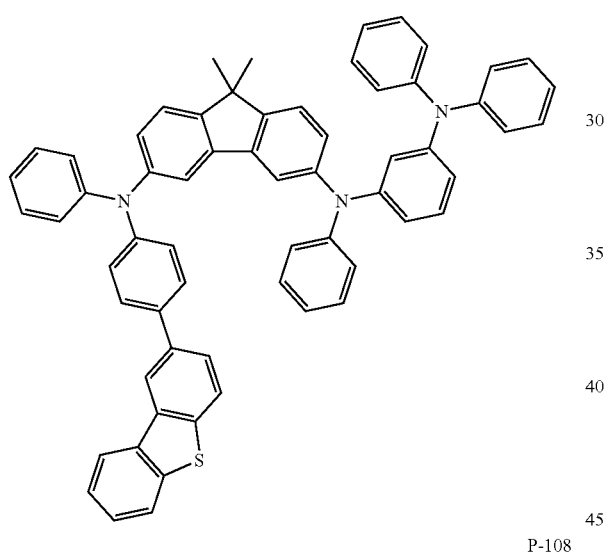
P-108
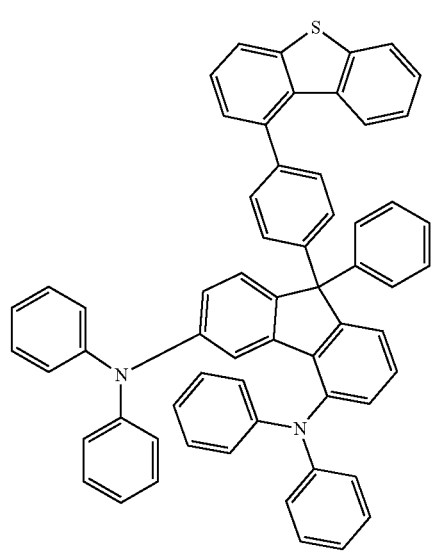
P-110
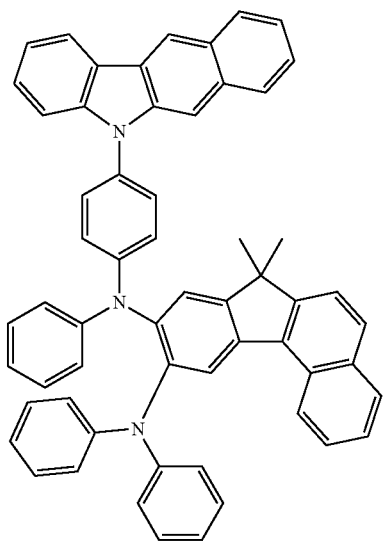

P-111
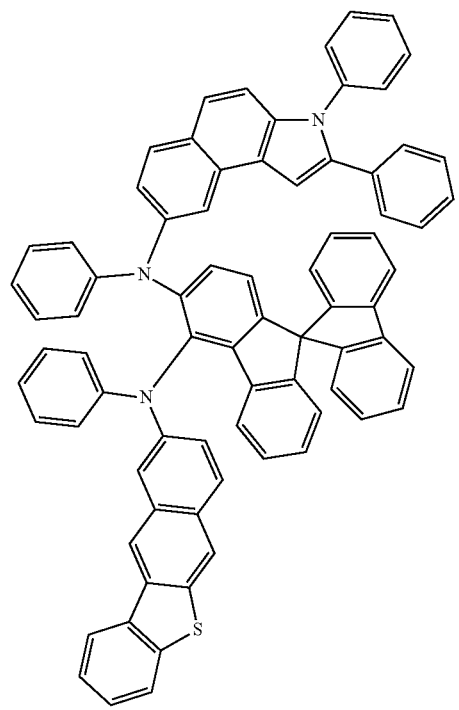
P-112
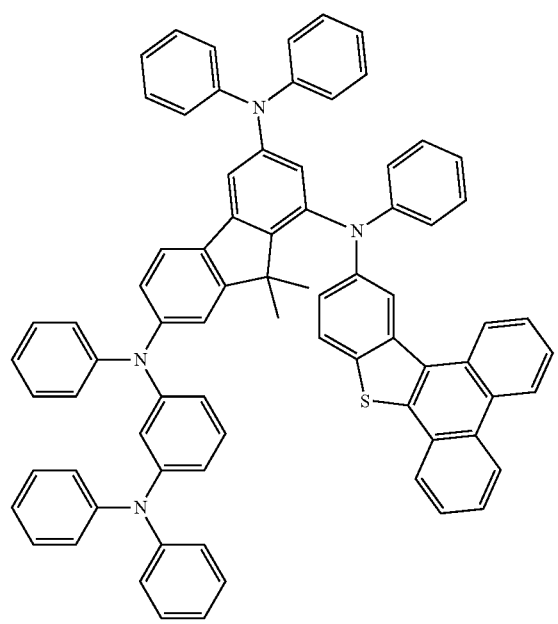
P-113
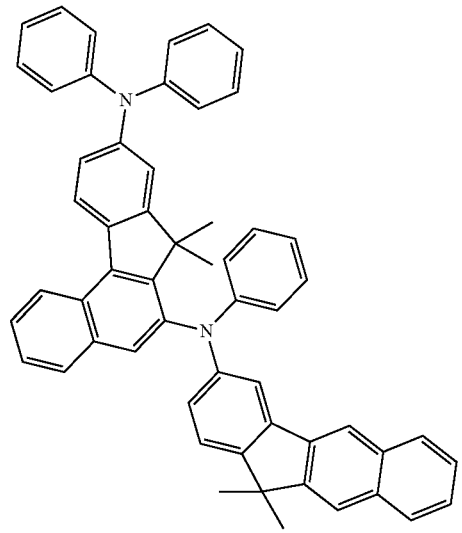
P-114
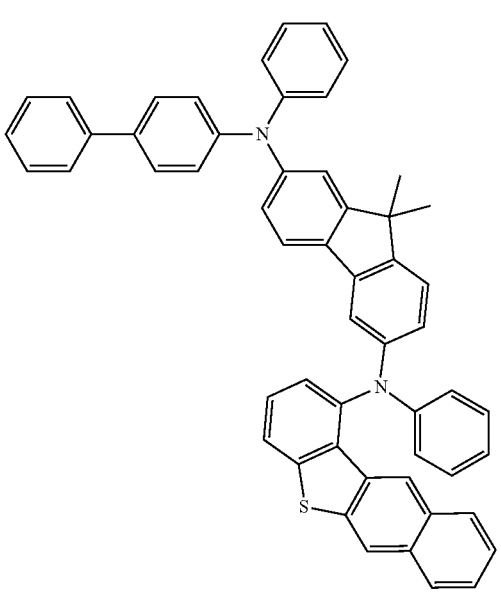
P-115

P-116
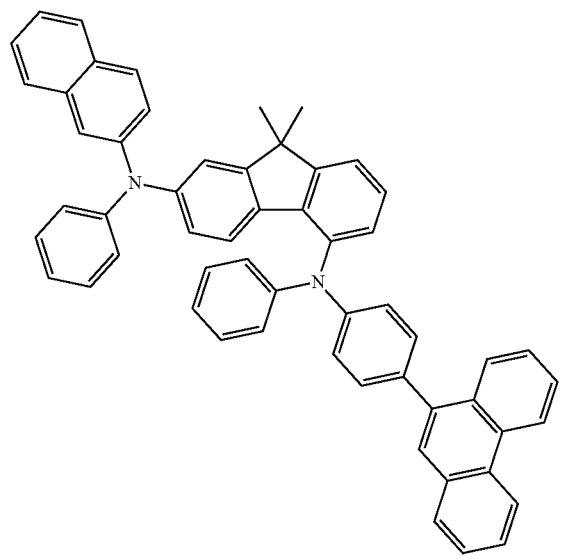
P-118
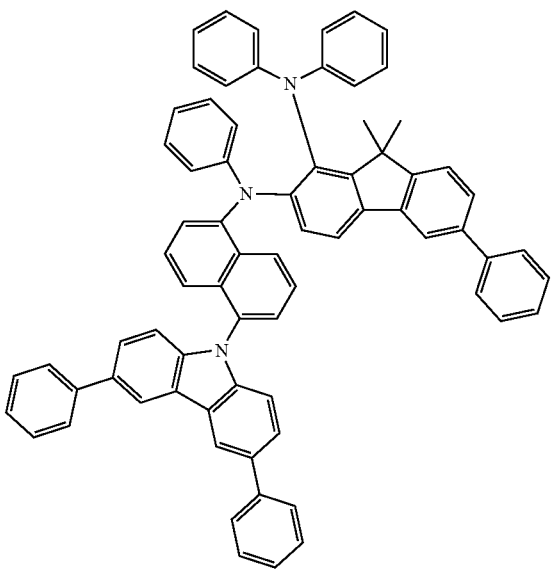
P-119
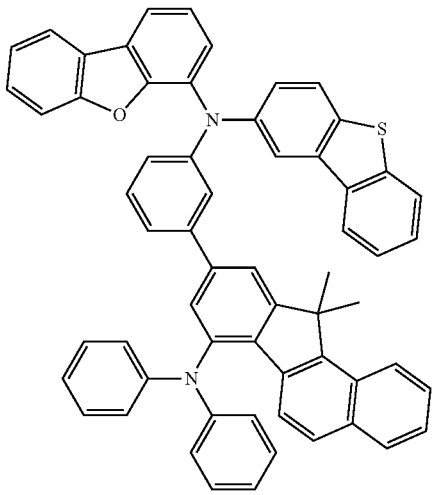
P-117
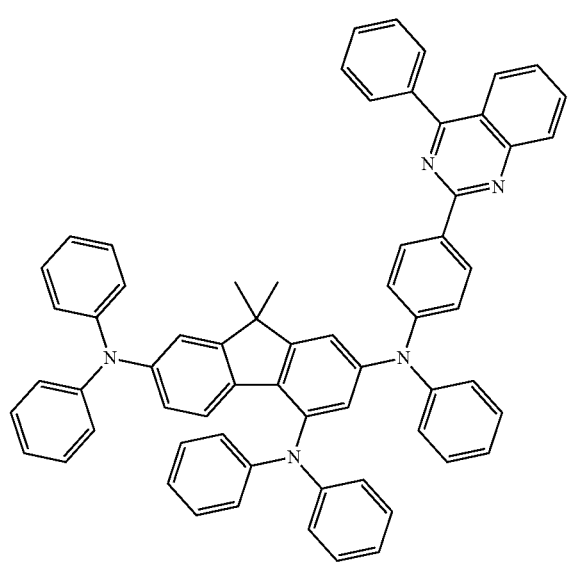
P-120
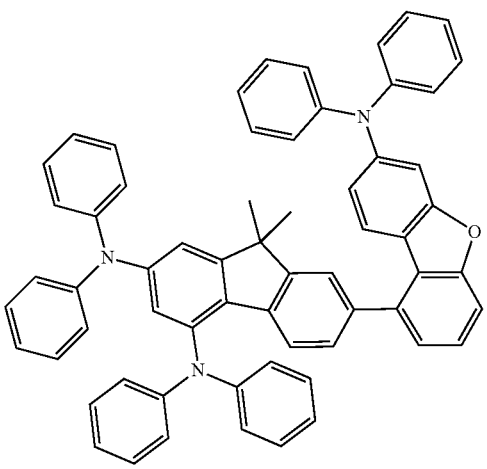

P-121
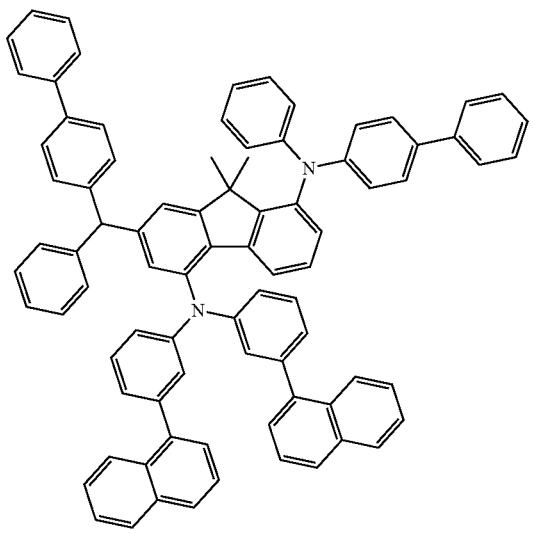
P-122
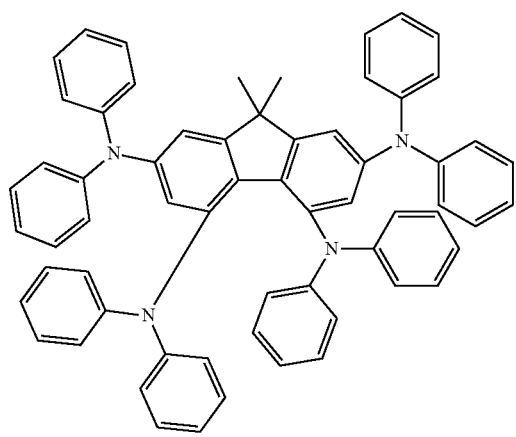
P-123
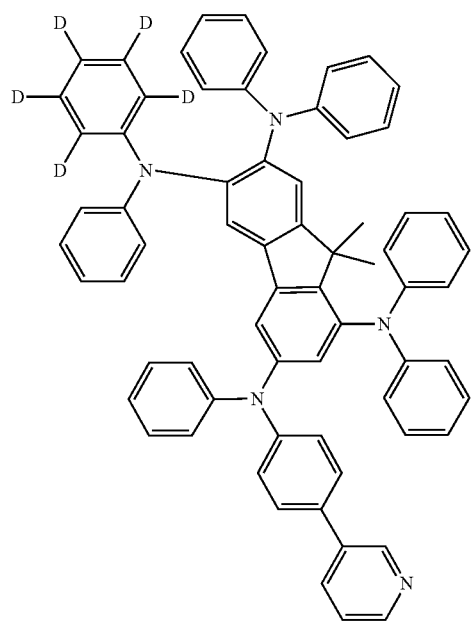
P-124
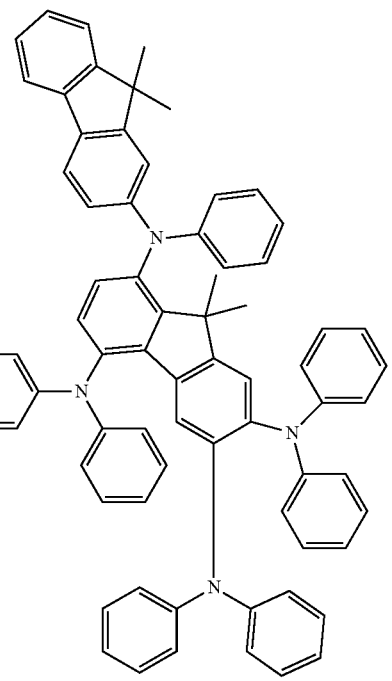
P-125
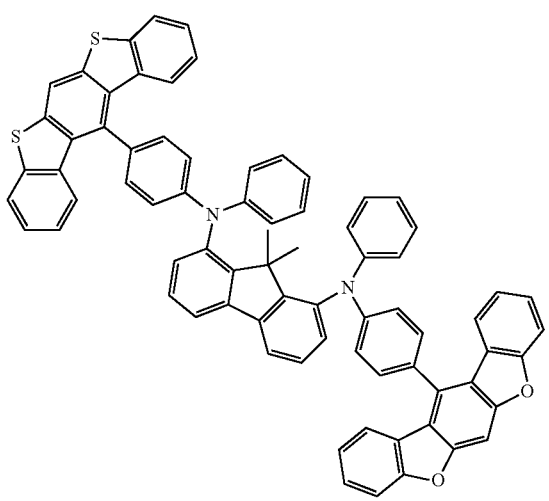
P-126
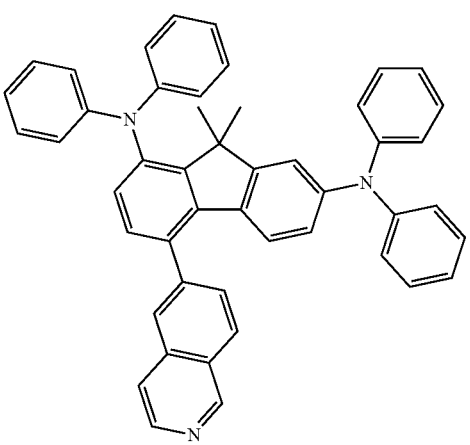

P-127
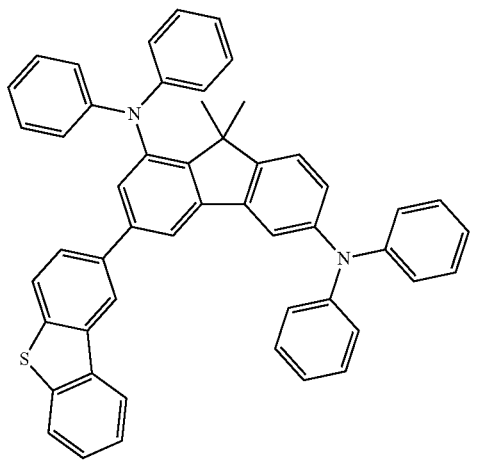
P-128
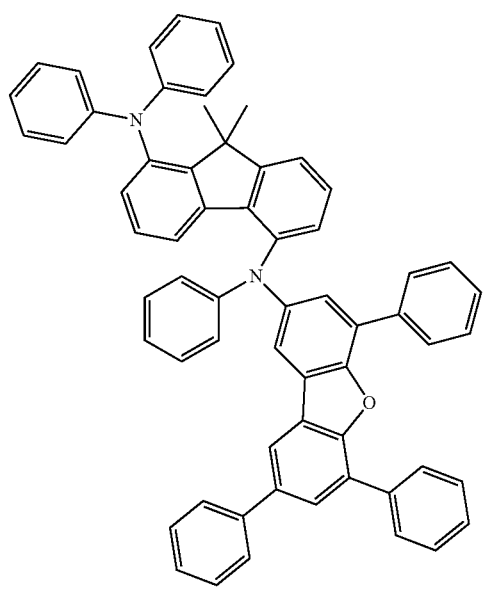
P-129
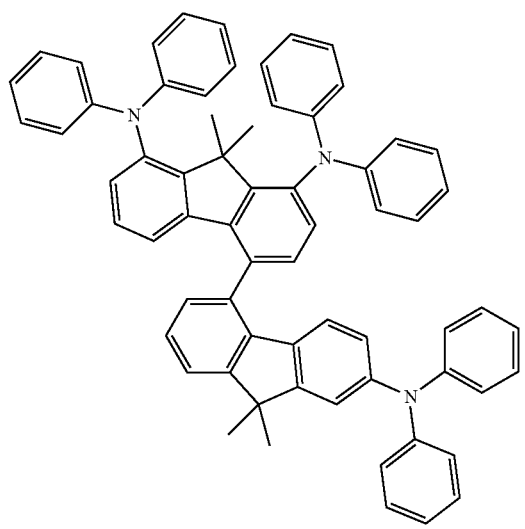
P-130
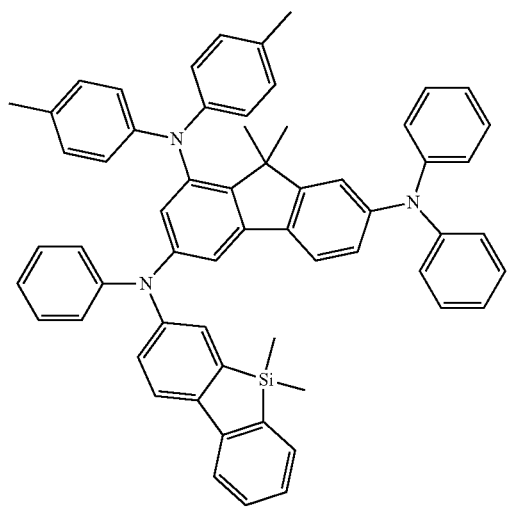
P-131
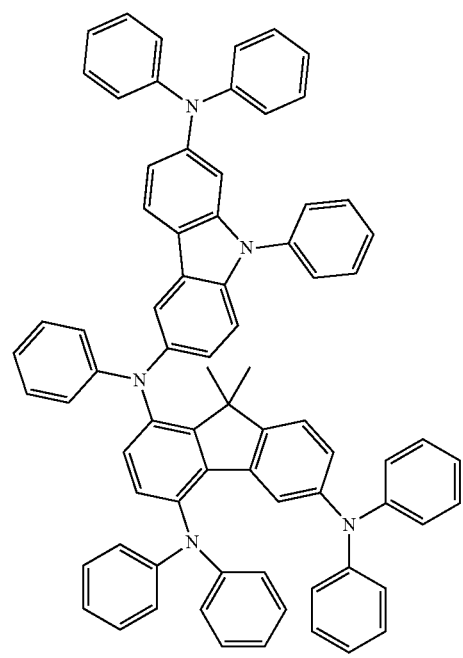
P-132
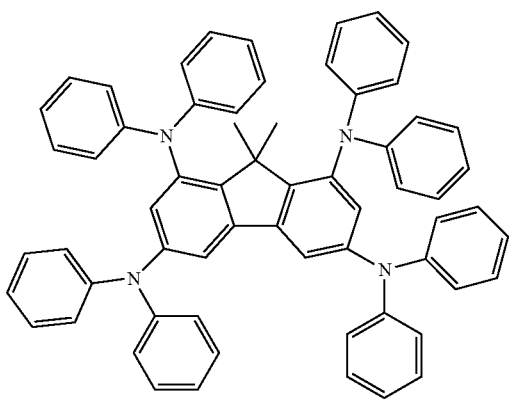

P-133
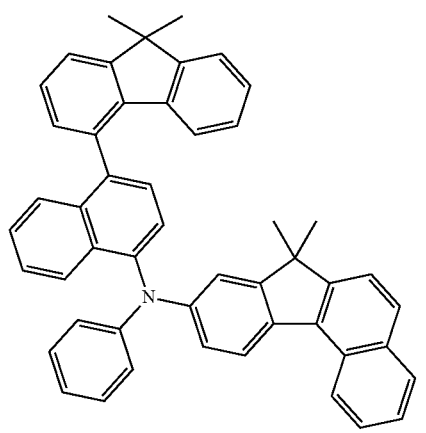
P-134
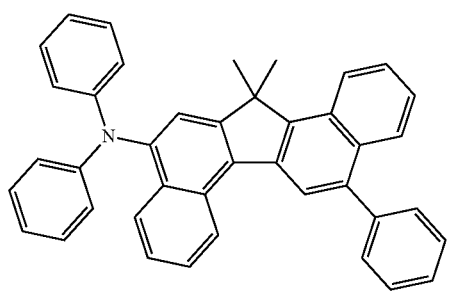
P-135
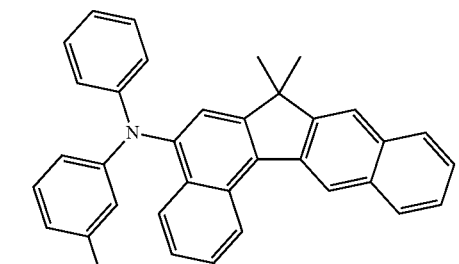
P-136
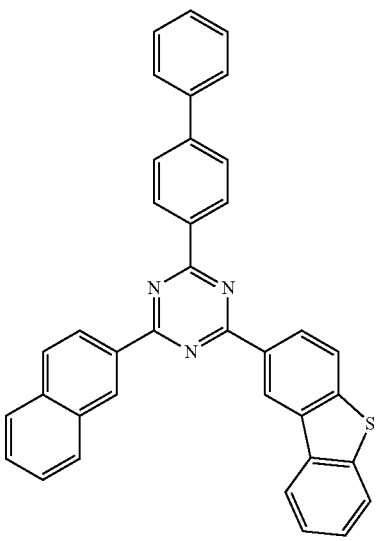
12. The organic electric element of claim 4, wherein the compound represented by Formula 12 is one of the following compounds:
P2-1
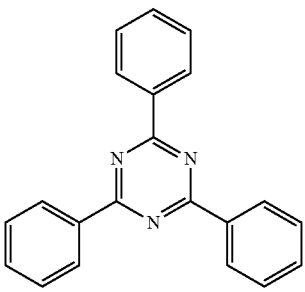
P2-2
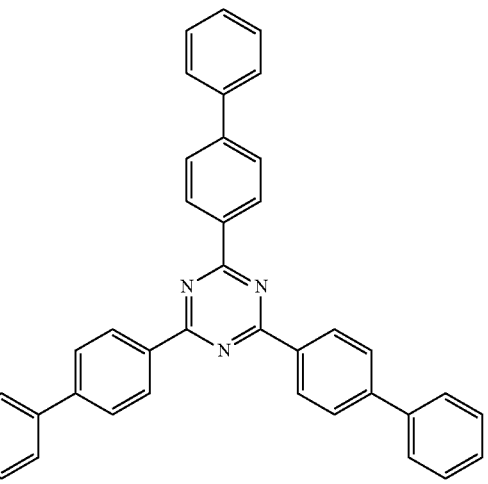
P2-3

P2-4
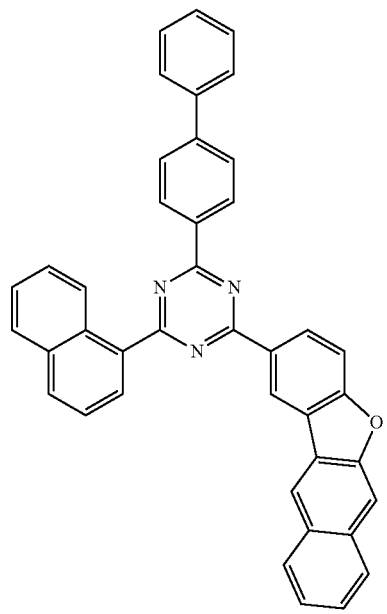
P2-7
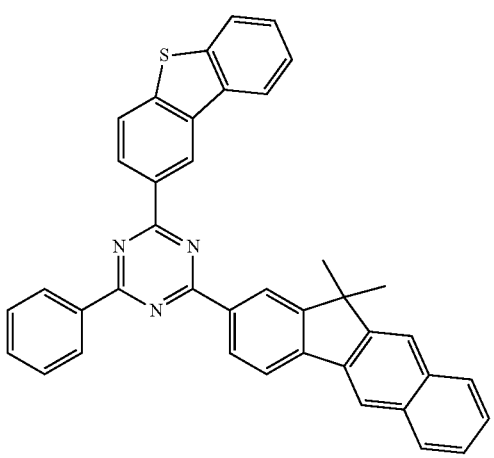
P2-4
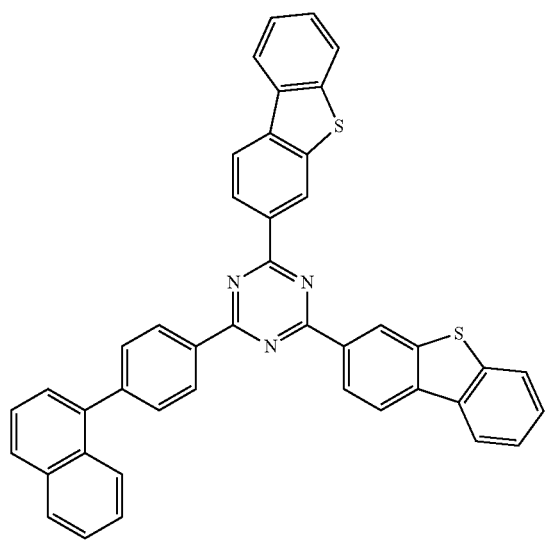
P2-8
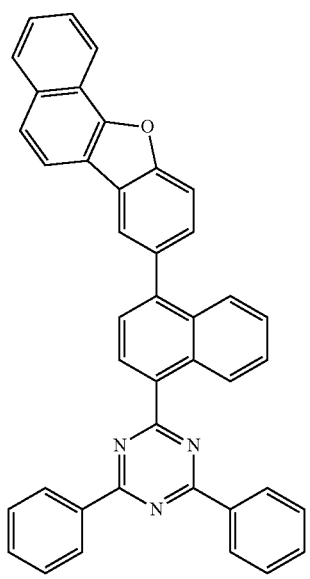
P2-6
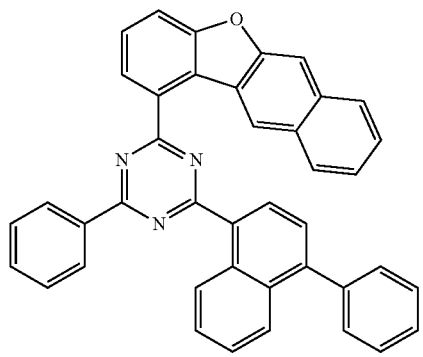
P2-9
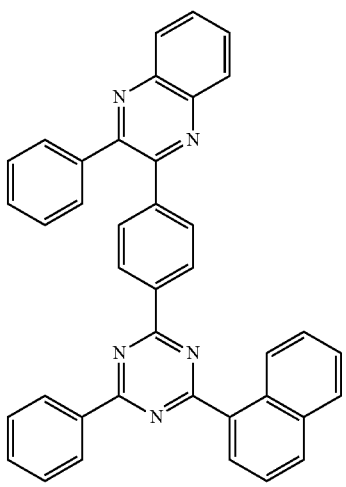

1p;2p
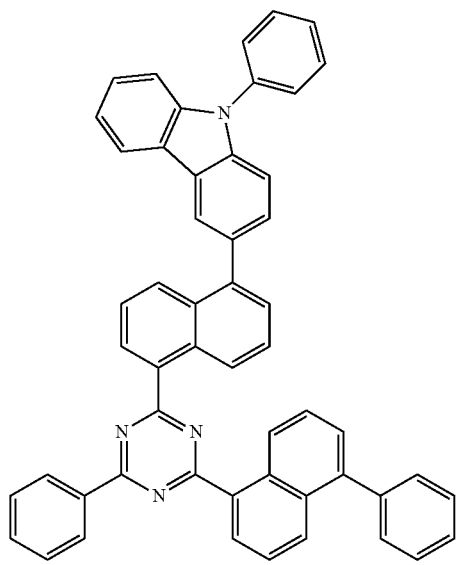
P2-11
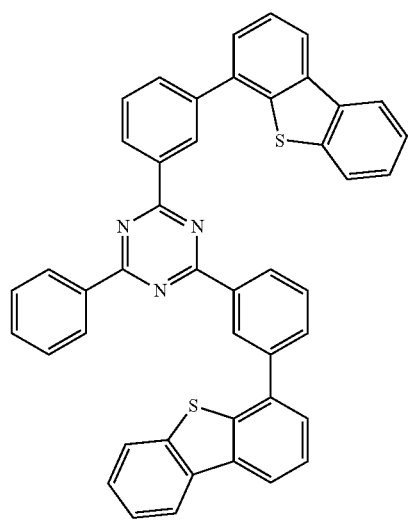
P2-10
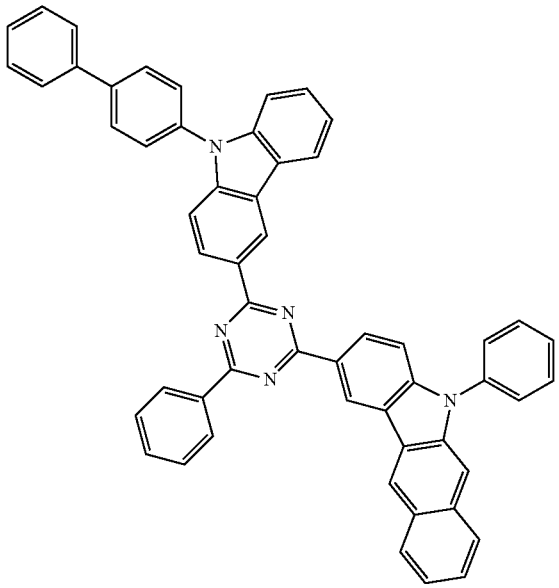
P2-12
P2-13
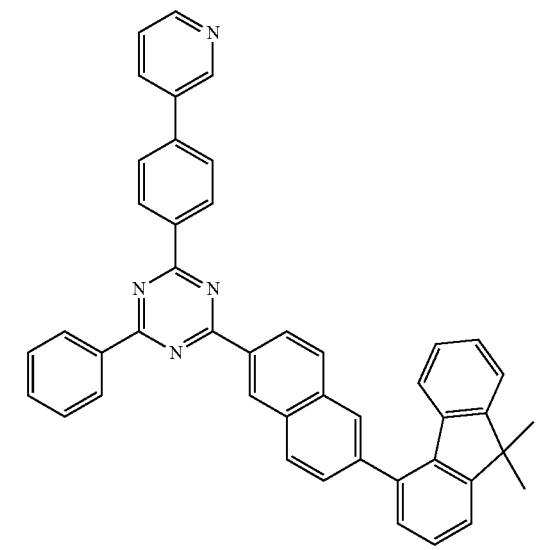
P2-14
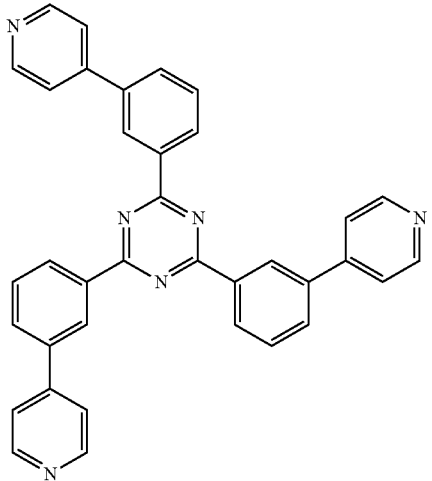

P2-15
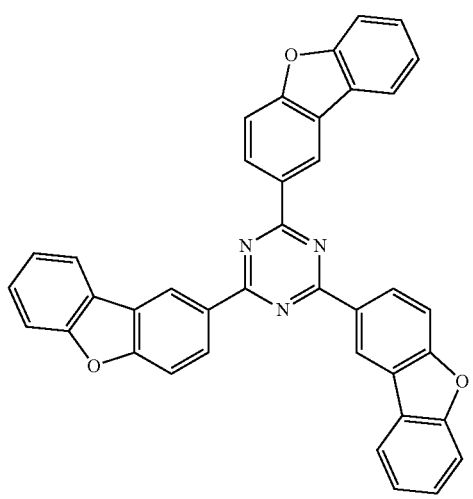
P2-18
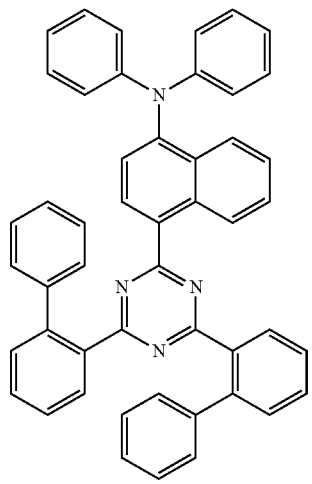
P2-16
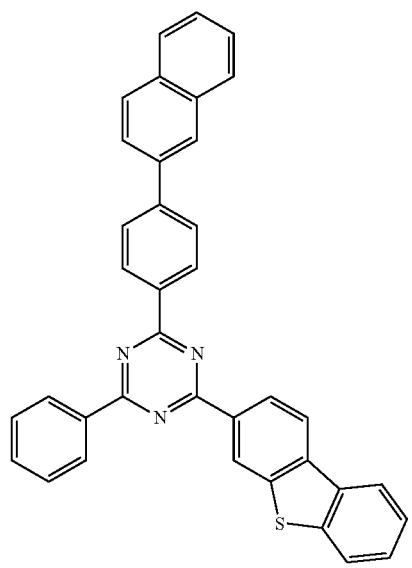
P2-19
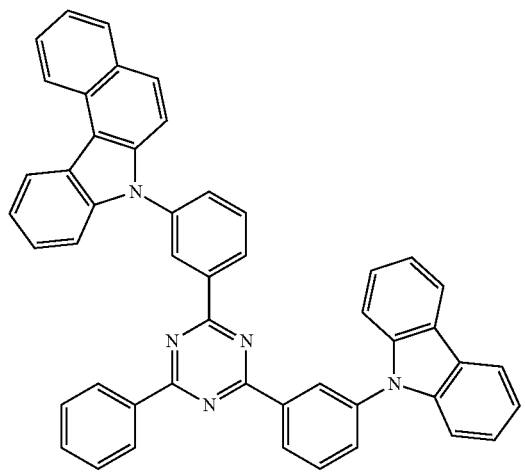
P2-17
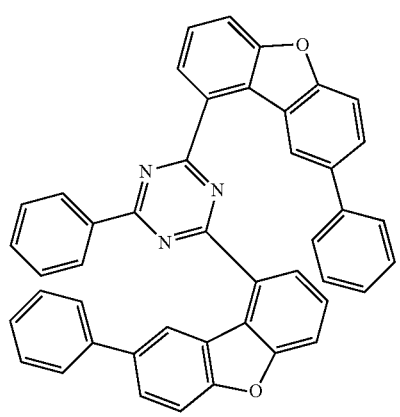
P2-20
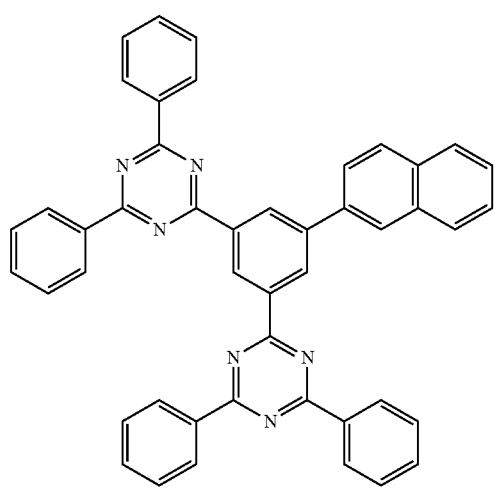

P2-21 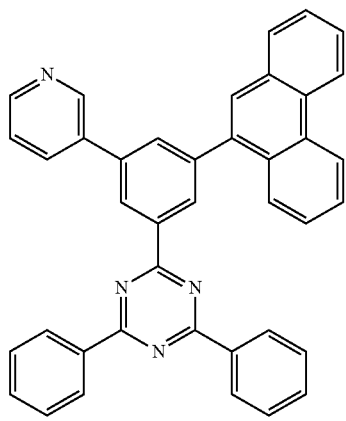
P2-24 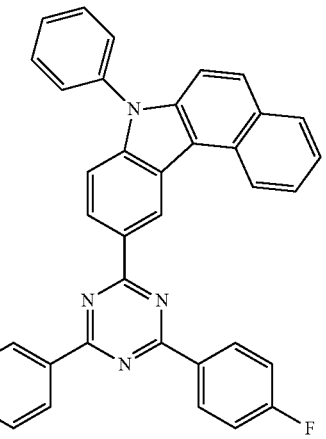
P2-22 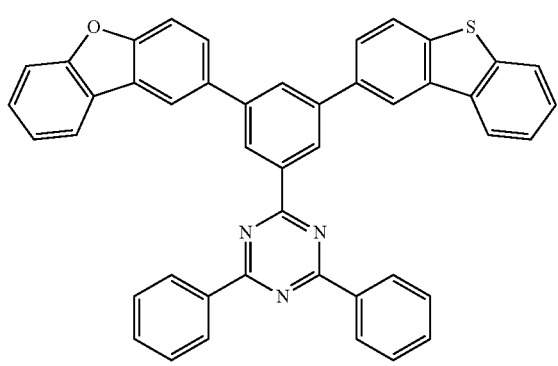
P2-25 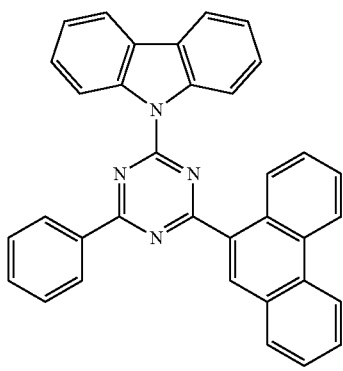
P2-23 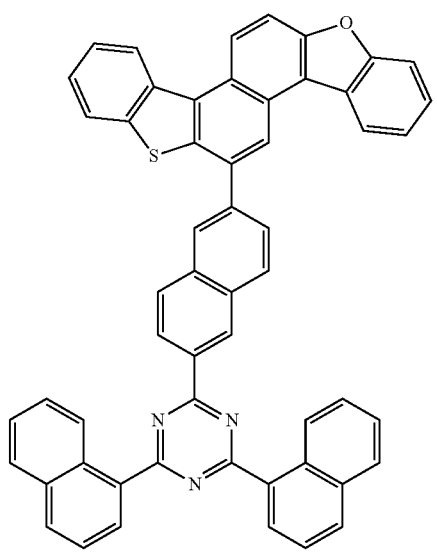
P2-26 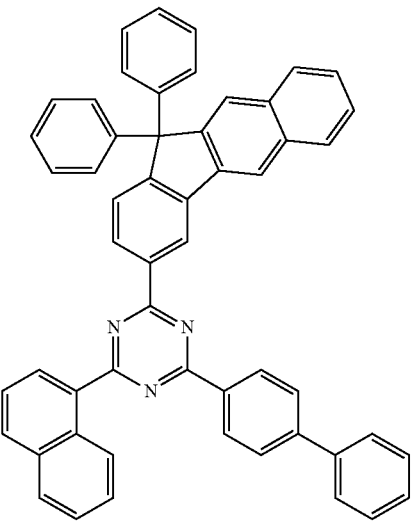

P2-27
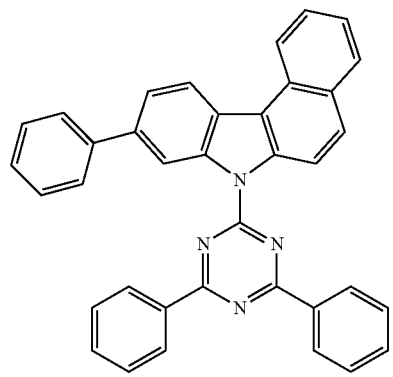
P2-31
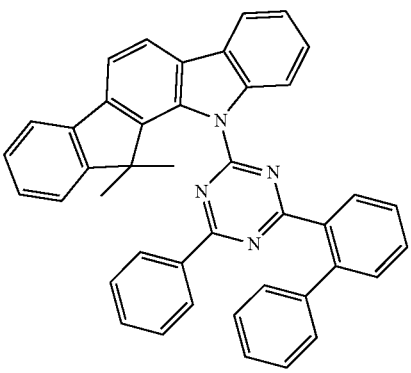
P2-28
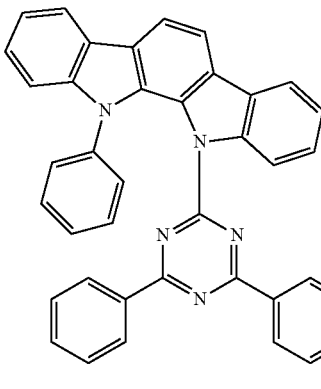
P2-32
P2-29
P2-33
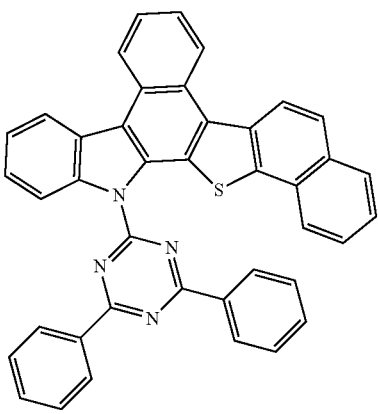
P2-30
P2-34
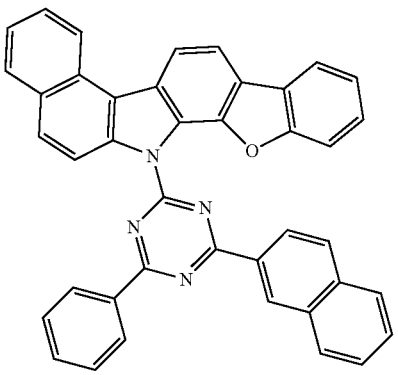

P2-35
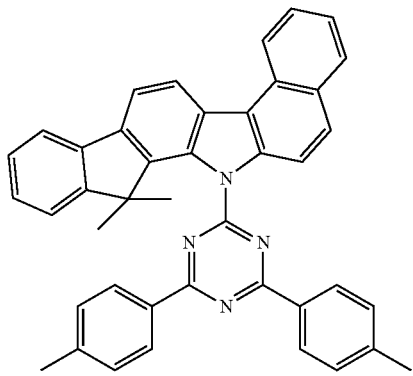
P2-36
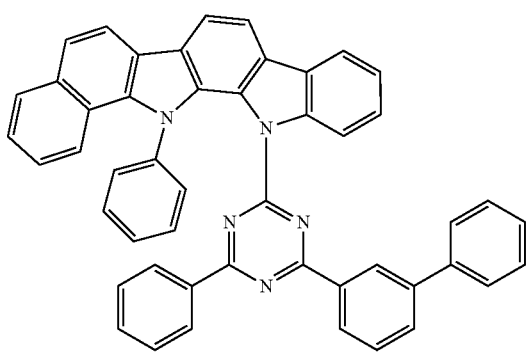
P2-37
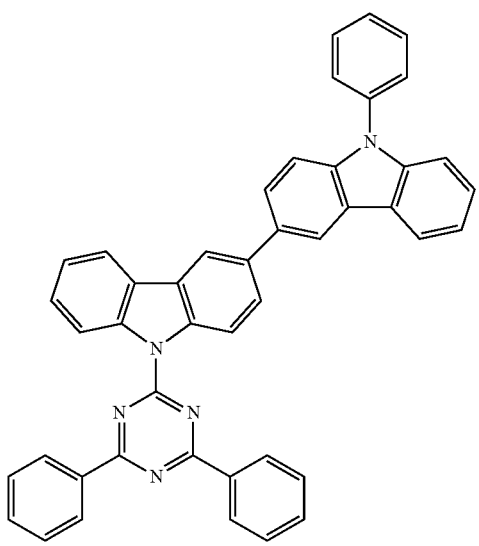
P2-38
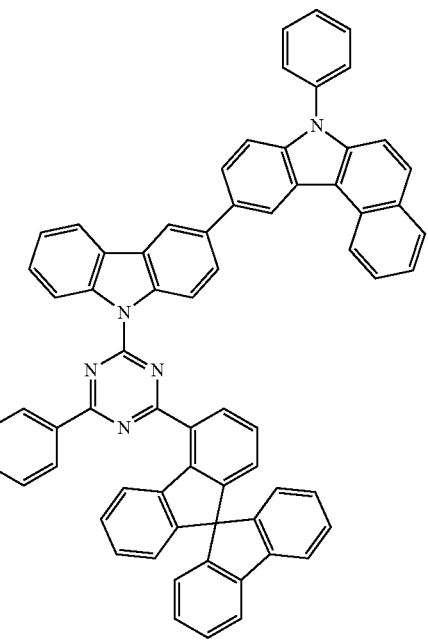
P2-39
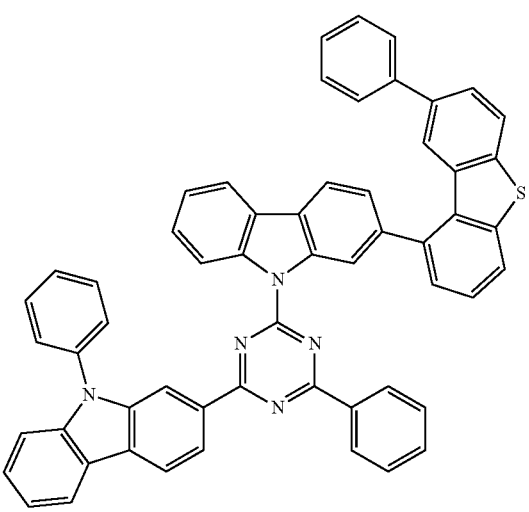

P2-40
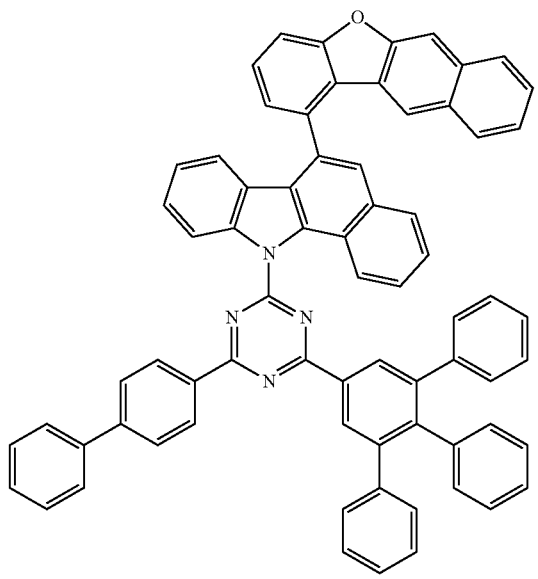
P2-41
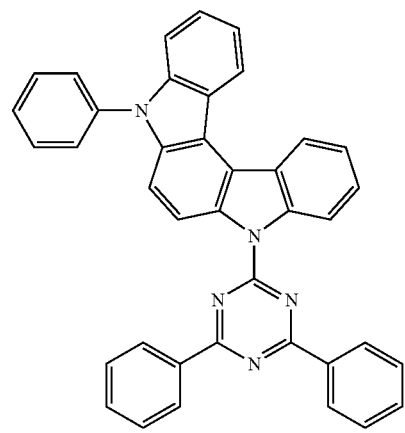
P2-42
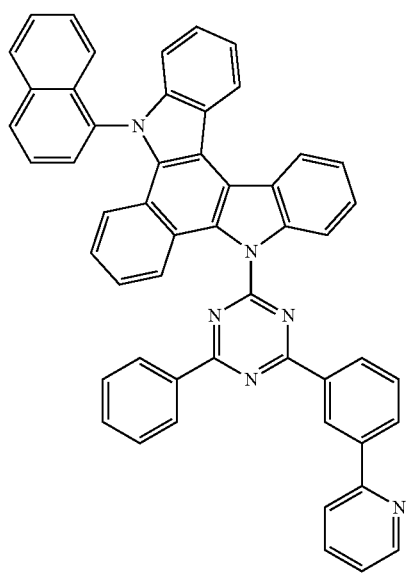
P2-43
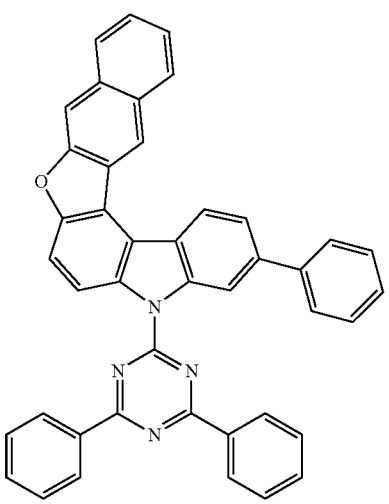
P2-44
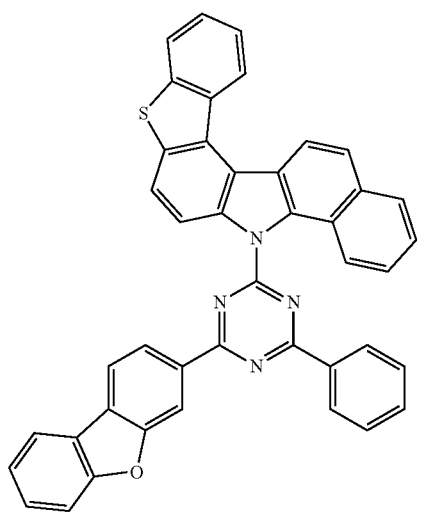
P2-45
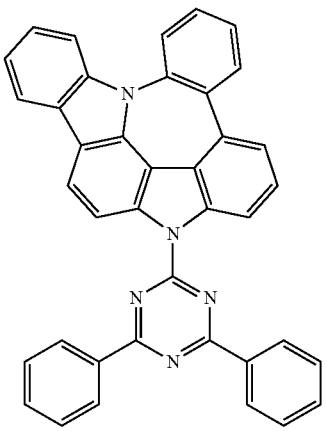

P2-46
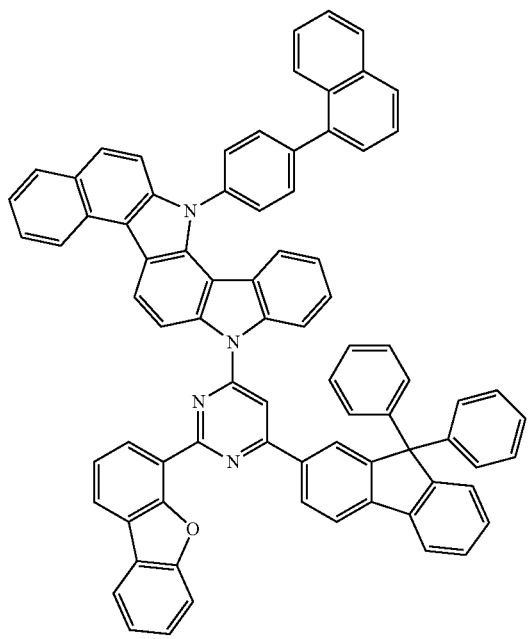
P2-47
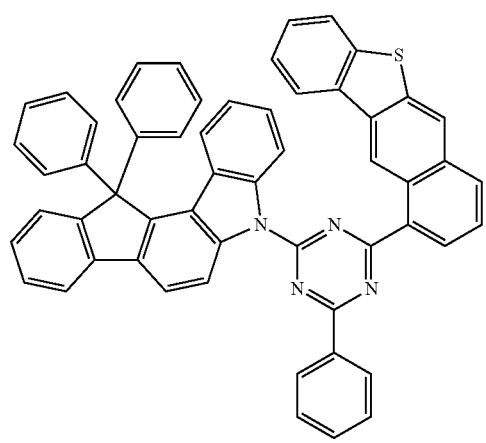
P2-48
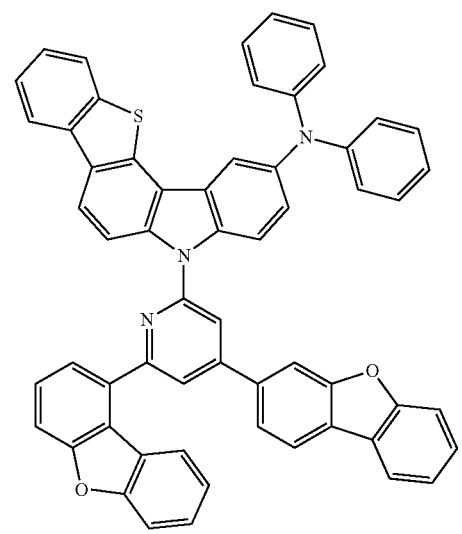
P2-49
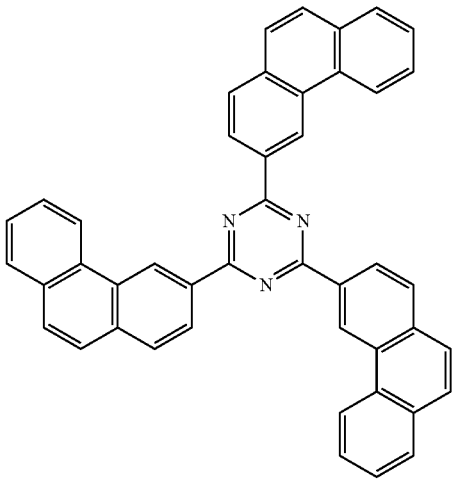
P2-50
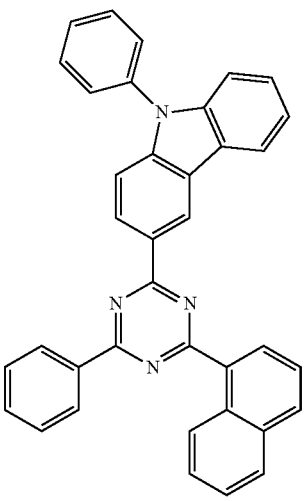
P2-51
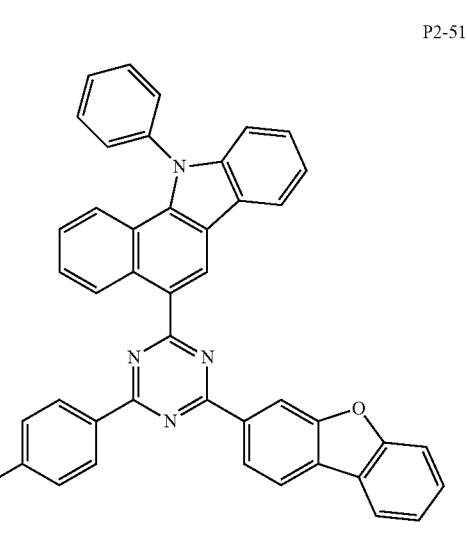

P2-52
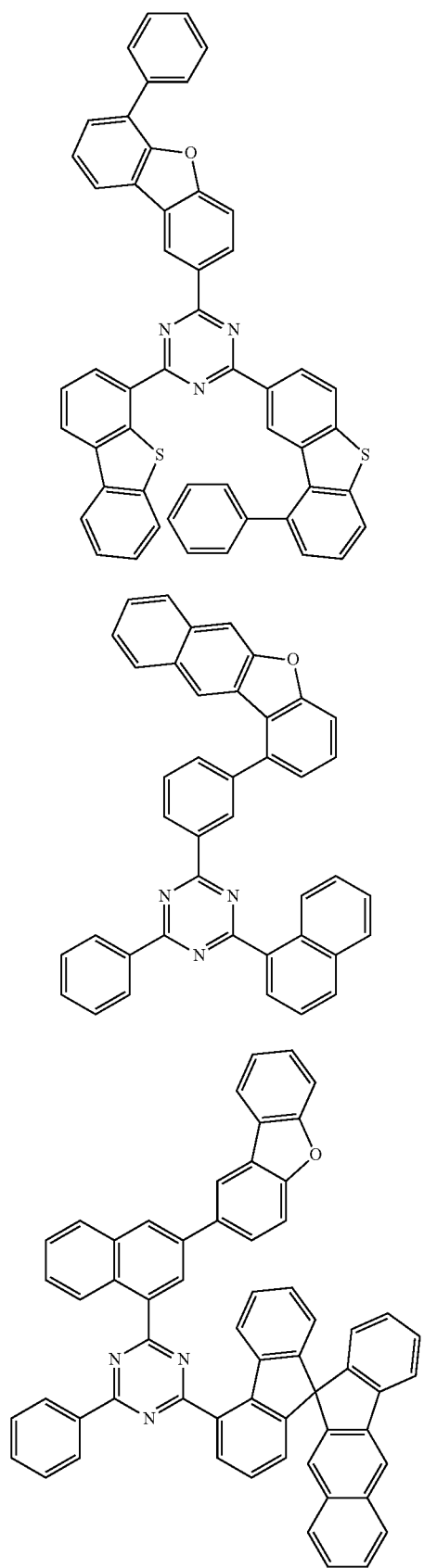
P2-53
P2-54
P2-55
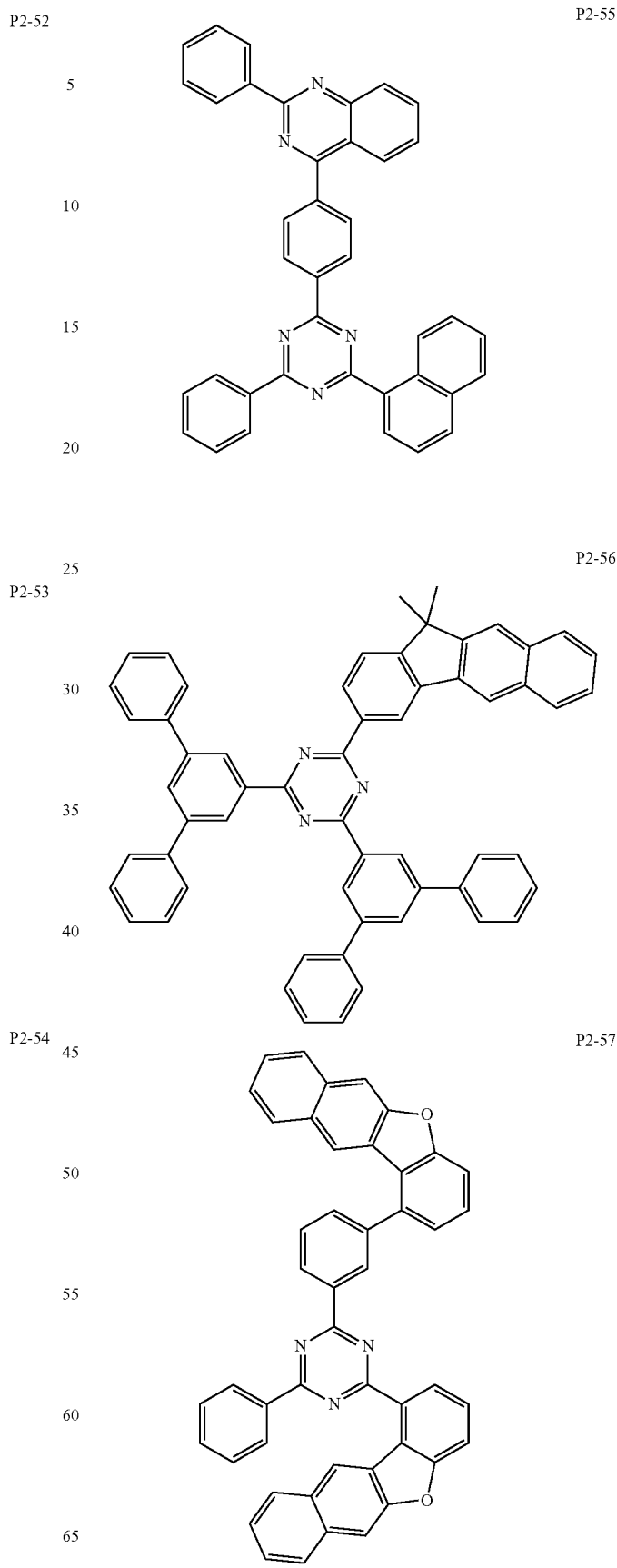
P2-56
P2-57

P2-58
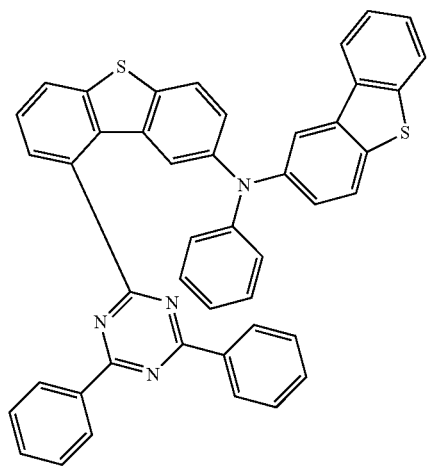
P2-59
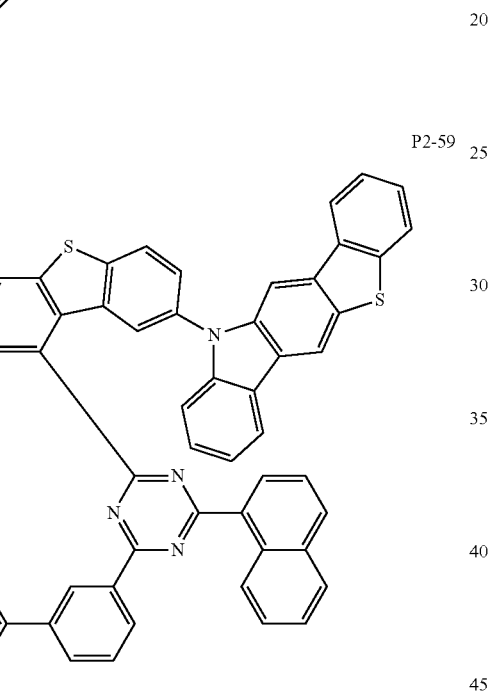
P2-60
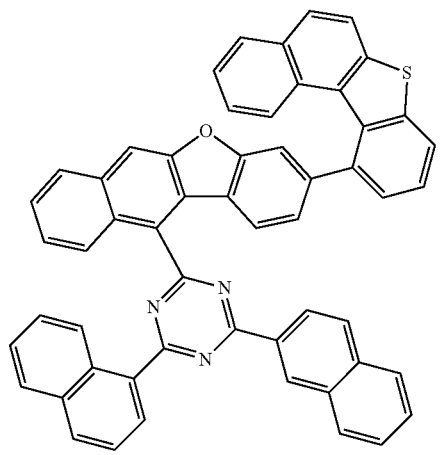
P2-61
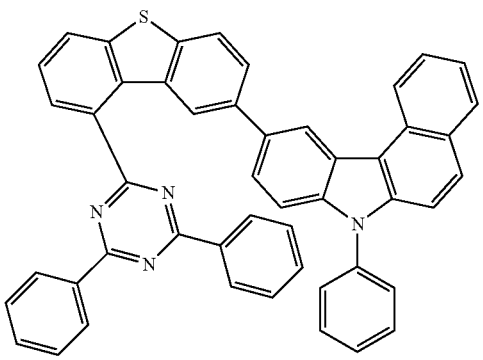
P2-62
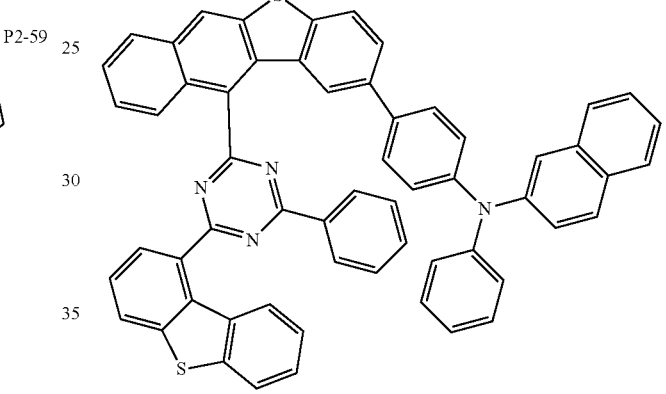
P2-63
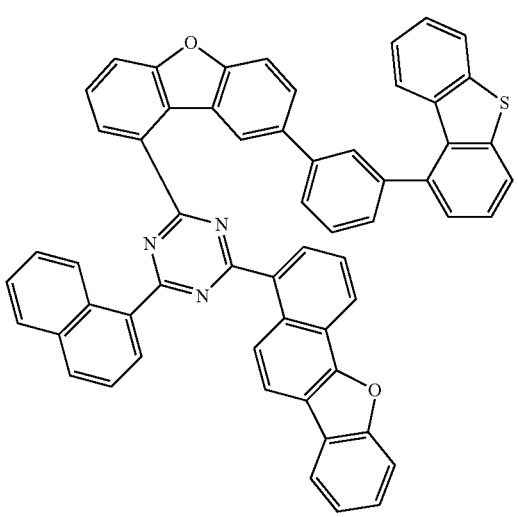

P2-64
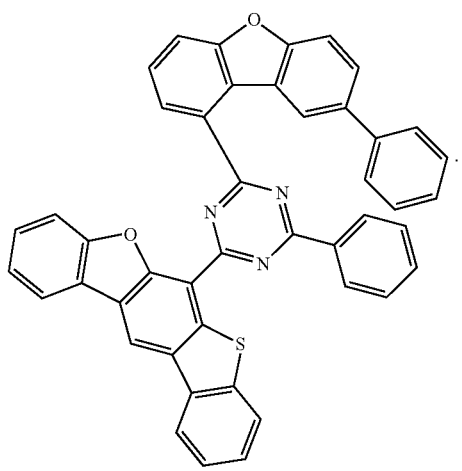
P2-67
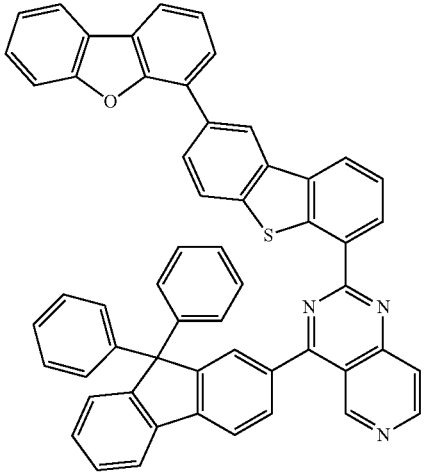
13. The organic electric element of claim 4, wherein the compound represented by Formula 13 is one of the following compounds:
P2-65
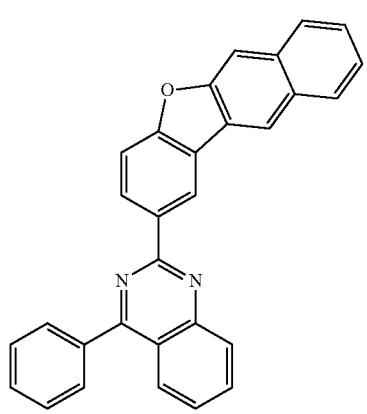
P2-68
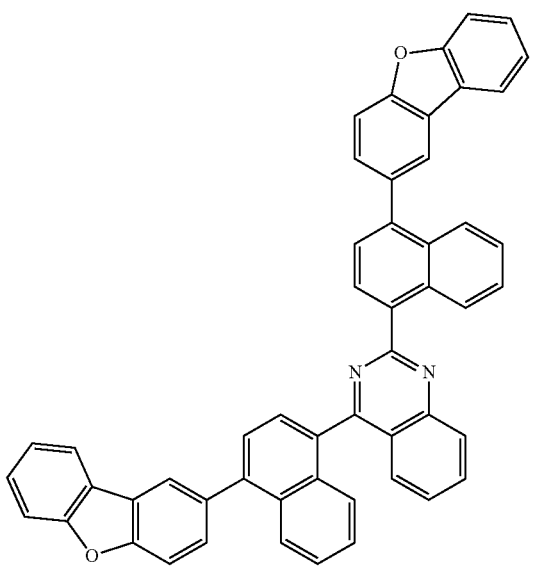
P2-66
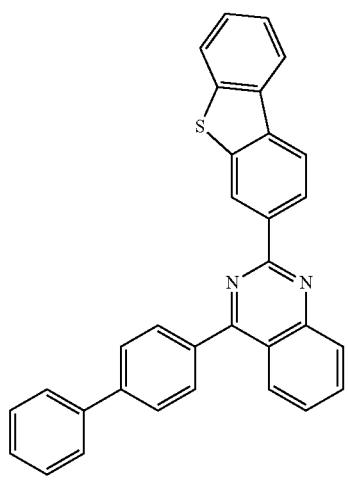
P2-69
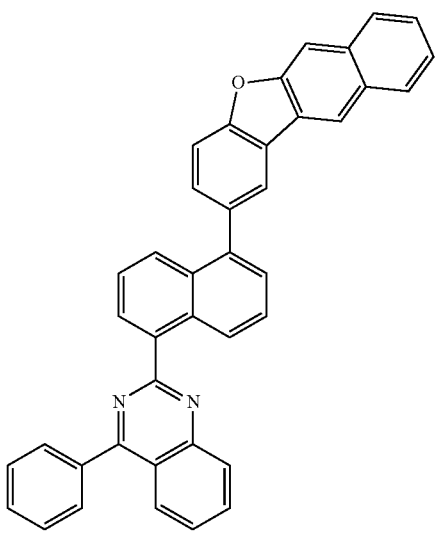

P2-70
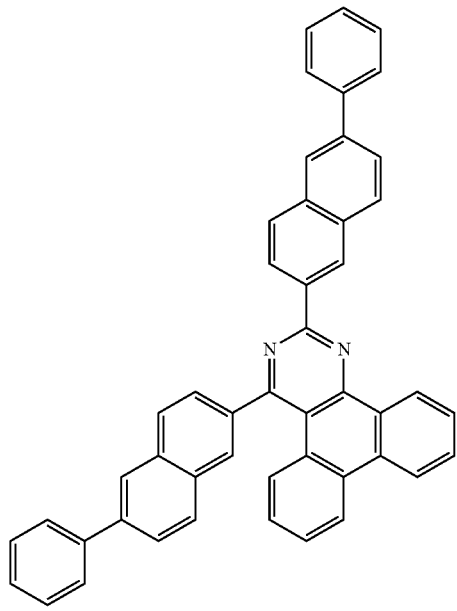
P2-71
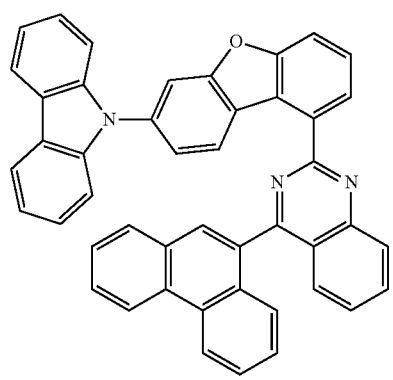
P2-72
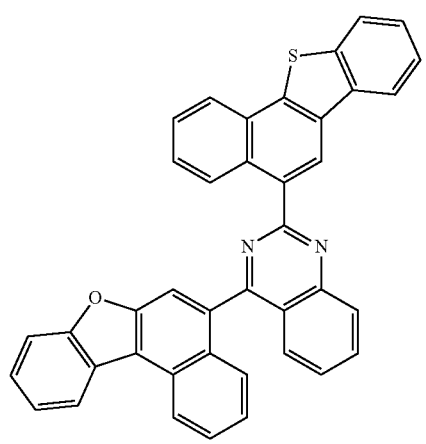
P2-73
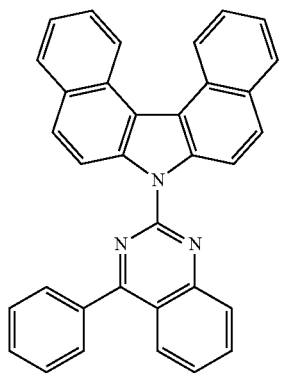
P2-74
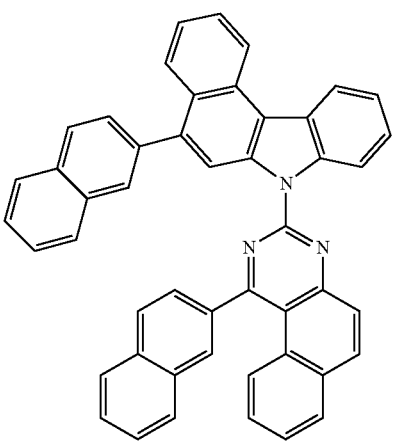
P2-75
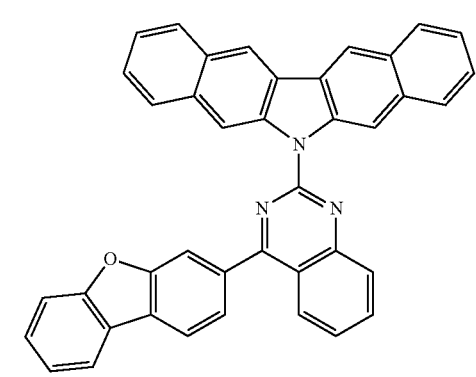
P2-76
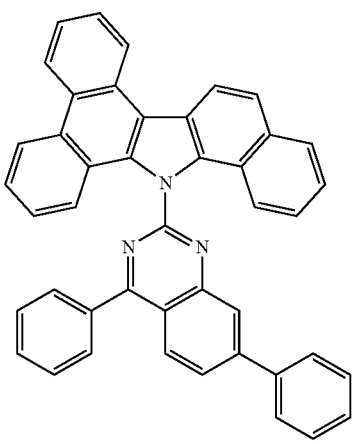

P2-77
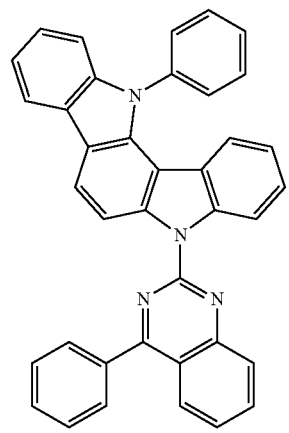
P2-78
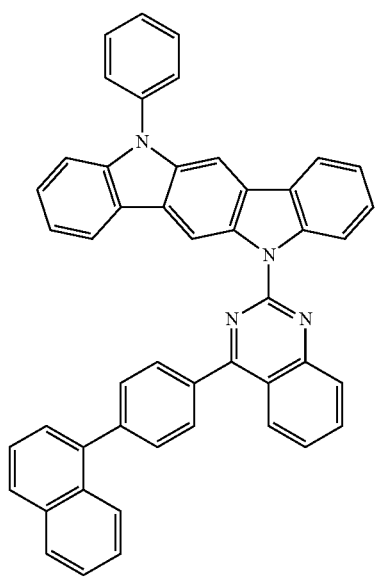
P2-79
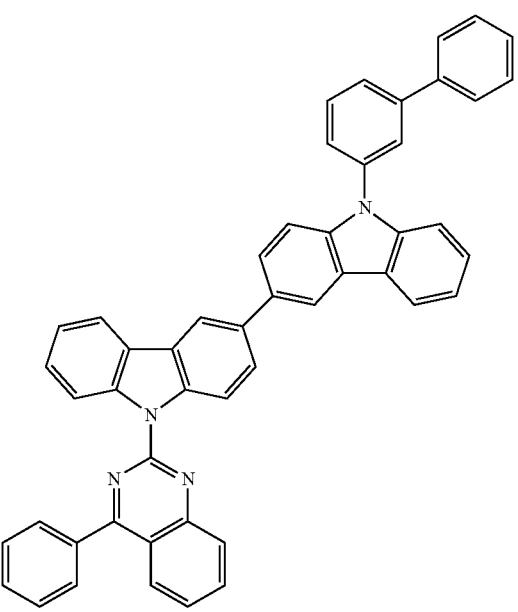
P2-80
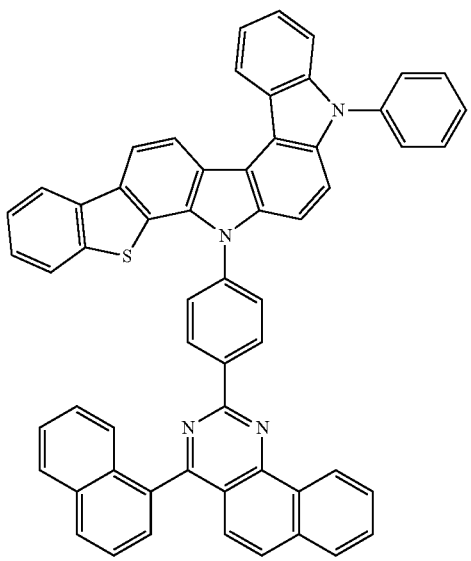
P2-81

213
-continued
P2-82
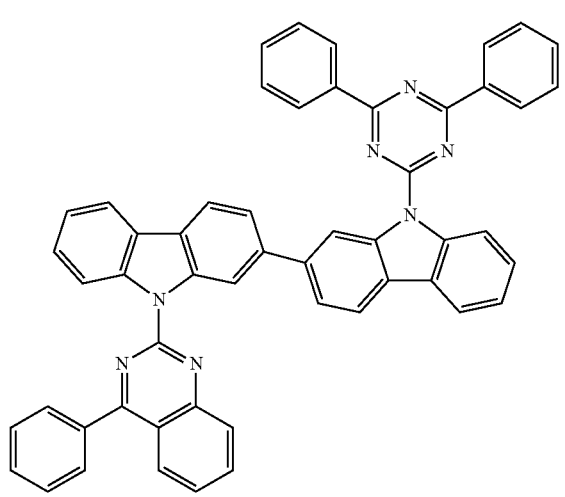
P2-83
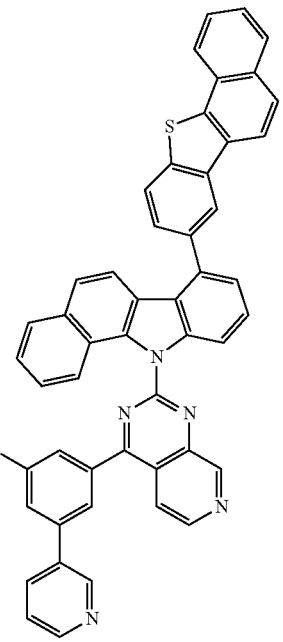
P2-84
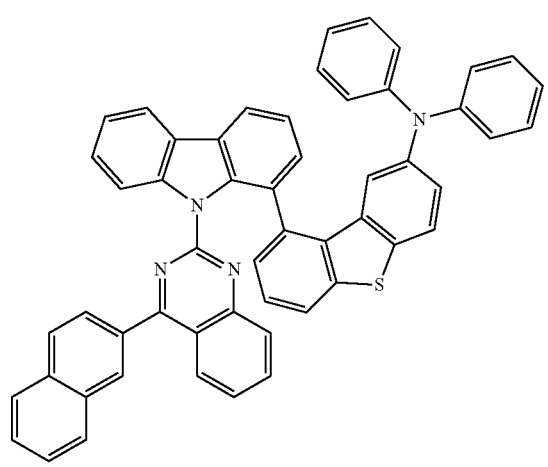
214
-continued
P2-85
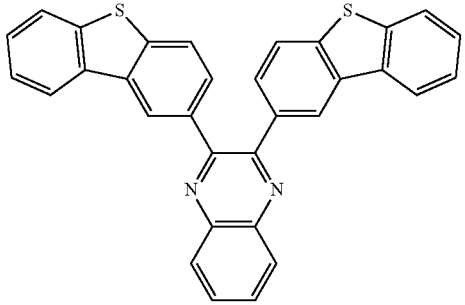
P2-86
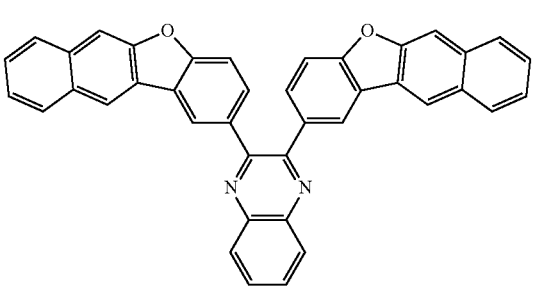
P2-87
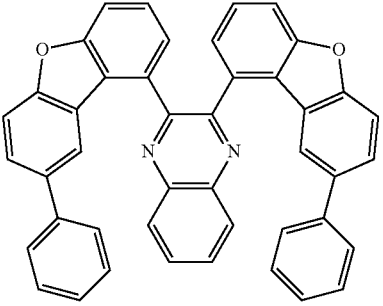
P2-88
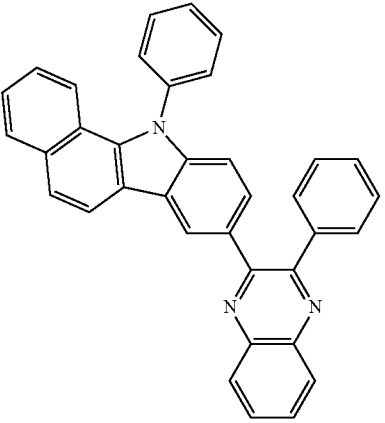

P2-89
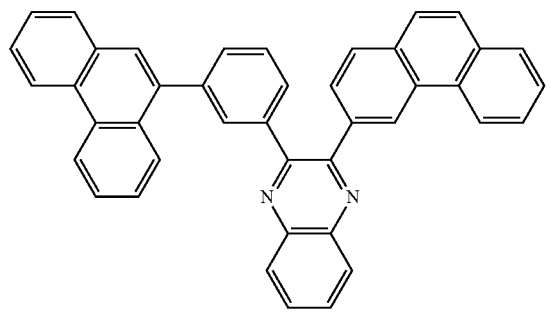
P2-90
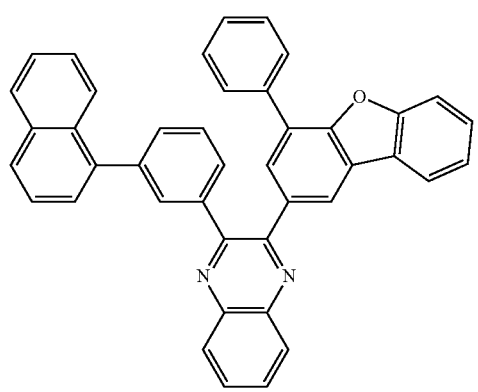
P2-91
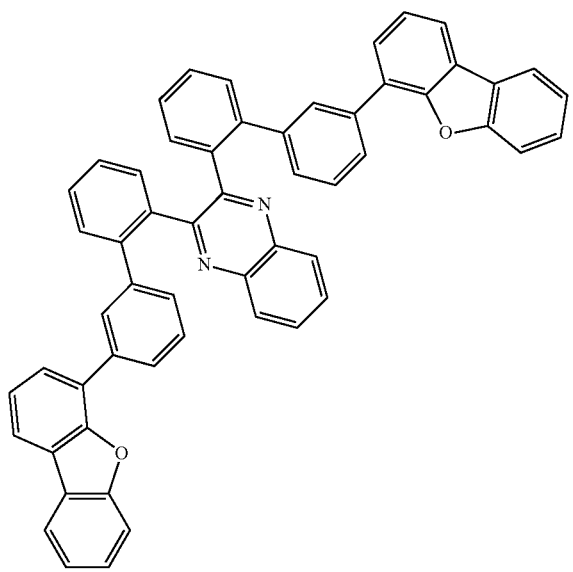
P2-92
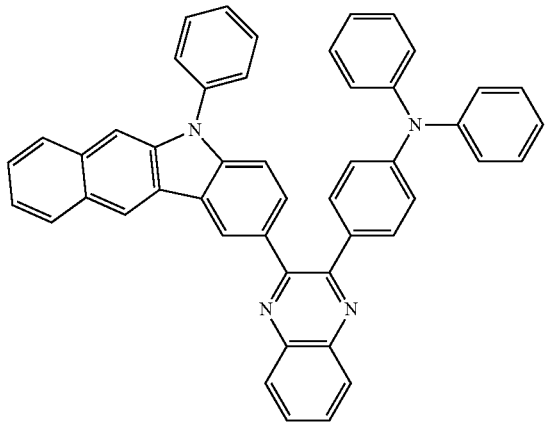
P2-93
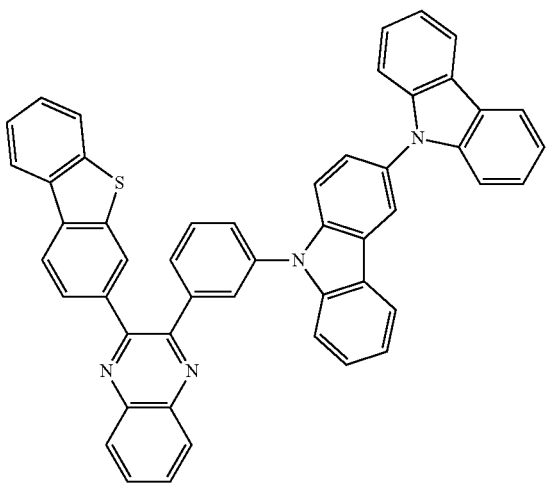
P2-94
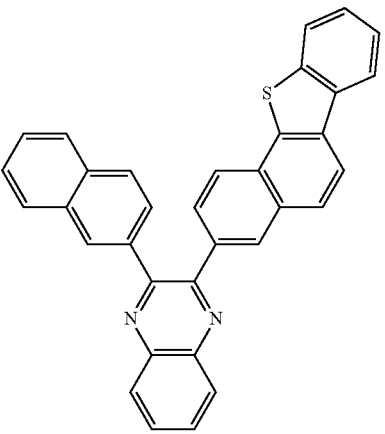

-continued
P2-95
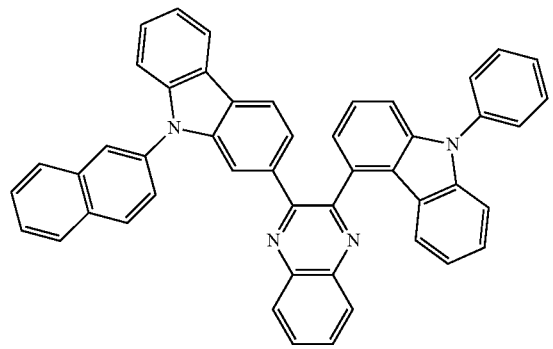
P2-96
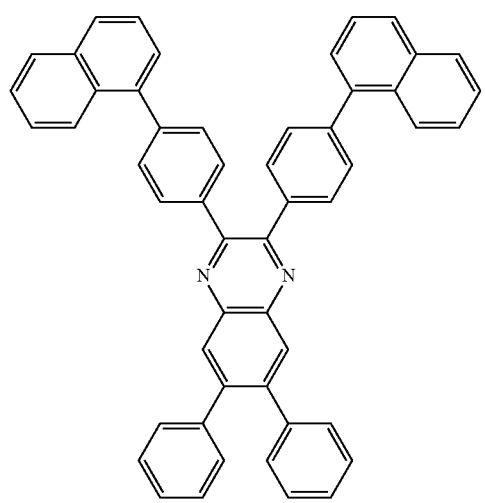
P2-97
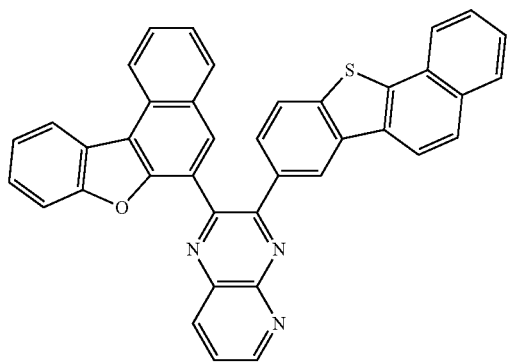
-continued
P2-98
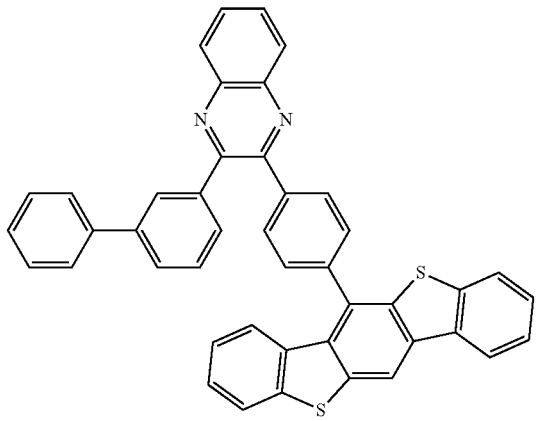
P2-99
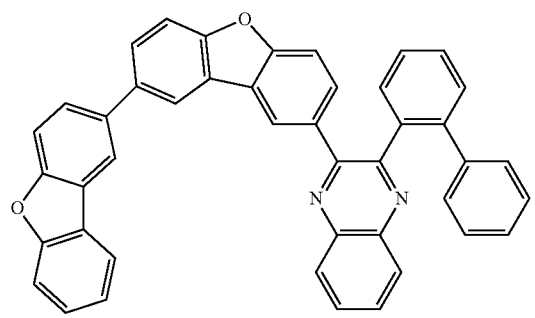
P2-100
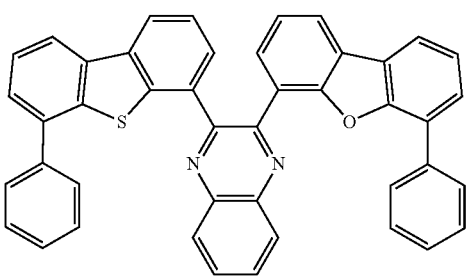
P2-101
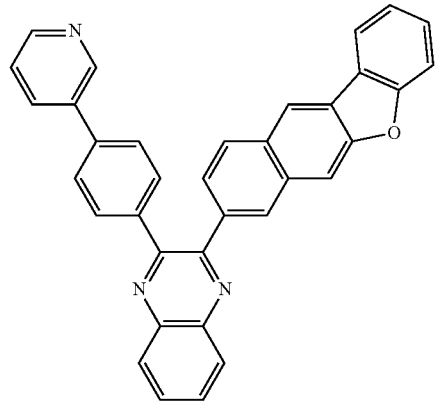

P2-102
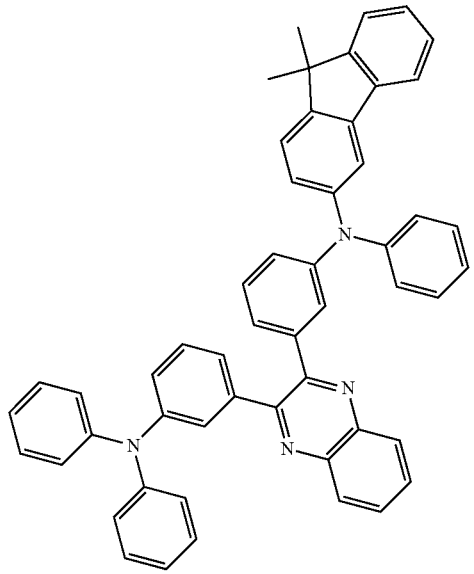
P2-103
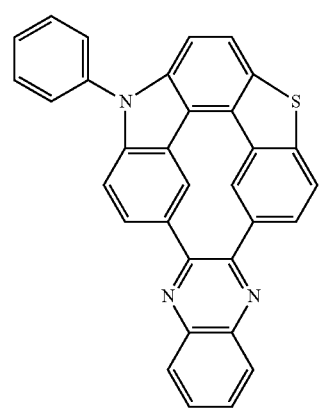
P2-104
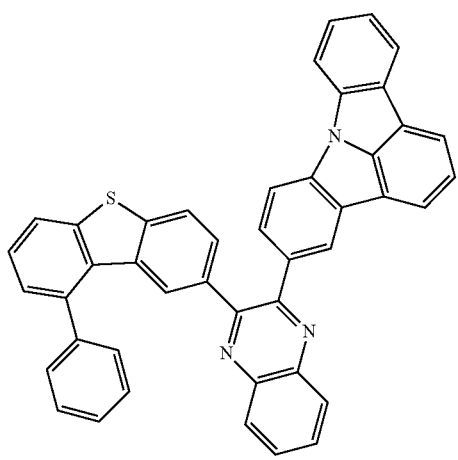
P2-105
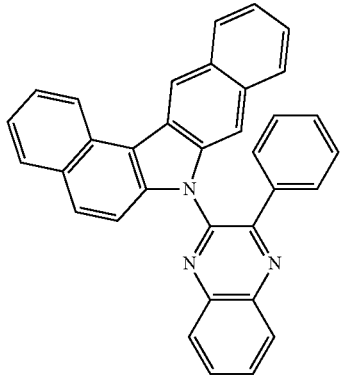
P2-106
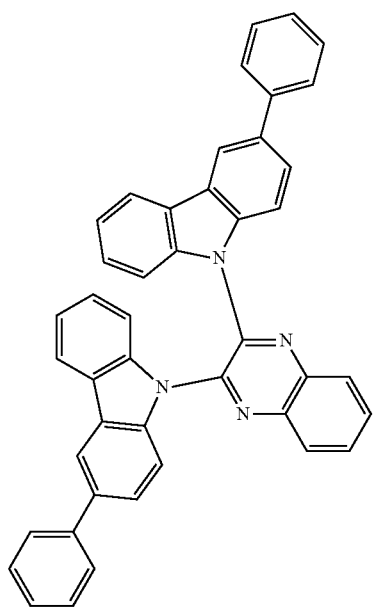
P2-107
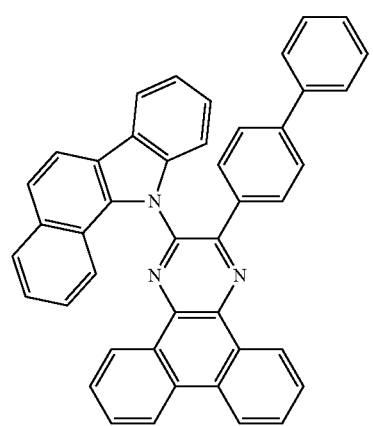

P2-108
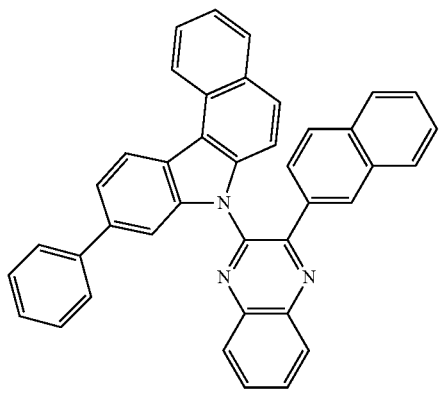
P2-109
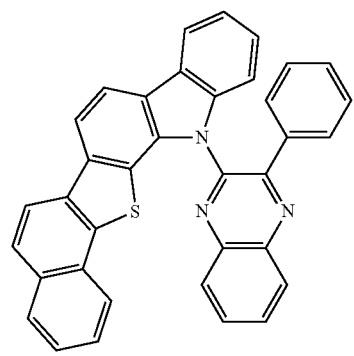
P2-110
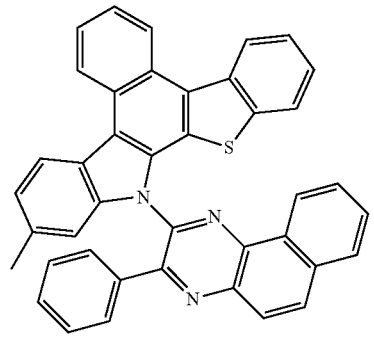
P2-111
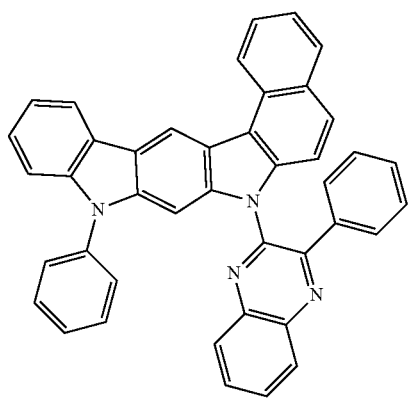
P2-112
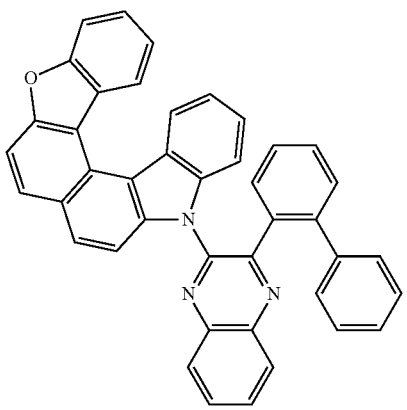
P2-113
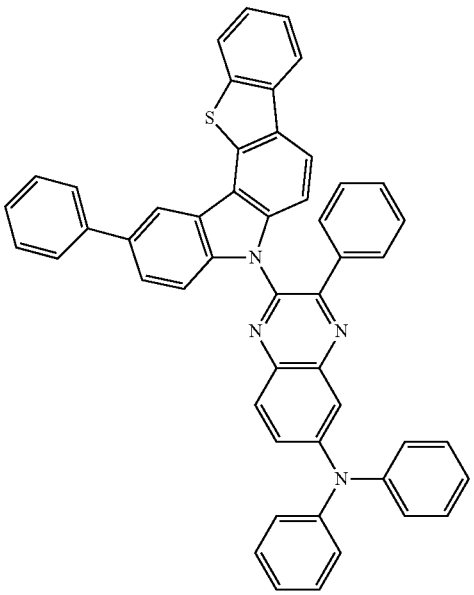
P2-114
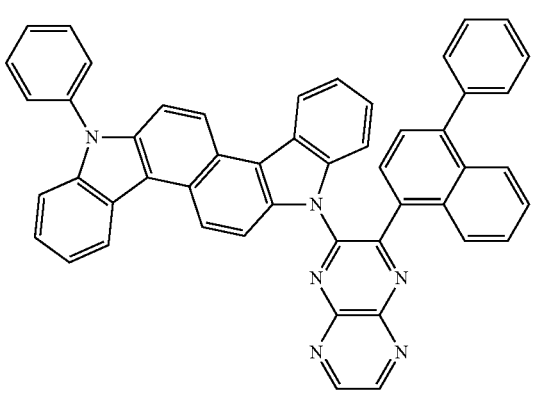

-continued
P2-115
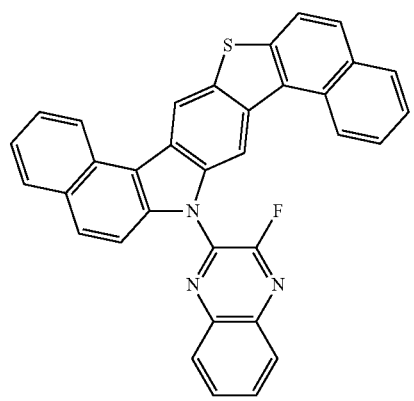
P2-116
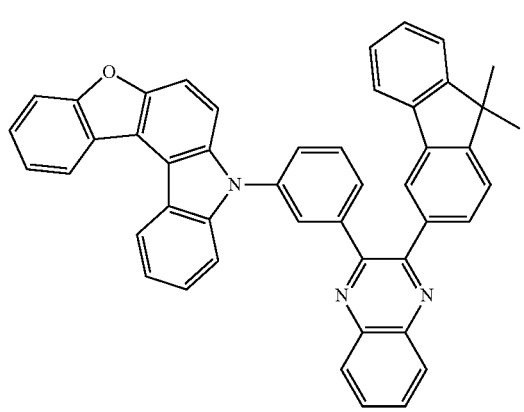
P2-117
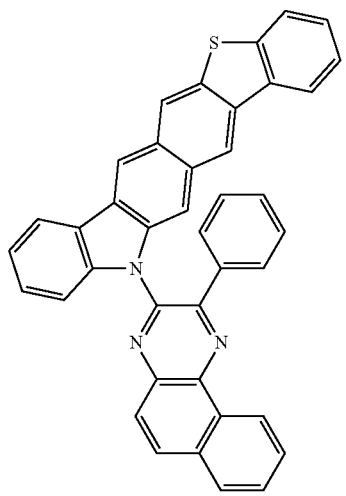
-continued
P2-118
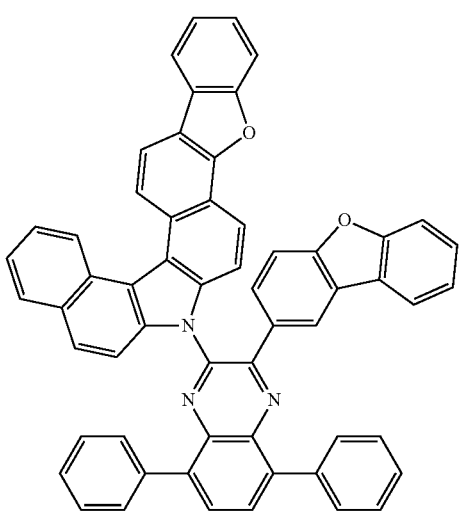
P2-119
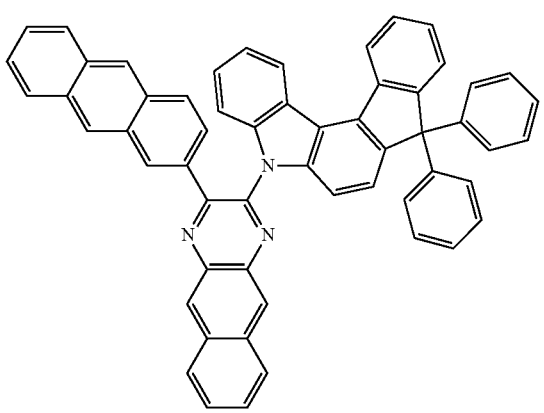
P2-120
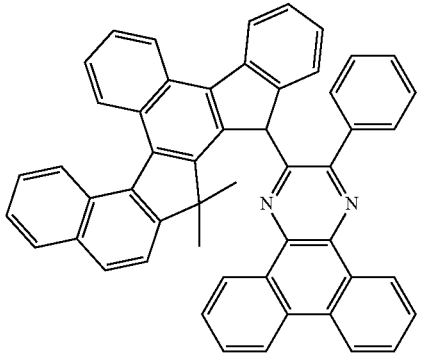

-continued
P2-121
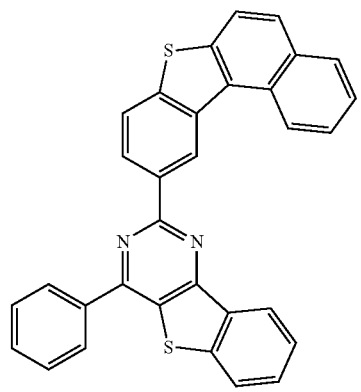
P2-122
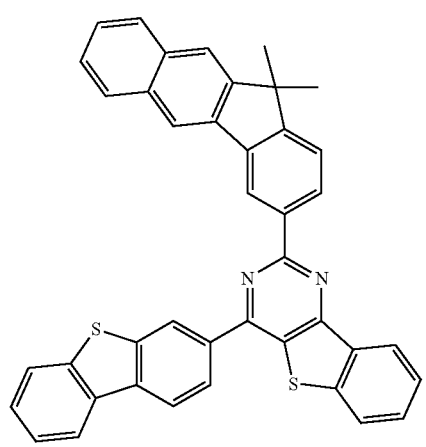
P2-123
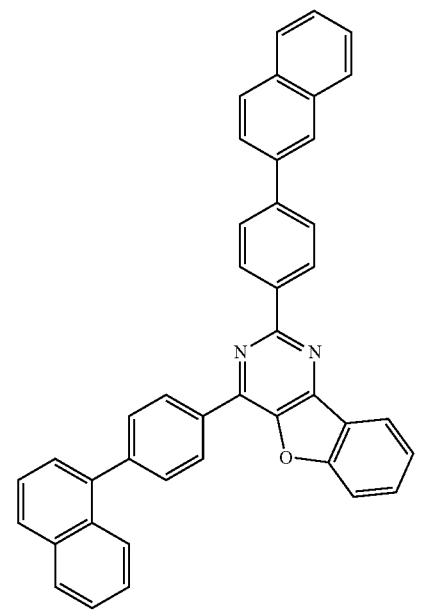
-continued
P2-124
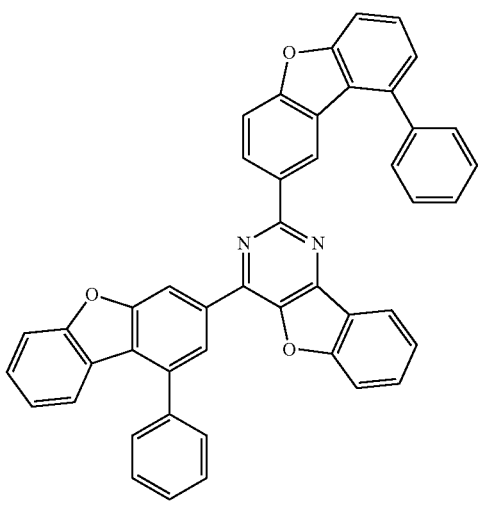
P2-125
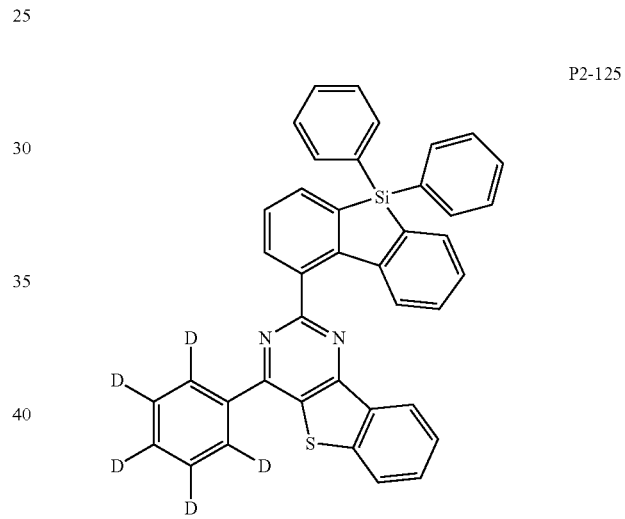
P2-126
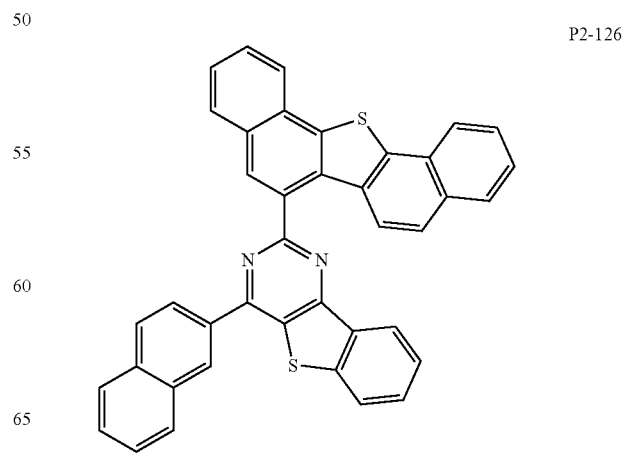

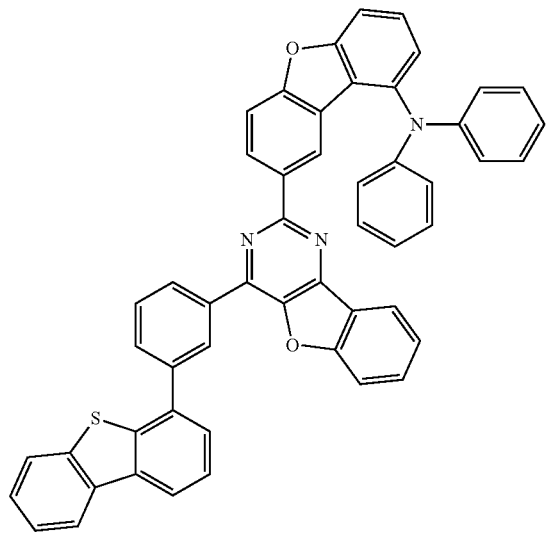
P2-127
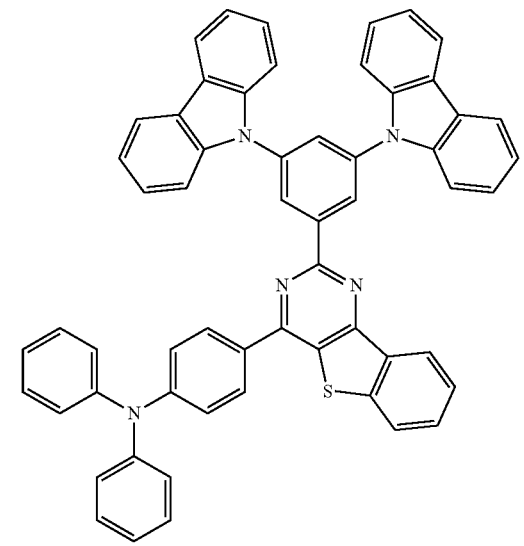
P2-130
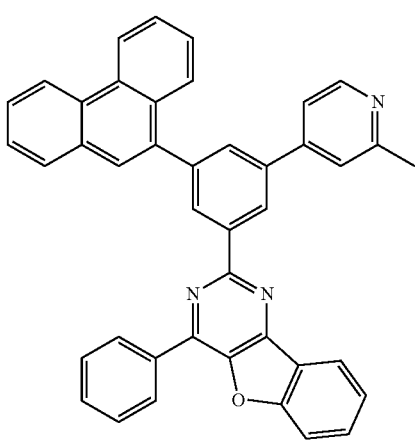
P2-128
P2-131
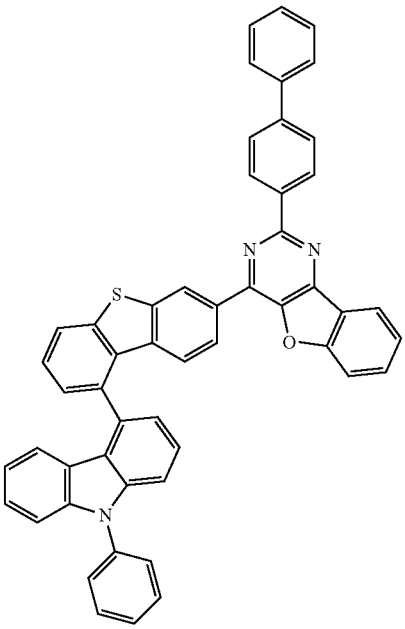
P2-129
P2-132

P2-133
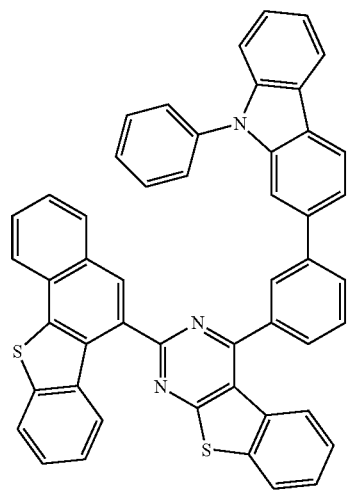
P2-134
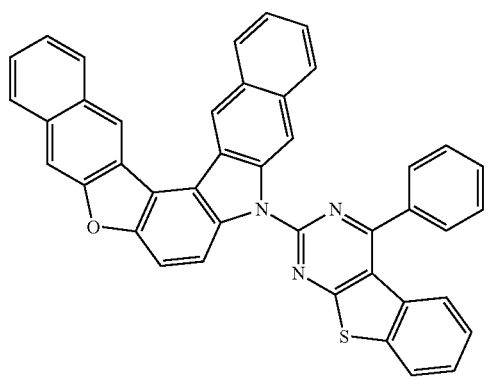
P2-135
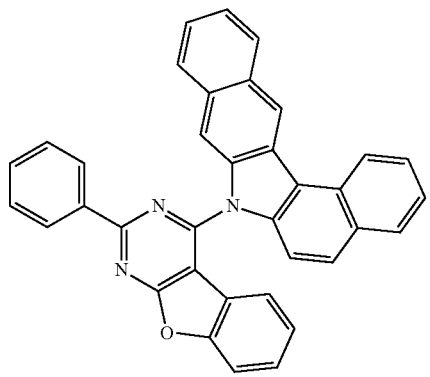
P2-136
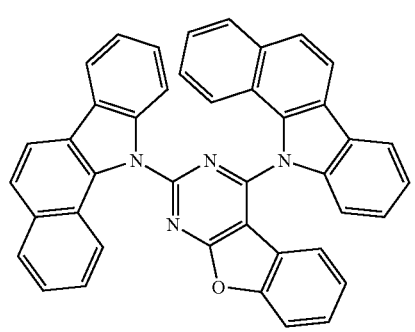
P2-137
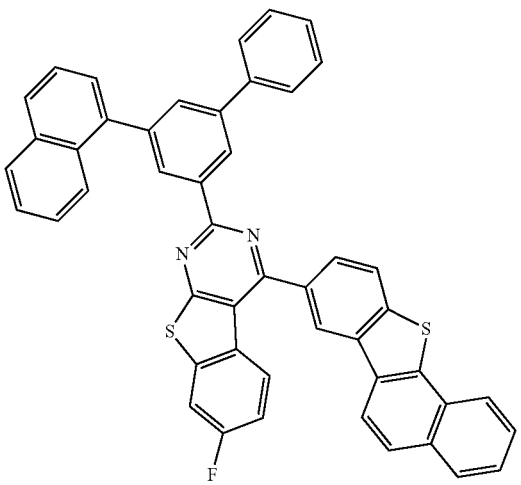
P2-138
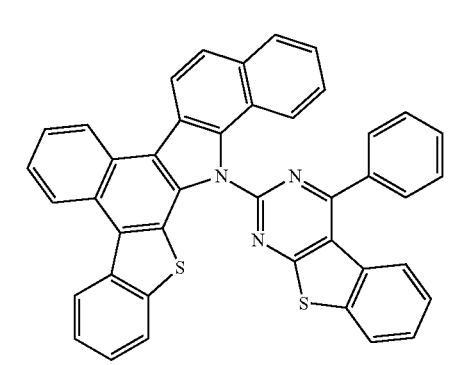
P2-139
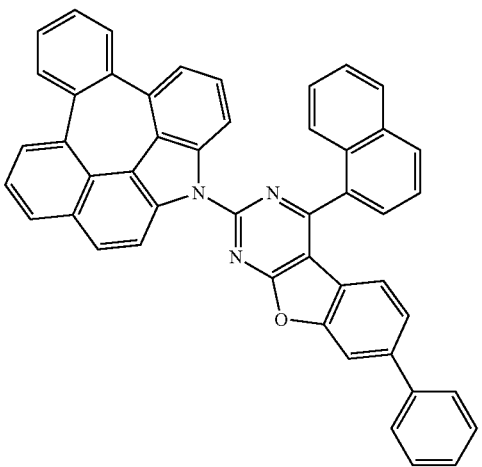

-continued
P2-140
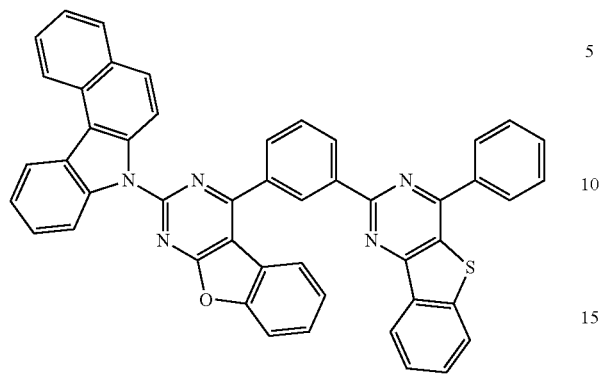
P2-141
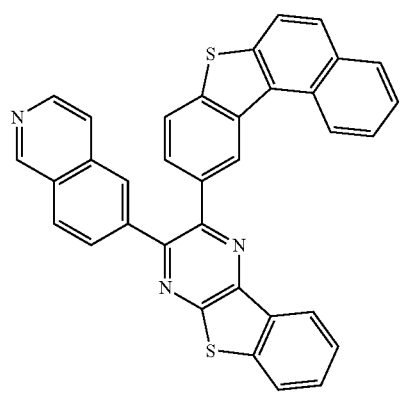
P2-142
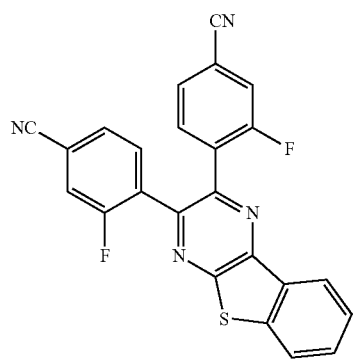
P2-143
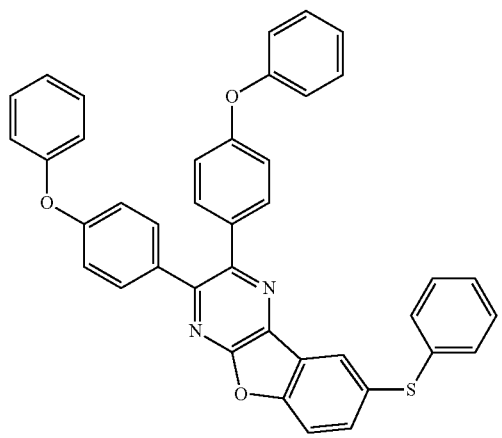
P2-144
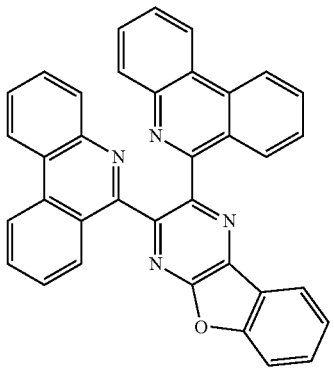
P2-145
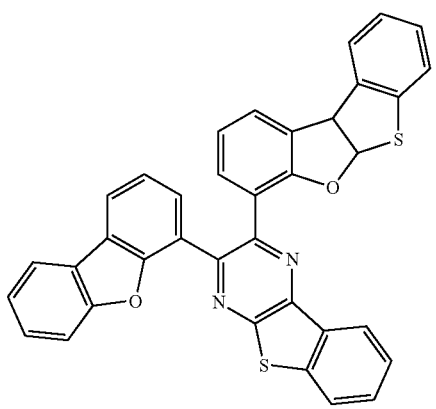
P2-146
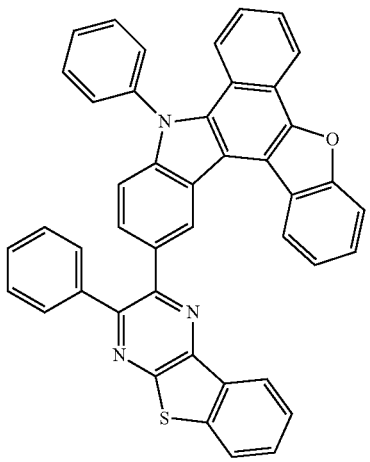

P2-147
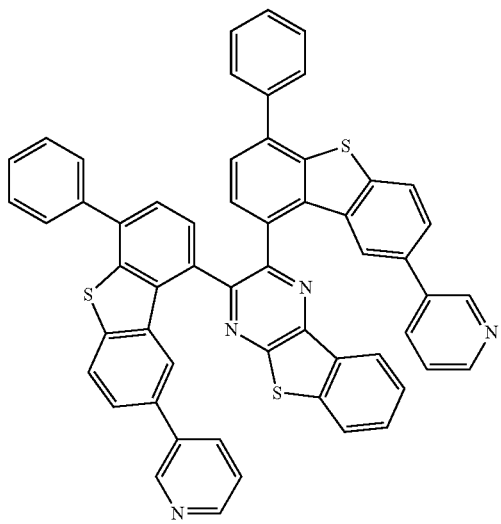
P2-148
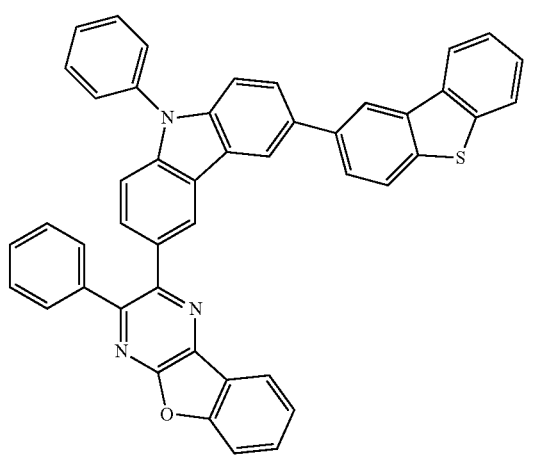
P2-149
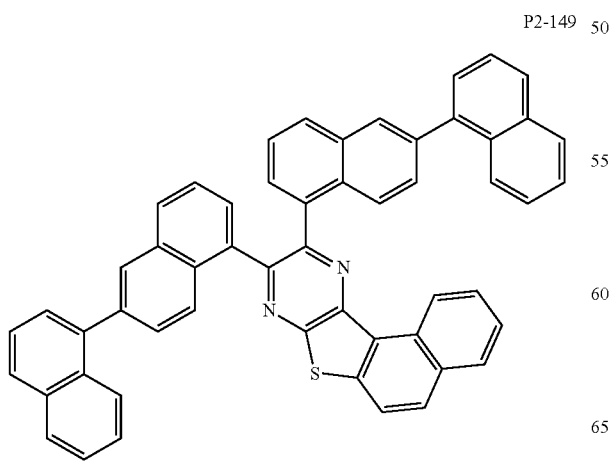
P2-150
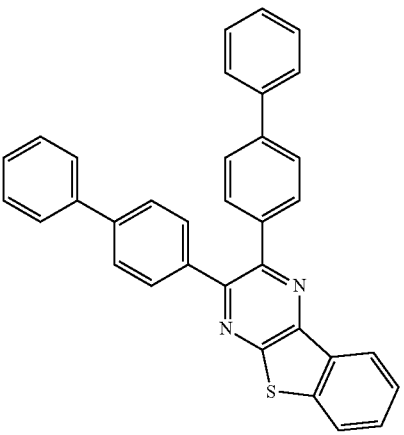
P2-151
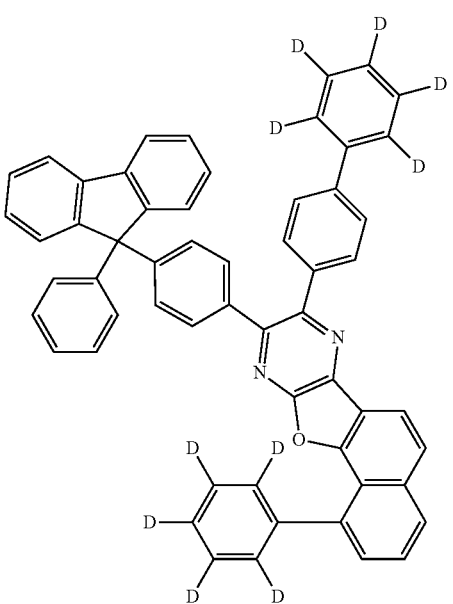

-continued

P2-152

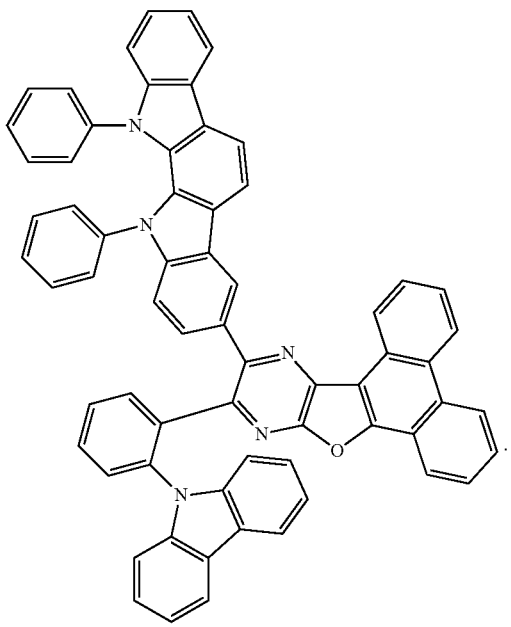

14. An organic electric element, comprising:
an anode;
a cathode; and
an organic material layer formed between the anode and the cathode, the organic material layer comprising:
a light emitting layer;
a hole transport layer formed between the light emitting layer and the anode; and
an emission-auxiliary layer formed between the hole transport layer and the light emitting layer,
wherein the hole transport layer, the emission-auxiliary layer and the light emitting layer comprise a compound of Formula 1, respectively:

[Formula 1]

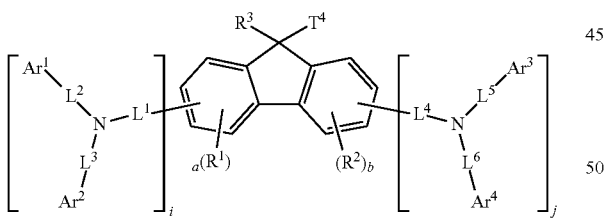

wherein:
$R^1$ and $R^2$ are each independently selected from the group consisting of hydrogen, deuterium, halogen, a cyano group, a nitro group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a $C_1$-$C_{30}$ alkyl group, a $C_2$-$C_{30}$ alkenyl group, a $C_2$-$C_{30}$ alkynyl group, a $C_1$-$C_{30}$ alkoxyl group, a $C_6$-$C_{30}$ aryloxy group and a $C_6$-$C_{30}$ arylthio group, and adjacent groups may be bonded to each other to form a ring,
a and b are each an integer of 0 to 4, and when each of these is an integer of 2 or more, a plurality of $R^1$s are each the same as or different from each other and a plurality of $R^2$s are each the same as or different from each other,
$R^3$ and $R^4$ are each independently selected from the group consisting of hydrogen, deuterium, halogen, a cyano group, a nitro group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a $C_1$-$C_{30}$ alkyl group, a $C_2$-$C_{30}$ alkenyl group, a $C_2$-$C_{30}$ alkynyl group, a $C_1$-$C_{30}$ alkoxyl group, a $C_6$-$C_{30}$ aryloxy group and -L'-N($R_a$)($R_b$), and $R^3$ and $R^4$ may be bonded to each other to form a ring,
$Ar^1$ to $Ar^4$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, and a $C_3$-$C_{60}$ aliphatic ring,
$L^1$ to $L^6$ are each independently selected from the group consisting of a single bond, a $C_6$-$C_{60}$ arylene group, a fluorenylene group, a $C_3$-$C_{60}$ aliphatic ring, and a $C_2$-$C_{60}$ heterocyclic group comprising at least one heteroatom selected from the group consisting of O, N, S, Si and P,
i and j are each an integer of 0 to 2, and when both i and j are 0, one of $R^3$ and $R^4$ contain -L'-N($R_a$)($R_b$),
when i is an integer of 2, a plurality of $Ar^1$s, a plurality of $Ar^2$s, a plurality of $L^1$s, a plurality of $L^2$s, a plurality of $L^3$s are the same as or different from each other,
when j is an integer of 2, a plurality of $Ar^3$s, a plurality of $Ar^4$s, a plurality of $L^4$s, a plurality of $L^5$s, a plurality of $L^6$s are the same as or different from each other,
L' is selected from the group consisting of a single bond, a $C_6$-$C_{60}$ arylene group, a fluorenylene group, a $C_3$-$C_{60}$ aliphatic ring, and a $C_2$-$C_{60}$ heterocyclic group comprising at least one heteroatom selected from the group consisting of O, N, S, Si and P,
$R_a$ and $R_b$ are each independently selected from the group consisting of a $C_6$-$C_{60}$ aryl group, a fluorenyl group, a $C_3$-$C_{60}$ aliphatic ring, and a $C_2$-$C_{60}$ heterocyclic group comprising at least one heteroatom selected from the group consisting of O, N, S, Si and P, and
$R^1$ to $R^4$, $Ar^1$ to $Ar^4$, $L^1$ to $L^6$, L', $R_a$, $R_b$, the ring formed by adjacent groups or by $R^3$ and $R^4$ may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ aliphatic ring group, a $C_7$-$C_{20}$ arylalkyl group, $C_8$-$C_{20}$ arylalkenyl group and -L'-N($R_a$)($R_b$),
wherein the organic material layer comprises two or more stacks, and the stacks each comprise a hole transport layer, a light emitting layer, and an electron transport layer formed sequentially on the anode.

15. The organic electric element of claim 14, wherein the organic material layer further comprises a charge generation layer formed between the two or more stacks.

16. The organic electric element of claim 1, further comprising a layer for improving luminous efficiency on one side of the anode and/or the cathode, wherein the one side is not facing the organic material layer.

17. An electronic device comprising a display device and a control unit for driving the display device, wherein the display device comprises the organic electric element of claim 1.

18. The electronic device of claim 17, wherein the organic electric element is selected from the group consisting of an organic light emitting diode, an organic solar cell, an organic photo conductor, an organic transistor, an element for monochromatic illumination and a quantum dot display.

\* \* \* \* \*